United States Patent
Prag

(10) Patent No.: US 10,982,252 B2
(45) Date of Patent: Apr. 20, 2021

(54) BACTERIAL SYSTEMS FOR ANALYZING UBIQUITYLATED POLYPEPTIDES

(71) Applicant: Technology Innovation Momentum Fund (Israel) Limited Partnership, Tel-Aviv (IL)

(72) Inventor: Gali Prag, Pardes Hannah-Karkur (IL)

(73) Assignee: Technology Innovation Momentum Fund (Israel) Limited Partnership, Tel-Aviv (IL)

( * ) Notice: Subject to any disclaimer, the term of this patent is extended or adjusted under 35 U.S.C. 154(b) by 146 days.

(21) Appl. No.: 16/322,956

(22) PCT Filed: Aug. 8, 2017

(86) PCT No.: PCT/IL2017/050876
§ 371 (c)(1),
(2) Date: Feb. 3, 2019

(87) PCT Pub. No.: WO2018/029682
PCT Pub. Date: Feb. 15, 2018

(65) Prior Publication Data
US 2019/0185902 A1 Jun. 20, 2019

Related U.S. Application Data

(60) Provisional application No. 62/371,881, filed on Aug. 8, 2016.

(51) Int. Cl.
*C12Q 1/02* (2006.01)
*C12Q 1/48* (2006.01)
*C12N 9/10* (2006.01)

(52) U.S. Cl.
CPC ............ *C12Q 1/025* (2013.01); *C12N 9/104* (2013.01); *C12Q 1/48* (2013.01); *C07K 2319/95* (2013.01); *G01N 2333/9015* (2013.01); *G01N 2333/9108* (2013.01); *G01N 2500/02* (2013.01); *G01N 2500/10* (2013.01)

(58) Field of Classification Search
CPC ...................................................... C12Q 1/48
See application file for complete search history.

(56) References Cited

U.S. PATENT DOCUMENTS

| | | | |
|---|---|---|---|
| 2003/0049688 A1 | 3/2003 | Michnick et al. | |
| 2004/0043386 A1 | 3/2004 | Pray et al. | |
| 2006/0194262 A1 | 8/2006 | Xu et al. | |
| 2007/0059731 A1 | 3/2007 | Kerppola | |
| 2009/0298089 A1 | 12/2009 | Rossner et al. | |
| 2011/0287963 A1 | 11/2011 | Delisa et al. | |

FOREIGN PATENT DOCUMENTS

| WO | WO 2018/029682 | 2/2018 |
|---|---|---|
| WO | WO 2019/030759 | 2/2019 |
| WO | WO 2020/079687 | 4/2020 |

OTHER PUBLICATIONS

Chakraborty et al., Nature Communications, 2015, pp. 1-12 as printed.*
International Search Report and the Written Opinion dated Jan. 12, 2020 From the International Searching Authority Re. Application No. PCT/IL2019/051122. (14 Pages).
Levin-Kravets et al. "*E. coli*-Based Selection and Expression Systems for Discovery, Characterisation, and Purification of Ubiquitylated Proteins", The Ubiquitin Proteasome System: Methods and Protocols, Methods in Molecular Biology, 1844(Chap.11): 155-166, Sep. 22, 2018.
International Preliminary Report on Patentability dated Feb. 21, 2019 From the International Bureau of WIPO Re. Application No. PCT/IL2017/050876. (11 Pages).
International Search Report and the Written Opinion dated Nov. 13, 2018 From the International Searching Authority Re. Application No. PCT/IL2018/050880. (12 Pages).
International Search Report and the Written Opinion dated Oct. 25, 2017 From the International Searching Authority Re. Application No. PCT/IL2017/050876. (20 Pages).
Chen et al. "Random Dissection to Select for Protein Split Sites and Its Application in Protein Fragment Complementation", Protein Science, 18(2): 399-409, Published Online Dec. 29, 2008. Figs. 1, 2.
Ciechanover et al. "The Ubiquitin Proteasome System in Neurodegenerative Diseases: Sometimes the Chicken, Sometimes the Egg", Neuron, 40(2): 427-446, Oct. 9, 2003. p. 430, Right col., 2nd Para-p. 434, Right col., Last Para, p. 436, Left col., 2nd Para.
Keren-Kaplan et al. "Purification and Crystallization of Mono-Ubiquitylated Ubiquitin Receptor Rpn10", Acta Crystallographica Section F, F68(9): 1120-1123, Sep. 1, 2012.
Keren-Kaplan et al. "Synthetic Biology Approach to Reconstituting the Ubiquitylation Cascade in Bacteria", The EMBO Journal, 31(2): 378-390, Published Online Nov. 11, 2011. p. 378, First Para-p. 379, First Para, p. 381, Left col., 2nd Para, p. 386, Left col., Last Para, Fig. 1.
Keren-Kaplan et al. "Synthetic Biology Approach to Reconstituting the Ubiquitylation Cascade in Bacteria", The EMBO Journal, Supplementary Material, p. 1-28, 2011.
Levin-Kravets et al. "A Bacterial Genetic Selection System for Ubiquitylation Cascade Discovery", Nature Methods, Supplementary Materials, 11 P., Published Online Oct. 3, 2016.
Levin-Kravets et al. "A Bacterial Genetic Selection System for Ubiquitylation Cascade Discovery", Neture Methods, 13(11): 945-952, Published Online Oct. 3, 2016. Abstract, p. 945, Left col., First Para-p. 946, Right col., First Para, Figs.1, 4.
Miao et al. "A HECT E3 Ubiquitin Ligase Negatively Regulates *Arabidopsis* Leaf Senescence Through Degradation of the Transcription Factor WRKY53", The Plant Journal, 63(2): 179-188, Published Online May 11, 2010. p. 180, Last Para-p. 181, Right col., First Para, Fig.1d, 1e, p. 187, Left col., 2nd Para-Right col., 2nd Para.

(Continued)

*Primary Examiner* — Bin Shen

(57) ABSTRACT

Bacterial systems for analyzing ubiquitination of proteins is disclosed herein. Kits for analyzing the ubiquitination and methods for carrying out the analysis are also disclosed.

18 Claims, 27 Drawing Sheets
(23 of 27 Drawing Sheet(s) Filed in Color)
Specification includes a Sequence Listing.

(56) References Cited

OTHER PUBLICATIONS

Roxburgh et al. "Small Molecules That Bind the Mdm2 RING Stabilize and Activate P53", Carcinogenesis, 33(4): 791-798, Published Online Feb. 2, 2012. p. 792, Left col., Last Para, p. 794, Left col., Last Para, Figs.4A.
Shekhawat et al. "Split-Protein Systems: Beyond Binary Protein-Protein Interactions", Current Opinion in Chemical Biology, 15(6): 789-797, Available Online Nov. 7, 2011. Abstract, p. 2, First Para.
Su et al. "A Novel E3 Ubiquitin Ligase Substrate Screen Identifies Rho Guanine Dissociation Inhibitor as a Substrate of Gene Related to Anergy in Lymphocytes", The Journal of Immunology, 177(11): 7559-7566, Dec. 2006.
Supplementary European Search Report and the European Search Opinion dated Mar. 17, 2020 From the European Patent Office Re. Application No. 17838924.3. (10 Pages).
Maculins et al. "A Generic Platform for Cellular Screening Against Ubiquitin Ligases", Scientific Reports, XP055673723, 6(1): 18940-1-18940-10, Published Online Jan. 8, 2016.

\* cited by examiner

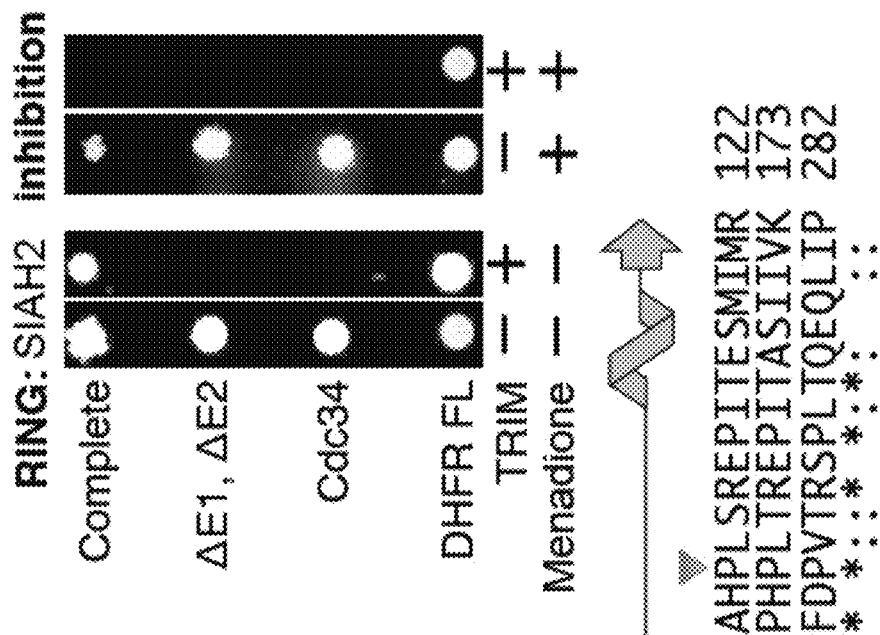
FIG. 2A
FIG. 2B
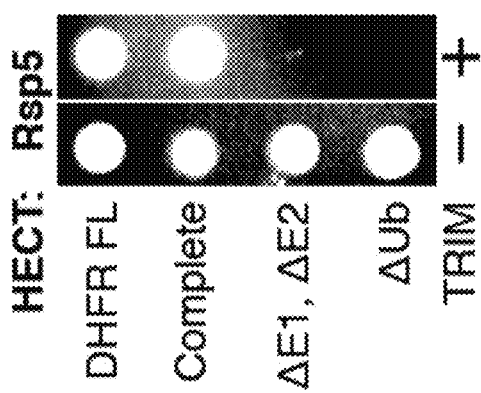
```
ECs3488  CSLYD-KDTLVQLVETGGAHPLSREPITESMIMR  122
ECs2156  CTLFD-AAAFSRLVGEGLPHPLTREPITASIIVK   173
HS_CHIP  IT-YDRKDIEEHLQRVGHFDPVTRSPLTQEQLIP   282
         :* :*    ** * * * * *:;*
```
FIG. 2C

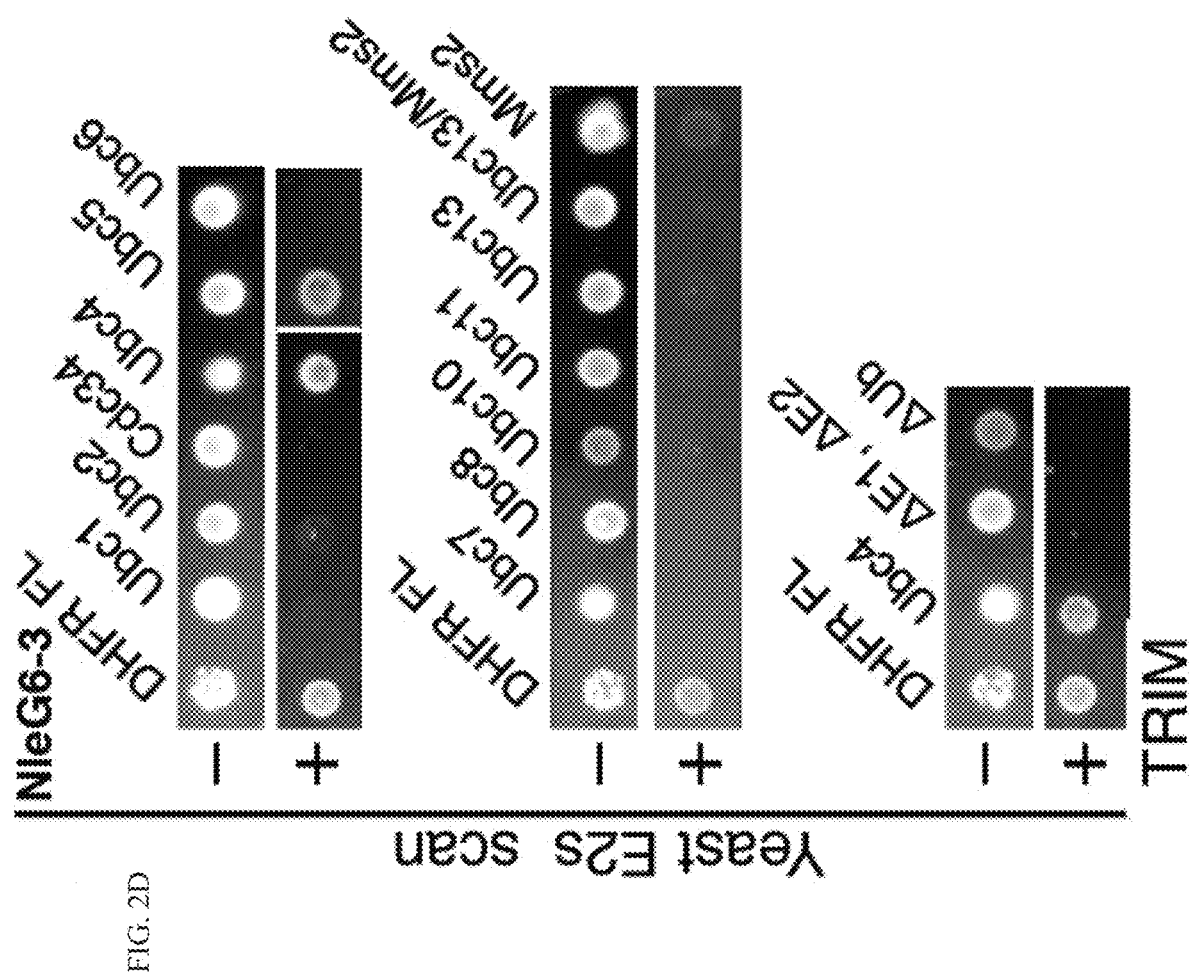

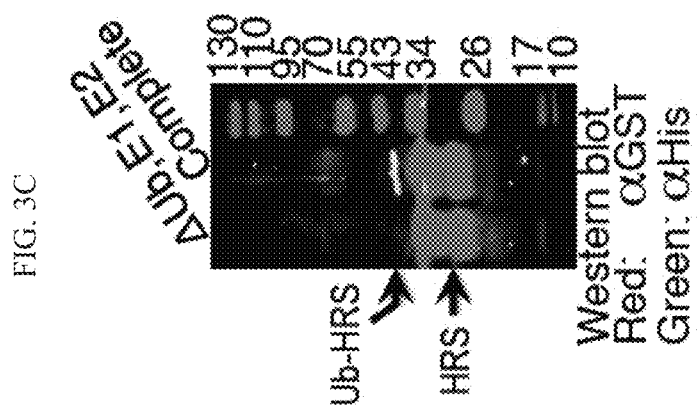

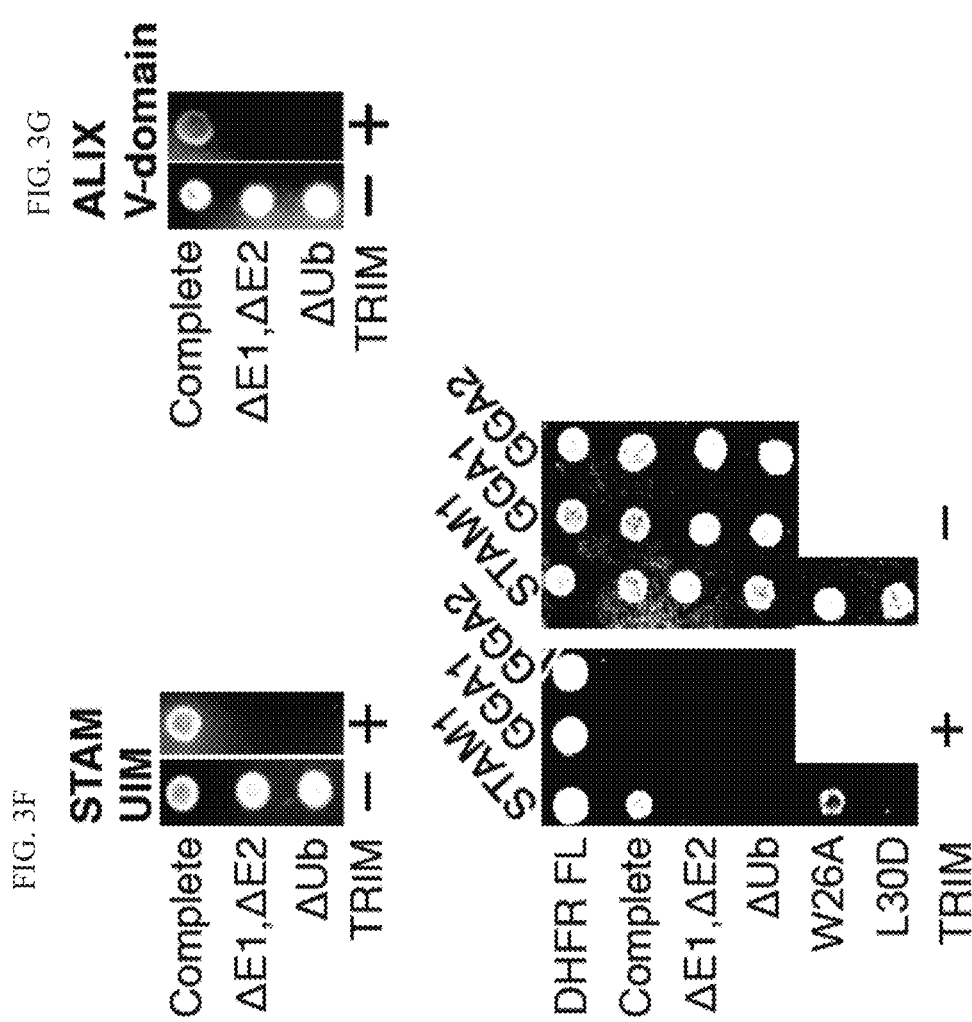

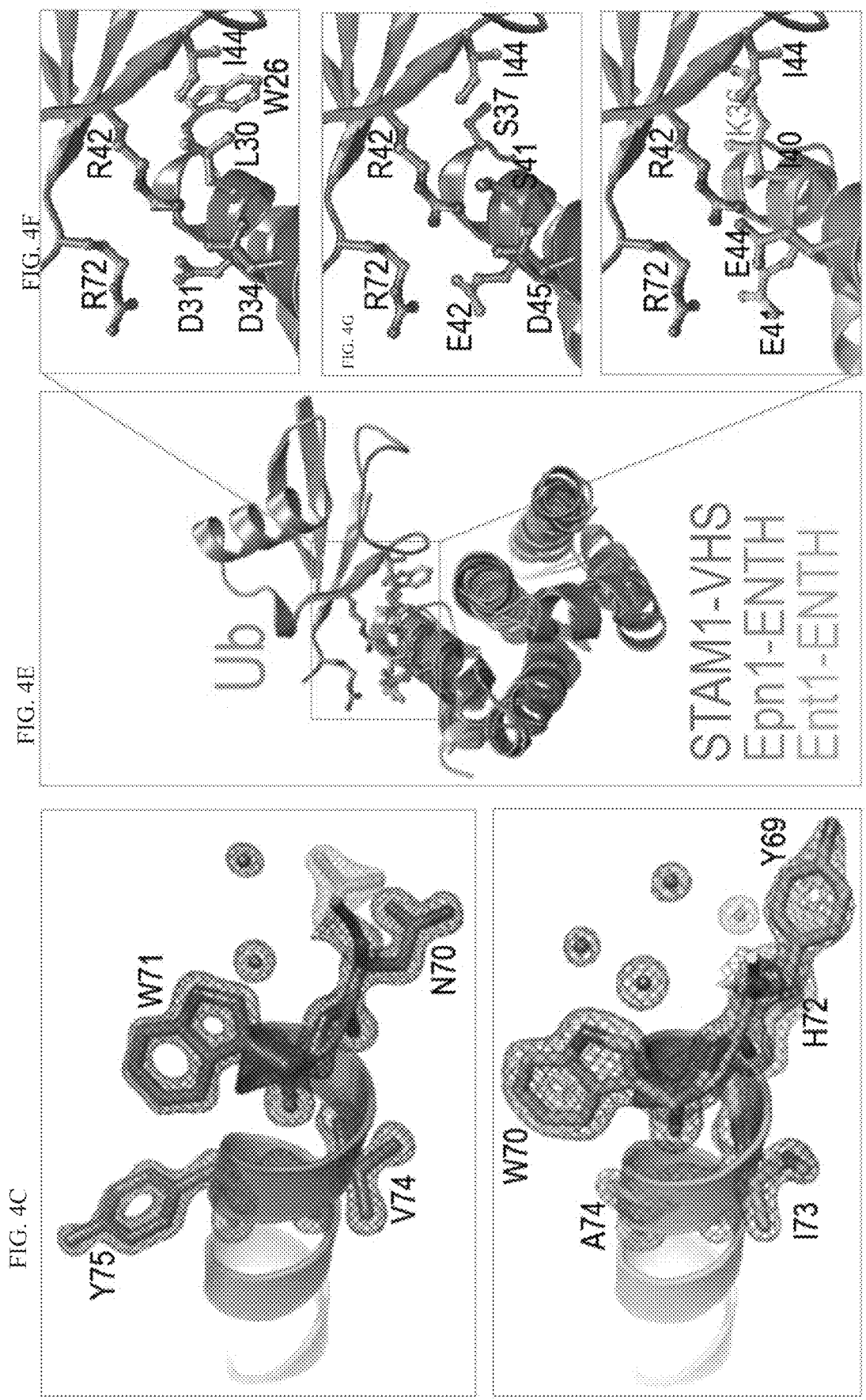

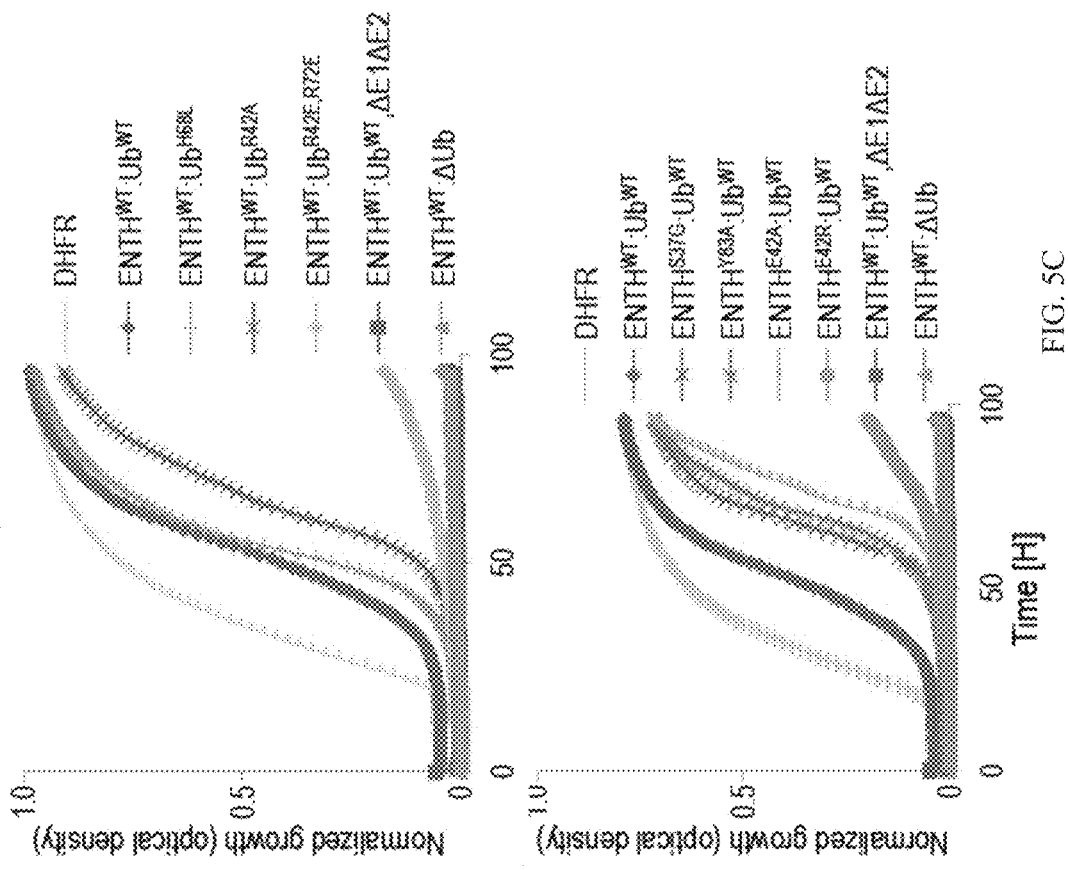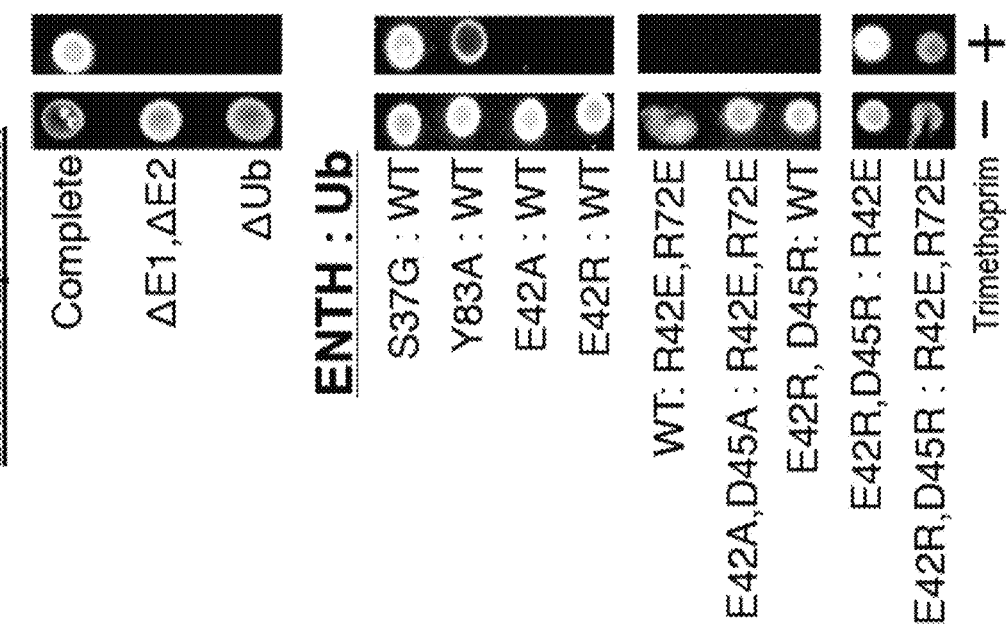

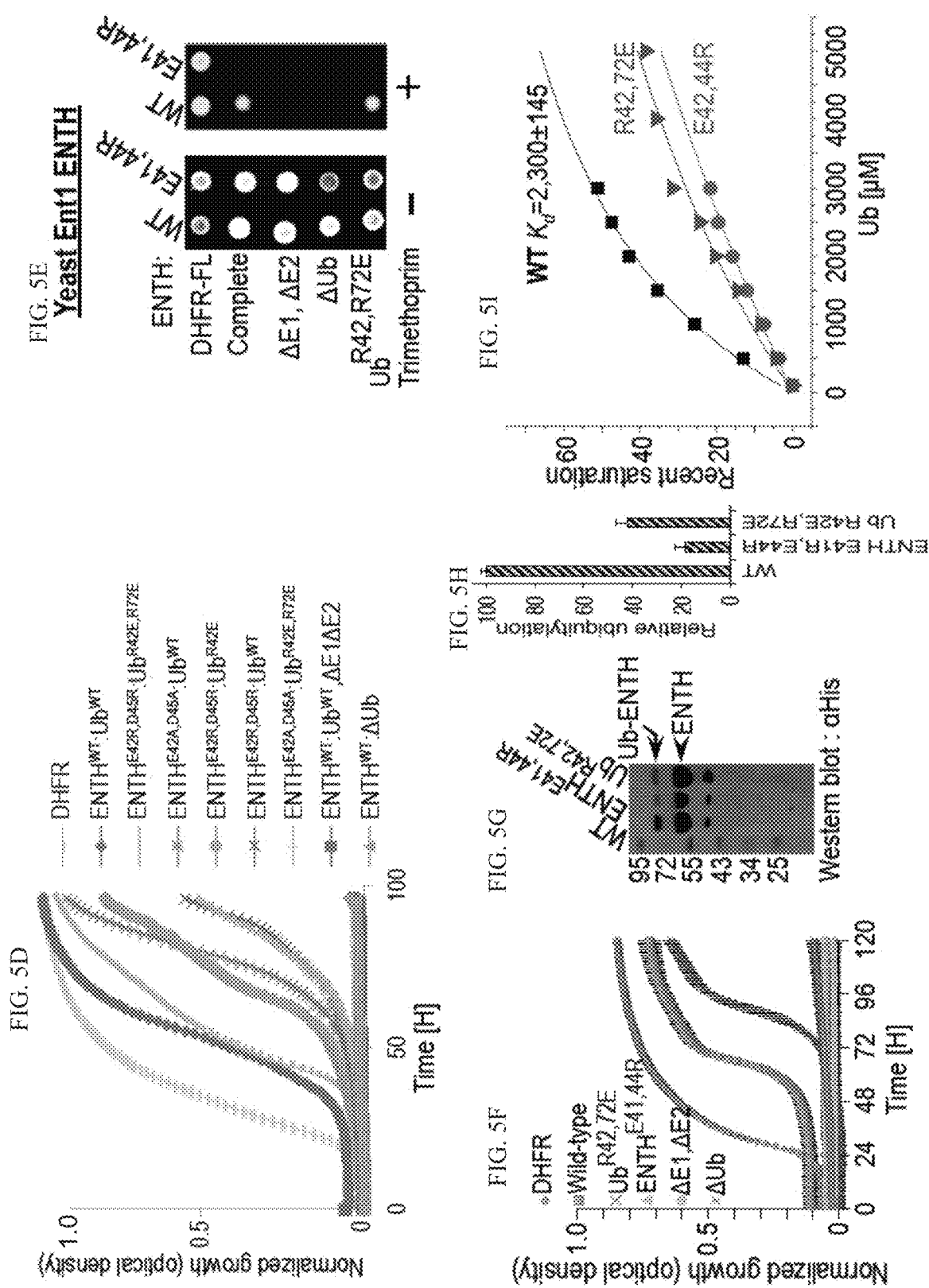

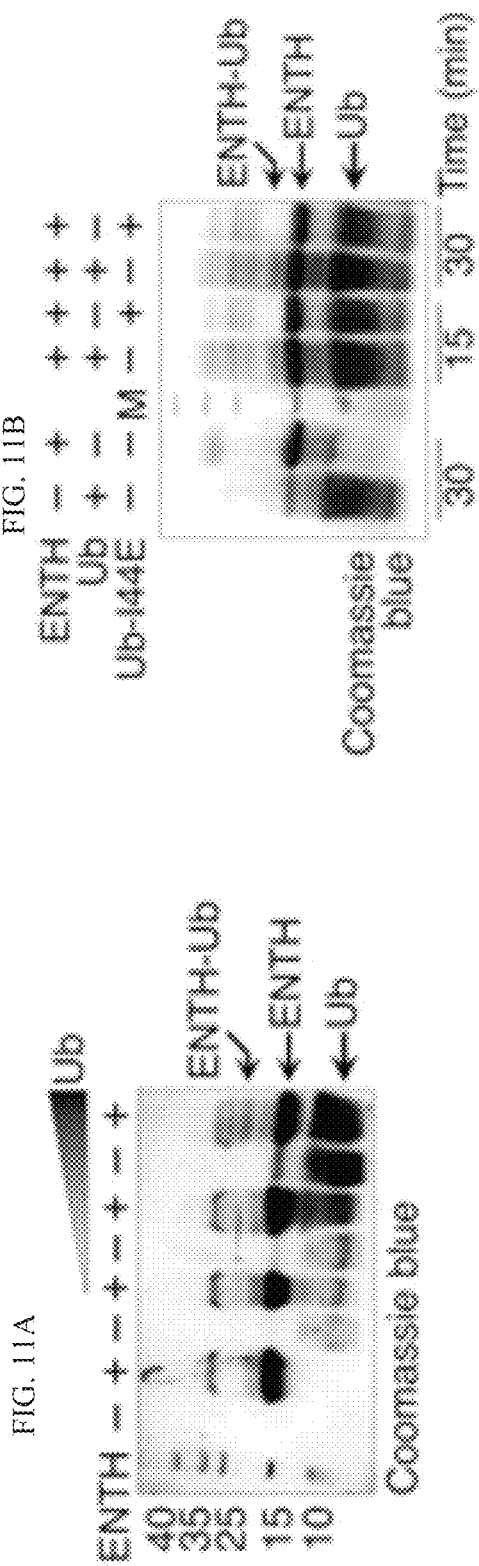
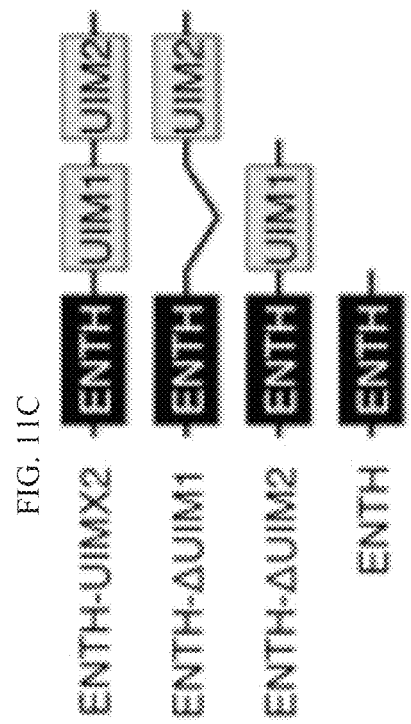
FIG. 11A
FIG. 11B
FIG. 11C

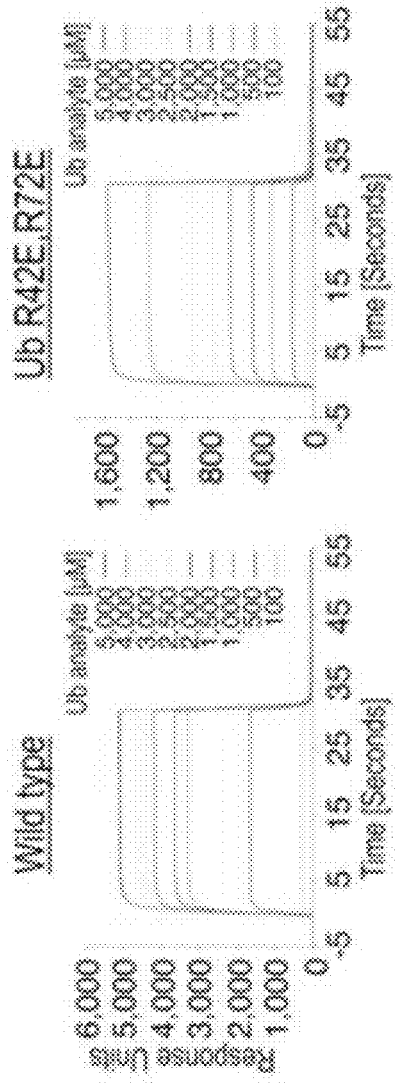
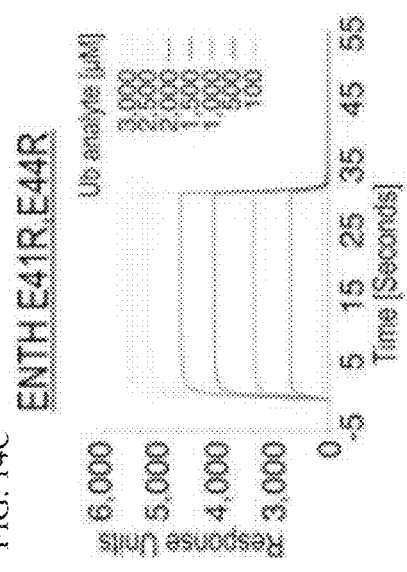
FIG. 14A Wild type
FIG. 14B Ub R42E,R72E
FIG. 14C ENTH E41R,E44R

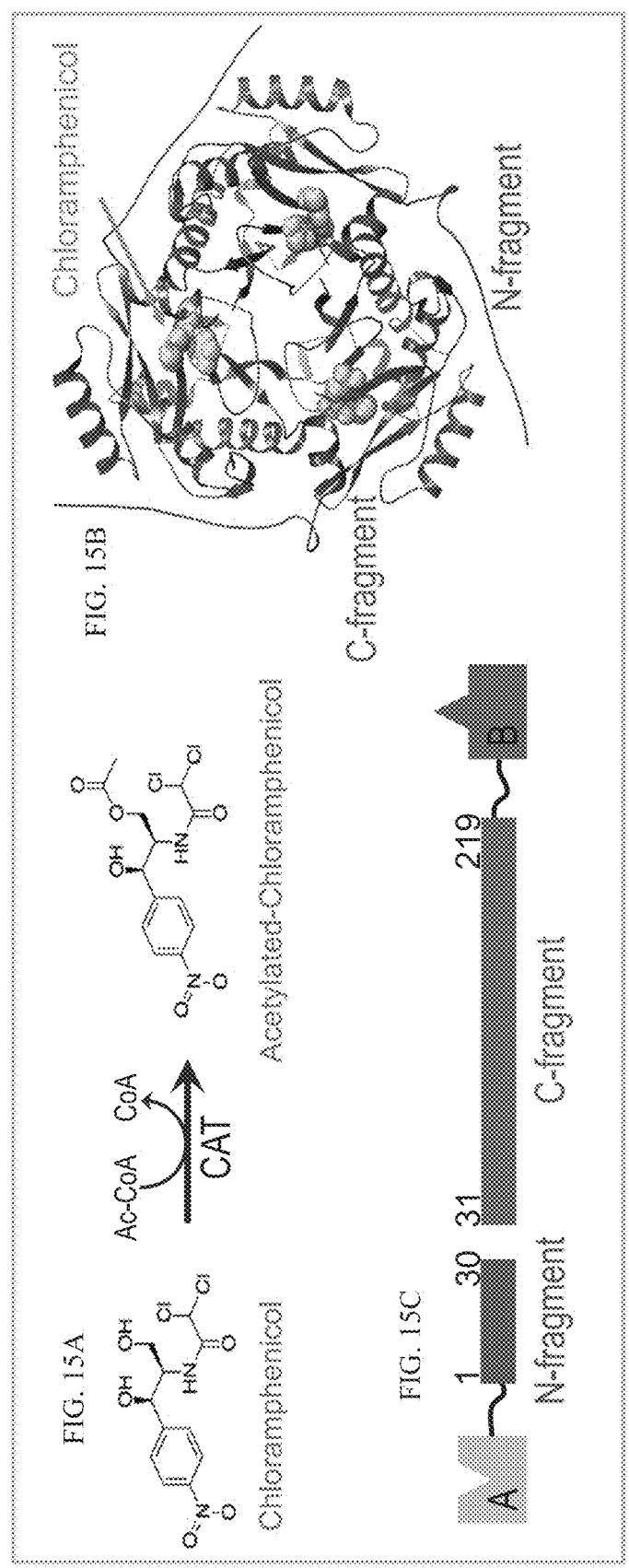

BACTERIAL SYSTEMS FOR ANALYZING UBIQUITYLATED POLYPEPTIDES

RELATED APPLICATIONS

This application is a National Phase of PCT Patent Application No. PCT/IL2017/050876 having International filing date of Aug. 8, 2017, which claims the benefit of priority under 35 USC § 119(e) of U.S. Provisional Patent Application No. 62/371,881 filed on Aug. 8, 2016. The contents of the above applications are all incorporated by reference as if fully set forth herein in their entirety.

SEQUENCE LISTING STATEMENT

The ASCII file, entitled 76523SequenceListing.txt, created on Feb. 3, 2019 comprising 264,259 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to bacterial systems for analyzing ubiquitylated polypeptides.

Ubiquitin (Ub) plays a pivotal role in numerous aspects of cellular processes. Therefore, aberrations in the Ub system are involved in a large number of pathologies, including various forms of cancer such as breast and colon cancer, neurodegenerative diseases such as Parkinson's and Alzheimer's diseases, and infectious diseases such as HIV and Ebola. Consequently, there is a critical need for a detailed understanding of the Ub system. Although there have been significant advances in understanding the ubiquitination process, much less is known about the downstream processes. These include substrate recognition by specific enzymatic interactions in the Ub system, and specific interactions between these enzymes and their substrates. In humans, for example, there are 2 E1 Ub-activating enzymes, 34 Ub-conjugating enzymes and more than 600 E3 Ub-ligases. These enzymes work on presumably several thousands of protein substrates, where specificity is mainly achieved by the E2:E3 and E3:Substrates interactions.

Another factor which impedes the researchers' efforts to fully characterize Ub cascades is the presence of deubiquitinating enzymes (DUBs) which rapidly reverse the ubiquitination signal. The half-life time of ubiquitylated proteins is thus extremely short. Specifically, it has been shown that about 100 DUBs that exist reverse the modification in a highly specific manner.

Background art includes Keren-Kaplan et al., The EMBO Journal (2012) 31, 378-390 and Su et al., J Immunol 2006;177;7559-7566.

SUMMARY OF THE INVENTION

According to an aspect of some embodiments of the present invention there is provided a method of identifying an agent which regulates the activity or amount of a ubiquitinating enzyme or deubiquitinating enzyme comprising:

(a) contacting a bacterial cell with the agent, wherein the bacterial cell outputs a detectable or selectable signal which correlates with the ubiquitination level of a substrate; and (b) measuring the level or the rate of accumulation of the detectable or selectable signal, wherein a change in the level as compared to the level in the absence of the agent, is indicative of an agent which regulates the activity or amount of the ubiquitinating or deubiquitinating enzyme.

According to an aspect of some embodiments of the present invention there is provided a method of determining whether an enzyme is capable of ubiquitinating a test substrate, the method comprising (a) expressing the enzyme in a bacterial cell;

(b) expressing ubiquitin in the bacterial cell, wherein the ubiquitin is attached to a first polypeptide fragment;

(c) expressing the test substrate in the bacterial cell, wherein the substrate is attached to a second polypeptide fragment, wherein the first polypeptide fragment associates with the second polypeptide fragment to generate a reporter polypeptide on ubiquitination of the test substrate; and (d) analyzing for the presence of the reporter polypeptide in the bacterial cell, wherein a presence of the reporter polypeptide is indicative that the enzyme is capable of ubiquitinating the test substrate.

According to an aspect of some embodiments of the present invention there is provided a method of identifying a polypeptide substrate for a ubiquitinating enzyme, the method comprising:

(a) expressing a plurality of candidate polypeptide substrates in a bacterial cell population, wherein each of the candidate polypeptide substrates is attached to an identical first polypeptide fragment;

(b) expressing the ubiquitinating enzyme in the bacterial cell population;

(c) expressing ubiquitin in the bacterial cell population, wherein the ubiquitin is attached to a second polypeptide fragment, wherein the second polypeptide fragment associates with the first polypeptide fragment to generate a reporter polypeptide on ubiquitination of the substrate; and (d) analyzing in bacterial colonies of the bacterial cell population for a presence or absence of the reporter polypeptide, wherein a presence of the reporter polypeptide is indicative of expression of a substrate for the ubiquitinating enzyme.

According to an aspect of some embodiments of the present invention there is provided a kit comprising:

(i) a first polynucleotide which encodes a first polypeptide fragment which is operably linked to a bacterial regulatory sequence, and a cloning site, wherein a position of the cloning site is selected such that upon insertion of a sequence which encodes a test polypeptide into the cloning site, following expression in a bacterial cell, a fusion protein is generated which comprises the test polypeptide in frame with the first polypeptide fragment; and (ii) a second polynucleotide comprising a second nucleic acid sequence encoding a second polypeptide fragment which is attached to ubiquitin, the second nucleic acid sequence being operably linked to a bacterial regulatory sequence, wherein the first polypeptide fragment associates with the second polypeptide fragment to generate a reporter polypeptide dependent on ubiquitination of the test polypeptide.

According to one embodiment, the ubiquitinating enzyme is a ubiquitin E3-ligase.

According to another embodiment, the ubiquitin E3-ligase is selected from the group consisting of Siah2, Smurf1, MDM2, BRCA1, PARKIN, UBE3A, TRIM5, NEDD4, UBR5 and Huwe1.

According to one embodiment, the ubiquitin E3-ligase is selected from the group consisting of Siah2, PARKIN, Smurf1, MDM2, BRCA1, MURF1, TRIM32 ITCH, UBE3B and UBE3A.

According to one embodiment, the substrate is selected from the group consisting of PHD3, SPROUTY2, Mitofusin 1, 2, MIRO, NEMO, SMADs, TβR-I, P53, S5A, HHR23, EPHEXIN5, ARC, PPARα, cyclin-B, Cdc25C, Calmodulin.

According to one embodiment, the regulates comprises downregulates.

According to one embodiment, the regulates comprises upregulates.

According to one embodiment, the ubiquitinating enzyme further comprises an E1 ligase and an E2 ligase.

According to one embodiment, the bacterial cell expresses:

(a) the ubiquitinating enzyme or the deubiquitinating enzyme;
(b) ubiquitin attached to a first polypeptide fragment; and
(c) the substrate attached to a second polypeptide fragment, wherein the first polypeptide fragment associates with the second polypeptide fragment to generate a reporter polypeptide on ubiquitination of the substrate.

According to one embodiment, the reporter polypeptide comprises a selectable polypeptide.

According to one embodiment, the selectable polypeptide is a split antibiotic resistance polypeptide.

According to one embodiment, the antibiotic resistance polypeptide is DHFR or B lactamase.

According to one embodiment, the first polypeptide fragment is attached to the ubiquitin via a linker.

According to one embodiment, the second polypeptide fragment is attached to the substrate via a linker.

According to one embodiment, the reporter polypeptide is an optically detectable signal.

According to one embodiment, the detectable polypeptide is selected from the group consisting of a split fluorescent polypeptide, a split luminescent polypeptide and a split phosphorescent polypeptide.

According to one embodiment, the analyzing is effected by bimolecular complementation of an antibiotic resistance protein.

According to one embodiment, the method further comprises expressing all the enzymes of the ubiquitinating enzyme cascade of the enzyme.

According to one embodiment, the reporter polypeptide is a detectable polypeptide or a selectable polypeptide.

According to one embodiment, the enzyme is selected from the group consisting of E3 ligase, ubiquitin E1-activating enzyme and ubiquitin E2 conjugating enzyme.

According to one embodiment, the test substrate comprises an E3 ligase or Rpn10.

According to one embodiment, the enzyme is a ubiquitin E1-activating enzyme, the method further comprises expressing in the bacterial cell a ubiquitin E2 conjugating enzyme and ubiquitin E3-ligase.

According to one embodiment, the selectable polypeptide is a split antibiotic resistance polypeptide.

According to one embodiment, the antibiotic resistance polypeptide is DHFR or B lactamase.

According to one embodiment, the first polypeptide fragment is attached to the ubiquitin via a linker.

According to one embodiment, the second polypeptide fragment is attached to the substrate via a linker.

According to one embodiment, the detectable polypeptide is an optically detectable signal.

According to one embodiment, the detectable polypeptide is selected from the group consisting of a split fluorescent polypeptide, a split luminescent polypeptide and a split phosphorescent polypeptide.

According to one embodiment, the analyzing is effected by bimolecular complementation of an antibiotic resistance protein.

According to one embodiment, the first and the second polynucleotide comprise a bacterial origin of replication.

According to one embodiment, the reporter polypeptide is a selectable polypeptide.

According to one embodiment, the reporter polypeptide comprises a selection or detectable polypeptide.

According to one embodiment, the kit further comprises a third polynucleotide which encodes at least one ubiquitinating enzyme.

According to one embodiment, the first polynucleotide and/or the second polynucleotide comprises a sequence which encodes at least one ubiquitinating enzyme.

According to one embodiment, the at least one ubiquitinating enzyme comprises ubiquitin E1-activating enzyme or ubiquitin E2-conjugating enzyme.

According to one embodiment, the at least one ubiquitinating enzyme comprises ubiquitin E1-activating enzyme and ubiquitin E2-conjugating enzyme.

According to one embodiment, the at least one ubiquitinating enzyme comprises E3 ligase.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
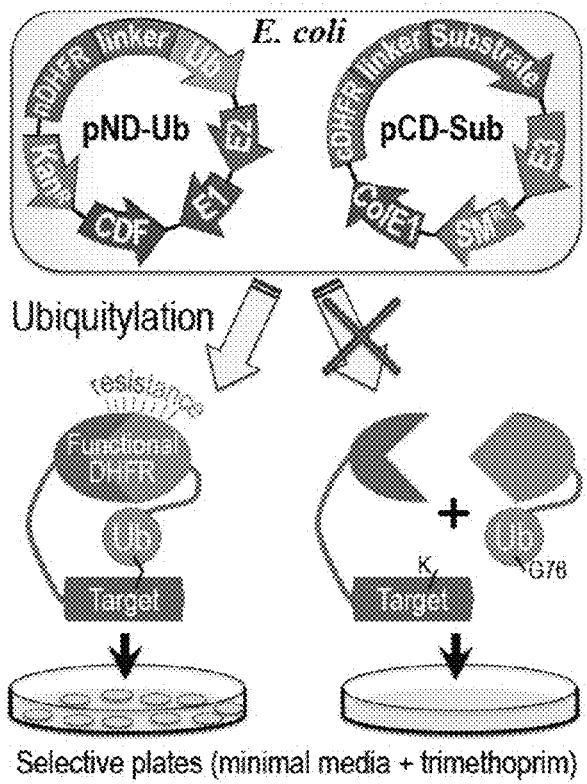

FIGS. 1A-D—Bacterial genetics approach for selection of ubiquitylated proteins. (A) A scheme demonstrates the constructed system for selection in bacteria. The ubiquitination apparatus is expressed from two compatible plasmids each harbors different antibiotic resistance and origin of replication, facilitating co-transformation and selection of the vectors regardless of ubiquitination. pND-Ub denotes the N-terminal fragment of DHFR fused to Ub. pCD-Sub denotes the C-terminal fragment of DHFR fused to a ubiquitination substrate. A complete system confers antibiotic resistance and bacterial growth in the presence of trimethoprim (TRIM). Red cross represents bacteria that express an incomplete system and therefore are not resistant to the selective media. (B) Demonstrates the system functionality. Antibiotic resistance (10 μgr/ml TRIM) is attained only when a complete ubiquitination cascade of Vps9 including wheat Uba1, yeast Ubc4, and yeast Rsp5 are co-expressed with split DHRF fragments fused to Ub and Vps9. (C) Shows that cognate E3-ligase (Rsp5) is necessary for Vps9 ubiquitination and antibiotic resistance. (D) Non-covalent interaction between Vps9 and Ub does not confer resistance for TRIM concentrations above 0.1 μg/ml. Ubiquitination—refers to complete ubiquitination cascade; binding—refers to incomplete ubiquitination cascade ($\Delta E1, \Delta E2$).

FIGS. 2A-G—Identification and characterization of NleG6-3 as E3-ligase.

(A) Bacteria that co-express cDHFR fusion to the E3-ligases Rsp5 (representative of the HECT family) with its cognate ubiquitination apparatus including Ubc4 is labeled 'complete'. Deletions of E1, E2 or Ub are indicated. (B) Bacteria that co-express cDHFR fusion to the E3-ligases Siah2 (representative of the RING family) with its cognate ubiquitination apparatus including UbcH5a is labeled 'complete'. Deletions of E1, E2, Ub or substitution of the UbcH5a with Cdc34 are indicated. The right panel shows Siah2 inhibition by menadione. (C) Shows sequence alignment derived from PSI-BLAST search using human CHIP as probe against the EHEC proteome. ECs3488 CSLYDKDTLVQLVETGGAHPLSREPITESMIMR—SEQ ID NO: 1; ECs2156 CTLFDAAAFSRLVGEGLPHPL-TREPITASIIVK—SEQ ID NO: 2; HS_CHIP ITY-DRKDIEEHLQRVGHFDPVTRSPLTQEQLIP—SEQ ID NO: 3. The full length sequence of the NleG6-3 ligase is as set forth by SEQ ID NO: 4.

(D) Yeast E2s scan for the E3-ligase ECs3488 (NleG6-3). (E) Self-ubiquitination of NleG6-3 by human UbcH5b/c. (F) Shows homology based model of NleG6-3 (orang) super imposed on the structure of EHEC NleG2-3 (blue) and Human CHIP:Ubch5b complex grey and magenta (respectively). Zooming into the predicted interface with highlighted critical binding residues. (G) Employment of the selection system for mutational analysis of the predicted E2:E3 interface.

FIGS. 3A-I—The bacterial selection system facilitates the identification and characterization of Ub-receptors. UBDs promote self-ubiquitination and therefore can be detected by the bacterial selection system. The cDHFR was fused to various UBDs in the pCD-Sub, and co-expressed in the selection system without E3-ligase. (A) Ubiquitination promoted by Hrs was used to validate the system performance. (B) Structure of the Hrs dsUIM:Ub complex (PDB code 2D3G) shows the interacting residues. (C) Western blot analysis demonstrates the formation of a covalent bond between Ub and GST-dsUIM fusion. $His_6$-Ub was co-expressed with E1 and Ubc4 along with GST-dsUIM. The protein was purified on GSH beads and subjected for western blot with anti GST (red) and anti-Histag (green). The yellow band that migrated at the molecular size of the ubiquitylated protein was detected by both antibodies. (D) The E1 inhibitor PYR41 attenuates bacterial growth only in the non-permissive conditions. Bacteria were grown in 96-well plates supplemented with PYR41 and/or TRIM as indicated. The relative growth rates at the log phase are shown with standard deviation (n=9). (E-H) Show the growth phenotypes of assorted UBDs in the selection system. e. Yeast Rpn10; f. Human STAM1-UIM; g. Human Alix-V domain; h. Yeast Hse1-VHS domain. (I) The binding of Ub to the VHS domains of human STAM1, GGA1 and GGA2 were examined in the selection system. Critical STAM1-VHS residues known to bind Ub were mutated and the growth phenotype was tested.

FIGS. 4A-J—Structural insight into a predicted ENTH:Ub interface.

(A-B) The selection system identified Epsin1-ENTH domains from yeast (Saccharomyces cerevisiae) Ent1 and from zebrafish (Danio rerio) Epn1 function as UBDs. Co-expression of these ENTH domains with the ubiquitination apparatus in the selection system conferred antibiotic resistance and promoted bacterial growth under non-permissive conditions. Structures of the zebrafish and yeast Epsin1 ENTH domains are presented. (C-D) Show the 2mFo-DFc sigma-A maps of the fish and the yeast proteins to 2.2 and 1.8 σ (respectively) of the final refined models. (E) The superimposition of the fish and the yeast ENTH structures on top of the STAM1-VHS:Ub complex (pdb code 3LDZ). Average Cα RMSD are 1.5 Å and 1.7 Å, respectively. The models were energetically minimized and carefully inspected. (F) Zoom in into crystal structure of the VHS:Ub interface (3LDZ). (G-H) Model of the ENTH:Ub complexes. (I) and (J) show zoom in into the interface of the model complexes.

FIGS. 5A-I—Characterization of the ENTH:Ub binding interface.

Structure-based mutants at the predicted ENTH:Ub interface were constructed and characterized. (A) Growth phenotypes of the zebrafish ENTH and Ub mutants in the selection system. (B) Growth curves of Ub wild type and mutants derived from the time-lapse scanning of the spots (density was analyzed by Fiji). (C) As shown in b, but for ENTH mutants. (D) As shown in b and c but for reciprocal mutations. (E) Growth phenotypes of the yeast ENTH and Ub mutants in the selection system. (F) As shown in b, but for yeast ENTH and Ub mutants. (G) The ubiquitination yield for wild-type and indicated mutants of the yeast $His_6$-MBP-ENTH were evaluated. The apo and ubiquitylated proteins were purified on amylose beads as described[17], resolved on SDS-PAGE and detected by western blot with anti His-tag antibody. (H) Quantification of the ubiquitination yields shown in (G). The ubiquitylated/apo ratio is presented as a percentage of the wild-type ratio. Values were averaged from four independent experiments, and standard deviation error bars are presented. (I) Surface Plasmon Resonance (SPR) analysis of the yeast ENTH:Ub binding affinity of wild-type and mutant proteins. Fitting to binding curves was carried out with a single-site-binding model using the OriginLab software. Standard errors derived from three independent measurements are indicated.

FIGS. 6A-D—Sem1 is a ubiquitination substrate of Rsp5.

Screening of pCD-Sub yeast fusion library revealed Sem1 as potential ubiquitination substrate of Rsp5 in the bacterial selection system. (A) Spots growth at the indicated hours post seeding shows that Rsp5 significantly promotes Sem1 ubiquitination (compare complete system that contains Rsp5 with a ΔRsp5 cascades). A 30 minutes intervals time-lapse movie of the scans can be found in the supplementary data. (B) Growth curves derived from quantification of the scans using 'Time Series Analyzer' in Fiji. Values are average of eight spots with standard deviation bars. (C) Detection of Sem1 ubiquitination in E. coli. Purified $His_6$-MBP-Semi from E. coli that co-express ubiquitination apparatus[17] was resolved on SDS-PAGE and detected by western-bolt with anti-Histag antibody. (D) Sem1 is a ubiquitination substrate of Rsp5 in vivo in yeast. $His_6$-Sem1 was expressed from Gal inducible promoter in wild-type or rsp5-1 yeast cells. Cultures grew at 25° C. (permissive conditions). Prior induction temperature was shift to 37° C. or remained as indicated.

His₆-Sem1 was purified under denatured conditions, resolved and detected as in (C).

FIGS. 7A-F—Functional analysis of the vWA:Ub binding patch. (A) Scheme showing a bacterial genetic selection system for ubiquitination (B) Ubiquitination addicted bacterial growth on selective (+Trimethoprim) or non-selective plates. A single scan of the plates 98 hours post seeding is shown. (C) Shows quantitation of ubiquitination dependent bacterial growth. Average density of individual spots monitored by scanning the plates in 1 hour intervals was plotted. Efficiency was calculated as the max growth density divided by the time of half max growth. NSG-no significant growth. (D) Shows a representative SPR response curves for the vWA:Ub complex. (E) Single model binding analysis of SPR affinity measurements of Rpn10:Ub wt and the indicated mutants. Kd values are indicated (right; NB-no binding). (F) Comparison between the relative growth of wt or mutant spots and the SPR measured association constants ($K_a$). Pearson product-moment correlation coefficient is r=0.99 (p<0.001).

Figure 8A:
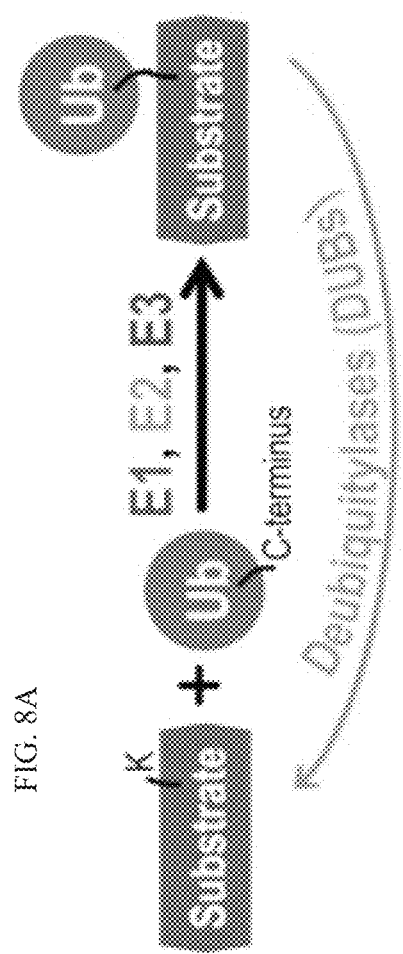
Figure 8B:
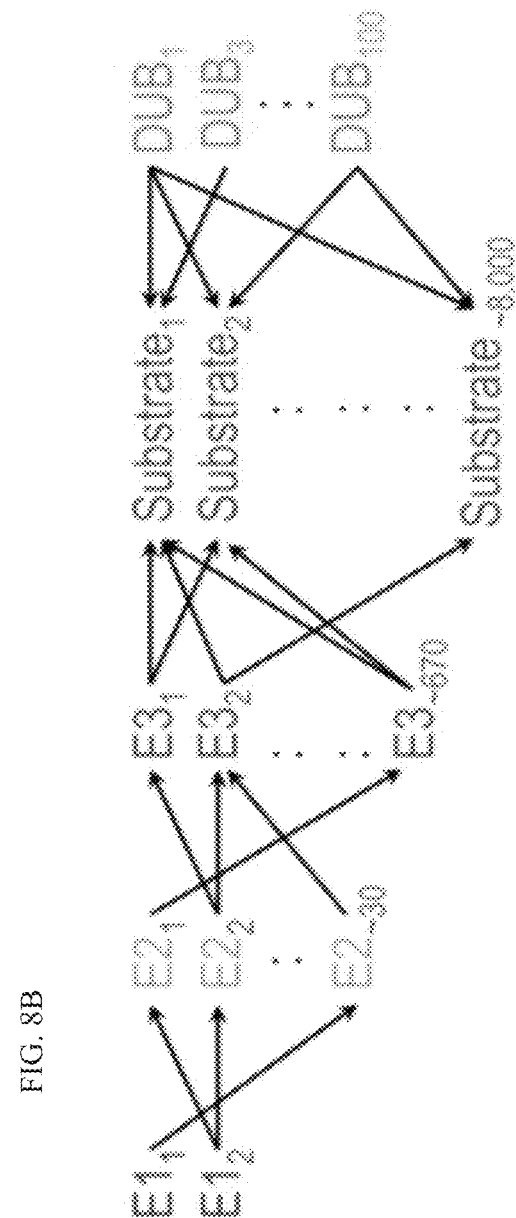

FIGS. 8A-B—Schemes show two of the major hurdles that pose challenges in assigning specific associations of components along ubiquitin cascades.

(A) Ubiquitination is rapidly reversed by deubiquitylases. In human there are about hundred deubiquitinating enzymes (DUBs) which efficiently and rapidly remove the ubiquitin moiety from targeted proteins.

(B) Ubiquitination cascades are multiplex. For example eight different substrates were found for the BRCA1 E3-ligase. Similarly, 7 different E3-ligases were demonstrated to ubiquitylate p53.

Figure 9:
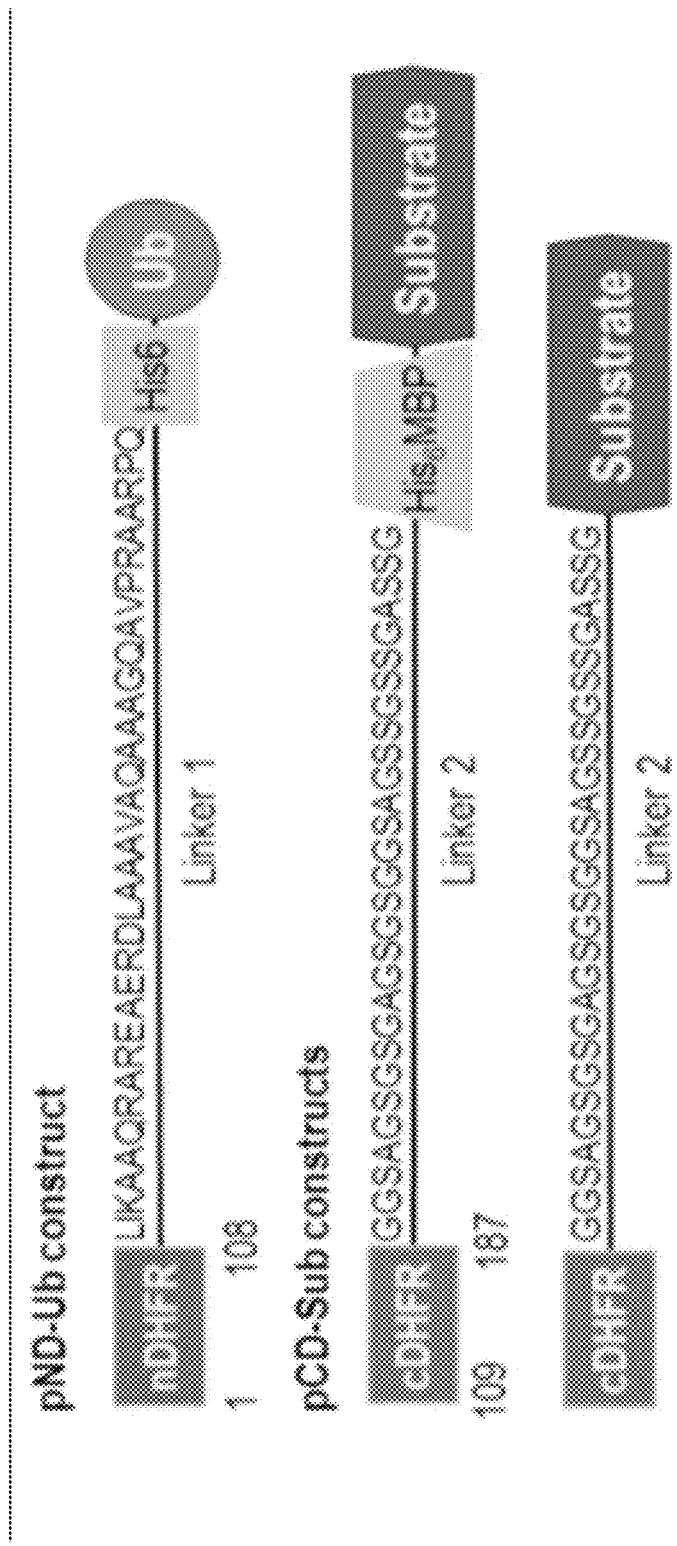

FIG. 9—Architecture and sequence of the linkers connecting the DHFR fragments to Ub and substrates. Schematic illustration of the constructs used in the selection system. pND-Ub vectors contain a N-Terminal DHFR fragment fused through the flexible linker (linker 1) to Ub. In the pCD-Sub the C-Terminal fragment of the DHFR was fused through the flexible linker (linker 2) to the His₆-MBP-substrate or directly to the substrate.

```
Linker1:
                                        SEQ ID NO: 5
LIKAAQRAREAERDLAAAVAQAAAGQAVPRAAPRQ- Linker2:
                                        SEQ ID NO: 6
GGSAGSGSGAGSGSGGSAGSSGSSGASSG-.
```

Figure 10:
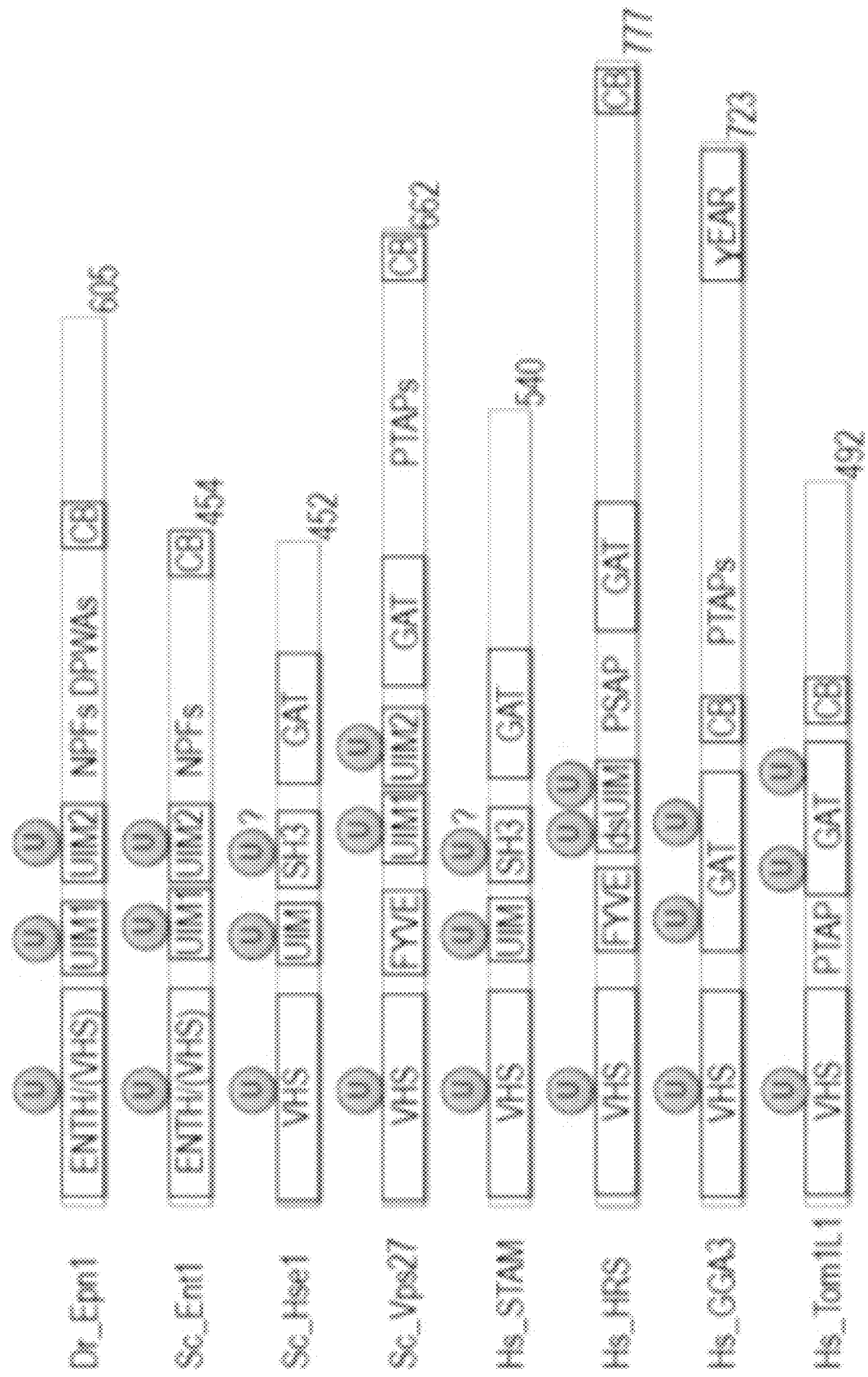
Figure 11D:
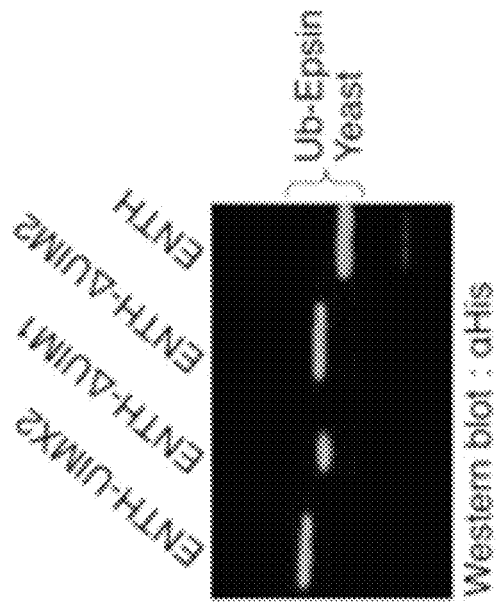
Figure 11E:
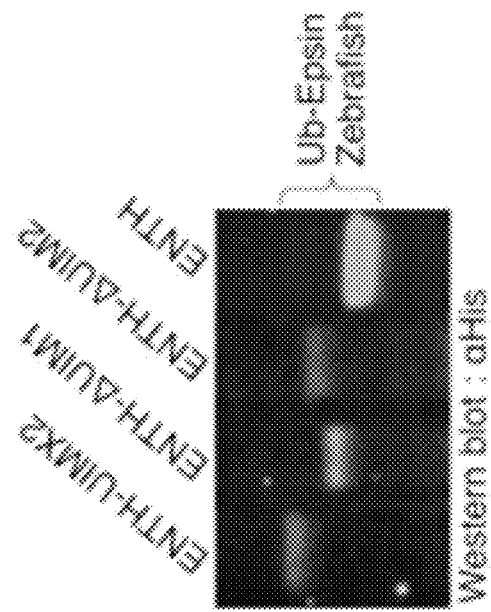

FIG. 10—Domain architecture of membrane associated Ub-receptors. Ub moieties mark the binding sites (orange circled U's).

FIGS. 11A-E—Ent1-ENTH domain directly binds ubiquitin. (A) Shows crosslinking assay of Ent1-ENTH domain with increased concentrations of Ub. A mild crosslinker, disuccinimidyl suberate (DSS) was used. Reactions were resolved by SDS-PAGE and Coomassie blue stained. (B) Shows crosslinking assay like in (A) of Ent1-ENTH domain with wild-type and Ub I44E mutant for various incubation times (as indicated). (C) Scheme of yeast and zebrafish Epsin-1 derivative constructs. (D). Ubiquitination of yeast Ent1 derivatives. (E). Ubiquitination of zebrafish Epn1 derivatives. His₆-Ub was co-expressed with E1 and Ubc4 along with GST-Epsin1 derivatives. Proteins were purified on GSH-beads and ubiquitination was detected by western blot using anti-Histag antibody as described in[17].

Figure 12B:
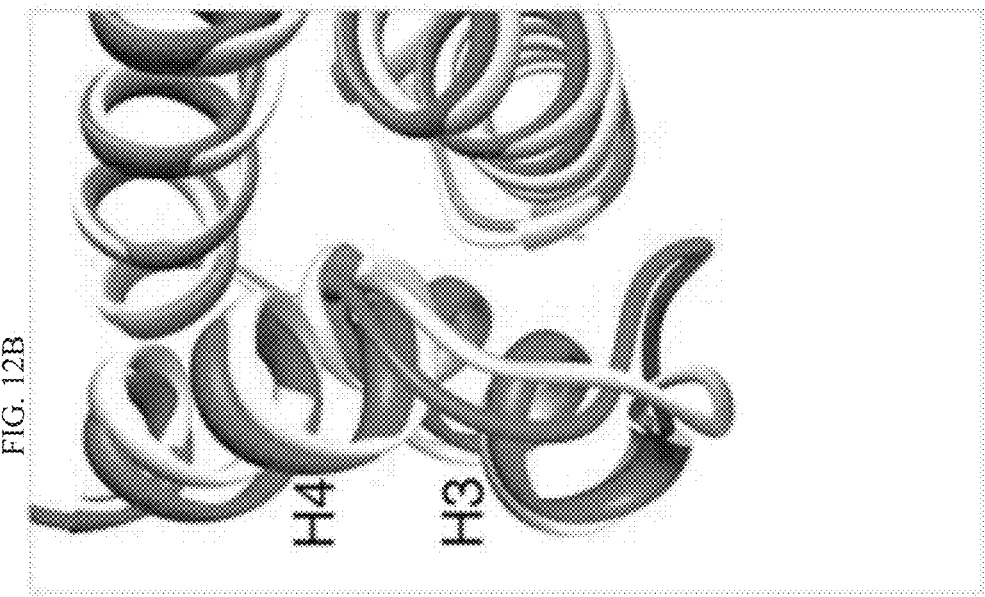
Figure 12A:
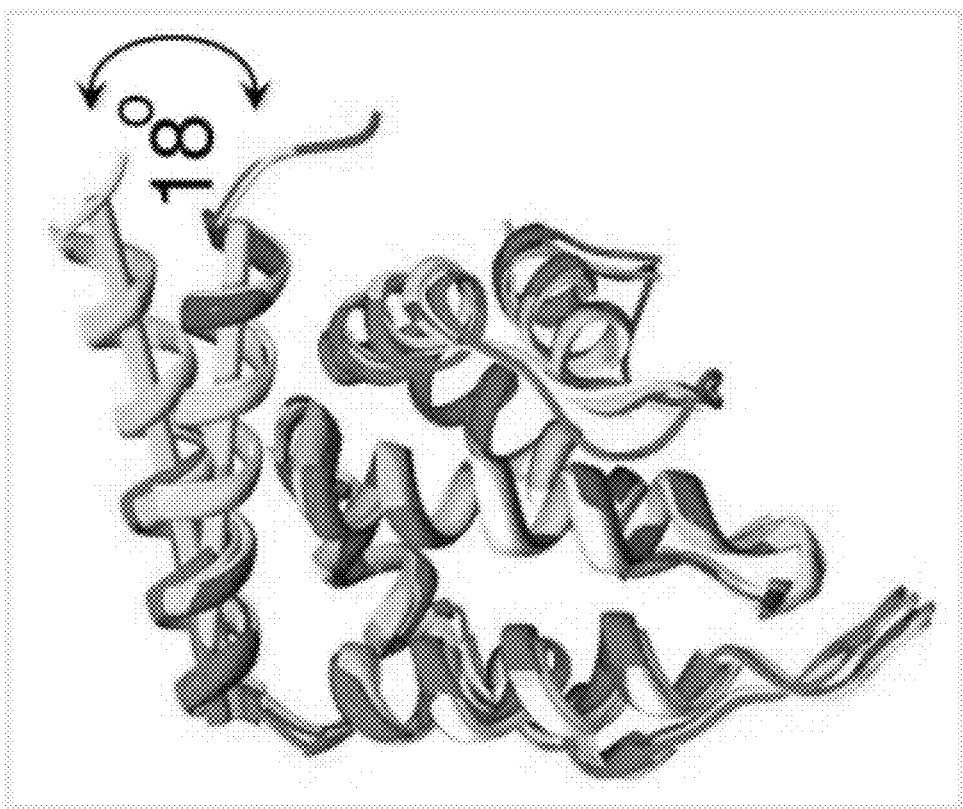

FIGS. 12A-B—Structural divergence within the ENTH domains. The coordinates of several ENTH domains including yeast (magenta), zebrafish (white), and three structures of rat ENTH domains (cyan, red and yellow), were superposed. The axis of helix-8 from each of the structures were calculated. Then the angles among the derived helices were compared (A). Structural differences between the loops tethering helices number 3 and 4 in yeast and zebrafish ENTH domains are presented (B).

Figure 13:
Figure 15D:
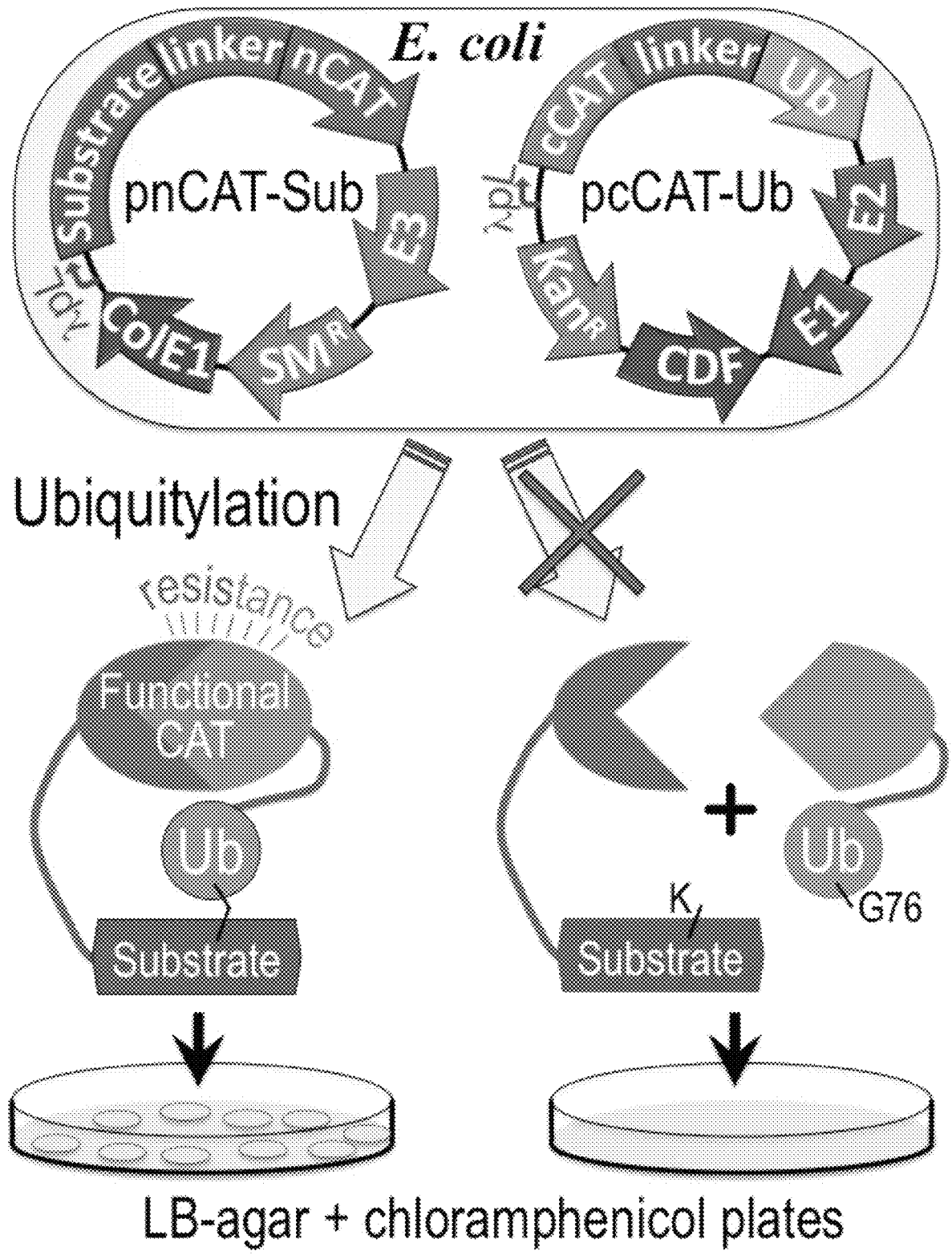

FIG. 13—ENTH/VHS domains can simultaneously associate with membranes and ubiquitin. Superimposing the ENTH complex with the lipid phosphatidylinositol-4,5-bisphosphate, GGA3-VHS complex with the Mannose-6P Receptor tail and the STAM1-VHS:Ub shows that membrane and Ub associations occur at opposite sides of the domain and therefore can occur simultaneously.

FIGS. 14A-C—Surface Plasmon Resonance (raw data). Sonograms of the SPR responses of the WT and the indicated mutants are presented.

FIGS. 15A-D—a schematic view of the split CAT bacterial selection system for ubiquitination.

A. The reaction executed by CAT (i.e. transfer of acetyl group from acetyl-CoA to chloramphenicol is shown.

B. Structure representation of assembled split CAT with chloramphenicol.

C. Linear representation of the split-CAT system.

D. cartoon view of the split CAT bacterial selection system.

FIGS. 16A-D—Split-CAT system detects ubiquitination.

A. Shows E3 independent uniquitination of the Ub-binding domain VHS of yeast Hse1.

B. The split CAT system shows significant higher growth efficiency that shortens the experimental time. Shown is UBE3A dependent ubiquitination of Rpn10 in the split CAT and DHFR selection system.

C. Mutation in UBE3A E3 ligase (G738E) that causes Angelman-syndrome phenotype.

D. The split CAT system facilitates the study of E3 ligases that cannot be purified from E. Coli such as UBE3B. Shown is UBE3B dependent ubiquitination of Rpn10 in the split CAT system. Kaufman syndrome mutation (G781R) in UBE3B shows a phenotype.

Figures 17A, 17B:

FIGS. 17A-B illustrate the DNA sequence and the translation products of $CAT_f$ (FIG. 17A-SEQ ID NO: 63 and SEQ ID NO: 64) and the split-$CAT_f$ fragments (FIG. 17B-SEQ ID NOs: 65-68). Arrow marks the cleavage site that was chosen for the split protein fragments (top). The stop codon after residue Q30 and the initiation codon prior residue C31 are shown in the split protein fragments (bottom).

DESCRIPTION OF SPECIFIC EMBODIMENTS OF THE INVENTION

The present invention, in some embodiments thereof, relates to bacterial systems for analyzing the ubiquitination of polypeptides.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Figure 7A:
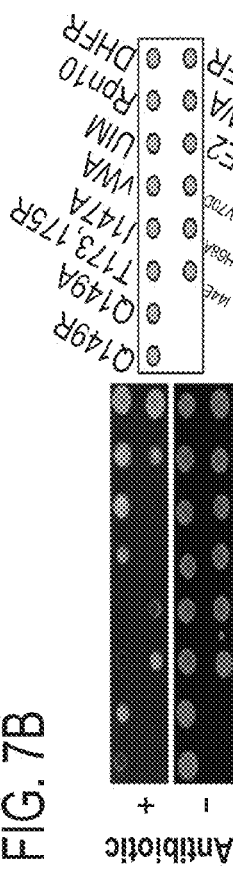
Figure 7B:
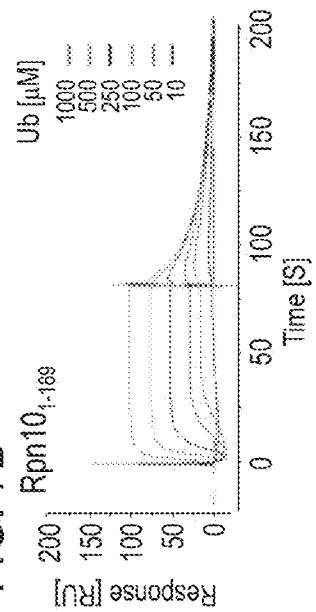
Figure 7C:
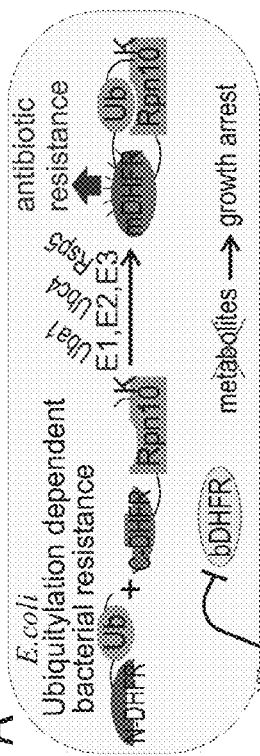
Figure 7D:
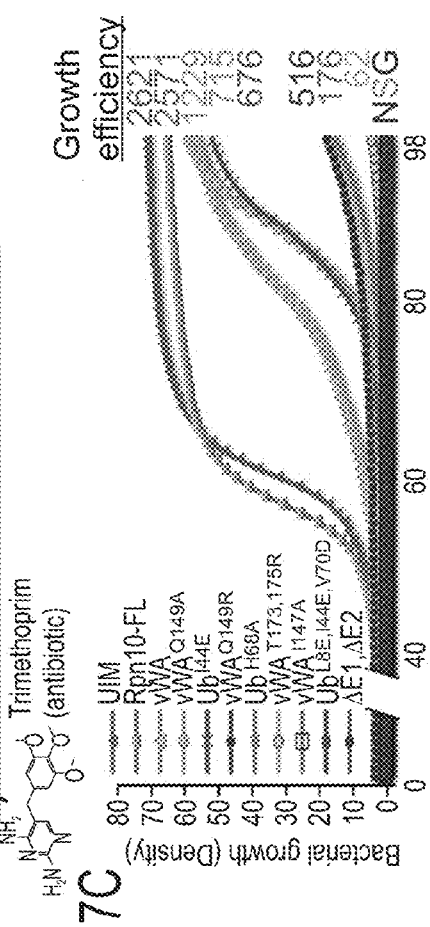
Figure 7E:
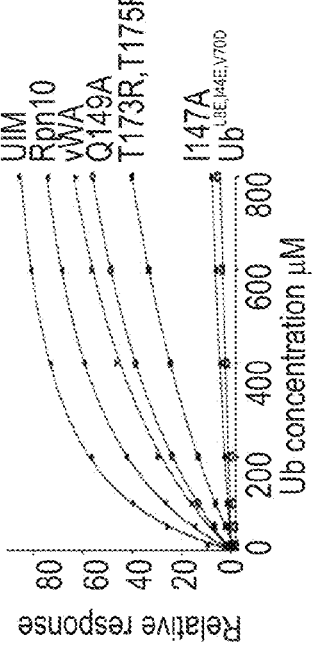
Figure 7F:
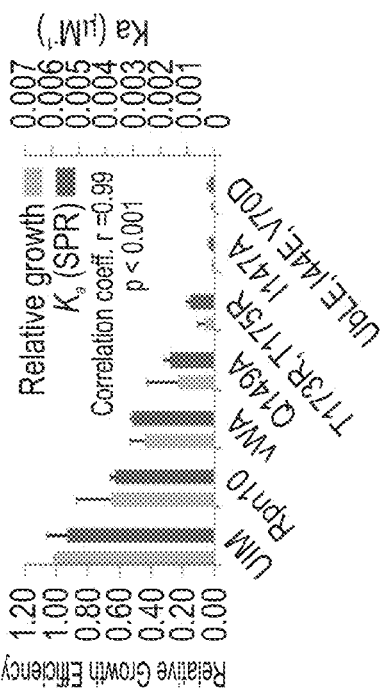

About one-third of the eukaryotic proteome undergoes ubiquitination, but most of the enzymatic cascades leading to substrate modification are still unknown. The present inventors have invented a genetic selection tool that utilizes E. coli, which lack deubiquitylases, to identify interactions along ubiquitination cascades. Co-expression of split antibiotic resistance protein tethered to ubiquitin and ubiquitination target together with a functional ubiquitination apparatus results in a covalent assembly of the resistance protein, giving rise to bacterial growth on selective media. The capability of the screening tool for small molecule modulators, in a high-throughput format is demonstrated herein. In addition, using a complete E2-library in the selection system, the present inventors identified and characterized an E3-ligase from the pathogenic bacteria EHEC. Furthermore, the present inventors identified ENTH as an ultraweak ubiquitin-binding domain, demonstrating the tool's high sensitivity. X-ray crystallography combined with bacterial selection studies facilitates structure-function analysis of the ENTH:ubiquitin interface. Moreover, study of the Rpn10: Ub non-covalent interaction (FIGS. 7A-F) demonstrated an excellent correlation between the growth efficiency under restrictive conditions of wild-type and mutants in the genetic selection system and the binding affinities measured by Surface Plasmon Resonance (SPR). FIG. 7F shows a comparison between the relative growth efficiency on selective media and the relative SPR association constants ($K_a$). Linear regression provides a Pearson correlation coefficient of r=0.99 (p <0.001).

These finding demonstrate that one can employ the system for drug discovery and improvements (hit-to-lead) as the ubiquitination dependent growth is highly correlated with the affinities along the cascade. Whilst further reducing the present invention to practice, the present inventors constructed and screened a yeast fusion library and discovered a novel physiological ubiquitination. Collectively, the developed system provides a robust high-throughput approach for genetic studies of ubiquitination cascades.

Thus, according to one aspect of the present invention there is provided a method of identifying an agent which regulates the activity or amount of a ubiquitinating enzyme or deubiquitinating enzyme comprising:

(a) contacting a bacterial cell with the agent, wherein the bacterial cell outputs a detectable or selectable signal which correlates with the ubiquitination level of a substrate; and (b) measuring the level or the rate of accumulation of the detectable or selectable signal, wherein a change in the level as compared to the level in the absence of the agent, is indicative of an agent which regulates the activity or amount of the ubiquitinating or deubiquitinating enzyme.

The method of this aspect of the present invention can screen for agents that upregulate or downregulate the activity and/or amount of the enzyme.

Agents that may be screened include small molecule agents, peptide agents, nucleic acid agents, antibodies, proteins, chemotherapeutic agents etc.

The screening assay of this aspect of the present invention uses bacteria that have been genetically modified to output a detectable or selectable signal which correlates with the ubiquitination level of a substrate.

Ubiquitination takes place by a cascade of enzyme activity (i.e. a plurality of enzymes which work together to bring about the same function—ubiquitination). For example, E1 activates the Ub; then Ub is transferred to E2. E2 together with E3 (or in many cases transfer the Ub to E3) recognize a specific target and ligate the Ub to the target protein.

Below is a list of the components of the assay which are expressed by the genetically modified bacteria of this aspect of the present invention, each of which will be described in detail herein below.

1. Ubiquitin;
2. Detectable signal;
3. At least one ubiquitinating or deubiquitinating enzyme; and
4. Substrate (target for ubiquitylation).

Any bacteria can be used for this assay so long as it lacks endogenous deubiquitinase activity and preferably also endogenous ubitquitinase activity. In one embodiment, the bacteria has at least 10 fold less endogenous deubiquitinase activity and endogenous ubiquitinase activity than a human cell. In another embodiment, the bacteria has at least 20 fold less endogenous deubiquitinase activity and endogenous ubiquitinase activity than a human cell.

Preferably the bacteria lack resistance to the selection markers in the current system. Examples of such bacteria include, but are not limited to *E. coli* K-12 derivatives including W3110, MG1655, DH5a, JM101, JM19, BL21, B834, XL1-Blue; also other non *E. coli* bacteria may be used.

According to a particular embodiment, the bacteria used in the system are of the genus *Escherichia*, such as for example *E. Coli*.

In order to express the components of the assay, a polynucleotide sequence encoding the elements described above is preferably ligated into a nucleic acid construct suitable for bacterial cell expression. Such a nucleic acid construct includes a promoter sequence for directing transcription of the polynucleotide sequence in the cell in a constitutive or inducible manner.

The phrase "an isolated polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase; or synthetically synthesized by assembled from short oligonucleotide.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

The nucleic acid construct (also referred to herein as an "expression vector") of some embodiments of the invention includes additional sequences which render this vector suitable for replication and integration in prokaryotes, eukaryotes, or preferably both (e.g., shuttle vectors). In addition, a typical cloning vector may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

Exemplary promoters contemplated by the present invention include, but are not limited to polyoma, Simian Virus 40

(SV40), adenovirus, retroviruses, hepatitis-B virus and cytomegalovirus promoters. According to a particular embodiment, the promoter is a bacterial promoter.

Constitutive promoters suitable for use with the present invention are promoter sequences which are active under most environmental conditions and most types of bacterial cells such as an unregulated bacteriophage lambda left promoter (pL) or pTac which presents high leakiness.

Enhancer elements can stimulate transcription up to 1,000 fold from linked homologous or heterologous promoters. Enhancers are active when placed downstream or upstream from the transcription initiation site. Many enhancing elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

In a preferred embodiment, the vector comprises a bacterial replication of origin.

The expression vector of some embodiments of the invention can further include additional polynucleotide sequences that allow, for example, the translation of several proteins from a single mRNA such as an internal ribosome entry site (IRES) and sequences for genomic integration of the promoter-chimeric polypeptide.

The use of bacterial operon architecture for multi-gene expression, where a single promoter is followed by several open reading frames (ORFs) each contains a ribosome-binding site (Shine-Dalgarno sequence) facilitates the co-expression of the multi-protein complex of the ubiquitination apparatus.

It will be appreciated that the individual elements comprised in the expression vector can be arranged in a variety of configurations. For example, enhancer elements, promoters and the like, and even the polynucleotide sequence(s) encoding the fusion protein can be arranged in a "head-to-tail" configuration, may be present as an inverted complement, or in a complementary configuration, as an anti-parallel strand. While such variety of configuration is more likely to occur with non-coding elements of the expression vector, alternative configurations of the coding sequence within the expression vector are also envisioned.

Exemplary methods of introducing the polynucleotides of the present invention into prokaryotic cells are well known in the art—these include, but are not limited to, transforming with a recombinant bacteriophage DNA, plasmid DNA or cosmid DNA expression vector containing the relevant gene sequences.

Other than containing the necessary elements for the transcription and translation of the inserted coding sequence, the expression construct of some embodiments of the invention can also include sequences engineered to enhance stability, production or isolation of the expressed peptide fragments.

Examples of bacterial constructs include the pET series of *E. Coli* expression vectors (see for example Studier et al (1990) Methods in Enzymol 185:60-89) in which their T7 promoter was replaced with the constitutive active bacteriophage pH (left promoter). Other vectors that may be used are those that belong to the pZE vector family (e.g. pZE21), those that belong to the pCloDF (containing a pCloDF13 origin) and pACYC (containing a p15A origin of replication).

Ubiquitin

The term "ubiquitin" as used herein refers to either mammalian ubiquitin having a sequence as set forth in SEQ ID NO: 7 or yeast ubiquitin having a sequence as set forth in SEQ ID NO: 8.

Detectable Signal

In one example, the detectable signal is a fluorescent protein or an enzyme producing a colorimetric reaction. Exemplary proteins that generate a detectable signal include, but are not limited to green fluorescent protein (Genbank Accession No. AAL33912), alkaline phosphatase (Genbank Accession No. AAK73766), peroxidase (Genbank Accession No. NP_568674), histidine tag (Genbank Accession No. AAK09208), Myc tag (Genbank Accession No. AF329457), biotin ligase tag (Genbank Accession No. NP_561589), orange fluorescent protein (Genbank Accession No. AAL33917), beta galactosidase (Genbank Accession No. NM_125776), Fluorescein isothiocyanate (Genbank Accession No. AAF22695) and strepavidin (Genbank Accession No. S11540).

In another example, the detectable signal is a luminescent protein such as products of bacterial luciferase genes, e.g., the luciferase genes encoded by Vibrio harveyi, Vibrio fischeri, and Xenorhabdus luminescens, the firefly luciferase gene FFlux, and the like.

In one embodiment, the selection is dominant selection, which typically uses a drug to arrest growth of a host cell. Those cells which would express a protein conveying drug resistance would survive the selection. The use of split marker allows the detection of ubiquitination events as further described below.

In order to output a detectable or selectable signal which correlates with the ubiquitination level of a substrate, the present inventors contemplate using a split polypeptide, wherein one fragment of the polypeptide is linked to ubiquitin and the other fragment of the polypeptide is linked to the substrate. When the polypeptide is expressed as two "split" fragments, there is no detectable or selectable signal. However, when the two fragments are brought close enough together (i.e. on ubiquitination of the substrate) they form a functional protein that emits a detectable or selectable signal—i.e. generate a reporter polypeptide.

According to a particular embodiment, the split polypeptide combines to generate a reporter polypeptide which is fluorescent, luminescent, phosphorescent or one that confers antibiotic resistance.

Examples of split polypeptides contemplated by the present invention include, but are not limited to beta lactamase, dihydrofolate reductase (DHFR), focal adhesion kinase, enhanced GFP, horseradish peroxidase, Infrared fluorescent protein IFP1.4 (an engineered chromophore-binding domain (CBD) of a bacteriophytochrome from *Deinococcus radiodurans*) LacZ (beta-galactosidase)' Luciferase, TEV (Tobacco etch virus protease).

According to a particular embodiment the split polypeptide provides resistance to an antibiotic when combined, but the bacteria is susceptible to the antibiotic when split. Preferably, the split polypeptide provides resistance to a bacteristatic antibiotic when combined. Examples of bacteriostatic antibiotics include but are not limited to trimethoprim and chloramphenicol.

In the case of trimethoprim, a split DHFR protein may be expressed. Specifically the use of selective media which lack thymidine, glycine, serine or methionine and contains the trimethoprim antibiotic allows the selection of genes required for the ubiquitination process.

In the case of chloramphenicol, a split chloramphenicol acetyl transferase (CAT) enzyme can be expressed.

As used herein, the term CAT refers to an enzyme (EC 2.3.1.28) that catalyzes the acetyl-S-CoA-dependent acetylation of chloramphenicol at the 3-hydroxyl group.

The CAT of this embodiment may have an amino acid sequence that is at least 90%, 91%, 92%, 93%, 94%, 95%, 96%, 97%, 98%, 99% or 100% homologous or identical to the sequence as set forth in SEQ ID NO: 64, as determined using the Standard protein-protein BLAST [blastp] software of the NCBI. An exemplary DNA sequence that encodes full length CAT is set forth in SEQ ID NO: 63.

In one embodiment the N-terminal fragment comprises a first portion of the catalytic active site of the CAT—e.g. the N terminal fragment typically contains the first 28 or 30 amino acids of the native CAT. The C-terminal fragment comprises the second portion of the catalytic active site of the CAT—for example, the C terminal fragment typically contains the rest of the sequence of the native CAT. The N-terminal fragment associates with the C-terminal fragment to generate an active CAT that is capable of acetylating chloramphenicol.

In one embodiment, the N terminus of the N-terminal fragment is linked to the C terminus of the substrate or ubiquitin (preferably via a linker).

In another embodiment, the C terminus of the C-terminal fragment is linked to the N terminus of the substrate or ubiquitin (preferably via a linker)—see for example FIG. 15C.

Preferably, the first amino acid of the C-terminal fragment is a small amino acid residue—for example cysteine or alanine. Thus, the C terminal fragment may begin with cysteine 31 (wherein the numbering is according to SEQ ID NO: 64), or alanine 29 (wherein the numbering is according to SEQ ID NO: 64). Other small amino acid residues include glycine, alanine, serine, proline, threonine, aspartate and asparagine.

By being small, the first amino acid of the C-terminal fragment after the formyl-methionine is causes the latter to be posttranslationally removed from the N-terminus (of the C-terminus fragment) hence salvaging the active site arrangement as seen by the activity.

In one embodiment, the N-terminal fragment comprises/consists of the amino acid sequence as set forth in SEQ ID NO: 67.

The C-terminal fragment comprises/consists of the amino acid sequence as set forth in SEQ ID NOs: 68.

The N-terminal fragment may be encoded by the nucleic acid sequence as set forth in SEQ ID NO: 65.

The C-terminal fragment may be encoded by the nucleic acid sequence as set forth in SEQ ID NO: 66.

The DNA and protein sequence of an exemplary split CAT is illustrated in FIG. 17B.

As mentioned, in order to generate the recombinant bacteria of the above described embodiment, the bacteria are genetically modified to express at least two polypeptide fragments—one of the polypeptide fragments being the split polypeptide fragment linked to ubiquitin and the other polypeptide fragment being the conjugate pair of the split polypeptide which is linked to the substrate.

In one embodiment, the split polypeptide fragment is directly linked to ubiquitin or substrate. In another embodiment, the split polypeptide fragment is linked to the ubiquitin or substrate via a peptide linker. The linker should be of a length and flexibility that allows functional stability of the reporter polypeptide. The linker is preferably between 10-500 amino acids, more preferably between 20 and 200 amino acids and more preferably between 20-100 amino acids. Exemplary peptide linkers that can be used are set forth in SEQ ID NOs: 5 or 6.

The first fragment of the reporter polypeptide which is linked to ubiquitin may be encoded on the same nucleic acid construct as the second fragment of the reporter polypeptide which is linked to the substrate. Alternatively, the first fragment of the reporter polypeptide which is linked to ubiquitin may be encoded on a different nucleic acid construct as the second fragment of the reporter polypeptide which is linked to the substrate. This embodiment is illustrated in FIG. 1A. Care should be taken when building the constructs such that the expression level of the first fragment is similar to the expression level of the second fragment. Thus for example, the promoter which is used to express the first fragment may be identical to the promoter used to express the second fragment.

In bacterial systems, a number of expression vectors can be advantageously selected depending upon the use intended for the polypeptide expressed. Specifically, the use of different selection markers such as $Kan^R$ and $Strep^R$) and different origin of replications (such as ColiE1 and CloDF13) is contemplated.

Ubiquitinating Enzyme

As used herein, the term "ubiquitinating enzyme" refers to ubiquitin-activating enzymes (E1s), ubiquitin-conjugating enzymes (E2s) or ubiquitin ligases (E3s). Collectively they have the EC number EC 6.3.2.19.

In one embodiment, the ubiquitinating enzyme is a human ubiquitinating enzyme.

Ubiquitin-activating enzymes (E1s) have the EC number EC 6.2.1.45, ubiquitin-conjugating enzymes have the EC number EC 2.3.2.23 and ubiquitin ligases have the EC number 2.3.2.27.

Amino acid sequences of exemplary E1s contemplated by the present invention include, but are not limited to SEQ ID NOs: 9-16.

Amino acid sequences of exemplary E2s contemplated by the present invention are set forth by SEQ ID NOs: 17-36.

Table 1, herein below provides nomenclature and most common synonyms used for E2 ubiquitin conjugating enzymes. The E2 nomenclature is in accordance with that used by the Human Genome Organization.

TABLE 1

| Human Genome Organization Nomenclature | Synonym |
| --- | --- |
| UBE2V2 | UEV2/MMS2 |
| UBE2D1 | UBC4/5/UBCH5A |
| UBE2D2 | UBC4/5/UBCH5B |
| UBE2D4 | HBUCE1 |
| UBE2D3 | UBC4/5 |
| UBE2W | FLJ11011 |
| UBE2B | UBC2/HHR6B/RAD6B/E217K |
| UBE2L6 | RIGB/UBCH8 |
| UBE2N | UBC13 |
| UBE2L3 | UBCH7 |
| UBE2G1 | UBC7/E217K |
| UBE2H | UBC8/E220K |
| UBE2M | UBC12 |
| UBE2F | NCE2 |
| UBE2E2 | UBCH8 |
| UBE2E3 | UBCH9/UBCM2 |
| UBE2S | E224K |
| UBE2U | MGC35130 |
| UBE2R1 | CDC34 |
| UBE2R2 | UBC3B/CDC34B |
| UBE2Z | HOYS7 |
| UBE2J2 | NCUBE2 |
| Probable ubiquitin-conjugating enzyme E2 FLJ25076 | LOC134111/FLJ25076 |
| AKTIP | FTS/FT1 |
| UBE2J1 | NCUBE1 |
| UBE2V1 | UEV1/CROC1 |
| UBE2Q2 | DKFZ/UBCI |
| UBE2Q1 | NICE5 |
|  | TSG101/VPS23/SG10 |
| UEVLD | UEV3 |

In one embodiment, the ubiquitinating enzyme is an E3 ligase.

Exemplary E3 ligases contemplated by the present invention include, but are not limited to Siah2, Smurf1, MDM2, BRCA1, PARKIN, UBE3A, TRIMS, NEDD4, UBR5, Huwel, Arkadia, ITCH, MuRF1, TRAF6, Trim32, UBR4, UBE3B and UBE3D.

According to a particular embodiment, the E3 ligase is selected from the group consisting of Siah2, Smurf1, MDM2, BRCA1, PARKIN, UBE3A, UBE3B, MURF1, TRIM32, TRIMS, NEDD4, UBR5 and Huwel.

In another embodiment the E3 ligase is Siah2, Smurf1, MDM2, BRCA1, PARKIN or UBE3A.

Amino acid sequences of exemplary E3s contemplated by the present invention are set forth in SEQ ID NOs: 37-62.

Below is a brief description of exemplary E3 ligases contemplated by the present invention and some of their exemplary substrates.

Seven in Absentia Homolog 2 (SIAH2):

SIAH2 is a RING finger type ubiquitin ligases with a catalytic RING domain on its N-terminus, followed by two zinc fingers and a C-terminal substrate binding domain.

Siah2 is an E3 ubiquitin ligase implicated in diverse biological processes including p38/JNK/NF-kB signaling pathways, DNA damage, estrogen signaling, programmed cell death, Ras/Raf pathway, mitosis, and hypoxia.

Siah2 targets numerous substrates for degradation including TRAF2 (ketoglutarate dehydrogenase), Spry2 (Sprouty2), and the prolyl hydroxylase PHD3.

Siah2 also limits its own availability through self-ubiquitination and degradation.

Siah2 play a key role in hypoxia, through the regulation of HIF-1α transcription stability and activity via regulation of PHD3 stability.

Smad Ubiquitination Regulatory Factor-I (Smurf1)

Smurf1 is a NEDD4-like Class IV HECT (homologous to E6-AP carboxylterminus) family E3 ligase with catalytic activity.

Smurf1 has been linked to several important biological pathways, including the bone morphogenetic protein pathway, the non-canonical Wnt pathway, and the mitogen-activated protein kinase pathway.

Smurfs possess three functional domains: an N-terminal protein kinase C (PKC)-related C2 domain which binds to phospholipids, targeting Smurfs to intracellular membranes, a central region containing two to four WW (tryptophan residues) protein—interacting domains which mediate ligase-substrate associations through interactions with a variety of proline-rich (PPXY) motifs and proline-containing phosphoserine/phosphothreonine sequences of the protein substrate, and a C-terminal HECT domain, responsible for ubiquitin transfer from a conserved cysteine residue at position 716 to a lysine residue in a substrate protein.

Smurf1 promotes p53 degradation by enhancing the activity of the E3 ligase MDM2. Smurf1 stabilizes MDM2 by enhancing the heterodimerization of MDM2 with MDMX, during which Smurf1 interacts with MDM2 and MDMX.

Smurf1 is also a key negative regulator of transforming growth factor (TGF)-β/bone morphogenetic protein (BMP) signaling pathway.

Mouse Double Minute 2 Homolog (MDM2)

MDM2 also known as E3 ubiquitin-protein ligase Mdm2 is an important negative regulator of the p53 tumor suppressor.

Mdm2 protein functions both as an E3 ubiquitin ligase that recognizes the N-terminal trans-activation domain (TAD) of the p53 tumor suppressor and as an inhibitor of p53 transcriptional activation.

Mdm2 contains a C-terminal RING domain (amino acid residues 430-480), which contains a Cis3-His2-Cis3 consensus that coordinates two molecules of zinc. These residues are required for zinc binding, which is essential for proper folding of the RING domain. The RING domain of Mdm2 confers E3 ubiquitin ligase activity and is sufficient for E3 ligase activity in Mdm2 RING autoubiquitination. The RING domain of Mdm2 is unique in that it incorporates a conserved Walker A or P-loop motif characteristic of nucleotide binding proteins, as well as a nucleolar localization sequence.

Mdm2 is capable of auto-polyubiquitination, and in complex with p300, a cooperating E3 ubiquitin ligase, is capable of polyubiquitinating p53. In this manner, Mdm2 and p53 are the members of a negative feedback control loop that keeps the level of p53 low in the absence of p53-stabilizing signals.

BRCA1

BRCA1-BARD1 constitutes a heterodimeric RING finger complex of the BRCA1/BRCA2-containing complex (BRCC) that contains significant ubiquitin ligase activity.

BRCA1 plays critical roles in the repair of chromosomal damage (error-free repair of DNA double-strand breaks), cell cycle checkpoint control, and genomic stability.

BRCA1 forms several distinct complexes through association with different adaptor proteins, and each complex forms in a mutually exclusive manner.

BRCA1 combines with other tumor suppressors, DNA damage sensors and signal transducers to form a large multi-subunit protein complex known as the BRCA1-associated genome surveillance complex (BASC).

The BRCA1 protein associates with RNA polymerase II, and through the C-terminal domain, also interacts with histone deacetylase complexes. Thus, this protein plays a role in transcription, DNA repair of double-strand breaks ubiquitination, transcriptional regulation as well as other functions Parkin:

Parkin is a RING-between-RING E3 ligase that functions in the covalent attachment of ubiquitin to specific substrates.

It is best known for regulating the disposal of dysfunctional mitochondria (together with PINK1, a serine threonine kinase) via mitochondrial autophagy (i.e., mitophagy).

Upon loss of mitochondrial membrane potential, PINK1 becomes stabilized and activated on the outer mitochondrial membrane (OMM), resulting in recruitment and activation of Parkin.

Parkin facilitates ubiquitination of a broad number of targets expressed on the OMM (e.g., TOM20, Mitofusins, VDAC, Fis1) resulting in recruitment of the autophagy machinery, autophagosome formation and mitochondrial clearance.

In addition to its established role in mitophagy and UPS, Parkin impacts other neuroprotective cellular pathways, including TNFα signaling, and Wnt/β catenin signaling, and is also a putative tumor suppressor.

UBE3A (Gene Coding for E6-Associated Protein; E6-AP):

This ligase promotes the ubiquitylation and degradation of p53. E6-AP was subsequently shown to ubiquitylate proteins independent of E6 and to serve an independent secondary function as a transcriptional co-activator of nuclear estrogen receptors. E6-AP has been implicated in a broad range of processes (e.g. cell growth, synaptic formation and function, etc.) and has been shown to have many different target substrates (e.g., HHR23A, CDKN1B, MCMI, etc.).

Tripartite motif-5 (TRIMS):

This ligase is a RING finger E3 ligase a key anti-viral restriction factor and directly involved in inhibiting HIV-1 replication.

Neural Precursor Cell Expressed Developmentally Downregulated 4 (NEDD4-1):

Nedd4-1 ubiquitinates a number of substrates, including ENaC, ADRB2, AMPA, Notch, pAKT, VEGFR2, EPS15, LATS1, and MDM2.

The vacuolar protein sorting protein Alix recruits NEDD4 to HIV-1 Gag protein to facilitate HIV-1 release via a mechanism that involves Alix ubiquitination.

NEDD4 also binds and ubiquitinates the latent membrane protein 2A (LMP2A) of the Epstein-Bar virus (EBV) to activate B-cell signal transduction.

Ubiquitin Protein Ligase E3 Component n-Recognin 5 (UBR5):

This ligase is also known as EDD (E3 identified by Differential Display), EDD1, HHYD, KIAA0896, or DD5.

URB5 acts as a general tumor suppressor by ubiquitinating, which increases p53 levels and induces cell senescence. UBR5 also ubiquitinates TopBP1, a topo-isomerase that intervenes in DNA damage response.

HUWE1:

HUWE1 (also known as ARF-BP1, MULE, LASU1, or HECTH9) is an E3 ligase that regulates the stability of diverse cellular substrates and, in consequence, numerous physiological processes, including DNA replication and damage repair, cell proliferation and differentiation, and apoptosis.

HUWE1 substrates include both tumor promoters (e.g., N-MYC, C-MYC, MCL1) and suppressors (e.g., p53, MYC, MIZ1).

HUWE1 has demonstrated both pro-oncogenic and tumor-suppressor functions in different tumor models.

HUWE1 belongs to the HECT (Homologous to E6AP C-Terminus)-family of ubiquitin E3 ligases.

Other additional E3 ligases and their substrates are provided in Table 2, herein below.

TABLE 2

| Ligase | Substrate | Function |
| --- | --- | --- |
| AMFR | KAI1 | AMFR is also known as gp78. AMFR is an integral ER membrane protein and functions in ER-associated degradation (ERAD). AMFR has been found to promote tumor metastasis through ubiquitination of the metastasis suppressor, KAI1. |
| APC/Cdc20 | Cyclin B | The anaphase promoting complex/cyclosome (APC/C) is a multiprotein complex with E3 ligase activity that regulates cell cycle progression through degradation of cyclins and other mitotic proteins. APC is found in a complex with CDC20, CDC27, SPATC1, and TUBG1. |
| APC/Cdh1 | Cdc20, Cyclin B, Cyclin A, Aurora A, Securin, Skp2, Claspin | The anaphase promoting complex/cyclosome (APC/C) is a multiprotein complex with E3 ligase activity that regulates cell cycle progression through degradation of cyclins and other mitotic proteins. The APC/C-Cdh1 dimeric complex is activated during anaphase and telophase, and remains active until onset of the next S phase. |
| C6orf157 | Cyclin B | C6orf157 is also known as H10BH. C6orf157 is an E3 ubiquitin ligase that has been shown to ubiquitinate cyclin B. |
| Cbl | | Cbl-b and c-Cbl are members of the Cbl family of adaptor proteins that are highly expressed in hematopoietic cells. Cbl proteins possess E3 ubiquitin ligase activity that downregulates numerous signaling proteins and RTKs in several pathways such as EGFR, T cell and B cell receptors, and integrin receptors. Cbl proteins play an important role in T cell receptor signaling pathways. |

TABLE 2-continued

| Ligase | Substrate | Function |
|---|---|---|
| CBLL1 | CDH1 | CBLL1 is also known as Hakai. CBLL1 is an E3 ubiquitin ligase that ubiquitinates the phosphorylated form of E-Cadherin, causing its degradation and loss of cell-cell adhesions. |
| CHFR | PLK1, Aurora A | CHFR is an E3 ubiquitin ligase that functions as a mitotic stress checkpoint protein that delays entry into mitosis in response to stress. CHFR has been shown to ubiquitinate and degrade the kinases PLK1 and Aurora A. |
| CHIP | HSP70/90, iNOS, Runx1, LRRK2 | CHIP is an E3 ubiquitin ligase that acts as a co-chaperone protein and interacts with several heat shock proteins, including HSP70 and HSP90, as well as the non-heat shock proteins iNOS, Runx1 and LRRK2. |
| DTL (Cdt2) | p21 | DTL is an E3 ubiquitin ligase that complexes with Cullin4 and DDB1, and promotes p21 degradation after UV damage. |
| E6-AP | p53, Dlg | E6-AP is also known as UBE3A. E6-AP is a HECT domain E3 ubiquitin ligase that interacts with Hepatitis C virus (HCV) core protein and targets it for degradation. The HCV core protein is central to packaging viral DNA and other cellular processes. E6-AP also interacts with the E6 protein of the human papillomavirus types 16 and 18, and targets the p53 tumor-suppressor protein for degradation. |
| HACE1 | | HACE1 is an E3 ubiquitin ligase and tumor suppressor. Aberrant methylation of HACE1 is frequently found in Wilms' tumors and colorectal cancer. |
| HECTD1 | | HECTD1 is an ubiquitin E3 ligase required for neural tube closure and normal development of the mesenchyme. |
| HECTD2 | | HECTD2 is a probable E3 ubiquitin ligase and may act as a susceptibility gene for neurodegeneration and prion disease. |
| HECTD3 | | HECTD3 is a probable E3 ubiquitin ligase and may play a role in cytoskeletal regulation, actin remodeling, and vesicle trafficking. |
| HECW1 | DVL1, mutant SOD1, p53 | HECW1 is also known as NEDL1. HECW1 interacts with p53 and the Wnt signaling protein DVL1, and may play a role in p53-mediated cell death in neurons. |
| HECW2 | p73 | HECW2 is also known as NEDL2. HECW2 ubiquitinates p73, which is a p53 family member. Ubiquitination of p73 increases protein stability. |
| HERC2 | RNF8 | HERC2 belongs to a family of E3 ubiquitin ligases involved in membrane trafficking events. HERC2 plays a role in the DNA damage response through interaction with RNF8. |
| HERC3 | | HERC3 belongs to a family of E3 ubiquitin ligases involved in membrane trafficking events. HERC3 interacts with hPLIC-1 and hPLIC-2 and localizes to the late endosomes and lysosomes. |
| HERC4 | | HERC4 belongs to a family of E3 ubiquitin ligases involved in membrane trafficking events. HERC4 is highly expressed in testis and may play a role in spermatogenesis. |
| HERC5 | | HERC5 belongs to a family of E3 ubiquitin ligases involved in membrane trafficking events. HERC5 is induced by interferon and other pro-inflammatory cytokines and plays a role in interferon-induced ISG15 conjugation during the innate immune response. |
| HUWE1 | N-Myc C-, Myc, p53, Mcl-1, TopBP1 | HUWE1 is also known as Mule. HUWE1 is a HECT domain E3 ubiquitin ligase that regulates degradation of Mcl-1 and therefore regulates DNA damage-induced apoptosis. HUWE1 also controls neuronal differentiation by destabilizing N-Myc, and regulates p53-dependent and independent tumor suppression via ARF. |
| HYD | CHK2 | HYD is also known as EDD or UBR5. HYD is a regulator of the DNA damage response and is overexpressed in many forms of cancer. |
| ITCH | MKK4, RIP2, Foxp3 | ITCH plays a role in T cell receptor activation and signaling through ubiquitination of multiple proteins including MKK4, RIP2 and Foxp3. Loss of ITCH function leads to an aberrant immune response and T helper cell differentiation. |
| LNX1 | NUMB | LNX1 is an E3 ubiquitin ligase that plays a role in cell fate determination during embryogenesis through regulation of NUMB, the negative regulator of Notch signaling. |
| mahogunin | | Mahogunin is an E3 ubiquitin ligase involved in melanocortin signaling. Loss of mahogunin function leads to neurodegeneration and loss of pigmentation, and may be the mechanism of action in prion disease. |
| MARCH-I | HLA-DRβ | MARCH1 is an E3 ubiquitin ligase found on antigen presenting cells (APCs). MARCH1 ubiquitinates MHC class II proteins and downregulates their cell surface expression. |
| MARCH-II | | MARCH-II is a member of the MARCH family of E3 ubiquitin ligases. It associates with syntaxin6 in the endosomes and helps to regulate vesicle trafficking. |

TABLE 2-continued

| Ligase | Substrate | Function |
|---|---|---|
| MARCH-III | | MARCH-III is a member of the MARCH family of E3 ubiquitin ligases. MARCH-III associates with syntaxin6 in the endosomes and helps to regulate vesicle trafficking. |
| MARCH-IV | MHC class I | MARCH-IV is a member of the MARCH family of E3 ubiquitin ligases. MARCH-IV ubiquitinates MHC class I proteins and downregulates their cell surface expression. |
| MARCH-VI | | MARCH-VI is also known as TEB4 and is a member of the MARCH family of E3 ubiquitin ligases. It localizes to the endoplasmic reticulum and participates in ER-associated protein degradation. |
| MARCH-VII | gp190 | MARCH-VII is also known as axotrophin. MARCH-VII was originally identified as a neural stem cell gene, but has since been shown to play a role in LIF signaling in T lymphocytes through degradation of the LIF-receptor subunit, gp190. |
| MARCH-VIII | B7-2, MHC class II | MARCH-VIII is also known as c-MIR. MARCH-VIII causes the ubiquitination/degradation of B7-2, which is a co-stimulatory molecule for antigen presentation. MARCH-VIII has also been shown to ubiquitinate MHC class II proteins. |
| MARCH-X | | MARCH-X is also known as RNF190. MARCH-X is a member of the MARCH family of E3 ubiquitin ligases. The putative role of MARCH-X is not currently known. |
| MDM2 | p53 | MDM2, an E3 ubiquitin ligase for p53, plays a central role in regulation of the stability of p53. Akt-mediated phosphorylation of MDM2 at Ser166 and Ser186 increases its interaction with p300, allowing MDM2-mediated ubiquitination and degradation of p53. |
| MEKK1 | c-Jun, Erk | MEKK1 is a well known protein kinase of the STE11 family. MEKK1 phosphorylates and activates MKK4/7, which in turn activates JNK1/2/3. MEKK1 contains a RING finger domain and exhibits E3 ubiquitin ligase activity toward c-Jun and Erk. |
| MIB1 | Delta, Jagged | Mindbomb homolog 1 (MIB1) is an E3 ligase that facilitates the ubiquitination and subsequent endocytosis of the Notch ligands, Delta and Jagged. |
| MIB2 | Delta, Jagged | Mind Bomb 2 (MIB2) is an E3 ligase that positively regulates Notch Signaling. MIB2 has been shown to play a role in myotube differentiation and muscle stability. MIB2 ubiquitinates NMDAR subunits to help regulate synaptic plasticity in neurons. |
| MycBP2 | Fbxo45, TSC2 | MycBP2 is an E3 ubiquitin ligase also known as PAM. MycBP2 associates with Fbxo45 to play a role in neuronal development. MycBP2 also regulates the mTOR pathway through ubiquitination of TSC2. |
| NEDD4 | | NEDD4 is an E3 ubiquitin ligase highly expressed in the early mouse embryonic central nervous system. NEDD4 downregulates both neuronal voltage-gated Na+ channels (NaVs) and epithelial Na+ channels (ENaCs) in response to increased intracellular Na+ concentrations. |
| NEDD4L | Smad2 | NEDD4L is an E3 ubiquitin ligase highly expressed in the early mouse embryonic central nervous system. NEDD4L has been shown to negatively regulate TGF-β signaling by targeting Smad2 for degradation. |
| Parkin | | Parkin is an E3 ubiquitin ligase that has been shown to be a key regulator of the autophagy pathway. Mutations in Parkin can lead to Parkinson's Disease. |
| PELI1 | TRIP, IRAK | PELI1 is an E3 ubiquitin ligase that plays a role in Toll-like Receptor (TLR3 and TLR4) signaling to NF-κB via the TRIP adaptor protein. PELI1 has also been shown to ubiquitinate IRAK. |
| Pirh2 | TP53 | Pirh2 is also known as RCHY1. Pirh2 is a RING domain E3 ubiquitin ligase. Pirh2 binds p53 and promotes proteosomal degradation of p53 independent of MDM2. Pirh2 gene expression is controlled by p53, making this interaction part of an autoinhibitory feedback loop. |
| PJA1 | ELF | PJA1 is also known as PRAJA. PJA1 plays a role in downregulating TGF-β signaling in gastric cancer via ubiquitination of the SMAD4 adaptor protein ELF. |
| PJA2 | | PJA2 is an E3 ubiquitin ligase found in neuronal synapses. The exact role and substrates of PJA2 are unclear. |
| RFFL | p53 | RFFL is also known as CARP2 and is an E3 ubiquitin ligase that inhibits endosome recycling. RFFL also degrades p53 through stabilization of MDM2. |
| RFWD2 | MTA1, p53, FoxO1 | RFWD2 is also known as COP1. RFWD2 is an E3 ubiquitin ligase that ubiquitinates several proteins involved in the DNA damage response and apoptosis including MTA1, p53, and FoxO1. |
| Rictor | SGK1 | Rictor interacts with Cullin1-Rbx1 to form an E3 ubiquitin ligase complex, and promotes ubiquitination and degradation of SGK1. |

TABLE 2-continued

| Ligase | Substrate | Function |
|---|---|---|
| RNF5 | JAMP, paxillin | RNF5 is also known as RMA5. RNF5 plays a role in ER-associated degradation of misfolded proteins and ER stress response through ubiquitination of JAMP. RNF5 also plays a role in cell motility and has been shown to ubiquitinate paxillin. |
| RNF8 | H2A, H2AX | RNF8 is a RING domain E3 ubiquitin ligase that plays a role in the repair of damaged chromosomes. RNF8 ubiquitinates Histone H2A and H2A.X at double-strand breaks (DSBs) which recruits 53BP1 and BRCA1 repair proteins. |
| RNF19 | SOD1 | RNF19 is also known as Dorfin. Accumulation and aggregation of mutant SOD1 leads to ALS disease. RNF19 ubiquitinates mutant SOD1 protein, causing a decrease in neurotoxicity. |
| RNF190 | | see MARCH-X |
| RNF20 | Histone H2B | RNF20 is also known as BRE1. RNF20 is an E3 ubiquitin ligase that monoubiquitinates Histone H2B. H2B ubiquitination is associated with areas of active transcription. |
| RNF34 | Caspase-8, -10 | RNF34 is also known as RFI. RNF34 inhibits death receptor mediated apoptosis through ubiquitination/degradation of caspase-8 and -10. |
| RNF40 | Histone H2B | RNF40 is also known as BRE1-B. RNF40 forms a protein complex with RNF20 resulting in the ubiquitination of Histone H2B. H2B ubiquitination is associated with areas of active transcription. |
| RNF125 | | RNF125 is also known as TRAC-1. RNF125 has been shown to positively regulate T cell activation. |
| RNF128 | | RNF128 is also known as GRAIL. RNF128 promotes T cell energy and may play a role in actin cytoskeletal organization in T cell/APC interactions. |
| RNF138 | TCF/LEF | RNF138 is also known as NARF. RNF138 is associated with Nemo-like Kinase (NLK) and suppresses Wnt/β-Catenin signaling through ubiquitination/degradation of TCF/LEF. |
| RNF168 | H2A, H2A.X | RNF168 is an E3 ubiquitin ligase that helps protect genome integrity by working together with RNF8 to ubiquitinate Histone H2A and H2A.X at DNA double-strand breaks (DSB). |
| SCF/β-TrCP | IκBα, Wee1, Cdc25A, β-Catenin | SCF/β-TrCP is an E3 ubiquitin ligase complex composed of SCF (SKP1-CUL1-F-box protein) and the substrate recognition component, β-TrCP (also known as BTRC). SCF/β-TrCP mediates the ubiquitination of proteins involved in cell cycle progression, signal transduction, and transcription. SCF/β-TrCP also regulates the stability of β-catenin and participates in Wnt signaling. |
| SCF/FBW7 | Cyclin E, c-Myc, c-Jun | SCF/FBW7 is an E3 ubiquitin ligase complex composed of SCF (SKP1-CUL1-F-box protein) and the substrate recognition component, FBW7. SCF/FBW7 mediates the ubiquitination of proteins involved in cell cycle progression, signal transduction, and transcription. Target proteins for SCF/FBW7 include the phosphorylated forms of c-Myc, Cyclin E, Notch intracellular domain (NICD), and c-Jun. Defects in FBXW7 may be a cause of breast cancer. |
| SCF/Skp2 | p27, p21, Fox01 | SCF/Skp2 is an E3 ubiquitin ligase complex composed of SCF (SKP1-CUL1-F-box protein) and the substrate recognition component, Skp2. SCF/Skp2 mediates the ubiquitination of proteins involved in cell cycle progression (specifically the G1/S transition), signal transduction, and transcription. Target proteins for SCF/Skp2 include the phosphorylated forms of p27Kip1, p21Waf1/Cip1, and FoxO1. |
| SHPRH | PCNA | SHPRH is an E3 ubiquitin ligase that plays a role in DNA replication through ubiquitination of PCNA. PCNA ubiquitination prevents genomic instability from stalled replication forks after DNA damage. |
| SIAH1 | β-catenin, Bim, TRB3 | SIAH1 is an E3 ubiquitin ligase that plays a role in inhibition of Wnt signaling through ubiquitination of β-catenin. SIAH1 has also been shown to promote apoptosis through upregulation of Bim, and to ubiquitinate the signaling adaptor protein TRB3. |
| SIAH2 | HIPK2, PHD1/3 | SIAH2 is an E3 ubiquitin ligase that plays a role in hypoxia through ubiquitination and degradation of HIPK2. SIAH2 also ubiquitinates PHD1/3, which regulates levels of HIF-1α in response to hypoxia. |
| SMURF1 | Smads | SMURF1 is an E3 ubiquitin ligase that interacts with BMP pathway Smad effectors, leading to Smad protein ubiquitination and degradation. Smurf1 negatively regulates osteoblast differentiation and bone formation in vivo. |
| SMURF2 | Smads, Mad2 | SMURF2 is an E3 ubiquitin ligase that interacts with Smads from both the BMP and TGF-β pathways. SMURF2 also regulates the mitotic spindle checkpoint through ubiquitination of Mad2. |
| TOPORS | p53, NKX3.1 | TOPORS is an E3 ubiquitin ligase and a SUMO ligase. TOPORS ubiquitinates and sumoylates p53, which |

TABLE 2-continued

| Ligase | Substrate | Function |
|---|---|---|
| | | regulates p53 stability. TOPORS has also been shown to ubiquitinate the tumor suppressor NKX3.1. |
| TRAF6 | NEMO, Akt1 | TRAF6 is an E3 ubiquitin ligase that functions as an adaptor protein in IL-1R, CD40, and TLR signaling. TRAF6 promotes NF-κB signaling through K63 polyubiquitination of IKK, resulting in IKK activation. TRAF6 has also been shown to ubiquitinate Akt1, causing its translocation to the cell membrane. |
| TRAF7 | | TRAF7 is an E3 ubiquitin ligase and SUMO ligase that functions as an adaptor protein in TNF Receptor and TLR signaling. TRAF7 has been shown to be capable of self-ubiquitination and plays a role in apoptosis via MEKK3-mediated activation of NF-κB. |
| TRIM63 | Troponin I, MyBP-C, MyLC1/2 | TRIM63 is also known as Murf-1. TRIM63 is a muscle-specific E3 ubiquitin ligase whose expression is upregulated during muscle atrophy. TRIM63 has been shown to ubiquitinate several important muscle proteins including troponin I, MyBP-C, and MyLC1/2. |
| UBE3B | | UBE3B is an E3 ubiquitin ligase identified through sequence analysis. The specific substrates and cellular function of UBE3B is currently unknown. |
| UBE3C | | UBE3C is an E3 ubiquitin ligase also known as KIAA10. UBE3C is highly expressed in muscle and may interact with the transcriptional regulator TIP120B. |
| UBR1 | | UBR1 is an E3 ubiquitin ligase responsible for proteasomal degradation of misfolded cytoplasmic proteins. UBR1 has also been shown to be a ubiquitin ligase of the N-end rule proteolytic pathway, which regulates degradation of short-lived proteins. |
| UBR2 | Histone H2A | UBR2 is an E3 ubiquitin ligase that has been shown to ubiquitinate histone H2A, resulting in transcriptional silencing. UBR2 is also part of the N-end rule proteolytic pathway. |
| UHRF2 | PCNP | UHRF2 is also known as NIRF. UHRF2 is a nuclear protein that may regulate cell cycle progression through association with Chk2. UHRF2 also ubiquitinates PCNP and has been shown to play a role in degradation of nuclear aggregates containing polyglutamine repeats. |
| VHL | HIF-1α | VHL is the substrate recognition component of the ECV (Elongin B/C, Cullen-2, VHL) E3 ubiquitin ligase complex responsible for degradation of the transcription factor HIF-1α. Ubiquitination and degradation of HIF-1α takes place only during periods of normoxia, but not during hypoxia, thereby playing a central role in the regulation of gene expression by oxygen. |
| WWP1 | ErbB4 | WWP1 is an E3 ubiquitin ligase commonly found to be overexpressed in breast cancer. WWP1 has been shown to ubiquitinate and degrade ErbB4. Interestingly, the WWP1 homolog in C. elegans was found to increase life expectancy in response to dietary restriction. |
| WWP2 | Oct-4 | WWP2 is an E3 ubiquitin ligase that has been shown to ubiquitinate/degrade the stem cell pluripotency factor Oct-4. WWP2 also ubiquitinates the transcription factor EGR2 to inhibit activation-induced T cell death. |
| ZNRF1 | | ZNRF1 is an E3 ubiquitin ligase highly expressed in neuronal cells. ZNRF1 is found in synaptic vesicle membranes and may regulate neuronal transmissions and plasticity. |

The term "deubiquitinating" enzyme refers to an enzyme that cleaves ubiquitin from proteins.

According to a specific embodiment, the deubiquitinating enzyme is a cysteine protease or a metalloprotease.

Exemplary deubiquitinating enzymes which may be expressed in the system include USP7 that is known to deubiquitinate MDM2, USP47, USP2, USP7, USP15, USP9X, USP28, USP30.

The ubiquitinating or deubiquitinating enzymes may be expressed from the same expression constructs as the substrate and the ubiquitin or on separate constructs.

Substrates

Examples of substrates include polypeptides that are known to be ubiquitinated in vivo in humans by E3 ligase or deubiquitinated in vivo by deubiquitinating enzymes.

According to a specific embodiment, the substrate is one that is known to be ubiquitinated differentially in a disease such as cancer.

Exemplary substrates that may be expressed in the bacteria have been described herein above.

According to a particular embodiment, the substrate is selected from the group consisting of PHD3, SPROUTY2, Mitofusin 1, 2, MIRO, NEMO, SMADs, TβR-I, P53, S5A, HHR23, EPHEXIN5, ARC, PPARα, cyclin-B, Cdc25C and Calmodulin.

It will be appreciated that as well as expressing the substrate and the ubiquitin (together with the split reporter polypeptide), the recombinant bacteria should also express the ubiquitinating or deubiquitinating enzyme.

In one embodiment, the bacteria express at least one E1 enzyme, at least one E2 enzyme and at least one E3 enzyme.

Preferably, the bacteria expresses the E2 enzyme that is a cognate pair for the E3 enzyme.

In another embodiment, the bacteria expresses at least one deubiquitinating enzyme.

An exemplary system is illustrated in FIG. 1A, whereby the E1 and E2 enzyme are expressed from the same construct as the ubiquitin and the E3 enzyme is expressed from the same construct as the substrate.

In another embodiment, the E1 and E2 enzyme are expressed from the same construct as the substrate and the E3 enzyme is expressed from the same construct as the ubiquitin.

In still a further embodiment, the E1 and E2 enzyme are expressed from the same construct as the substrate and/or the ubiquitin and the E3 enzyme is expressed from an additional expression construct.

The additional expression construct from which the E3-ligase is expressed may use a different selection marker as that used for the other constructs (e.g. Amp$^R$ selection marker). It may also use a different origin of replication such as p15A. The promoter for this expression construct may be inducible or constitutive. In one embodiment, the promoter is a weak constitutive promoter such as the pTac promoter which is leaky without the addition of inducer (IPTG). The present inventors contemplate using a kit for easy preparation of the expression constructs.

Such a kit may comprise:

(i) a first polynucleotide which encodes a first polypeptide fragment which is operably linked to a bacterial regulatory sequence, and a cloning site, wherein a position of the cloning site is selected such that upon insertion of a sequence which encodes a test polypeptide (i.e. the substrate) into the cloning site, following expression in a bacterial cell, a fusion protein is generated which comprises the test polypeptide in frame with the first polypeptide fragment; and (ii) a second polynucleotide comprising a second nucleic acid sequence encoding a second polypeptide fragment which is attached to ubiquitin, the second nucleic acid sequence being operably linked to a bacterial regulatory sequence, wherein the first polypeptide fragment associates with the second polypeptide fragment to generate a reporter polypeptide (e.g. selectable polypeptide, as further described herein above) dependent on ubiquitination of the test polypeptide.

The first polynucleotide and the second polynucleotide may be on the same expression vector or on a separate expression vector. If present on different expression vectors, then preferably each polynucleotide sequence comprises a bacterial origin of replication.

The kit may comprise a third polynucleotide which encodes at least one ubiquitinating enzyme. Alternatively, the first polynucleotide and/or the second polynucleotide may comprise a sequence which encodes the ubiquitinating enzyme (e.g. E1, E2 and/or E3).

Once an agent has been identified as a regulator of a ubiquitinating or deubiquitinating enzyme, therapeutic potential thereof may be tested using other known in-vitro tests. The candidate agent's therapeutic potential may also be tested in animal models the related disease (e.g. cancer).

Once its therapeutic potential has been corroborated, pharmaceutical compositions comprising same may be synthesized.

It will be appreciated that the system described herein can be manipulated to determine whether an enzyme is capable of ubiquitinating a test substrate.

In this embodiment, the enzyme is expressed in a bacterial cell, as well as the ubiquitin (which is attached to the first polypeptide fragment (as described herein above) and the test substrate (which is attached to the second fragment (as described herein above).

The method may be used to test many different E3 enzymes in various combinations with E2 and E1.

The method proceeds by analyzing for the presence of the reporter polypeptide in the bacterial cell—a presence or amount of the reporter polypeptide is indicative that the enzyme is capable of ubiquitinating the test substrate.

In another aspect, the system described herein can be used to determine whether an enzyme is capable of ubiquitinating a test substrate.

The method of this aspect of the present invention comprises:

(a) expressing a plurality of candidate polypeptide substrates in a bacterial cell population, wherein each of the candidate polypeptide substrates is attached to an identical first polypeptide fragment (as described herein above);

(b) expressing the ubiquitinating enzyme in the bacterial cell population;

(c) expressing ubiquitin in the bacterial cell population, wherein the ubiquitin is attached to a second polypeptide fragment (as described herein above), wherein the second polypeptide fragment associates with the first polypeptide fragment to generate a reporter polypeptide on ubiquitination of the substrate; and (d) analyzing in bacterial colonies of the bacterial cell population for a presence or absence of the reporter polypeptide, wherein a presence of the reporter polypeptide is indicative of expression of a substrate for the ubiquitinating enzyme.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, biophysical, bacterial genetics and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Plasmid Construction

Selection system for ubiquitination: Two sets of *E. coli*-compatible expression vectors were constructed. Ubiquitin and different substrates were fused to two fragments of the murine DHFR, under control of a constitutive lambda phage promoter pLtetO1 (see FIG. 1A).

The pND-Ub vector is based on a modified pZE21 vector, contacting the pLtetO1. The mouse cDNA of the nDHFR fragment (residues 1-108) was PCR-amplified and sub-cloned between the KpnI and PacI sites (the PacI site was inserted into the vector by PCR) into the pZE21 vector. Then a flexible linker was constructed using a two-step PCR method and digested with PacI and NotI (the NotI site was inserted into the vector by PCR) and cloned into the vector downstream to the pLtetO1-nDHFR. Ubiquitination apparatus cassettes containing a $His_6$-Ub-E2-E1 were PCR-amplified from pGEN plasmids expressing different E2s or Ub mutants and sub-cloned as fusion to the C-terminus of the nDHFR-linker1 into the NotI and AvrII endonuclease recognition sites.

The pCD-Sub vector was constructed based on a pCDF-duet vector. The T7 promoter was substituted with pLtetO1. The cDHFR fragment (residues 109-187) was PCR-amplified and subcloned under the pLtetO1 promoter at the MluI and AscI endonuclease recognition sites (the AscI site was inserted by PCR). A second linker was fused to the N-terminus of MBP and cloned into the AscI site. Substrates were PCR-amplified and sub-cloned into SacII and SpeI sites downstream and in-frame with the cDHFR-linker2-MBP. In some vectors the MBP was removed. Some vectors were prepared by complete chemical synthesis assembly[48].

Cloning into expression, purification and detection vectors: The ENTH domain of zebrafish $Epn1_{(18-157)}$ and the dsUIM of human $Hrs_{(257-276)}$ were subcloned into the pGST-parallel2 vector between BamHI and EcoRI endonuclease recognition sites. The ENTH domain of yeast $Ent1_{(1-152)}$ was subcloned into the pCDF-duet vector fused to $His_6$-MBP as previously described ($pCOG21^{17}$). For detection of ubiquitination in bacteria, yeast Sem1 was subcloned into pCDF-duet vector fused to $His_6$-MBP. For yeast expression and purification $His_6$-Sem1 was subcloned into pGREG600 by recombineering that also removed the GFP from the vector.

The structure and sequences of all vectors were confirmed by restriction endonuclease and DNA-sequencing analyses.

Site-directed mutagenesis: Point mutations were introduced using the ExSite approach (Stratagene). The entire vector was amplified using Phusion DNA polymerase. Parental DNA was digested by DpnI and the DNA was blunt ligated. All mutants were sequenced to ensure that the desired mutations were introduced and that no other mutations occurred.

Ubiquitination-dependent *E. coli* growth assay: *E. coli* W3110 (from Ezra Yagil laboratory at TAU) were co-transformed with the pND-Ub and the pCD-Sub plasmids and plated on LB agar supplemented with 34 μg/ml kanamycin and 25 μg/ml streptomycin. 5 ml of liquid LB medium supplemented with the same antibiotic concentrations were inoculated with a single colony and left to grow overnight at 37° C. The culture was harvested and washed twice with 5 ml of minimal Davis medium. The optical density ($OD_{600}$) was measured and adjusted to 0.2. Two and a half microliters of the diluted cultures from each sample were spotted on agar Davis plates containing 0, 0.5, 5, 10, 20 or 50 μg/ml of TRIM. The plates were incubated for 2-3 days at 30° C. and photographed with a UV camera in identical conditions. Each spotting assay was repeated at least 6 times.

Selection experiments in solution growth media: Overnight cultures in LB medium (supplemented with 30 μg/ml kanamycin and 25 μg/ml streptomycin) were harvested and re-suspended in Davis minimal medium. Diluted cells ($OD_{600}$, 0.2) were grown at 30° C. in 96-well plates containing 0.2 ml Davis medium supplemented with 0, 1, 5, 7, 10 and 12 μg/ml TRIM and with or without 100 μM Pyr-41. Growth rates were monitored by measuring the optical density ($OD_{595}$) using a microplate spectrophotometer. Doubling time was calculated for early logarithmic growth ($OD_{595}$ between 0.02 and 0.2). All experiments were performed at least 9 times (n=9).

Genetic Selection Assays for Characterization of Structural Based Mutants.

Data collection: *E. coli* W3110 expressing the pND-Ubs, pCD-Subs (and sometimes also an Ampicillin resistance plasmid that constitutively expresses E3-ligase) grew to logarithmic phase at 37° C. in 5 ml of LB medium supplemented with 23 μg/ml Kanamycin, 16 μg/ml Streptomycin and 33 μg/ml Ampicillin. The culture was harvested and washed once with 5 ml of minimal Davis medium. The bacterial density was adjusted to OD600 nm value of 0.3. Culture samples (2.5 μl each) were spotted on Davis agar Petri dishes containing 10 μg/ml trimethoprim. Culture in each experiment was spotted usually three to four times. Most experiments were repeated at least three to four times (therefore 9<n>16). Time-lapse (30 or 60 minutes) scanning took place in 26° C. incubator using a regular A4/US-letter office scanner (Epson Perfection V37)[40].

Image analysis: Images were read into Fiji as a stack using 'import →image sequence'. The spots density were measured using the *Time Series Analyzer* V3 (Balaji J 2007; a Java ARchive ImageJ/Fiji plugin that can be downloaded and installed from www(dot)rsb(dot)info(dot)nih(dot)gov/ij/plugins/time-series(dot)html). Regions Of Interest (ROIs) were specified (typically as 20X20 ovals) of and their total intensities (bacterial densities) were integrated and plotted where 'Z-axis' is the image time index. Similarly, the background was measured and calculated and subtracted from the collected data. Logistic regressions of growth curves were calculated using Origin. A single parameter that describes growth efficiency was calculated as follows: the growth curve slope at the 'half max density' was extracted and divided by its time index.

Protein purification: Proteins were purified from *E. coli* using affinity tags as previously described[17]. For crystallization purposes, proteins were concentrated to 5-20 mg/ml using centricon (Amicon Ultra), in a final solution of 50 mM Tris-HCl (pH 8.0), 150 mM NaCl, and 5 mM dithiothreitol (DTT).

Western-blot analysis: Following separation on SDS-PAGE, samples were transferred onto a nitrocellulose membrane and incubated with rabbit anti-His epitope tag antibody (1:20 000 dilution, Rockland) or mouse anti-GST antibody (1:200, Santa Cruz), and infrared dye coupled goat anti-mouse secondary antibody (1:12 000, LI-COR). Blots were scanned using an Odyssey system (LI-COR Biosciences) at 700 and 800 nm.

Crystallization and data collection: Crystallization and data collection and processing of yeast Ent1-ENTH have been reported[60]. Purified Zebrafish Epn1-ENTH was concentrated to 10 mg/ml and was crystallized in 0.1M $KPO_4$ pH 7.0 and 19% PEG 3,350 at 20° C. Crystals were cryo-protected with 25% ethylene glycol and were frozen in liquid nitrogen. Data were collected at the ID29 beamline (ESRF, Grenoble) and processed with HKL2000 software[61]

Structure determination and refinement: Structure of ENTH domains were solved by molecular replacement (MR); 1H0A[37] was used for searching model with PHASER[62]. To facilitate the MR search, the first 17 residues were removed and alanine reduction was exerted to the non-conserved residues. Model building and refinement were carried out with PHENIX[63], Refmac5[64] and COOT[65].

Ubiquitylated-Rpn10 was purified from E.coli and crystallized as previously described 5,35. It was found that the extremely thin crystals (1-3 μm) were highly sensitive to radiation damage. BEST software was used, which precisely predicted an efficient data-collection strategy to achieve a full completeness dataset for these C2 space-group crystals, with only 95 images at oscillation steps of 1.75°. Data were collected at the ID14-4 beamline (ESRF) at wavelength of λ=0.93930 Å under cryo conditions of 100° K. The structure was determined by molecular replacement using PHASER 42, where the Rpn10-vWA domain from S. pombe (PDB 2X5N) and Ub (PDB 1UBQ) 41 were used as initial search models. PHENIX auto-build was used to provide an initial model. Model-building and refinement were carried out with PHENIX 43, Refmac5 44 and COOT 45. The geometry parameters of the isopetide bond were restrained within the refinement process in PHENIX. The structure was validated with PROCHECK 46 and the PDB validation tool. Statistics of Ramachandran analysis yielded 98.7% of the residues were found in the most favored or additional allowed regions and 1.3% were found in the generously allowed regions. None of the residues were found in disallowed regions. It was found that the linker tethering the vWA domain to the UIM has an intrinsic propensity for cleavage at the beginning of the hinge. Indeed, the linker spontaneously clipped-off during crystallization. Consequently, the crystallized protein contained the vWA domain (residues 1-191) and its conjugated Ub at K84. Interestingly, the structures of apo Rpn10 from S. cerevisiae and from S. pombe[18,24] also present truncated forms of the protein at the same location.

Crosslinking assays: Crosslinking was carried out using 0.5 mM disuccinimidyl substrate (DSS) as described by[66].

Surface plasmon resonance: Purified His$_6$-MBP-ENTH or mutants were immobilized on an Ni$^{+2}$ chip at a density of ~800U. Untagged Ub (analyte) was injected at a flow rate of 20 ml per min in 150 mM NaCl, 10 mM HEPES pH 7.0 and 0.010% poly-sorbate 20 at 24° C.; 500 mM imidazole was used for surface regeneration. To avoid immobilization of aggregated analyte the purified Ub was chromatographed by gel filtration and briefly sonicated immediately before SPR experiments. Data were processed with BioEvaluation and fitting carried out as a single-site-binding model with OriginLab. Standard errors derived from at least three samples.

SPR analysis of Rpn10-vWA:Ub and mutants non-covalent interactions. The experimental set-up comprised α-GST antibody immobilized on a CM5 chip according to the manufacturer's protocol (GE Healthcare). The ligands (Rpn10 derivatives) were expressed and purified as GST-fusion-proteins and captured on the chip. Free mono-Ub was the analyte. Prior to each experiment the ligand and the analyte proteins were subjected to size exclusion chromatography. Each measurement was taken in triplicate. The experiment comprised 90-100 seconds for binding, 300-350 s for dissociation. Wild-type and mutant Ub analytes were injected at a flow rate of 10 ml/min in 10 mM HEPES pH 7.0, 150 mM NaCl, and 0.005% polysorbate-20 at 25° C. At the end of each experiment, the ligands were removed and surface regeneration was achieved by flowing 10 mM glycine-HCl pH 2.6, followed by sequential washing steps of 1-2 min with 0.1% SDS, 10 mM NaOH. Data were processed using Biacore BIAevaluation software. A single-site-binding model was used for curve fitting of the binding data (Sigma Plot). For plotting, data were scaled such that Rmax=100.

Detection of ubiquitination in vivo: pScHis$_6$-Sem1 plasmid was transformed into the SEY6210, rsp5::HIS3, pDsRed415-rsp5$^{WT}$ and rsp5-1 (rsp5$^{L733S}$) MATa ura3-52, his3-200, trp1-901, lys2-801, suc2-9, leu2-3 strains and grew at 26 in 50 ml of YPD medium (2% glucose) supplemented with 200 μg/ml G418. At log phase the cultures were harvested and the pastes were washed with DDW and transferred to 50 ml YPD medium (2% galactose) supplemented with 200 μg/ml G418. Each culture was divided into two flasks and grew at permissive (26° C.) and restrictive (37° C.) temperatures for additional 4 hours. The cultures were harvested and lysed in 2 ml cold 1.85 N NaOH, 7.5% β-mercaptoethano for 10 min on ice. Proteins were precipitated with the addition of half volume of 50% TCA (final concentration of 25% TCA) and collected by centrifugation (18,000 rpm 20 min). The pellet was resuspended and washed with 3 ml ice-cold 80% acetone, and collected by centrifugation (18,000 rpm 5 min). Then the pellet was re-suspended in 1.5 ml resuspension buffer (6 M guanidine HCl, 100 mM Tris-HCl, 100 mM NaCl, 0.1% triton X-100, pH 8.8) and incubated at 25° C. for 1 hour while rotating. The protein fraction incubated 20 min at 4° C. with 70 μl Ni+2 resin and washed twice with resuspension buffer followed by two washes with buffer 2 (8M urea, 100 mM Tris-HCl pH 8.8, 100 mM NaCl, 0.1% triton X-100) and two washes with buffer 3 (50 mM Tris-HCl pH 7.5, 150 mM NaCl). The Ni+2 beads were boiled in Laemmli buffer and separated by SDS-PAGE followed by western blot analysis with anti-His6 antibody.

Library construction: Yeast GST-tagged ORFs (GE collection) were pooled from 384 pins plated cultures and plasmids were isolated as a pool. The GST fusion genes were PCR amplified. The PCR products were size fractionated (350 to 3000 bp) by gel electrophoresis followed by PCR purification using PureLink, kit (Invitrogen) and sub-cloned in-frame with cDHFR to the pCD-Sub vector by recombineering. The resulted library was transformed to DH5α cells and kept in −80° C. Isolated plasmids of the library were transformed to W3110 competent cells that contained the pND-Ub and constitutively expressed E3-ligase plasmids. Followed transformation the bacteria were plated on selective media.

Accession codes: Atomic coordinates and structure factors for the crystal structures of *Saccharomyces cerevisiae* Ent1-ENTH and *Danio rerio* Epn1-ENTH domains have been deposited in the Protein Data Bank under ID codes rcsb079376 and rcsb074441 respectively.

Results

Construction of a Selection System for Ubiquitination Events in Bacteria

A system was generated for genetic screening of ubiquitination events in *E. coli*. In this system, two fragments of a split reporter gene are tethered to Ub and a ubiquitination substrate and are co-expressed along with ubiquitination apparatus in *E. coli* (FIG. 1A). Specifically, the N-terminal fragment of murine dihydrofolate reductase (nDHFR) was fused to the N-terminus of Ub (in a plasmid denoted pND-Ub) and the C-terminal fragment of DHFR (cDHFR) to the N-terminus of the substrate (in a plasmid denoted pCD-Sub). Pending on substrate ubiquitination, the two DHFR fragments are assembled into a functional enzyme conferring antibiotic [trimethoprim (TRIM)] resistance and growth on selective media[19]. The DHFR fragments were tethered to Ub and to the substrate with long linkers designed to confer flexible but stable characteristics facilitating the functional assembly of the reporter (FIG. 9). The system has a polycistronic architecture in which ubiquitination apparatus and the substrate are co-expressed from two or three compatible vectors (FIG. 1A). Synthetic operons are expressed from a constitutive promoter [an unregulated λ-phage left promoter (pL)], suitable for bacterial genetic studies.

Figure 1B:
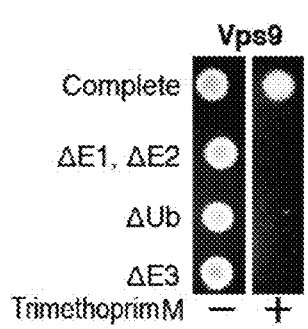
Figure 1C:
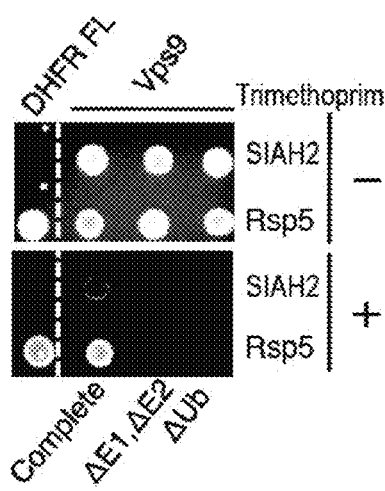

To assess the functionality of the system, the well-characterized Ub-receptor Vps9[15-17] was fused to cDHFR (pCD-Sub) and co-expressed together with Rsp5 (E3) and the pND-Ub vector that expresses E1 and yeast Ubc4 (E2). It was found that the W3110 strain provided the best genetic background under the described experimental conditions. Bacteria expressing a complete ubiquitination system for Vps9 grew under both permissive and non-permissive conditions (FIG. 1B). However, strains lacking Ub or E1/E2 did not grow on selective media. To demonstrate that the developed system maintains the known E3:substrate specificity, Rsp5 was replaced with Siah2, a non-cognate E3-ligase. Bacteria grew only when the cognate E3 was expressed (FIG. 1C), even though Siah2 was functional in the selection system, as it promoted self-ubiquitination (FIG. 2B).

Figure 1D:
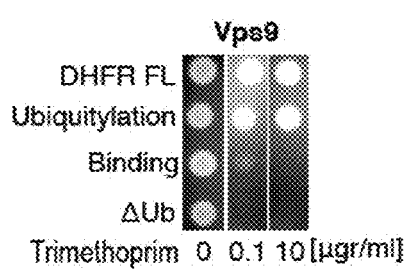

The split DHFR system was originally developed for identification of non-covalent protein-protein interactions[19], suggesting that the selection system may detect non-covalent UBDs:Ub interactions. Since UBDs present a fairly low affinity to Ub[14], different antibiotic concentrations were tested to identify suitable growth conditions for Vps9:Ub non-covalent interactions. Although Vps9 presents one of the highest UBD:Ub measured affinities[15,16], growth was found only at antibiotic concentration of 0.1 μg/ml (FIG. 1D). Since such antibiotic concentration is limited for selection, it seems that the developed system is selective only for ubiquitination events.

The Ubiquitination Selection System Facilitates Identification and Characterization of E3s Most E3-ligases undergo self-ubiquitination[20]. The developed selection system thus provides a straightforward tool for their identification and characterization as self-ubiquitination is predicted to confer antibiotic resistance. Yeast Rsp5 and human Siah2, representatives of the HECT and the RING ligases, respectively, were fused to cDHFR. Growth phenotypes were observed under non-permissive conditions, only when all the required ubiquitination components were co-expressed (FIGS. 2A-B).

Siah2 inhibition by menadione may play an important role in cancer therapy[21]. As the engineered bacteria became addicted to self-ubiquitination of Siah2, its inhibition was predicted to present growth arrest phenotype. FIG. 2B (right) shows a growth arrest phenotype in the presence of menadione only under the addictive conditions. Similarly, Cdc34, a non-cognate E2, did not support growth. The developed system could thus be employed for screening of potential drugs. It was suggested that some E3s use one E2 to attach the first Ub and a different E2 for building the Ub-chain[22]. The present system may facilitate the identification of such E2s.

Identification of a Novel E3-Ligase and its Cognate E2s

To demonstrate the system's ability to identify a novel E3-ligase, the present inventors focused on a U-box family from the pathogenic enterohaemorrhagic *E. coli* (EHEC). They used the well-characterized human ligase CHIP as a probe in a PSI-BLAST search against the EHEC proteome. The search retrieved an uncharacterized sequence, ECs3488, as a potential ligase containing a conserved 35-amino-acid sequence with 22% identity to a helix-loop-helix-beta region of the CHIP U-box domain[23] (FIG. 2C). ECs3488, also named NleG6-3, has been postulated as an E3-ligase, but its expression and function have never been demonstrated[24,25]. ECs3488 was cloned as a fusion with cDHFR and screened against a full yeast library of E2s, resulting in the identification of Ubc4/5 as cognate E2s for the putative E3-ligase (FIG. 2D). Then, the ligase functionality was examined with the human E2 orthologs UbcH5B/C (FIG. 2E).

Figures 2F, 2G:
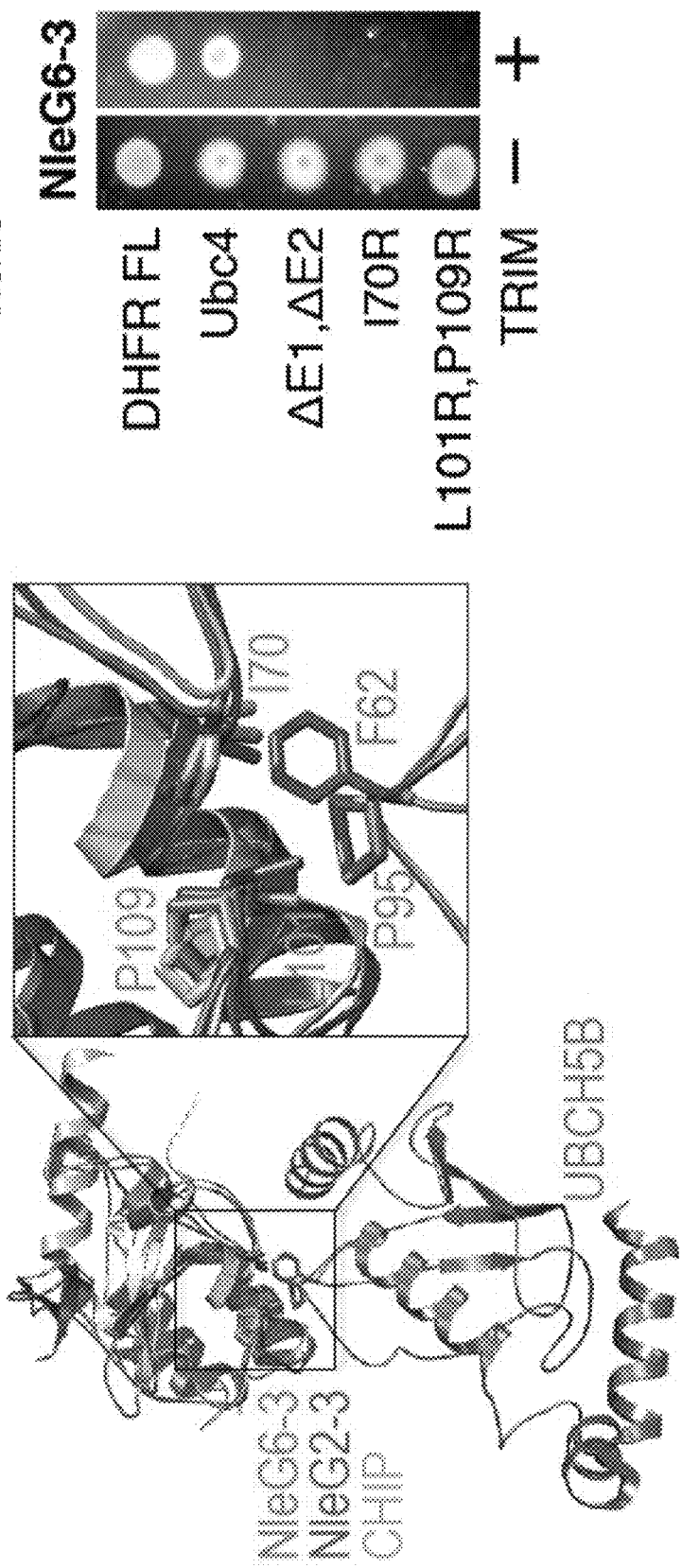

Based on the structures of NleG2-3 and of the CHIP:UbcH5a complex (PDB 2KKX and 2OXQ)[24] structural model for the ECs3488:E2 interface was built (FIG. 2F) and the selection system was used to assess the model. The results corroborated the structural model, as the ECs3488:E2-binding mutants presented significant growth arrest phenotypes (FIG. 2G).

Selection Approach for Identification and Characterization of UBDs

Figure 3B:
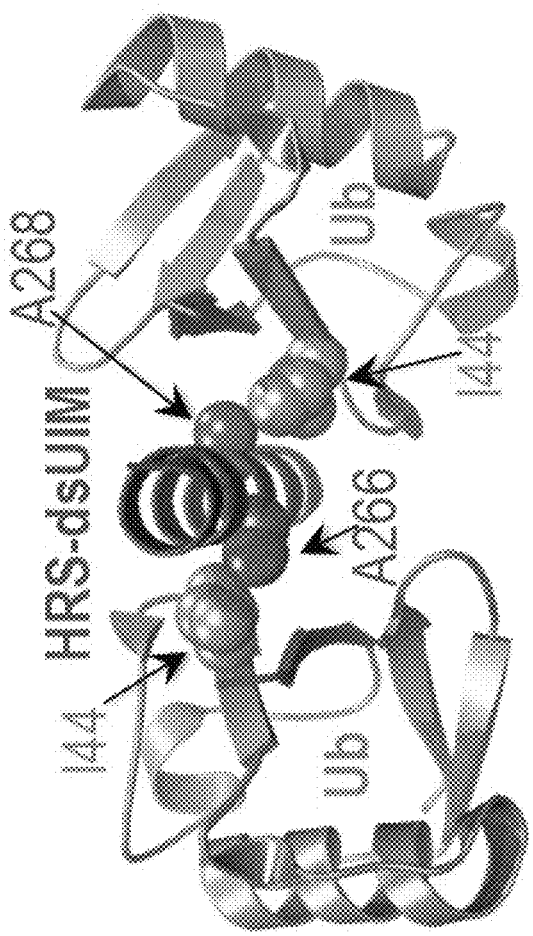
Figure 3A:
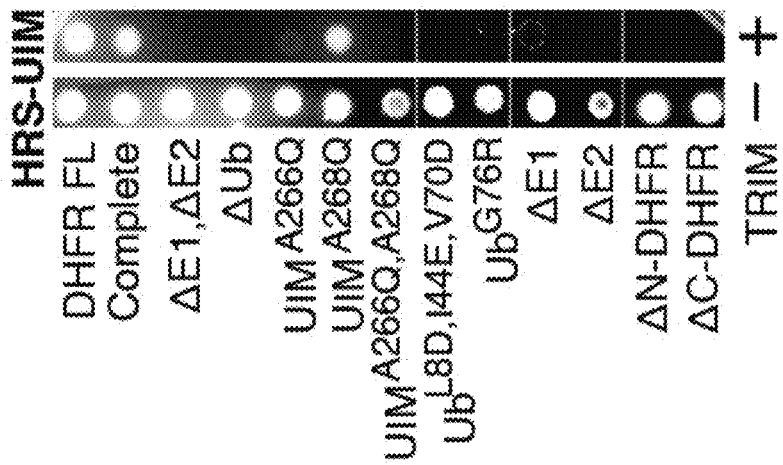

Ubiquitin binding domains (UBDs) usually bind mono-Ub with low affinity, ranging from 2 μM to 2100 μM[15,26], posing a challenge to biochemical and biophysical studies. The selection system stabilizes the dynamic and weak UBD:Ub non-covalent interactions by forming a covalent bond between Ub and Ub-receptor (i.e. ubiquitination) in the bacteria. The present inventors assessed the ability of the system to sense low affinity UBD by tethering the double-sided UIM (dsUIM) of Hrs as substrate[27,28] (FIG. 3A). The structures of Hrs:STAM (also known as ESCRT-0 complex) and particularly its dsUIM:Ub complex, were determined and facilitated detailed molecular assessment[29,30]. The E3-independent self-ubiquitination of most Ub-receptors and the promiscuous function of Ubc4/5 subfamily members aided in the analysis. Available lysine residues for ubiquitination do not necessarily need to be part of the UBD as was demonstrated for several UIM and UBA proteins[31]. Alanine residues at each face of the dsUIM were demonstrated to interact with the Ub 144 hydrophobic patch (FIG. 3B). Indeed, it was found that the A266Q, A268Q double mutant presented a growth arrest phenotype. Similarly, I44-patch mutant abolished bacterial growth. The phenotype of Ub-G76R demonstrated that growth is also dependent on ubiquitination. Furthermore, Western-blot analysis showed that a covalent bond between Ub and Hrs is generated (FIG. 3C). Finally, it was demonstrated that the growth is dependent on a functional ubiquitination apparatus by omitting the E1/E2 enzymes (FIG. 3A) or by administration of the E1 inhibitor, PYR-41[32] (FIG. 3D).

The system's functionality with other structurally different UBDs, including the proteasomal receptor Rpn10, human STAM1-UIM and ALIX-V domains[33] and the yeast Hse 1-VHS domain[26], that together are involved in multivesicular and retroviruses budding, was furthered verified/validated (FIGS. 3E-H).

Similar to ESCRT-0 (STAM, HRS and Hse1) components, GGAs proteins also utilize UBDs to transport ubiquitylated-cargo from Golgi to the multivesicular body. An affinity of 2100 μM was demonstrated to the GGA3-VHS:Ub complex[26]. Critical tryptophan and leucine residues were identified in STAM1 and other VHS domains that bind Ub at the I44 patch. Moreover, the VHS domains of GGA1 and 2, which naturally lack the critical leucine, do not bind Ub. It was demonstrated that despite the weak affinity, the selection system distinguished between these phenotypes (FIG. 3I).

One benefit of a bacterio static antibiotic like trimethoprim is that it enables the accumulation of functional DHFR assemblies, due to the ubiquitination, up-to a threshold level that is sufficient to confer resistance while not harming the bacteria. Thus, the developed system may provide a supersensitive readout for genetic identification and characterization of potential UBDs, without the need to purify them.

ENTH is a UBD

Figure 4B:
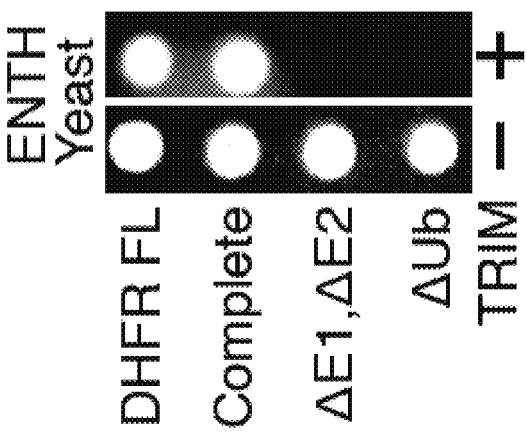
Figure 4A:
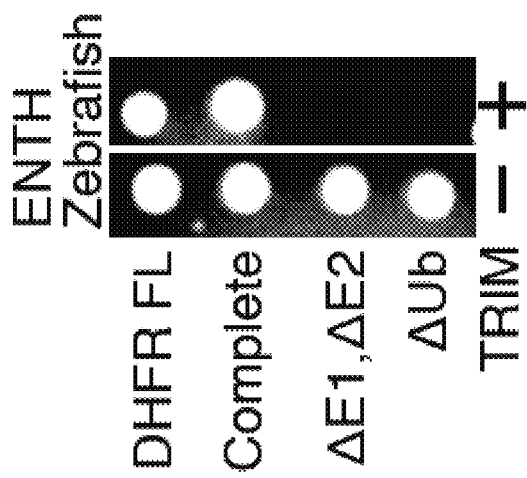
Figure 4J:
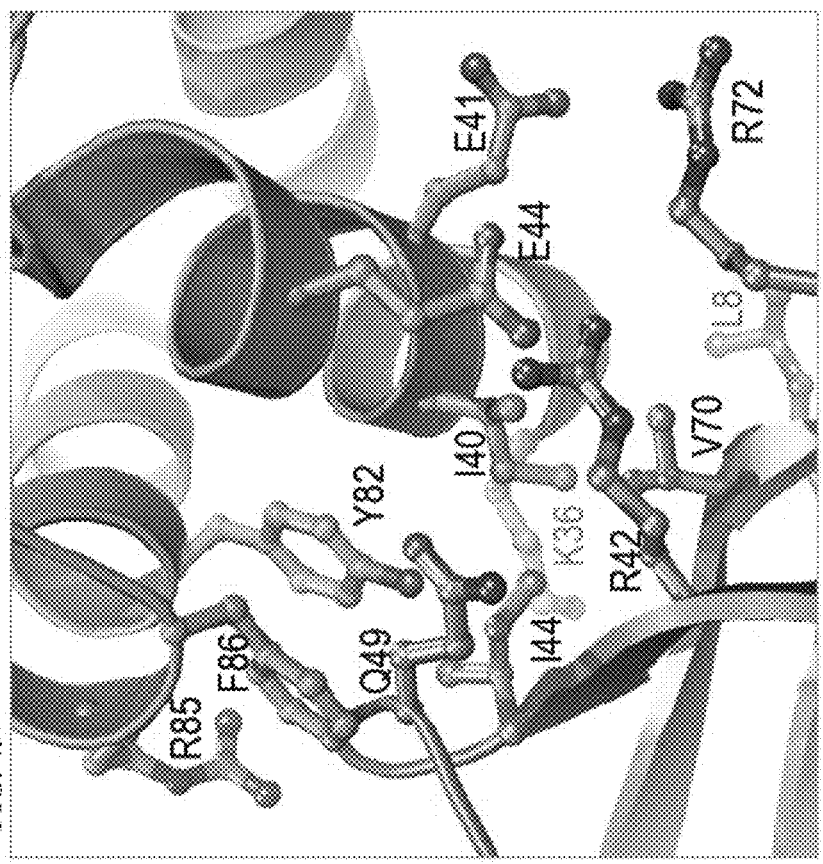
Figure 4I:
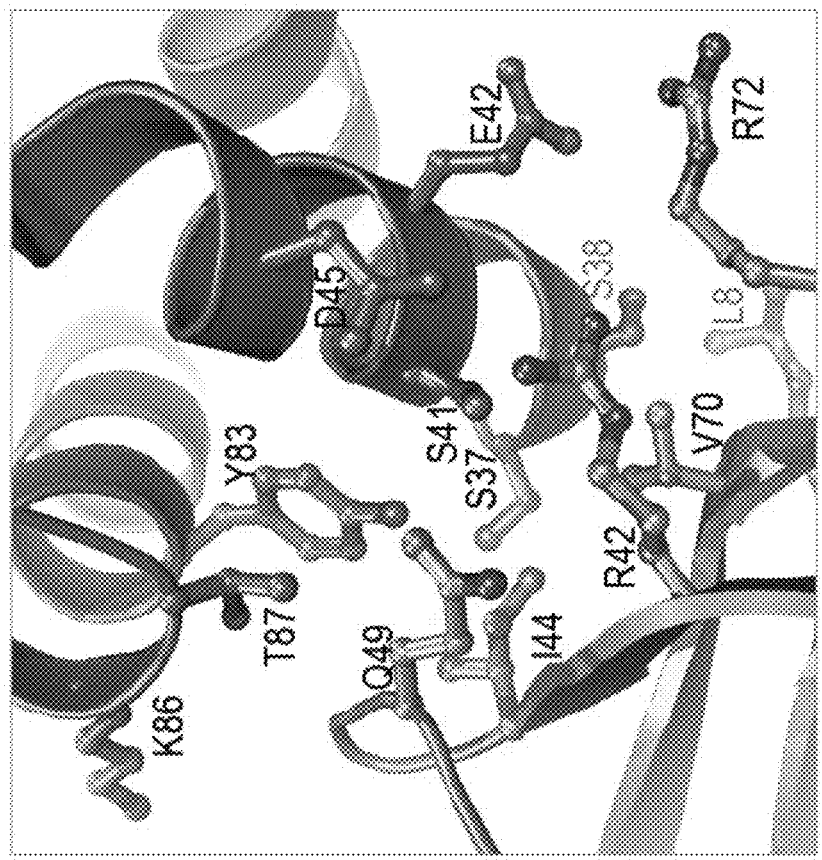

The present inventors next sought to challenge the system to detect a novel ultraweak-affinity UBD. ENTH domains assume a similar fold to that of VHS[34]. Moreover, Epsin proteins possess a similar architecture to the Ub-receptors Hrs, STAM and GGAs by harboring VHS/ENTH, two Ub binding patches (dsUIM or 2xUIM or GAT domains) followed by a long flexible linker containing endocytic machinery binding elements including a clathrin-binding box (FIG. 10). Therefore, although ENTH probably lacks the critical tryptophan or leucine residues[26], it was speculated that it too binds Ub. The selection system was employed and it was demonstrated that cDHFR-ENTH domains of yeast and zebrafish promote growth on selective media in an E3-independent manner (FIGS. 4A-B). This suggests that these ENTH domains directly bind Ub~E2. Indeed, biochemical crosslinking assays and purification/detection of ubiquitylated yeast Entl derivatives from *E. coli*[17] strongly support the genetic data suggesting that ENTH directly binds Ub (FIG. 11A-E).

Structure of ENTH Domain Provides Insight into Mechanism of Ub Recognition

To obtain high resolution information on the ENTH:Ub interaction, the present inventors tried to crystalize the complex. Probably due to the ultraweak affinity (see quantification below), only crystals of apo ENTH or Ub were obtained. The structures of yeast (Sc_ENTH) and zebrafish (Zf_ENTH) domains were determined by molecular replacement to 1.95 Å and 1.41 Å resolutions respectively (Table 3 and FIGS. 4C-J).

TABLE 3

Crystallographic Data and Refinement Statistics

| Construct | Z.f ENTH | S.c ENTH |
|---|---|---|
| Data Collection | | |
| X-ray source | ESRF ID29 | ESRF ID29 |
| Wavelength (Å) | 0.978 | 0.978 |
| Space group | P1 | P 21 21 21 |
| Cell dimensions | | |
| a, b, c, (Å) | a = 42.364, b = 51.724, c = 64.639 | a = 32.69, b = 35.46, c = 110.62 |
| α, β, γ (°) | α = 89.333, β = 76.373, γ = 79.737 | α = β = γ = 90 |
| Resolution (Å) | 1.4-62.79 (1.409-1.425)$^a$ | |
| R-merge¶ (%) | 7.5 (3.2) | 0.166 |
| I/σI | 5.3 (4.4) | 6.79 (1.50) |
| Completeness (%) | 94.0 (88.97) | 99.18 (99.58) |
| Redundancy | 3.4 (3.0) | |
| Observed reflections | 325,868 | 37572 |
| Unique reflections | 95136 (9256) | 9806 (1429) |
| Refinement | | |
| Resolution | 1.41-62.79 $^a$(1.41-1.425) | 1.95-55.42 $^a$(1.95-2.0) |
| $R_{work}/R_{free}$ | 0.1545/0.2015 | 0.1862/0.2364 |
| Number of atoms | 6022 | 1254 |
| Protein | 5189 | 137 |
| Ligand/ion | 10 | |
| Water | 823 | 97 |
| average B factor (Å$^2$) | 17.5 | 19.00 |
| Solvent (%) | 28.83 | 29.40 |
| r.m.s. deviations | | |
| Bond lengths (Å) | 0.009 | 0.018 |
| Bond angles (°) | 1.134 | 1.30 |
| Ramachandran (%) | | |
| Favored | 94.1 | 96 |
| Additional allowed | 5.7 | 4.0 |
| Outliers | 0.2 | 0.0 |
| Disallowed | 0.0 | 0.0 |
| PDB code | 5LP0 | 5LOZ |

¶R-merge = Σhkl Σi|Ii(hkl) − (I(hkl))|/Σhkl Σi Ii(hkl), where Ii(hkl) is the intensity of the ith observation of reflection hkl and <I(hkl)> is the average intensity of reflection hkl.
$^a$Outer resolution shell High-quality electron density maps (FIGS. 4C-D) showed that although these structures are highly similar, apparent differences can be seen in the loop tethering helices-3 and 4 and the angle between the superhelix structure and helix-8 (FIGS. 12A-B).

To generate a structural model of the ENTH:Ub complex, the ENTH domains were superimposed onto the STAM1-VHS:Ub complex[26,35,36]. The models showed that the STAM1 W26 and L30 Ub-binding residues were naturally substituted with S37 and S41 in Zf_ENTH and K36 and I40 in Sc_ENTH. (FIGS. 4C-J). Intriguingly, these models suggest that Ub R42 and R72 form electrostatic interactions with E42 and D45 or E41 and E44 of Zf_ENTH and Sc_ENTH, respectively. Both models predicted additional interactions that seemed to contribute little to the binding.

Intriguingly, superimposing the ENTH:Ub model onto the structure of ENTH complex with the membrane lipid phosphatidylinositol-4,5-bisphosphate[37] shows that ENTH binds Ub and the membrane lipid at opposite sites (FIG. 13), suggesting that ENTH can bind Ub while associated with the membrane. Similarly, superimposing the VHS:Ub complex onto the VHS:M6PR-tail (the acidic-cluster-dileucine sorting signal of the mannose-6-phosphate receptor) complex[38,39], shows the same phenomenon, suggesting that both VHS and ENTH domains can recognize ubiquitylated-transmembrane-cargo while associated with the membrane.

Genetic Approach for Structural Validation of the ENTH: Ub Interface

ENTH domains lack the critical Trp or Ile, suggesting that cumulative interactions of peripheral residues compensate for its role in Ub binding. To evaluate the contributions of specific residues to the ENTH:Ub interaction, point mutations were introduced at the predicted interface. The growth rates were monitored by time-lapse scanning the bacteria using a simple A4/US-letter scanner with a modified control software[40]. To quantify the growth rates, a simple Fiji[41] based time series analyzer procedure was applied to measure a typical stack of 100-200 scans (see details in the Materials and Methods section) by means of optical density (FIGS. 5B-5F).

Ala mutagenesis or exchanging the charge of the acidic residues of Zf_ENTH demonstrated growth arrest phenotypes (FIGS. 5A,C,D). A similar phenotype, though less severe for the Ub R42E, R72E mutant, was found when the acidic residues of the yeast protein were mutated, suggesting slight structural differences between these complexes. Remarkably, a permutation cycle in which the Zf_ENTH E42 and D45 residues were replaced with arginine residues, and Ub R42 and R72 were replaced with glutamic residues, restored growth (FIG. 5D). This result reflects the accuracy level of the structural model and the high sensitivity of the selection system. Moreover, the Ub R42E, R72E mutant could not suppress the Zf_ENTH E42A, D45A mutant, signifying the importance of these electrostatic interactions. The Zf_ENTH S37G and Y83A mutants, predicted to provide lesser contributions to the binding, indeed yielded minor but significant growth phenotypes (FIG. 5A). Taken together, the results of this mutational analysis strongly corroborate the structural model and demonstrate the power of the developed system to detect and quantify relatively minor differences in protein-protein interactions along Ub pathways.

The yields of ubiquitination of the Sc_ENTH wild-type and mutant proteins were biochemically quantified (FIGS. 5G-H). The ENTH E41R, E44R and the Ub R42E, R72E double mutants significantly reduced the ubiquitination yield by about 60-80%.

Finally, to biophysically corroborate the data and to quantify the affinity of the ENTH:Ub complex, Surface Plasmon Resonance (SPR) measurements were performed with immobilized Sc_ENTH and free mono-Ub (FIG. 5I). Ultraweak binding with $K_d$ of 2,300 µM was found for the wild-type complex. This result is compatible with our model and previous measurements of homologous VHS:Ub complexes in Hrs, Vps27 and GGA3, which present affinities of 1,400, 1,500 and 2,100 µM, respectively[26]. Interestingly, the Ub R42E, R72E or Sc_ENTH E41R, E44R mutants showed saturation binding curves that could be fit to a single binding model (FIG. 5I and FIGS. 14A-C) with respective estimated affinities 2.6 fold and 3.5 fold lower than that of the wild-type. Notably, for these mutants, the Ub (analyte) concentrations were too low to obtain accurate $K_d$ values, as reflected in the high standard errors. Together, the correlation between the SPR measurements, the genetic and biochemical data provides a rough estimation for the sensitivity of the selection system in monitoring Ub binding.

Ultraweak (~3,000 μM) protein-protein interactions are significant as they regulate various biological functions[42,43]. Typically, K63-tri-Ub chains constitute the main signal for clathrin-dependent membrane protein trafficking[44-46]. Therefore, Ub-receptors decoding this signal usually possess three Ub-binding patches[47] (FIGS. 11A-E). Avidity and/or cooperative of tandem UBDs render selectivity of these Ub-receptors. The contribution of the VHS domain to the total affinity and selectivity of VHS-UIM proteins has been thoroughly studied[26,35]. Therefore, the ultraweak affinity described herein should be considered in the context of full-length Epsin, which contains two additional UIMs.

Identification of Sem1 as Ubiquitination Target of Rsp5

Figure 6B:
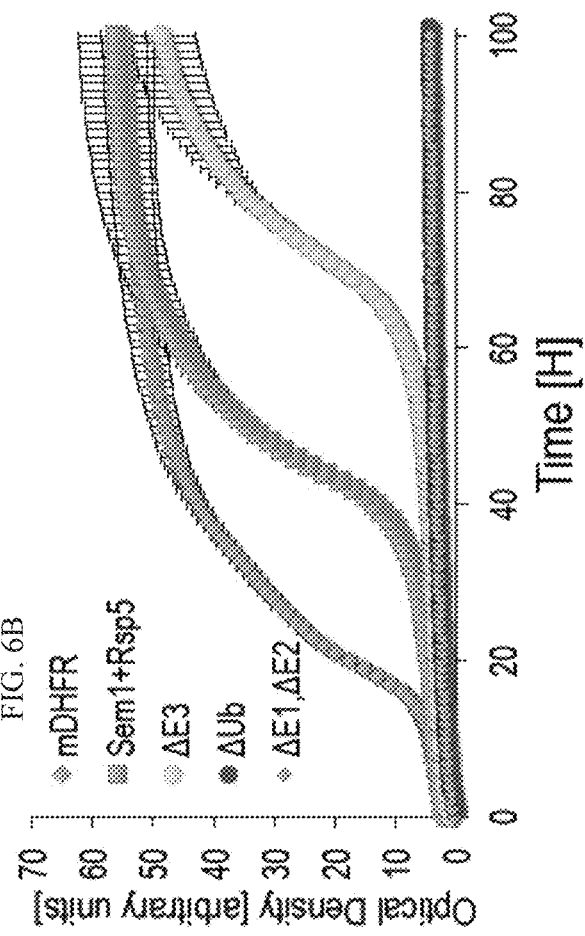
Figure 6A:
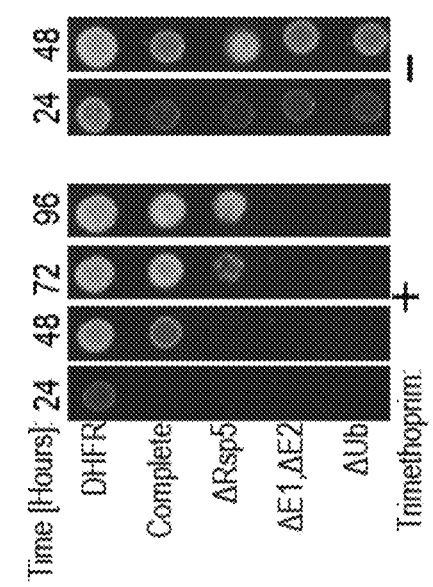
Figures 6C, 6D:
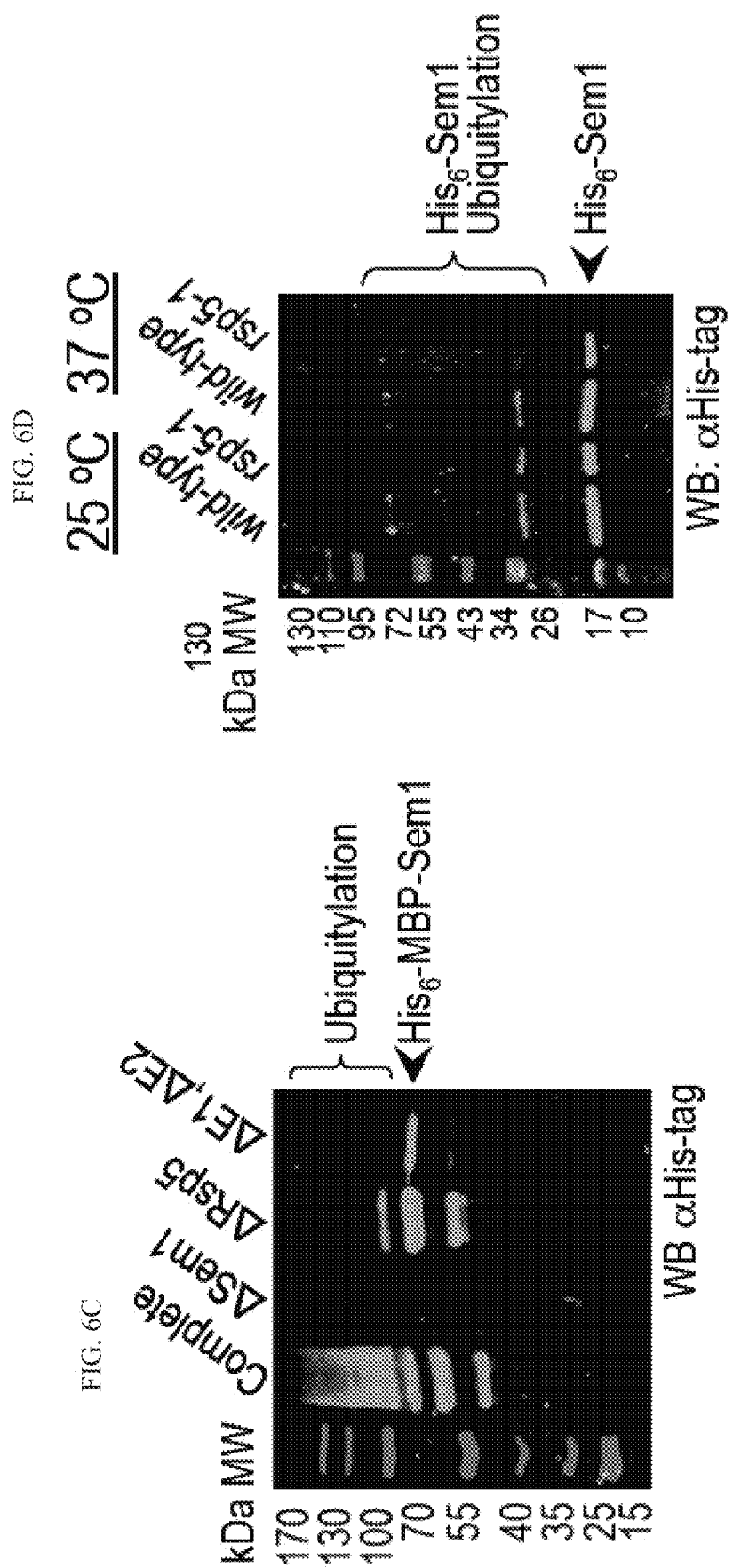

One of the greatest challenges in the Ub field is to identify association between E3-ligases and their cognate ubiquitination targets (FIGS. 6A-D). To demonstrate the potential of the developed system to address this challenge, the present inventors constructed a whole genome yeast fusion library in-frame with cDHFR and screened the library against Rsp5. The entire array of yeast GST-tagged ORFs (GE collection) were amalgamated and plasmids were isolated as a pool. The plasmid library was PCR-amplified and the products were subcloned into the developed selection system by Gibson assembly[48]. As many Ub-receptors may undergo E3-independent ubiquitination, the present inventors expected to obtain false positive growth of these ORFs, and therefore they employed an assay for E3-independent ubiquitination. They compared the growth rates of the positive colonies with and without Rsp5 using the scanner as described above. Less than 100 positive colonies were identified (from 10 Petri dishes). Most of them showed very similar growth rates in the presence or absence of Rsp5. However, the colony of Sem1 demonstrated significantly higher growth rates when Rsp5 was co-expressed. Sem1 and its human orthologue DSS 1 (Deleted Split-hand/Split-foot) are involved in critical processes including development, proteasome assembly, DNA repair and cancer[49-53]. As DSS1 possesses two conserved UBDs[54], Sem1 was tested to see if it underwent E3-independet ubiquitination. It was found that Rsp5 significantly promoted Sem1 ubiquitination (FIGS. 6A-B). Moreover, detection of ubiquitylated $His_6$-MBP-Sem1 from E. coli showed highly similar results (FIG. 6C). Since this is the first report for Sem1 ubiquitination, the present inventors tested if Sem1 undergoes Rsp5 dependent ubiquitination in vivo in yeast. Ubiquitination was detected in yeast extracts of wild-type and a temperature sensitive rsp5 allele, rsp5-1. Expression of galactose dependent $His_6$-Sem1 at permissive and restrictive temperatures showed that Rsp5 is a bona-fide ligase of Sem1, as unlike the wt, the ubiquitination in rsp5-1 was detected at 26° C. but not at 37° C. (FIG. 6D).

Use of Chloramphenicol Acetyl Transferase (CAT) as a Selection Marker

Figure 16A:
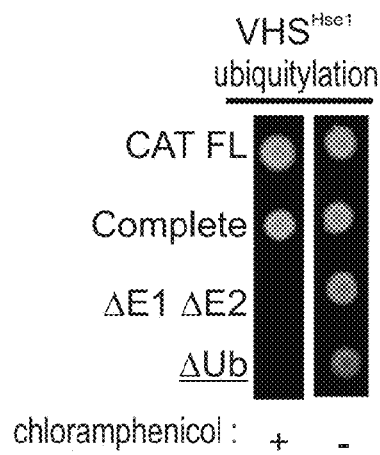

Based on the crystal structure of $CAT_I$ in its apo and complex with chloramphenicol (PDB accessions 3U9B and 3U9F) the present inventors designed a split-CAT system. To test if the newly designed split-CAT system can identify ubiquitination events, they tethered a ubiquitylation target to the nCAT fragment and Ub to the cCAT fragment (FIGS. 15A-D). The fused proteins were co-expressed with their cognate ubiquitylation apparatus and bacteria were spotted on selective media (rich agar supplemented with 7-10 mg of chloramphenicol per ml). At first, a simple ubiquitylation cascade was tested consisting of Ub-receptor (a Ub-Binding Domain UBD containing protein) as the ubiquitylation target. Specifically, the Ub-receptor of Hse1-VHS domain tethered to the nCAT was co-expressed with nCAT tethered to Ub. Wheat E1 (Uba1) and the yeast E2 (Ubc4) were also expressed. As shown in FIG. 16A expression of the complete ubiquitylation cascade of VHS domain tethered to the split-CAT system presented growth phenotype. However, when the ubiquitylation enzymes E1 and E2 or Ub were removed growth arrest phenotypes were found.

Figure 16B:
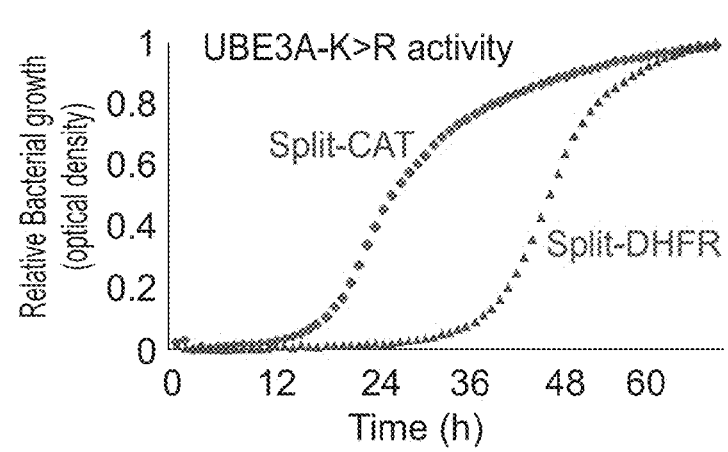

To compare the growth efficiency between the split-DHFR vs. the split-CAT systems, a UBE3A (also known as E6AP) Rpn10 ubiquitylation dependent cascade was constructed in both systems. A K>R mutation within UBE3A was constructed which results in a constitutive hyperactive E3-ligase. This ligase was expressed from a $3^{rd}$ vector under the regulation of the leaky promoter pTac (i.e. without the addition of IPTG) in bacteria that express Ub, Rpn10, Uba1 (E1) and UBCH7 (E2). FIG. 16B shows a significant difference in growth efficiency between the two systems.

Figure 16C:
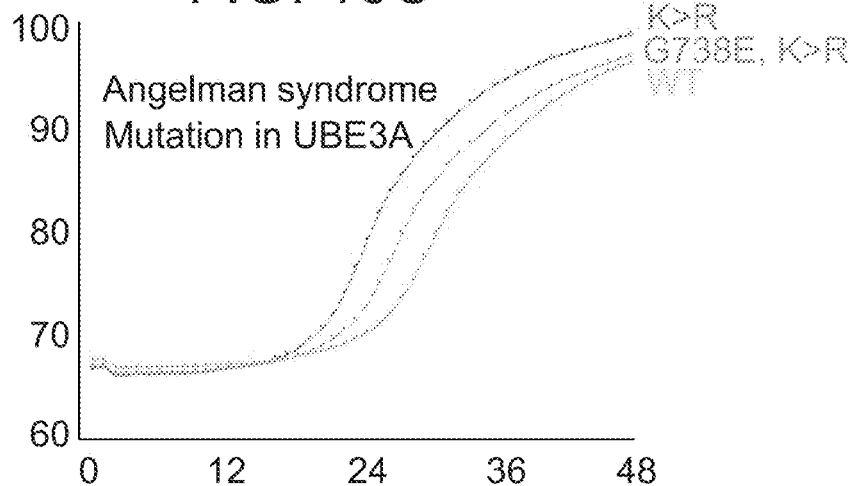
Figure 16D:
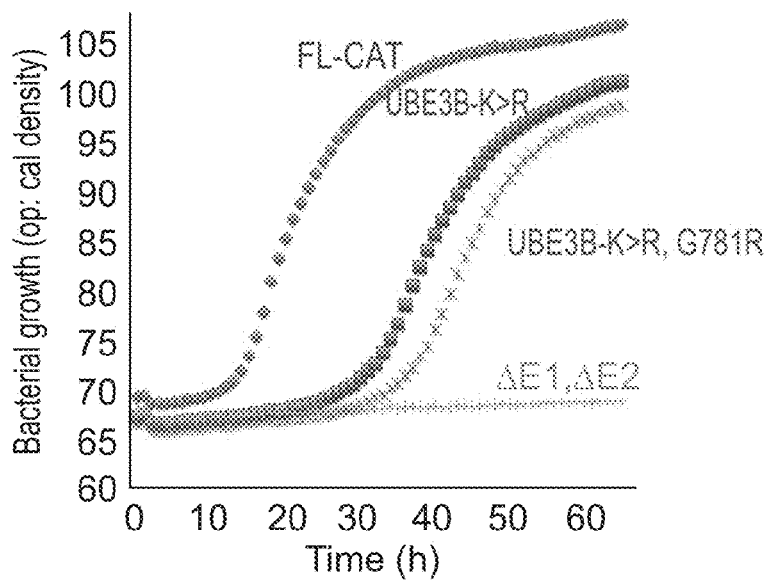

To demonstrate the system application to study the effect of point mutations an Angelman syndrome (AS) mutation was introduced into UBE3A and bacterial growth was analyzed in wild-type (self-arrested), K>R mutant (hyperactive) and AS mutation on the background of the K>R mutation (FIG. 16C). It was found that the K>R mutation resulted in a higher efficient growth phenotype while the AS mutation resulted in a decreased efficient growth phenotype compared with the WT enzyme. Similarly, the function of UBE3B a HECT E3 Ub-ligase that presents a difficulty in purification in its active from and which is involved in Kaufman Syndrome (KS; Flex et al. 2013) was also assessed in the system. Using the selection system, the critical lysine residue that undergoes self-ubiquitylation that lead to allosteric restrain of the enzyme was identified and a K>R unrestrained mutant was constructed. KS mutation on the background of the UBE3B K>R demonstrated a growth phenotype (FIG. 16D).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

1. Weissman, A. M., Shabek, N. & Ciechanover, A. The predator becomes the prey: regulating the ubiquitin system by ubiquitylation and degradation. *Nature reviews. Molecular cell biology* 12, 605-620 (2011).
2. Wild, P. et al. Phosphorylation of the autophagy receptor optineurin restricts Salmonella growth. *Science* 333, 228-233 (2011).
3. Nalepa, G., Rolfe, M. & Harper, J. W. Drug discovery in the ubiquitin-proteasome system. *Nat Rev Drug Discov* 5, 596-613 (2006).

4. Mizushima, N., Levine, B., Cuervo, A. M. & Klionsky, D. J. Autophagy fights disease through cellular self-digestion. *Nature* 451, 1069-1075 (2008).
5. Ciechanover, A. & Brundin, P. The ubiquitin proteasome system in neurodegenerative diseases: sometimes the chicken, sometimes the egg. *Neuron* 40, 427-446 (2003).
6. Bachmair, A., Finley, D. & Varshaysky, A. In vivo half-life of a protein is a function of its amino-terminal residue. *Science* 234, 179-186 (1986).
7. Deshaies, R. J. & Joazeiro, C. A. RING domain E3 ubiquitin ligases. *Annu Rev Biochem* 78, 399-434 (2009).
8. Hershko, A., Ciechanover, A., Heller, H., Haas, L. A. & Rose, A. I. Proposed role of ATP in protein breakdown: Conjugation of proteins with multiple chains of the polypeptide of ATP-dependent proteolysis. *Proc Natl Acad Sci USA* 77, 1783-1786 (1980).
9. Li, W. et al. Genome-wide and functional annotation of human E3 ubiquitin ligases identifies MULAN, a mitochondrial E3 that regulates the organelle's dynamics and signaling. *PLoS One* 3, e1487 (2008).
10. Wilkinson, K. D., Urban, M. K. & Haas, A. L. Ubiquitin is the ATP-dependent proteolysis factor I of rabbit reticulocytes. *J Biol Chem* 255, 7529-7532 (1980).
11. Hicke, L., Schubert, H. L. & Hill, C. P. Ubiquitin-binding domains. *Nat Rev Mol Cell Biol* 6, 610-621 (2005).
12. Di Fiore, P. P., Polo, S. & Hofmann, K. When ubiquitin meets ubiquitin receptors: a signalling connection. *Nat Rev Mol Cell Biol* 4, 491-497 (2003).
13. Hoeller, D. et al. Regulation of ubiquitin-binding proteins by monoubiquitination. *Nat Cell Biol* 8, 163-169 (2006).
14. Hurley, J. H., Lee, S. & Prag, G. Ubiquitin-binding domains. *Biochem J* 399, 361-372 (2006).
15. Prag, G. et al. Mechanism of ubiquitin recognition by the CUE domain of Vps9p. *Cell* 113, 609-620 (2003).
16. Shih, S. C. et al. A ubiquitin-binding motif required for intramolecular monoubiquitylation, the CUE domain. *EMBO J* 22, 1273-1281 (2003).
17. Keren-Kaplan, T. et al. Synthetic biology approach to reconstituting the ubiquitylation cascade in bacteria. *EMBO J* 31, 378-390 (2012).
18. Keren-Kaplan, T. & Prag, G. Purification and crystallization of mono-ubiquitylated ubiquitin receptor Rpn10. *Actacrystallographica. Section F, Structural biology and crystallization communications* 68, 1120-1123 (2012).
19. van den Bogaart, G. et al. Synaptotagmin-1 may be a distance regulator acting upstream of SNARE nucleation. *Nat Struct Mol Biol* 18, 805-812 (2011).
20. Lorick, K. L. et al. RING fingers mediate ubiquitin-conjugating enzyme (E2)-dependent ubiquitination. *Proc Natl Acad Sci USA* 96, 11364-11369 (1999).
21. Shah, M. et al. Inhibition of Siah2 ubiquitin ligase by vitamin K3 (menadione) attenuates hypoxia and MAPK signaling and blocks melanoma tumorigenesis. *Pigment cell & melanoma research* 22, 799-808 (2009).
22. Windheim, M., Peggie, M. & Cohen, P. Two different classes of E2 ubiquitin-conjugating enzymes are required for the mono-ubiquitination of proteins and elongation by polyubiquitin chains with a specific topology. *Biochem J* 409, 723-729 (2008).
23. Bhaysar, A. P., Guttman, J. A. & Finlay, B. B. Manipulation of host-cell pathways by bacterial pathogens. *Nature* 449, 827-834 (2007).
24. Wu, B. et al. NleG Type 3 effectors from enterohaemorrhagic Escherichia coli are U-Box E3 ubiquitin ligases. *PLoS pathogens* 6, e1000960 (2010).
25. Tobe, T. et al. An extensive repertoire of type III secretion effectors in Escherichia coli O157 and the role of lambdoid phages in their dissemination. *Proc Natl Acad Sci USA* 103, 14941-14946 (2006).
26. Ren, X. & Hurley, J. H. VHS domains of ESCRT-0 cooperate in high-avidity binding to polyubiquitinated cargo. *EMBO J* 29, 1045-1054 (2010).
27. Oldham, C. E., Mohney, R. P., Miller, S. L., Hanes, R. N. & O'Bryan, J.P. The ubiquitin-interacting motifs target the endocytic adaptor protein epsin for ubiquitination. *Curr Biol* 12, 1112-1116 (2002).
28. Polo, S. et al. A single motif responsible for ubiquitin recognition and monoubiquitination in endocytic proteins. *Nature* 416, 451-455 (2002).
29. Hirano, S. et al. Double-sided ubiquitin binding of Hrs-UIM in endosomal protein sorting. *Nat Struct Mol Biol* 13, 272-277 (2006).
30. Prag, G. et al. The Vps27/Hse1 complex is a GAT domain-based scaffold for ubiquitin-dependent sorting. *Dev Cell* 12, 973-986 (2007).
31. Hoeller, D. et al. E3-independent monoubiquitination of ubiquitin-binding proteins. *Mol Cell* 26, 891-898 (2007).
32. Yang, Y. et al. Inhibitors of ubiquitin-activating enzyme (E1), a new class of potential cancer therapeutics. *Cancer research* 67, 9472-9481 (2007).
33. Keren-Kaplan, T. et al. Structure-based in silico identification of ubiquitin-binding domains provides insights into the ALIX-V:ubiquitin complex and retrovirus budding. *EMBO J* 32, 538-551 (2013).
34. Misra, S., Beach, B. M. & Hurley, J. H. Structure of the VHS domain of human Tom1 (target of myb 1): insights into interactions with proteins and membranes. *Biochemistry* 39, 11282-11290 (2000).
35. Lange, A. et al. Evidence for cooperative and domain-specific binding of the signal transducing adaptor molecule 2 (STAM2) to Lys63-linked diubiquitin. *J Biol Chem* 287, 18687-18699 (2012).
36. Hong, Y.H. et al. Identification of a novel ubiquitin binding site of STAM1 VHS domain by NMR spectroscopy. *FEBS letters* 583, 287-292 (2009).
37. Ford, M. G. et al. Curvature of clathrin-coated pits driven by epsin. *Nature* 419, 361-366 (2002).
38. Misra, S., Puertollano, R., Kato, Y., Bonifacino, J. S. & Hurley, J. H. Structural basis for acidic-cluster-dileucine sorting-signal recognition by VHS domains. *Nature* 415, 933-937 (2002).
39. Shiba, T. et al. Structural basis for recognition of acidic-cluster dileucine sequence by GGA1. *Nature* 415, 937-941 (2002).
40. Levin-Reisman, I. et al. Automated imaging with ScanLag reveals previously undetectable bacterial growth phenotypes. *Nat Methods* 7, 737-739 (2010).
41. Schindelin, J. et al. Fiji: an open-source platform for biological-image analysis. *Nat Methods* 9, 676-682 (2012).
42. Vaynberg, J. et al. Structure of an ultraweak protein-protein complex and its crucial role in regulation of cell morphology and motility. *Mol Cell* 17, 513-523 (2005).
43. Malovannaya, A. et al. Analysis of the human endogenous coregulator complexome. *Cell* 145, 787-799 (2011).
44. Huang, F. et al. Lysine 63-linked polyubiquitination is required for EGF receptor degradation. *Proc Natl Acad Sci USA* 110, 15722-15727 (2013).
45. Vina-Vilaseca, A. & Sorkin, A. Lysine 63-linked Polyubiquitination of the Dopamine Transporter Requires WW3 and WW4 Domains of Nedd4-2 and UBE2D Ubiquitin-conjugating Enzymes. *Journal of Biological Chemistry* 285, 7645-7656 (2010).
46. MacGurn, J. A., Hsu, P. C. & Emr, S. D. Ubiquitin and membrane protein turnover: from cradle to grave. *Annu Rev Biochem* 81, 231-259 (2012).
47. Rahighi, S. & Dikic, I. Selectivity of the ubiquitin-binding modules. *FEBS letters* 586, 2705-2710 (2012).
48. Gibson, D. G. et al. Enzymatic assembly of DNA molecules up to several hundred kilobases. *Nat Methods* 6, 343-345 (2009).
49. Crackower, M. A. et al. Characterization of the split hand/split foot malformation locus SHFM1 at 7q21.3-q22.1 and analysis of a candidate gene for its expression during limb development. *Human molecular genetics* 5, 571-579 (1996).
50. Funakoshi, M., Li, X., Velichutina, I., Hochstrasser, M. & Kobayashi, H. Sem1, the yeast ortholog of a human BRCA2-binding protein, is a component of the proteasome regulatory particle that enhances proteasome stability. *J Cell Sci* 117, 6447-6454 (2004).
51. Jantti, J., Landenranta, J., Olkkonen, V. M., Soderlund, H. & Keranen, S. SEMI, a homologue of the split hand/split foot malformation candidate gene Dss1, regulates exocytosis and pseudohyphal differentiation in yeast. *Proc Natl Acad Sci USA* 96, 909-914 (1999).
52. Marston, N. J. et al. Interaction between the product of the breast cancer susceptibility gene BRCA2 and DSS1, a protein functionally conserved from yeast to mammals *Mol Cell Biol* 19, 4633-4642 (1999).
53. Ma, Y. Y. et al. Identification of the deleted in split hand/split foot 1 protein as a novel biomarker for human cervical cancer.
54. Honda, R., Tanaka, H. & Yasuda, H. Oncoprotein MDM2 is a ubiquitin ligase E3 for tumor suppressor p53. *FEBS letters* 420, 25-27 (1997).
55. Chatterjee, C., McGinty, R. K., Fierz, B. & Muir, T. W. Disulfide-directed histone ubiquitylation reveals plasticity in hDot1L activation. *Nat Chem Biol* 6, 267-269 (2010).
56. Chen, J., Ai, Y., Wang, J., Haracska, L. & Zhuang, Z. Chemically ubiquitylated PCNA as a probe for eukaryotic translesion DNA synthesis. *Nat Chem Biol* 6, 270-272 (2010).
57. Kumar, K. S., Spasser, L., Erlich, L. A., Bavikar, S. N. & Brik, A. Total Chemical Synthesis of Di-ubiquitin Chains. *Angew Chem Int Ed Engl* 49, 9126-9131 (2010).
58. Kamadurai, H. B. et al. Mechanism of ubiquitin ligation and lysine prioritization by a HECT E3. *eLife* 2, e00828 (2013).
59. Du, Y., Xu, N., Lu, M. & Li, T. hUbiquitome: a database of experimentally verified ubiquitination cascades in humans. *Database: the journal of biological databases and curation* 2011, bar055 (2011).
60. Scott, D. C., Monda, J. K., Bennett, E. J., Harper, J. W. & Schulman, B. A. N-terminal acetylation acts as an avidity enhancer within an interconnected multiprotein complex. *Science* 334, 674-678 (2011).
61. Otwinowski, Z. & Minor, W. Processing of X-ray diffraction data collected in oscillation mode. *Methods Enzymology* 176, 307-326 (1997).
62. McCoy, A. J. Solving structures of protein complexes by molecular replacement with Phaser. *Acta crystallographica. Section D, Biological crystallography* 63, 32-41 (2007).
63. Adams, P. D. et al. PHENIX: building new software for automated crystallographic structure determination. *Actacrystallographica. Section D, Biological crystallography* 58, 1948-1954 (2002).
64. Murshudov, G. N., Vagin, A. A. & Dodson, E. J. Refinement of macromolecular structures by the maximum-likelihood method. *Actacrystallographica. Section D, Biological crystallography* 53, 240-255 (1997).
65. Emsley, P. & Cowtan, K. Coot: model-building tools for molecular graphics. *Actacrystallographica. Section D, Biological crystallography* 60, 2126-2132 (2004).
66. Mizuno, E., Kawahata, K., Kato, M., Kitamura, N. & Komada, M. STAM proteins bind ubiquitinated proteins on the early endosome via the VHS domain and ubiquitin-interacting motif. *Mol Biol Cell* 14, 3675-3689 (2003).
67. Adhya, S. L., Court, D. L., Friedman, D. I. & Gottesman, M. E. Obituary—Amos Oppenheim (31 Oct. 1934 to 24 Sep. 2006). *Molecular Microbiology* 67, 685-686 (2008).

What is claimed is:

1. A method of identifying an agent which regulates the activity or amount of a ubiquitinating enzyme or deubiquitinating enzyme comprising:
   (a) contacting a bacterial cell with the agent, wherein the bacterial cell expresses: (i) said ubiquitinating enzyme or said deubiquitinating enzyme; (ii) ubiquitin attached to a first polypeptide fragment; and (iii) a substrate attached to a second polypeptide fragment, wherein said first polypeptide fragment associates with said second polypeptide fragment to generate a reporter polypeptide on ubiquitination of said substrate as a detectable or selectable signal which correlates with the ubiquitination level of the substrate; and
   (b) measuring the level or the rate of accumulation of said detectable or selectable signal, wherein a change in the level as compared to the level in the absence of said agent, is indicative of an agent which regulates the activity or amount of the ubiquitinating or deubiquitinating enzyme.

2. The method of claim 1, wherein said ubiquitinating enzyme is a ubiquitin E3-ligase.

3. The method of claim 2, wherein said ubiquitin E3-ligase is selected from the group consisting of Siah2, PARKIN, Smurf1, MDM2, BRCA1, MURF1, TRIM32 ITCH, UBE3B and UBE3A.

4. The method of claim 2, wherein said ubiquitinating enzyme further comprises an E1 ligase and an E2 ligase.

5. The method of claim 1, wherein the substrate is selected from the group consisting of PHD3, SPROUTY2, Mitofusin 1, 2, MIRO, NEMO, SMADs, TθR-I, P53, S5A, HHR23, EPHEXIN5, ARC, PPARα, cyclin-B, Cdc25C and Calmodulin.

6. The method of claim 1, wherein said reporter polypeptide comprises a selectable polypeptide.

7. The method of claim 6, wherein said selectable polypeptide is a split antibiotic resistance polypeptide.

8. The method of claim 1, wherein said first polypeptide fragment is attached to said ubiquitin via a linker and/or wherein said second polypeptide fragment is attached to said substrate via a linker.

9. The method of claim 1, wherein said reporter polypeptide is an optically detectable signal.

10. The method of claim 1, wherein said analyzing is effected by bimolecular complementation of an antibiotic resistance protein.

11. A method of determining whether an enzyme is capable of ubiquitinating a test substrate, the method comprising
   (a) expressing the enzyme in a bacterial cell;
   (b) expressing ubiquitin in said bacterial cell, wherein said ubiquitin is attached to a first polypeptide fragment;
   (c) expressing the test substrate in said bacterial cell, wherein said substrate is attached to a second polypeptide fragment, wherein said first polypeptide fragment associates with said second polypeptide fragment to generate a reporter polypeptide on ubiquitination of the test substrate; and
   (d) detecting the presence of said reporter polypeptide in the bacterial cell, wherein a presence of said reporter polypeptide is indicative that the enzyme is capable of ubiquitinating the test substrate.

12. The method of claim 11, further expressing all the enzymes of the ubiquitinating enzyme cascade of the enzyme.

13. The method of claim 11, wherein said reporter polypeptide is a detectable polypeptide or a selectable polypeptide.

14. The method of claim 13, wherein said selectable polypeptide is a split antibiotic resistance polypeptide.

15. The method of claim 13, wherein said detectable polypeptide is an optically detectable signal.

16. The method of claim 11, wherein said enzyme is selected from the group consisting of E3 ligase, ubiquitin E1-activating enzyme and ubiquitin E2 conjugating enzyme.

17. The method of claim 11, wherein said first polypeptide fragment is attached to said ubiquitin via a linker and/or wherein said second polypeptide fragment is attached to said substrate via a linker.

18. The method of claim 11, wherein said detecting is effected by bimolecular complementation of an antibiotic resistance protein.

* * * * *

SEQUENCE LISTING

<160> NUMBER OF SEQ ID NOS: 68

<210> SEQ ID NO 1
<211> LENGTH: 33
<212> TYPE: PRT
<213> ORGANISM: Artificial sequence
<220> FEATURE:
<223> OTHER INFORMATION: synthetic peptide

<400> SEQUENCE: 1

Cys Ser Leu Tyr Asp Lys Asp Thr Leu Val Gln Leu Val Glu Thr Gly
1               5                   10                  15

Gly Ala His Pro Leu Ser Arg Glu Pro Ile Thr Glu Ser Met Ile Met
            20                  25                  30

Arg

<210> SEQ ID NO 2
<211> LENGTH: 33
<212> TYPE: PRT
<213> ORGANISM: Artificial sequence
<220> FEATURE:
<223> OTHER INFORMATION: synthetic peptide

```
<400> SEQUENCE: 2

Cys Thr Leu Phe Asp Ala Ala Ala Phe Ser Arg Leu Val Gly Glu Gly
1               5                   10                  15

Leu Pro His Pro Leu Thr Arg Glu Pro Ile Thr Ala Ser Ile Ile Val
            20                  25                  30

Lys

<210> SEQ ID NO 3
<211> LENGTH: 33
<212> TYPE: PRT
<213> ORGANISM: Artificial sequence
<220> FEATURE:
<223> OTHER INFORMATION: synthetic peptide

<400> SEQUENCE: 3

Cys Thr Leu Phe Asp Ala Ala Ala Phe Ser Arg Leu Val Gly Glu Gly
1               5                   10                  15

Leu Pro His Pro Leu Thr Arg Glu Pro Ile Thr Ala Ser Ile Ile Val
            20                  25                  30

Lys

<210> SEQ ID NO 4
<211> LENGTH: 140
<212> TYPE: PRT
<213> ORGANISM: Artificial sequence
<220> FEATURE:
<223> OTHER INFORMATION: full length sequence of the NleG6-3 ligase

<400> SEQUENCE: 4

Met Glu Arg Arg Ala Val Ala Leu Glu Arg Gln Leu Asn Gly Gly Val
1               5                   10                  15

Asp Phe Leu Arg Ser Val Asn Asn Tyr Phe Gln Ser Val Met Ala Glu
            20                  25                  30

His Arg Glu Asn Lys Thr Ser Asn Lys Ile Leu Met Glu Lys Ile Asn
        35                  40                  45

Ser Cys Val Phe Gly Thr Asp Ser Asn His Phe Ser Cys Pro Glu Ser
    50                  55                  60

Phe Leu Thr Cys Pro Ile Thr Leu Asp Thr Pro Ala Asn Gly Val Phe
65                  70                  75                  80

Met Arg Asn Ser Gln Gly Ala Glu Ile Cys Ser Leu Tyr Asp Lys Asp
                85                  90                  95

Thr Leu Val Gln Leu Val Glu Thr Gly Gly Ala His Pro Leu Ser Arg
            100                 105                 110

Glu Pro Ile Thr Glu Ser Met Ile Met Arg Lys Asp Glu Cys His Phe
        115                 120                 125

Asp Ser Lys Lys Glu Ser Phe Val Ala Ser Asp Ala
    130                 135                 140

<210> SEQ ID NO 5
<211> LENGTH: 35
<212> TYPE: PRT
<213> ORGANISM: Artificial sequence
<220> FEATURE:
<223> OTHER INFORMATION: Flexible linker amino acid sequence

<400> SEQUENCE: 5

Leu Ile Lys Ala Ala Gln Arg Ala Arg Glu Ala Glu Arg Asp Leu Ala
1               5                   10                  15
```

Ala Ala Val Ala Gln Ala Ala Gly Gln Ala Val Pro Arg Ala Ala
            20                  25                  30

Pro Arg Gln
        35

<210> SEQ ID NO 6
<211> LENGTH: 29
<212> TYPE: PRT
<213> ORGANISM: Artificial sequence
<220> FEATURE:
<223> OTHER INFORMATION: Flexible linker amino acid sequence

<400> SEQUENCE: 6

Gly Gly Ser Ala Gly Ser Gly Ser Gly Ala Gly Ser Gly Ser Gly Gly
1               5                   10                  15

Ser Ala Gly Ser Ser Gly Ser Ser Gly Ala Ser Ser Gly
            20                  25

<210> SEQ ID NO 7
<211> LENGTH: 76
<212> TYPE: PRT
<213> ORGANISM: Artificial sequence
<220> FEATURE:
<223> OTHER INFORMATION: mammalian ubiquitin amino acid sequence

<400> SEQUENCE: 7

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 8
<211> LENGTH: 75
<212> TYPE: PRT
<213> ORGANISM: Artificial sequence
<220> FEATURE:
<223> OTHER INFORMATION: yeast ubiquitin amino acid sequence

<400> SEQUENCE: 8

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ser Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Leu Ser Asp Tyr Asn Ile Gln Lys Glu Ser
    50                  55                  60

Thr Leu His Leu Val Leu Arg Leu Arg Gly Gly
65                  70                  75

<210> SEQ ID NO 9
<211> LENGTH: 1051
<212> TYPE: PRT
<213> ORGANISM: Triticum aestivum

<400> SEQUENCE: 9

```
Met Leu Pro Arg Lys Arg Glu Ile Val Ala Gly Val Glu Asp Leu
1               5                   10                  15

Gln Lys Lys Thr Arg Ala Gly Glu Gly Glu Val Thr Arg Glu Glu Gly
                20                  25                  30

Asp Ala Ala Met Ala Gly Arg Gly Asn Glu Ile Asp Glu Asp Leu His
            35                  40                  45

Ser Arg Gln Leu Ala Val Tyr Gly Arg Glu Thr Met Lys Arg Leu Phe
    50                  55                  60

Gly Ser Asn Val Leu Val Ser Gly Leu Gln Gly Leu Gly Ala Glu Ile
65                  70                  75                  80

Ala Lys Asn Leu Val Leu Ala Gly Val Lys Ser Val Thr Leu His Asp
                85                  90                  95

Asp Gly Asn Val Glu Leu Trp Asp Leu Ser Ser Asn Phe Phe Leu Ser
            100                 105                 110

Glu Asn Asp Val Gly Gln Asn Arg Ala Gln Ala Cys Val Gln Lys Leu
            115                 120                 125

Gln Glu Leu Asn Asn Ala Val Leu Val Ser Ala Leu Thr Gly Asp Leu
    130                 135                 140

Thr Lys Glu His Leu Ser Lys Phe Gln Ala Val Val Phe Thr Asp Ile
145                 150                 155                 160

Ser Leu Asp Lys Ala Ile Glu Phe Asp Asp Tyr Cys His Ser Gln Gln
                165                 170                 175

Pro Pro Ile Ala Phe Ile Lys Ser Glu Val Arg Gly Leu Phe Gly Ser
            180                 185                 190

Val Phe Cys Asp Phe Gly Pro Glu Phe Thr Val Leu Asp Val Asp Gly
            195                 200                 205

Glu Glu Pro His Thr Gly Ile Val Ala Ser Ile Ser Asn Asp Asn Pro
210                 215                 220

Ala Leu Val Ser Cys Val Asp Asp Glu Arg Leu Glu Phe Gln Asp Gly
225                 230                 235                 240

Asp Leu Val Val Phe Ser Glu Val His Gly Met Thr Glu Leu Asn Asp
                245                 250                 255

Gly Lys Pro Arg Lys Val Lys Asn Ala Arg Pro Tyr Ser Phe Phe Leu
            260                 265                 270

Glu Glu Asp Thr Ser Ser Phe Gly Ala Tyr Val Arg Gly Gly Ile Val
            275                 280                 285

Thr Gln Val Lys Pro Pro Lys Val Ile Lys Phe Lys Pro Leu Lys Glu
            290                 295                 300

Ala Met Ser Glu Pro Gly Glu Phe Leu Met Ser Asp Phe Ser Lys Phe
305                 310                 315                 320

Glu Arg Pro Pro Leu Leu His Leu Ala Phe Gln Ala Leu Asp Lys Phe
                325                 330                 335

Arg Thr Glu Leu Ser Arg Phe Pro Val Ala Gly Ser Thr Asp Asp Val
            340                 345                 350

Gln Arg Val Ile Glu Tyr Ala Ile Ser Ile Asn Asp Thr Leu Gly Asp
            355                 360                 365

Arg Lys Leu Glu Glu Ile Asp Lys Lys Leu Leu His His Phe Ala Ser
370                 375                 380

Gly Ser Arg Ala Val Leu Asn Pro Met Ala Ala Met Phe Gly Gly Ile
385                 390                 395                 400

Val Gly Gln Glu Val Val Lys Ala Cys Ser Gly Lys Phe His Pro Leu
                405                 410                 415
```

```
Tyr Gln Phe Phe Tyr Phe Asp Ser Val Glu Ser Leu Pro Val Asp Pro
            420                 425                 430

Leu Glu Pro Gly Asp Leu Lys Pro Lys Asn Ser Arg Tyr Asp Ala Gln
        435                 440                 445

Ile Ser Val Phe Gly Ser Lys Leu Gln Asn Lys Leu Glu Glu Ala Lys
    450                 455                 460

Ile Phe Met Val Gly Gly Ala Leu Gly Cys Glu Phe Leu Lys Asn
465                 470                 475                 480

Leu Ala Leu Met Gly Ile Ser Cys Ser Gln Asn Gly Asn Leu Thr Leu
                485                 490                 495

Thr Asp Asp Val Ile Glu Lys Ser Asn Leu Ser Arg Gln Phe Leu
            500                 505                 510

Phe Arg Asp Trp Asn Ile Gly Gln Pro Lys Ser Thr Val Ala Ala Thr
        515                 520                 525

Ala Ala Met Val Ile Asn Pro Lys Leu His Val Glu Ala Leu Gln Asn
    530                 535                 540

Arg Ala Ser Pro Glu Thr Glu Asn Val Phe Asn Asp Ala Phe Trp Glu
545                 550                 555                 560

Asn Leu Asp Ala Val Asn Ala Leu Asp Asn Val Thr Ala Arg Met
                565                 570                 575

Tyr Ile Asp Ser Arg Cys Val Tyr Phe Gln Lys Pro Leu Leu Glu Ser
            580                 585                 590

Gly Thr Leu Gly Ala Lys Cys Asn Thr Gln Met Val Ile Pro His Leu
        595                 600                 605

Thr Glu Asn Tyr Gly Ala Ser Arg Asp Pro Pro Glu Lys Gln Ala Pro
    610                 615                 620

Met Cys Thr Val His Ser Phe Pro His Asn Ile Asp His Cys Leu Thr
625                 630                 635                 640

Trp Ala Arg Ser Glu Phe Glu Gly Leu Leu Glu Lys Thr Pro Thr Glu
                645                 650                 655

Val Asn Ala Phe Leu Ser Asn Pro Thr Thr Tyr Ile Ser Ala Ala Arg
            660                 665                 670

Thr Ala Gly Asp Ala Gln Ala Arg Asp Gln Leu Glu Arg Val Ile Glu
        675                 680                 685

Cys Leu Asp Arg Asp Lys Cys Glu Thr Phe Gln Asp Ser Ile Thr Trp
    690                 695                 700

Ala Arg Leu Lys Phe Glu Asp Tyr Phe Ser Asn Arg Val Lys Gln Leu
705                 710                 715                 720

Thr Phe Thr Phe Pro Glu Asp Ser Met Thr Ser Ser Gly Ala Pro Phe
                725                 730                 735

Trp Ser Ala Pro Lys Arg Phe Pro Arg Pro Val Glu Phe Ser Ser Ser
            740                 745                 750

Asp Gln Ser Gln Leu Ser Phe Ile Leu Ala Ala Ile Leu Arg Ala
        755                 760                 765

Glu Thr Phe Gly Ile Pro Ile Pro Glu Trp Ala Lys Thr Pro Asn Lys
    770                 775                 780

Leu Ala Ala Glu Ala Val Asp Lys Val Ile Val Pro Asp Phe Gln Pro
785                 790                 795                 800

Lys Gln Gly Val Lys Ile Val Thr His Glu Lys Ala Thr Ser Leu Ser
                805                 810                 815

Ser Ala Ser Val Asp Asp Ala Val Ile Glu Glu Leu Ile Ala Lys
            820                 825                 830

Leu Glu Glu Val Ser Lys Thr Leu Pro Ser Gly Phe His Met Asn Pro
```

-continued

```
                835                 840                 845
Ile Gln Phe Glu Lys Asp Asp Thr Asn Phe His Met Asp Val Ile
    850                 855                 860
Ala Gly Phe Ala Asn Met Arg Ala Arg Asn Tyr Ser Ile Pro Glu Val
865                 870                 875                 880
Asp Lys Leu Lys Ala Lys Phe Ile Ala Arg Ile Ile Pro Ala Ile
                885                 890                 895
Ala Thr Ser Thr Ala Met Ala Thr Gly Leu Val Cys Leu Glu Leu Tyr
                    900                 905                 910
Lys Ala Leu Ala Gly Gly His Lys Val Glu Asp Tyr Arg Asn Thr Phe
            915                 920                 925
Ala Asn Leu Ala Ile Pro Leu Phe Ser Ile Ala Glu Pro Val Pro Pro
            930                 935                 940
Lys Thr Ile Lys His Gln Glu Leu Ser Trp Thr Val Trp Asp Arg Trp
945                 950                 955                 960
Thr Val Thr Gly Asn Ile Thr Leu Arg Glu Leu Leu Glu Trp Leu Lys
                965                 970                 975
Glu Lys Gly Leu Asn Ala Tyr Ser Ile Ser Cys Gly Thr Ser Leu Leu
                980                 985                 990
Tyr Asn Ser Met Phe Pro Arg His  Lys Glu Arg Leu Asp  Arg Lys Val
                995                 1000                 1005
Val Asp  Val Ala Arg Glu Val  Ala Lys Met Glu Val  Pro Ser Tyr
     1010                1015                 1020
Arg Arg  His Leu Asp Val Val  Val Ala Cys Glu Asp  Asp Asp Asp
     1025                 1030                 1035
Asn Asp  Val Asp Ile Pro Leu  Val Ser Val Tyr Phe  Arg
     1040                 1045                 1050

<210> SEQ ID NO 10
<211> LENGTH: 1053
<212> TYPE: PRT
<213> ORGANISM: Triticum aestivum

<400> SEQUENCE: 10

Met Leu Pro Ser Lys Arg Pro Ser Asp Ala Ala Gly Asp Glu Asn
1               5                   10                  15
Gly Arg Gly Gly Asp Ala Arg Gly Pro Gly Ser Gly Arg Arg Ala
            20                  25                  30
Arg Ala Ala Ala Gly Ala Val Thr Ala Ala Pro Gln Glu Ile Asp Glu
            35                  40                  45
Asp Leu His Ser Arg Gln Leu Ala Val Tyr Gly Arg Glu Thr Met Arg
    50                  55                  60
Arg Leu Phe Ala Ser Asp Val Leu Val Ser Gly Leu Asn Gly Leu Gly
65              70                  75                  80
Ala Glu Ile Ala Lys Asn Leu Ala Leu Ala Gly Val Lys Ser Val Thr
                85                  90                  95
Ile His Asp Val Lys Thr Val Lys Met Trp Asp Leu Ser Gly Asn Phe
            100                 105                 110
Phe Leu Ser Glu Asp Asp Ile Gly Lys Asn Arg Ala Ala Ala Cys Val
            115                 120                 125
Ala Lys Leu Gln Glu Leu Asn Asn Ala Val Leu Ile Ser Ala Leu Thr
        130                 135                 140
Glu Glu Leu Thr Thr Glu His Leu Ser Lys Phe Gln Ala Val Val Phe
145                 150                 155                 160
```

-continued

```
Thr Asp Ile Asp Leu Asp Lys Ala Tyr Glu Phe Asp Tyr Cys His
            165                 170                 175
Asn His Gln Pro Pro Ile Ser Phe Ile Lys Ser Glu Val Cys Gly Leu
        180                 185                 190
Phe Gly Ser Val Phe Cys Asp Phe Gly Pro Lys Phe Thr Val Leu Asp
        195                 200                 205
Val Asp Gly Glu Asp Pro His Thr Gly Ile Ile Ala Ser Ile Ser Asn
    210                 215                 220
Asp Asn Pro Ala Leu Ile Ser Cys Val Asp Glu Arg Leu Glu Phe
225                 230                 235                 240
Gln Asp Gly Asp Leu Val Val Phe Ser Glu Val His Gly Met Thr Glu
                245                 250                 255
Leu Asn Asp Gly Lys Pro Arg Lys Val Lys Asn Ala Arg Pro Phe Ser
            260                 265                 270
Phe Ser Ile Glu Glu Asp Thr Ser Asn Phe Gly Ile Tyr Val Lys Gly
        275                 280                 285
Gly Ile Val Thr Gln Val Lys Glu Pro Lys Val Leu Cys Phe Lys Ala
    290                 295                 300
Leu Arg Asp Ala Met Thr Asp Pro Gly Glu Val Leu Leu Ser Asp Phe
305                 310                 315                 320
Ser Lys Phe Glu Arg Pro Pro Val Leu His Leu Ala Phe Gln Ala Leu
                325                 330                 335
Asp Lys Phe Lys Lys Asp His Gly Arg Cys Pro Ala Ala Gly Cys Glu
            340                 345                 350
Glu Asp Ala His Ser Phe Leu Lys Ile Ala Ala Ile Asn Glu Ala
        355                 360                 365
Ser Ala Asp Arg Lys Leu Asp Thr Ile Asp Glu Lys Leu Phe Arg Gln
    370                 375                 380
Phe Ala Ser Gly Ser Arg Ala Val Leu Asn Pro Met Ala Met Phe
385                 390                 395                 400
Gly Gly Ile Val Gly Gln Glu Val Val Lys Ala Cys Ser Gly Lys Phe
                405                 410                 415
His Pro Leu Asn Gln Phe Phe Tyr Phe Asp Ser Val Glu Ser Leu Pro
            420                 425                 430
Thr Tyr Pro Leu Glu Pro Gln Asp Leu Lys Pro Ser Asn Asn Arg Tyr
        435                 440                 445
Asp Ala Gln Val Ser Val Phe Gly Ser Lys Leu Gln Lys Lys Met Glu
    450                 455                 460
Glu Ala Asn Thr Phe Val Val Gly Ser Gly Ala Leu Gly Cys Glu Phe
465                 470                 475                 480
Leu Lys Asn Leu Ala Leu Met Gly Val Ser Cys Ser Ser Lys Gly Lys
                485                 490                 495
Leu Thr Ile Thr Asp Asp Ile Ile Glu Lys Ser Asn Leu Ser Arg
            500                 505                 510
Gln Phe Leu Phe Arg Asp Trp Asn Ile Gly Gln Ala Lys Ser Thr Val
        515                 520                 525
Ala Ala Thr Ala Ala Ser Ala Ile Asn Pro Ser Leu His Ile Asp Ala
    530                 535                 540
Leu Gln Asn Arg Ala Cys Pro Asp Thr Glu Asn Val Phe His Asp Thr
545                 550                 555                 560
Phe Trp Glu Gly Leu Asp Val Val Ile Asn Ala Leu Asp Asn Val Asn
                565                 570                 575
Ala Arg Met Tyr Met Asp Met Arg Cys Leu Tyr Phe Gln Lys Pro Leu
```

```
                580             585             590
Leu Glu Ser Gly Thr Leu Gly Ala Lys Cys Asn Ile Gln Met Val Ile
            595             600             605

Pro His Leu Thr Glu Asn Tyr Gly Ala Ser Arg Asp Pro Pro Glu Lys
        610             615             620

Gln Ala Pro Met Cys Thr Val His Ser Phe Pro His Asn Ile Asp His
625             630             635             640

Cys Leu Thr Trp Ala Arg Ser Glu Phe Glu Gly Leu Leu Glu Lys Thr
                645             650             655

Pro Asn Glu Val Asn Ser Phe Leu Ser Asn Pro Ala Gln Tyr Ala Ala
            660             665             670

Ala Met Arg Lys Ala Gly Asp Ala Gln Ala Arg Glu Leu Leu Glu Arg
        675             680             685

Val Ser Glu Cys Leu Asn Lys Asp Arg Cys Ser Thr Phe Asp Asp Cys
690             695             700

Ile Ser Trp Ala Arg Leu Lys Phe Glu Asp Tyr Phe Ser Asn Arg Val
705             710             715             720

Lys Gln Leu Thr Phe Thr Phe Pro Glu Asp Ala Ala Thr Ser Met Gly
            725             730             735

Ala Pro Phe Trp Ser Ala Pro Lys Arg Phe Pro Arg Ala Leu Gln Phe
        740             745             750

Ser Ala Ala Asp Gln Ser His Leu Asn Phe Ile Met Ser Ala Ser Ile
            755             760             765

Leu Arg Ala Glu Ser Phe Gly Val Ala Ile Pro Glu Trp Ala Lys Asp
        770             775             780

Thr Ser Lys Leu Ala Asp Val Val Asn Lys Ile Ala Val Pro Thr Phe
785             790             795             800

Glu Pro Lys Gln Gly Val Asn Ile Val Thr Asp Glu Lys Ala Ser Asn
            805             810             815

Leu Ser Ser Thr Ser Val Asp Asp Val Ala Val Ile Glu Asp Leu Leu
        820             825             830

Ala Lys Leu Gln Glu Tyr Ala Lys Met Leu Leu Pro Gly Phe Gln Met
        835             840             845

Lys Pro Ile Gln Phe Glu Lys Asp Asp Thr Asn Phe His Met Asp
        850             855             860

Leu Ile Ser Gly Leu Ala Asn Met Arg Ala Arg Asn Tyr Ser Ile Pro
865             870             875             880

Glu Val Asp Lys Leu Lys Ala Lys Phe Ile Ala Gly Arg Ile Ile Pro
            885             890             895

Ala Ile Ala Thr Ser Thr Ala Met Ala Thr Gly Leu Val Cys Leu Glu
        900             905             910

Leu Tyr Lys Val Ile Ala Gly His Pro Val Glu Asp Tyr Arg Asn
        915             920             925

Thr Phe Ala Asn Leu Ala Leu Pro Leu Phe Ser Met Ala Glu Pro Val
    930             935             940

Pro Pro Lys Val Met Lys His Lys Glu Thr Ser Trp Thr Val Trp Asp
945             950             955             960

Arg Trp Ser Val Gln Gly Asn Leu Thr Leu Ala Glu Leu Leu Gln Trp
            965             970             975

Phe Ala Asp Lys Gly Leu Thr Ala Tyr Ser Ile Ser Cys Gly Thr Ser
        980             985             990

Leu Leu Tyr Asn Asn Met Phe Ala Arg His Lys Asp Arg Leu Thr Lys
        995             1000            1005
```

-continued

```
Lys Val Val Asp Ile Ala Arg Glu Val Ala Lys Val Asp Val Pro
    1010                1015                1020

Glu Tyr Arg Arg His Leu Asp Ile Gly Val Ala Cys Glu Asp Glu
    1025                1030                1035

Asp Glu Asn Asp Val Asp Ile Pro Leu Val Ser Val Tyr Phe Arg
    1040                1045                1050

<210> SEQ ID NO 11
<211> LENGTH: 1058
<212> TYPE: PRT
<213> ORGANISM: Homo sapiens

<400> SEQUENCE: 11

Met Ser Ser Ser Pro Leu Ser Lys Lys Arg Val Ser Gly Pro Asp
1               5                   10                  15

Pro Lys Pro Gly Ser Asn Cys Ser Pro Ala Gln Ser Val Leu Ser Glu
            20                  25                  30

Val Pro Ser Val Pro Thr Asn Gly Met Ala Lys Asn Gly Ser Glu Ala
        35                  40                  45

Asp Ile Asp Glu Gly Leu Tyr Ser Arg Gln Leu Tyr Val Leu Gly His
    50                  55                  60

Glu Ala Met Lys Arg Leu Gln Thr Ser Ser Val Leu Val Ser Gly Leu
65                  70                  75                  80

Arg Gly Leu Gly Val Glu Ile Ala Lys Asn Ile Ile Leu Gly Gly Val
                85                  90                  95

Lys Ala Val Thr Leu His Asp Gln Gly Thr Ala Gln Trp Ala Asp Leu
            100                 105                 110

Ser Ser Gln Phe Tyr Leu Arg Glu Glu Asp Ile Gly Lys Asn Arg Ala
        115                 120                 125

Glu Val Ser Gln Pro Arg Leu Ala Glu Leu Asn Ser Tyr Val Pro Val
    130                 135                 140

Thr Ala Tyr Thr Gly Pro Leu Val Glu Asp Phe Leu Ser Gly Phe Gln
145                 150                 155                 160

Val Val Val Leu Thr Asn Thr Pro Leu Glu Asp Gln Leu Arg Val Gly
                165                 170                 175

Glu Phe Cys His Asn Arg Gly Ile Lys Leu Val Val Ala Asp Thr Arg
            180                 185                 190

Gly Leu Phe Gly Gln Leu Phe Cys Asp Phe Gly Glu Glu Met Ile Leu
        195                 200                 205

Thr Asp Ser Asn Gly Glu Gln Pro Leu Ser Ala Met Val Ser Met Val
    210                 215                 220

Thr Lys Asp Asn Pro Gly Val Val Thr Cys Leu Asp Glu Ala Arg His
225                 230                 235                 240

Gly Phe Glu Ser Gly Asp Phe Val Ser Phe Ser Glu Val Gln Gly Met
                245                 250                 255

Val Glu Leu Asn Gly Asn Gln Pro Met Glu Ile Lys Val Leu Gly Pro
            260                 265                 270

Tyr Thr Phe Ser Ile Cys Asp Thr Ser Asn Phe Ser Asp Tyr Ile Arg
        275                 280                 285

Gly Gly Ile Val Ser Gln Val Lys Val Pro Lys Lys Ile Ser Phe Lys
    290                 295                 300

Ser Leu Val Ala Ser Leu Ala Glu Pro Asp Phe Val Val Thr Asp Phe
305                 310                 315                 320

Ala Lys Phe Ser Arg Pro Ala Gln Leu His Ile Gly Phe Gln Ala Leu
```

-continued

```
                325                 330                 335
His Gln Phe Cys Ala Gln His Gly Arg Pro Pro Arg Pro Arg Asn Glu
            340                 345                 350
Glu Asp Ala Ala Glu Leu Val Ala Leu Ala Gln Ala Val Asn Ala Arg
            355                 360                 365
Ala Leu Pro Ala Val Gln Gln Asn Asn Leu Asp Glu Asp Leu Ile Arg
        370                 375                 380
Lys Leu Ala Tyr Val Ala Ala Gly Asp Leu Ala Pro Ile Asn Ala Phe
385                 390                 395                 400
Ile Gly Gly Leu Ala Ala Gln Glu Val Met Lys Ala Cys Ser Gly Lys
                405                 410                 415
Phe Met Pro Ile Met Gln Trp Leu Tyr Phe Asp Ala Leu Glu Cys Leu
            420                 425                 430
Pro Glu Asp Lys Glu Val Leu Thr Glu Asp Lys Cys Leu Gln Arg Gln
            435                 440                 445
Asn Arg Tyr Asp Gly Gln Val Ala Val Phe Gly Ser Asp Leu Gln Glu
        450                 455                 460
Lys Leu Gly Lys Gln Lys Tyr Phe Leu Val Gly Ala Gly Ala Ile Gly
465                 470                 475                 480
Cys Glu Leu Leu Lys Asn Phe Ala Met Ile Gly Leu Gly Cys Gly Glu
                485                 490                 495
Gly Gly Glu Ile Ile Val Thr Asp Met Asp Thr Ile Lys Ser Asn
            500                 505                 510
Leu Asn Arg Gln Phe Leu Phe Arg Pro Trp Asp Val Thr Lys Leu Lys
            515                 520                 525
Ser Asp Thr Ala Ala Ala Val Arg Gln Met Asn Pro His Ile Arg
530                 535                 540
Val Thr Ser His Gln Asn Arg Val Gly Pro Asp Thr Glu Arg Ile Tyr
545                 550                 555                 560
Asp Asp Asp Phe Phe Gln Asn Leu Asp Gly Val Ala Asn Ala Leu Asp
                565                 570                 575
Asn Val Asp Ala Arg Met Tyr Met Asp Arg Arg Cys Val Tyr Tyr Arg
            580                 585                 590
Lys Pro Leu Leu Glu Ser Gly Thr Leu Gly Thr Lys Gly Asn Val Gln
        595                 600                 605
Val Val Ile Pro Phe Leu Thr Glu Ser Tyr Ser Ser Gln Asp Pro
        610                 615                 620
Pro Glu Lys Ser Ile Pro Ile Cys Thr Leu Lys Asn Phe Pro Asn Ala
625                 630                 635                 640
Ile Glu His Thr Leu Gln Trp Ala Arg Asp Glu Phe Glu Gly Leu Phe
                645                 650                 655
Lys Gln Pro Ala Glu Asn Val Asn Gln Tyr Leu Thr Asp Pro Lys Phe
            660                 665                 670
Val Glu Arg Thr Leu Arg Leu Ala Gly Thr Gln Pro Leu Glu Val Leu
            675                 680                 685
Glu Ala Val Gln Arg Ser Leu Val Leu Gln Arg Pro Gln Thr Trp Ala
        690                 695                 700
Asp Cys Val Thr Trp Ala Cys His His Trp His Thr Gln Tyr Ser Asn
705                 710                 715                 720
Asn Ile Arg Gln Leu Leu His Asn Phe Pro Pro Asp Gln Leu Thr Ser
                725                 730                 735
Ser Gly Ala Pro Phe Trp Ser Gly Pro Lys Arg Cys Pro His Pro Leu
            740                 745                 750
```

```
Thr Phe Asp Val Asn Asn Pro Leu His Leu Asp Tyr Val Met Ala Ala
            755                 760                 765

Ala Asn Leu Phe Ala Gln Thr Tyr Gly Leu Thr Gly Ser Gln Asp Arg
        770                 775                 780

Ala Ala Val Ala Thr Phe Leu Gln Ser Val Gln Val Pro Glu Phe Thr
785                 790                 795                 800

Pro Lys Ser Gly Val Lys Ile His Val Ser Asp Gln Glu Leu Gln Ser
                805                 810                 815

Ala Asn Ala Ser Val Asp Asp Ser Arg Leu Glu Glu Leu Lys Ala Thr
            820                 825                 830

Leu Pro Ser Pro Asp Lys Leu Pro Gly Phe Lys Met Tyr Pro Ile Asp
        835                 840                 845

Phe Glu Lys Asp Asp Ser Asn Phe His Met Asp Phe Ile Val Ala
    850                 855                 860

Ala Ser Asn Leu Arg Ala Glu Asn Tyr Asp Ile Pro Ser Ala Asp Arg
865                 870                 875                 880

His Lys Ser Lys Leu Ile Ala Gly Lys Ile Ile Pro Ala Ile Ala Thr
                885                 890                 895

Thr Thr Ala Ala Val Val Gly Leu Val Cys Leu Glu Leu Tyr Lys Val
            900                 905                 910

Val Gln Gly His Arg Gln Leu Asp Ser Tyr Lys Asn Gly Phe Leu Asn
        915                 920                 925

Leu Ala Leu Pro Phe Phe Gly Phe Ser Glu Pro Leu Ala Ala Pro Arg
    930                 935                 940

His Gln Tyr Tyr Asn Gln Glu Trp Thr Leu Trp Asp Arg Phe Glu Val
945                 950                 955                 960

Gln Gly Leu Gln Pro Asn Gly Glu Glu Met Thr Leu Lys Gln Phe Leu
                965                 970                 975

Asp Tyr Phe Lys Thr Glu His Lys Leu Glu Ile Thr Met Leu Ser Gln
            980                 985                 990

Gly Val Ser Met Leu Tyr Ser Phe Phe Met Pro Ala Ala Lys Leu Lys
        995                 1000                1005

Glu Arg Leu Asp Gln Pro Met Thr Glu Ile Val Ser Arg Val Ser
    1010                1015                1020

Lys Arg Lys Leu Gly Arg His Val Arg Ala Leu Val Leu Glu Leu
    1025                1030                1035

Cys Cys Asn Asp Glu Ser Gly Glu Asp Val Glu Val Pro Tyr Val
    1040                1045                1050

Arg Tyr Thr Ile Arg
    1055

<210> SEQ ID NO 12
<211> LENGTH: 1058
<212> TYPE: PRT
<213> ORGANISM: Oryctolagus cuniculus

<400> SEQUENCE: 12

Met Ser Ser Ser Pro Leu Ser Lys Lys Arg Arg Val Ser Gly Pro Asp
1               5                   10                  15

Pro Lys Pro Gly Ser Asn Cys Ser Pro Ala Gln Ser Val Leu Pro Gln
                20                  25                  30

Val Pro Ser Ala Pro Thr Asn Gly Met Ala Lys Asn Gly Ser Glu Ala
            35                  40                  45

Asp Ile Asp Glu Gly Leu Tyr Ser Arg Gln Leu Tyr Val Leu Gly His
```

```
            50                  55                  60
Glu Ala Met Lys Arg Leu Gln Thr Ser Ser Val Leu Ser Gly Leu
 65                  70                  75                  80

Arg Gly Leu Gly Val Glu Ile Ala Lys Asn Ile Ile Leu Gly Gly Val
                     85                  90                  95

Lys Ala Val Thr Leu His Asp Gln Gly Thr Ala Gln Trp Ala Asp Leu
                100                 105                 110

Ser Ser Gln Phe Tyr Leu Arg Glu Asp Ile Gly Lys Asn Arg Ala
                115                 120                 125

Glu Val Ser Gln Pro Arg Leu Ala Glu Leu Asn Ser Tyr Val Pro Val
130                 135                 140

Thr Ala Tyr Thr Gly Pro Leu Val Glu Asp Phe Leu Ser Gly Phe Gln
145                 150                 155                 160

Val Val Val Leu Thr Asn Ser Pro Leu Glu Asp Gln Leu Arg Val Gly
                165                 170                 175

Glu Phe Cys His Ser Arg Gly Ile Lys Leu Val Val Ala Asp Thr Arg
                180                 185                 190

Gly Leu Phe Gly Gln Leu Phe Cys Asp Phe Gly Glu Glu Met Ile Leu
                195                 200                 205

Thr Asp Ser Asn Gly Glu Gln Pro Leu Ser Thr Met Val Ser Met Val
210                 215                 220

Thr Lys Asp Asn Pro Gly Val Val Thr Cys Leu Asp Glu Ala Arg His
225                 230                 235                 240

Gly Phe Glu Ser Gly Asp Phe Val Ser Phe Glu Val Gln Gly Met
                245                 250                 255

Thr Glu Leu Asn Gly Asn Gln Pro Ile Glu Ile Lys Val Leu Gly Pro
                260                 265                 270

Tyr Thr Phe Ser Ile Cys Asp Thr Ser Asn Phe Ser Asp Tyr Ile Arg
                275                 280                 285

Gly Gly Ile Val Ser Gln Val Lys Val Pro Lys Lys Ile Ser Phe Lys
                290                 295                 300

Ser Leu Ser Ala Ser Leu Ala Glu Pro Asp Phe Val Met Thr Asp Phe
305                 310                 315                 320

Ala Lys Phe Ser Arg Pro Ala Gln Leu His Ile Gly Phe Gln Ala Leu
                325                 330                 335

His Lys Phe Cys Ala Gln His Ser Arg Pro Arg Pro Arg Asn Glu
                340                 345                 350

Glu Asp Ala Ala Glu Leu Val Thr Leu Ala Arg Ala Val Asn Ser Lys
                355                 360                 365

Ala Ser Ser Ala Val Gln Gln Asp Ser Leu Asp Glu Asp Leu Ile Arg
                370                 375                 380

Asn Leu Ala Phe Val Ala Ala Gly Asp Leu Ala Pro Ile Asn Ala Phe
385                 390                 395                 400

Ile Gly Gly Leu Ala Ala Gln Glu Val Met Lys Ala Cys Ser Gly Lys
                405                 410                 415

Phe Met Pro Ile Met Gln Trp Leu Tyr Phe Asp Ala Leu Glu Cys Leu
                420                 425                 430

Pro Glu Asp Lys Glu Ser Leu Thr Glu Asp Lys Cys Leu Pro Arg Gln
                435                 440                 445

Asn Arg Tyr Asp Gly Gln Val Ala Val Phe Gly Ser Asp Leu Gln Glu
                450                 455                 460

Lys Leu Gly Arg Gln Lys Tyr Phe Leu Val Gly Ala Gly Ala Ile Gly
465                 470                 475                 480
```

-continued

```
Cys Glu Leu Leu Lys Asn Phe Ala Met Ile Gly Leu Gly Cys Gly Glu
            485                 490                 495
Asn Gly Glu Ile Ile Val Thr Asp Met Asp Thr Ile Glu Lys Ser Asn
        500                 505                 510
Leu Asn Arg Gln Phe Leu Phe Arg Pro Trp Asp Val Thr Lys Leu Lys
            515                 520                 525
Ser Asp Thr Ala Ala Ala Val His Gln Met Asn Pro His Ile Arg
530                 535                 540
Val Thr Ser His Gln Asn Arg Val Gly Pro Asp Thr Glu Arg Ile Tyr
545                 550                 555                 560
Asp Asp Asp Phe Phe Gln Thr Leu Asp Gly Val Ala Asn Ala Leu Asp
                565                 570                 575
Asn Val Asp Ala Arg Met Tyr Met Asp Arg Arg Cys Val Tyr Tyr Arg
            580                 585                 590
Lys Pro Leu Leu Glu Ser Gly Thr Leu Gly Thr Lys Gly Asn Val Gln
        595                 600                 605
Val Val Ile Pro Phe Leu Thr Glu Ser Tyr Ser Ser Ser Gln Asp Pro
            610                 615                 620
Pro Glu Lys Ser Ile Pro Ile Cys Thr Leu Lys Asn Phe Pro Asn Ala
625                 630                 635                 640
Ile Glu His Thr Leu Gln Trp Ala Arg Asp Glu Phe Glu Gly Leu Phe
                645                 650                 655
Lys Gln Pro Ala Glu Asn Val Asn Gln Tyr Leu Thr Asp Pro Lys Phe
            660                 665                 670
Val Glu Arg Thr Leu Arg Leu Ala Gly Thr Gln Pro Leu Glu Val Leu
        675                 680                 685
Glu Ala Val Gln Arg Ser Leu Val Leu Gln Leu Pro Gln Ser Trp Ala
690                 695                 700
Asp Cys Val Thr Trp Ala Cys His His Trp Thr Gln Tyr Ser Asn
705                 710                 715                 720
Asn Ile Arg Gln Leu Leu His Asn Phe Pro Pro Asp Gln Leu Thr Ser
                725                 730                 735
Ser Gly Ala Pro Phe Trp Ser Gly Pro Lys Arg Cys Pro His Pro Leu
            740                 745                 750
Thr Phe Asp Val Ser Asn Pro Leu His Leu Asp Tyr Val Met Ala Ala
        755                 760                 765
Ala Asn Leu Phe Ala Gln Thr Tyr Gly Leu Ala Gly Ser Gln Asp Arg
770                 775                 780
Ala Ala Val Ala Thr Leu Leu Gln Ser Val Gln Val Pro Glu Phe Thr
785                 790                 795                 800
Pro Lys Ser Gly Val Lys Ile His Val Ser Asp Gln Glu Leu Gln Ser
                805                 810                 815
Ala Asn Ala Ser Val Asp Asp Ser Arg Leu Glu Glu Leu Lys Ala Thr
            820                 825                 830
Leu Pro Ser Pro Asp Lys Leu Pro Gly Phe Lys Met Tyr Pro Ile Asp
        835                 840                 845
Phe Glu Lys Asp Asp Asp Ser Asn Phe His Met Asp Phe Ile Val Ala
850                 855                 860
Ala Ser Asn Leu Arg Ala Glu Asn Tyr Asp Ile Pro Pro Ala Asp Arg
865                 870                 875                 880
His Lys Ser Lys Leu Ile Ala Gly Lys Ile Ile Pro Ala Ile Ala Thr
                885                 890                 895
```

-continued

Thr Thr Ala Ala Val Val Gly Leu Val Cys Leu Glu Leu Tyr Lys Val
            900                 905                 910

Val Gln Gly His Arg His Leu Asp Ser Tyr Lys Asn Gly Phe Leu Asn
    915                 920                 925

Leu Ala Leu Pro Phe Phe Gly Phe Ser Glu Pro Leu Ala Ala Pro Arg
930                 935                 940

His Gln Tyr Tyr Asn Gln Glu Trp Thr Leu Trp Asp Arg Phe Glu Val
945                 950                 955                 960

Gly Leu Gln Pro Asn Gly Glu Glu Met Thr Leu Lys Gln Phe Leu
            965                 970                 975

Asp Tyr Phe Lys Thr Glu His Lys Leu Glu Ile Thr Met Leu Ser Gln
            980                 985                 990

Gly Val Ser Met Leu Tyr Ser Phe Phe Met Pro Ala Ala Lys Leu Lys
            995                 1000                1005

Glu Arg Leu Asp Gln Pro Met Thr Glu Ile Val Ser Arg Val Ser
1010                1015                1020

Lys Arg Lys Leu Gly Arg His Val Arg Ala Leu Val Leu Glu Leu
    1025                1030                1035

Cys Cys Asn Asp Glu Ser Gly Glu Asp Val Glu Val Pro Tyr Val
    1040                1045                1050

Arg Tyr Thr Ile Arg
    1055

<210> SEQ ID NO 13
<211> LENGTH: 1058
<212> TYPE: PRT
<213> ORGANISM: Bos taurus

<400> SEQUENCE: 13

Met Ser Ser Ser Pro Leu Ser Lys Lys Arg Arg Val Ser Gly Pro Asp
1               5                   10                  15

Pro Lys Pro Gly Ser Asn Cys Ser Pro Ala His Ser Val Leu Ser Glu
            20                  25                  30

Val Pro Ser Val Pro Ala Asn Gly Met Ala Lys Asn Val Ser Asp Ala
        35                  40                  45

Asp Ile Asp Glu Gly Leu Tyr Ser Arg Gln Leu Tyr Val Leu Gly His
    50                  55                  60

Glu Ala Met Lys Arg Leu Gln Thr Ser Ser Val Leu Val Ser Gly Leu
65                  70                  75                  80

Arg Gly Leu Gly Val Glu Ile Ala Lys Asn Ile Ile Leu Gly Gly Val
                85                  90                  95

Lys Ala Val Thr Leu His Asp Gln Gly Thr Ala Gln Trp Ala Asp Leu
            100                 105                 110

Ser Ser Gln Phe Tyr Leu Arg Glu Glu Asp Ile Gly Lys Asn Arg Ala
        115                 120                 125

Glu Val Ser Gln Pro Arg Leu Ala Glu Leu Asn Ser Tyr Val Pro Val
    130                 135                 140

Ser Ala Tyr Thr Gly Pro Leu Val Glu Asp Phe Leu Ser Asp Phe Gln
145                 150                 155                 160

Val Val Val Leu Thr Asn Ser Pro Leu Glu Asp Gln Leu Arg Val Gly
                165                 170                 175

Glu Phe Cys His Ser His Gly Ile Lys Leu Val Val Ala Asp Thr Arg
            180                 185                 190

Gly Leu Phe Gly Gln Leu Phe Cys Asp Phe Gly Glu Glu Met Ile Leu
        195                 200                 205

```
Thr Asp Ser Asn Gly Glu Gln Pro Leu Ser Ala Met Val Ser Met Val
    210                 215                 220
Thr Lys Asp Asn Pro Gly Val Val Thr Cys Leu Asp Glu Ala Arg His
225                 230                 235                 240
Gly Phe Glu Ser Gly Asp Phe Val Ser Phe Ser Glu Val Gln Gly Met
                245                 250                 255
Ile Glu Leu Asn Gly Ser Gln Pro Met Glu Ile Lys Val Leu Gly Pro
            260                 265                 270
Tyr Thr Phe Ser Ile Cys Asp Thr Ser Asn Phe Ser Asp Tyr Ile Arg
        275                 280                 285
Gly Gly Ile Val Ser Gln Val Lys Val Pro Lys Lys Ile Ser Phe Lys
    290                 295                 300
Ser Leu Pro Ala Ser Leu Ala Glu Pro Asp Phe Val Met Thr Asp Phe
305                 310                 315                 320
Ala Lys Tyr Ser Arg Pro Ala Gln Leu His Ile Gly Phe Gln Ala Leu
                325                 330                 335
His His Phe Cys Ala Gln His Gly Arg Ser Pro Arg Pro His Asn Glu
            340                 345                 350
Glu Asp Ala Ala Glu Leu Val Thr Ile Ala Gln Ala Val Asn Ala Arg
        355                 360                 365
Ser Leu Pro Ala Val Gln Gln Gly Ser Leu Asp Glu Asp Leu Ile Arg
    370                 375                 380
Lys Leu Ala Tyr Val Ala Ala Gly Asp Leu Ala Pro Ile Asn Ala Phe
385                 390                 395                 400
Ile Gly Gly Leu Ala Ala Gln Glu Val Met Lys Ala Cys Ser Gly Lys
                405                 410                 415
Phe Met Pro Ile Met Gln Trp Leu Tyr Phe Asp Ala Leu Glu Cys Leu
            420                 425                 430
Pro Glu Asp Lys Glu Ala Leu Thr Glu Asp Lys Cys Leu Pro Arg Gln
        435                 440                 445
Asn Arg Tyr Asp Gly Gln Val Ala Val Phe Gly Ser Asp Leu Gln Glu
    450                 455                 460
Arg Leu Gly Lys Gln Lys Tyr Phe Leu Val Gly Ala Gly Ala Ile Gly
465                 470                 475                 480
Cys Glu Leu Leu Lys Asn Phe Ala Met Ile Gly Leu Gly Cys Ala Glu
                485                 490                 495
Asp Gly Glu Ile Val Val Thr Asp Met Asp Thr Ile Glu Lys Ser Asn
            500                 505                 510
Leu Asn Arg Gln Phe Leu Phe Arg Pro Trp Asp Val Thr Lys Leu Lys
        515                 520                 525
Ser Asp Thr Ala Ala Ala Val Arg Gln Met Asn Pro His Ile Arg
    530                 535                 540
Val Thr Ser His Gln Asn Arg Val Gly Pro Asp Thr Glu Arg Ile Tyr
545                 550                 555                 560
Asp Asp Asp Phe Phe Gln Asn Leu Asp Gly Val Thr Asn Ala Leu Asp
                565                 570                 575
Asn Val Asp Ala Arg Met Tyr Met Asp Arg Arg Cys Val Tyr Tyr Arg
            580                 585                 590
Lys Pro Leu Leu Glu Ser Gly Thr Leu Gly Thr Lys Gly Asn Val Gln
        595                 600                 605
Val Val Ile Pro Phe Leu Thr Glu Ser Tyr Ser Ser Ser Gln Asp Pro
    610                 615                 620
```

```
Pro Glu Lys Ser Ile Pro Ile Cys Thr Leu Lys Asn Phe Pro Asn Ala
625                 630                 635                 640

Ile Glu His Thr Leu Gln Trp Ala Arg Asp Glu Phe Glu Gly Leu Phe
                645                 650                 655

Lys Gln Pro Ala Glu Asn Val Asn Gln Tyr Leu Thr Asp Pro Lys Phe
            660                 665                 670

Val Glu Arg Thr Leu Arg Leu Ala Gly Thr Gln Pro Leu Glu Val Leu
        675                 680                 685

Glu Ala Val Gln Arg Ser Leu Val Leu Gln Arg Pro Gln Thr Trp Ala
    690                 695                 700

Asp Cys Val Thr Trp Ala Cys His His Trp His Thr Gln Tyr Ser Asn
705                 710                 715                 720

Asn Ile Arg Gln Leu Leu His Asn Phe Pro Asp Gln Leu Thr Ser
                725                 730                 735

Ser Gly Ala Pro Phe Trp Ser Gly Pro Lys Arg Cys Pro His Pro Leu
            740                 745                 750

Thr Phe Asp Val Ser Asn Pro Leu His Leu Asp Tyr Val Ile Ala Ala
        755                 760                 765

Ala Asn Leu Phe Ala Gln Thr Tyr Gly Leu Thr Gly Ser Gln Asp Arg
    770                 775                 780

Ala Ala Val Ala Thr Leu Leu Gln Ser Val Gln Val Pro Glu Phe Thr
785                 790                 795                 800

Pro Lys Ser Gly Val Lys Ile His Val Ser Asp Gln Glu Leu Gln Ser
                805                 810                 815

Ala Asn Ala Ser Val Asp Asp Ser Arg Leu Glu Glu Leu Lys Ala Thr
            820                 825                 830

Leu Pro Ser Pro Glu Lys Leu Pro Gly Phe Lys Met Tyr Pro Ile Asp
        835                 840                 845

Phe Glu Lys Asp Asp Asp Thr Asn Phe His Met Asp Phe Ile Val Ala
    850                 855                 860

Ala Ser Asn Leu Arg Ala Glu Asn Tyr Asp Ile Pro Pro Ala Asp Arg
865                 870                 875                 880

His Lys Ser Lys Leu Ile Ala Gly Lys Ile Ile Pro Ala Ile Ala Thr
                885                 890                 895

Thr Thr Ala Ala Val Val Gly Leu Val Cys Leu Glu Leu Tyr Lys Val
            900                 905                 910

Val Gln Gly His Arg Gln Leu Asn Ser Tyr Lys Asn Gly Phe Leu Asn
        915                 920                 925

Leu Ala Leu Pro Phe Phe Gly Phe Ser Glu Pro Leu Ala Ala Pro Arg
    930                 935                 940

His Gln Tyr Tyr Asn Gln Glu Trp Thr Leu Trp Asp Arg Phe Glu Val
945                 950                 955                 960

Gln Gly Leu Gln Pro Asn Gly Glu Glu Met Thr Leu Lys Gln Phe Leu
                965                 970                 975

Asp Tyr Phe Lys Thr Glu His Lys Leu Glu Ile Thr Met Leu Ser Gln
            980                 985                 990

Gly Val Ser Met Leu Tyr Ser Phe Phe Met Pro Ala Ala Lys Leu Lys
        995                 1000                1005

Glu Arg Leu Asp Gln Pro Met Thr Glu Ile Val Ser Arg Val Ser
    1010                1015                1020

Lys Arg Lys Leu Gly Arg His Val Arg Ala Leu Val Leu Glu Leu
    1025                1030                1035

Cys Cys Asn Asp Glu Ser Gly Glu Asp Val Glu Val Pro Tyr Val
```

```
                          1040                1045                1050
         Arg Tyr   Thr Ile Arg
             1055

<210> SEQ ID NO 14
<211> LENGTH: 1024
<212> TYPE: PRT
<213> ORGANISM: Saccharomyces cerevisiae

<400> SEQUENCE: 14

Met Ser Ser Asn Asn Ser Gly Leu Ser Ala Ala Gly Glu Ile Asp Glu
1               5                   10                  15

Ser Leu Tyr Ser Arg Gln Leu Tyr Val Leu Gly Lys Glu Ala Met Leu
            20                  25                  30

Lys Met Gln Thr Ser Asn Val Leu Ile Leu Gly Leu Lys Gly Leu Gly
        35                  40                  45

Val Glu Ile Ala Lys Asn Val Val Leu Ala Gly Val Lys Ser Met Thr
    50                  55                  60

Val Phe Asp Pro Glu Pro Val Gln Leu Ala Asp Leu Ser Thr Gln Phe
65                  70                  75                  80

Phe Leu Thr Glu Lys Asp Ile Gly Gln Lys Arg Gly Asp Val Thr Arg
                85                  90                  95

Ala Lys Leu Ala Glu Leu Asn Ala Tyr Val Pro Val Asn Val Leu Asp
            100                 105                 110

Ser Leu Asp Asp Val Thr Gln Leu Ser Gln Phe Gln Val Val Val Ala
        115                 120                 125

Thr Asp Thr Val Ser Leu Glu Asp Lys Val Lys Ile Asn Glu Phe Cys
130                 135                 140

His Ser Ser Gly Ile Arg Phe Ile Ser Ser Glu Thr Arg Gly Leu Phe
145                 150                 155                 160

Gly Asn Thr Phe Val Asp Leu Gly Asp Glu Phe Thr Val Leu Asp Pro
                165                 170                 175

Thr Gly Glu Glu Pro Arg Thr Gly Met Val Ser Asp Ile Glu Pro Asp
            180                 185                 190

Gly Thr Val Thr Met Leu Asp Asp Asn Arg His Gly Leu Glu Asp Gly
        195                 200                 205

Asn Phe Val Arg Phe Ser Glu Val Glu Gly Leu Asp Lys Leu Asn Asp
210                 215                 220

Gly Thr Leu Phe Lys Val Glu Val Leu Gly Pro Phe Ala Phe Arg Ile
225                 230                 235                 240

Gly Ser Val Lys Glu Tyr Gly Glu Tyr Lys Lys Gly Gly Ile Phe Thr
                245                 250                 255

Glu Val Lys Val Pro Arg Lys Ile Ser Phe Lys Ser Leu Lys Gln Gln
            260                 265                 270

Leu Ser Asn Pro Glu Phe Val Phe Ser Asp Phe Ala Lys Phe Asp Arg
        275                 280                 285

Ala Ala Gln Leu His Leu Gly Phe Gln Ala Leu His Gln Phe Ala Val
290                 295                 300

Arg His Asn Gly Glu Leu Pro Arg Thr Met Asn Asp Glu Asp Ala Asn
305                 310                 315                 320

Glu Leu Ile Lys Leu Val Thr Asp Leu Ser Val Gln Gln Pro Glu Val
                325                 330                 335

Leu Gly Glu Gly Val Asp Val Asn Glu Asp Leu Ile Lys Glu Leu Ser
            340                 345                 350
```

-continued

```
Tyr Gln Ala Arg Gly Asp Ile Pro Gly Val Val Ala Phe Gly Gly
            355                 360                 365
Leu Val Ala Gln Glu Val Leu Lys Ala Cys Ser Gly Lys Phe Thr Pro
    370                 375                 380
Leu Lys Gln Phe Met Tyr Phe Asp Ser Leu Glu Ser Leu Pro Asp Pro
385                 390                 395                 400
Lys Asn Phe Pro Arg Asn Glu Lys Thr Thr Gln Pro Val Asn Ser Arg
                405                 410                 415
Tyr Asp Asn Gln Ile Ala Val Phe Gly Leu Asp Phe Gln Lys Lys Ile
            420                 425                 430
Ala Asn Ser Lys Val Phe Leu Val Gly Ser Gly Ala Ile Gly Cys Glu
        435                 440                 445
Met Leu Lys Asn Trp Ala Leu Leu Gly Leu Gly Ser Gly Ser Asp Gly
    450                 455                 460
Tyr Ile Val Val Thr Asp Asn Asp Ser Ile Glu Lys Ser Asn Leu Asn
465                 470                 475                 480
Arg Gln Phe Leu Phe Arg Pro Lys Asp Val Gly Lys Asn Lys Ser Glu
                485                 490                 495
Val Ala Ala Glu Ala Val Cys Ala Met Asn Pro Asp Leu Lys Gly Lys
            500                 505                 510
Ile Asn Ala Lys Ile Asp Lys Val Gly Pro Glu Thr Glu Glu Ile Phe
        515                 520                 525
Asn Asp Ser Phe Trp Glu Ser Leu Asp Phe Val Thr Asn Ala Leu Asp
    530                 535                 540
Asn Val Asp Ala Arg Thr Tyr Val Asp Arg Arg Cys Val Phe Tyr Arg
545                 550                 555                 560
Lys Pro Leu Leu Glu Ser Gly Thr Leu Gly Thr Lys Gly Asn Thr Gln
                565                 570                 575
Val Ile Ile Pro Arg Leu Thr Glu Ser Tyr Ser Ser Ser Arg Asp Pro
            580                 585                 590
Pro Glu Lys Ser Ile Pro Leu Cys Thr Leu Arg Ser Phe Pro Asn Lys
        595                 600                 605
Ile Asp His Thr Ile Ala Trp Ala Lys Ser Leu Phe Gln Gly Tyr Phe
    610                 615                 620
Thr Asp Ser Ala Glu Asn Val Asn Met Tyr Leu Thr Gln Pro Asn Phe
625                 630                 635                 640
Val Glu Gln Thr Leu Lys Gln Ser Gly Asp Val Lys Gly Val Leu Glu
                645                 650                 655
Ser Ile Ser Asp Ser Leu Ser Ser Lys Pro His Asn Phe Glu Asp Cys
            660                 665                 670
Ile Lys Trp Ala Arg Leu Glu Phe Glu Lys Lys Phe Asn His Asp Ile
    675                 680                 685
Lys Gln Leu Leu Phe Asn Phe Pro Lys Asp Ala Lys Thr Ser Asn Gly
690                 695                 700
Glu Pro Phe Trp Ser Gly Ala Lys Arg Ala Pro Thr Pro Leu Glu Phe
705                 710                 715                 720
Asp Ile Tyr Asn Asn Asp His Phe His Phe Val Val Ala Gly Ala Ser
                725                 730                 735
Leu Arg Ala Tyr Asn Tyr Gly Ile Lys Ser Asp Asp Ser Asn Ser Lys
            740                 745                 750
Pro Asn Val Asp Glu Tyr Lys Ser Val Ile Asp His Met Ile Ile Pro
        755                 760                 765
Glu Phe Thr Pro Asn Ala Asn Leu Lys Ile Gln Val Asn Asp Asp Asp
```

```
               770                 775                 780
Pro Asp Pro Asn Ala Asn Ala Asn Gly Ser Asp Glu Ile Asp Gln
785                 790                 795                 800

Leu Val Ser Ser Leu Pro Asp Pro Ser Thr Leu Ala Gly Phe Lys Leu
                805                 810                 815

Glu Pro Val Asp Phe Glu Lys Asp Asp Thr Asn His His Ile Glu
                820                 825                 830

Phe Ile Thr Ala Cys Ser Asn Cys Arg Ala Gln Asn Tyr Phe Ile Glu
                835                 840                 845

Thr Ala Asp Arg Gln Lys Thr Lys Phe Ile Ala Gly Arg Ile Ile Pro
850                 855                 860

Ala Ile Ala Thr Thr Thr Ser Leu Val Thr Gly Leu Val Asn Leu Glu
865                 870                 875                 880

Leu Tyr Lys Leu Ile Asp Asn Lys Thr Asp Ile Glu Gln Tyr Lys Asn
                885                 890                 895

Gly Phe Val Asn Leu Ala Leu Pro Phe Phe Gly Phe Ser Glu Pro Ile
                900                 905                 910

Ala Ser Pro Lys Gly Glu Tyr Asn Asn Lys Lys Tyr Asp Lys Ile Trp
                915                 920                 925

Asp Arg Phe Asp Ile Lys Gly Asp Ile Lys Leu Ser Asp Leu Ile Glu
                930                 935                 940

His Phe Glu Lys Asp Glu Gly Leu Glu Ile Thr Met Leu Ser Tyr Gly
945                 950                 955                 960

Val Ser Leu Leu Tyr Ala Ser Phe Phe Pro Pro Lys Lys Leu Lys Glu
                965                 970                 975

Arg Leu Asn Leu Pro Ile Thr Gln Leu Val Lys Leu Val Thr Lys Lys
                980                 985                 990

Asp Ile Pro Ala His Val Ser Thr Met Ile Leu Glu Ile Cys Ala Asp
                995                 1000                1005

Asp Lys Glu Gly Glu Asp Val Glu Val Pro Phe Ile Thr Ile His
                1010                1015                1020

Leu

<210> SEQ ID NO 15
<211> LENGTH: 1080
<212> TYPE: PRT
<213> ORGANISM: Arabidopsis thaliana

<400> SEQUENCE: 15

Met Leu His Lys Arg Ala Ser Glu Ala Asn Asp Lys Asn Asp Asn Thr
1               5                   10                  15

Ile Ile Gly Ser Asp Leu Ala Ser Ser Lys Lys Arg Arg Ile Asp Phe
                20                  25                  30

Thr Glu Ser Ser Ser Asp Lys Ser Ser Ser Ile Leu Ala Ser Gly Ser
            35                  40                  45

Ser Arg Gly Phe His Gly Asp Ser Val Val Gln Gln Ile Asp Met Ala
        50                  55                  60

Phe Gly Asn Ser Asn Arg Gln Glu Ile Asp Glu Asp Leu His Ser Arg
65                  70                  75                  80

Gln Leu Ala Val Tyr Gly Arg Glu Thr Met Arg Arg Leu Phe Ala Ser
                85                  90                  95

Asn Val Leu Ile Ser Gly Met His Gly Leu Gly Ala Glu Ile Ala Lys
                100                 105                 110

Asn Leu Ile Leu Ala Gly Val Lys Ser Val Thr Leu His Asp Glu Arg
```

-continued

```
            115                 120                 125
Val Val Glu Leu Trp Asp Leu Ser Ser Asn Phe Val Phe Ser Glu Asp
            130                 135                 140

Asp Val Gly Lys Asn Arg Ala Asp Ala Ser Val Gln Lys Leu Gln Asp
145                 150                 155                 160

Leu Asn Asn Ala Val Val Ser Ser Leu Thr Lys Ser Leu Asn Lys
            165                 170                 175

Glu Asp Leu Ser Gly Phe Gln Val Val Phe Ser Asp Ile Ser Met
            180                 185                 190

Glu Arg Ala Ile Glu Phe Asp Asp Tyr Cys His Ser His Gln Pro Pro
            195                 200                 205

Ile Ala Phe Val Lys Ala Asp Val Arg Gly Leu Phe Gly Ser Val Phe
            210                 215                 220

Cys Asp Phe Gly Pro Glu Phe Ala Val Leu Asp Val Asp Gly Glu Glu
225                 230                 235                 240

Pro His Thr Gly Ile Ile Ala Ser Ile Ser Asn Glu Asn Gln Ala Phe
                    245                 250                 255

Ile Ser Cys Val Asp Asp Glu Arg Leu Glu Phe Glu Asp Gly Asp Leu
                260                 265                 270

Val Val Phe Ser Glu Val Glu Gly Met Thr Glu Leu Asn Asp Gly Lys
            275                 280                 285

Pro Arg Lys Ile Lys Ser Thr Arg Pro Tyr Ser Phe Thr Leu Asp Glu
290                 295                 300

Asp Thr Thr Asn Tyr Gly Thr Tyr Val Lys Gly Ile Val Thr Gln
305                 310                 315                 320

Val Lys Gln Pro Lys Leu Leu Asn Phe Lys Pro Leu Arg Glu Ala Leu
                325                 330                 335

Lys Asp Pro Gly Asp Phe Leu Phe Ser Asp Phe Ser Lys Phe Asp Arg
                340                 345                 350

Pro Pro Leu Leu His Leu Ala Phe Gln Ala Leu Asp His Phe Lys Ala
                355                 360                 365

Glu Ala Gly Arg Phe Pro Val Ala Gly Ser Glu Glu Asp Ala Gln Lys
            370                 375                 380

Leu Ile Ser Ile Ala Thr Ala Ile Asn Thr Gly Gln Gly Asp Leu Lys
385                 390                 395                 400

Val Glu Asn Val Asp Gln Lys Leu Leu Arg His Phe Ser Phe Gly Ala
                405                 410                 415

Lys Ala Val Leu Asn Pro Met Ala Ala Met Phe Gly Gly Ile Val Gly
                420                 425                 430

Gln Glu Val Val Lys Ala Cys Ser Gly Lys Phe His Pro Leu Phe Gln
            435                 440                 445

Phe Phe Tyr Phe Asp Ser Val Glu Ser Leu Pro Ser Glu Pro Val Asp
            450                 455                 460

Ser Ser Asp Phe Ala Pro Arg Asn Ser Arg Tyr Asp Ala Gln Ile Ser
465                 470                 475                 480

Val Phe Gly Ala Lys Phe Gln Lys Lys Leu Glu Asp Ala Lys Val Phe
                485                 490                 495

Thr Val Gly Ser Gly Ala Leu Gly Cys Glu Phe Leu Lys Asn Leu Ala
                500                 505                 510

Leu Met Gly Val Ser Cys Gly Ser Gln Gly Lys Leu Thr Val Thr Asp
            515                 520                 525

Asp Asp Ile Ile Glu Lys Ser Asn Leu Ser Arg Gln Phe Leu Phe Arg
            530                 535                 540
```

```
Asp Trp Asn Ile Gly Gln Ala Lys Ser Thr Val Ala Ser Ala Ala
545                 550                 555                 560

Ala Val Ile Asn Pro Arg Phe Asn Ile Glu Ala Leu Gln Asn Arg Val
                565                 570                 575

Gly Ala Glu Thr Glu Asn Val Phe Asp Asp Ala Phe Trp Glu Asn Leu
            580                 585                 590

Thr Val Val Asn Ala Leu Asp Asn Val Asn Ala Arg Leu Tyr Val
        595                 600                 605

Asp Ser Arg Cys Leu Tyr Phe Gln Lys Pro Leu Leu Glu Ser Gly Thr
        610                 615                 620

Leu Gly Thr Lys Cys Asn Thr Gln Ser Val Ile Pro His Leu Thr Glu
625                 630                 635                 640

Asn Tyr Gly Ala Ser Arg Asp Pro Pro Glu Lys Gln Ala Pro Met Cys
                645                 650                 655

Thr Val His Ser Phe Pro His Asn Ile Asp His Cys Leu Thr Trp Ala
            660                 665                 670

Arg Ser Glu Phe Glu Gly Leu Leu Glu Lys Thr Pro Ala Glu Val Asn
        675                 680                 685

Ala Tyr Leu Ser Ser Pro Val Glu Tyr Thr Asn Ser Met Met Ser Ala
        690                 695                 700

Gly Asp Ala Gln Ala Arg Asp Thr Leu Glu Arg Ile Val Glu Cys Leu
705                 710                 715                 720

Glu Lys Glu Lys Cys Glu Thr Phe Gln Asp Cys Leu Thr Trp Ala Arg
                725                 730                 735

Leu Arg Phe Glu Asp Tyr Phe Val Asn Arg Val Lys Gln Leu Ile Tyr
            740                 745                 750

Thr Phe Pro Glu Asp Ala Ala Thr Ser Thr Gly Ala Pro Phe Trp Ser
        755                 760                 765

Ala Pro Lys Arg Phe Pro Arg Pro Leu Gln Tyr Ser Ser Ser Asp Pro
770                 775                 780

Ser Leu Leu Asn Phe Ile Thr Ala Thr Ala Ile Leu Arg Ala Glu Thr
785                 790                 795                 800

Phe Gly Ile Pro Ile Pro Glu Trp Thr Lys Asn Pro Lys Glu Ala Ala
                805                 810                 815

Glu Ala Val Asp Arg Val Ile Val Pro Asp Phe Glu Pro Arg Gln Asp
            820                 825                 830

Ala Lys Ile Val Thr Asp Glu Lys Ala Thr Thr Leu Thr Thr Ala Ser
        835                 840                 845

Val Asp Asp Ala Ala Val Ile Asp Leu Ile Ala Lys Ile Asp Gln
        850                 855                 860

Cys Arg His Asn Leu Ser Pro Asp Phe Arg Met Lys Pro Ile Gln Phe
865                 870                 875                 880

Glu Lys Asp Asp Thr Asn Tyr His Met Asp Val Ile Ala Gly Leu
            885                 890                 895

Ala Asn Met Arg Ala Arg Asn Tyr Ser Ile Pro Glu Val Asp Lys Leu
        900                 905                 910

Lys Ala Lys Phe Ile Ala Gly Arg Ile Pro Ala Ile Ala Thr Ser
        915                 920                 925

Thr Ala Met Ala Thr Gly Leu Val Cys Leu Glu Leu Tyr Lys Val Leu
        930                 935                 940

Asp Gly Gly His Lys Val Glu Ala Tyr Arg Asn Thr Phe Ala Asn Leu
945                 950                 955                 960
```

Ala Leu Pro Leu Phe Ser Met Ala Glu Pro Leu Pro Lys Val Val
            965                 970                 975

Lys His Arg Asp Met Ala Trp Thr Val Trp Asp Arg Trp Val Leu Lys
        980                 985                 990

Gly Asn Pro Thr Leu Arg Glu Val Leu Gln Trp Leu Glu Asp Lys Gly
        995                 1000                1005

Leu Ser Ala Tyr Ser Ile Ser Cys Gly Ser Cys Leu Leu Phe Asn
    1010                1015                1020

Ser Met Phe Thr Arg His Lys Glu Arg Met Asp Lys Lys Val Val
    1025                1030                1035

Asp Leu Ala Arg Asp Val Ala Lys Val Glu Leu Pro Pro Tyr Arg
    1040                1045                1050

Asn His Leu Asp Val Val Val Ala Cys Glu Asp Glu Asp Asp Asn
    1055                1060                1065

Asp Val Asp Ile Pro Leu Val Ser Ile Tyr Phe Arg
    1070                1075                1080

<210> SEQ ID NO 16
<211> LENGTH: 1058
<212> TYPE: PRT
<213> ORGANISM: Rattus norvegicus

<400> SEQUENCE: 16

Met Ser Ser Ser Pro Leu Ser Lys Lys Arg Arg Val Ser Gly Pro Asp
1               5                   10                  15

Pro Lys Pro Gly Ser Asn Cys Ser Ser Ala Gln Ser Val Leu Ser Glu
            20                  25                  30

Val Ser Ser Val Pro Thr Asn Gly Met Ala Lys Asn Gly Ser Glu Ala
        35                  40                  45

Asp Ile Asp Glu Ser Leu Tyr Ser Arg Gln Leu Tyr Val Leu Gly His
    50                  55                  60

Glu Ala Met Lys Met Leu Gln Thr Ser Ser Val Leu Val Ser Gly Leu
65                  70                  75                  80

Arg Gly Leu Gly Val Glu Ile Ala Lys Asn Ile Ile Leu Gly Gly Val
                85                  90                  95

Lys Ala Val Thr Leu His Asp Gln Gly Thr Thr Gln Trp Ala Asp Leu
            100                 105                 110

Ser Ser Gln Phe Tyr Leu Arg Glu Glu Asp Ile Gly Lys Asn Arg Ala
        115                 120                 125

Glu Val Ser Gln Pro Arg Leu Ala Glu Leu Asn Ser Tyr Val Pro Val
    130                 135                 140

Thr Ala Tyr Thr Gly Pro Leu Val Glu Asp Phe Leu Ser Gly Phe Gln
145                 150                 155                 160

Val Val Val Leu Thr Asn Ser Pro Leu Glu Glu Gln Leu Arg Val Gly
                165                 170                 175

Glu Phe Cys His Ser Arg Gly Ile Lys Leu Val Val Ala Asp Thr Arg
            180                 185                 190

Gly Leu Phe Gly Gln Leu Phe Cys Asp Phe Gly Glu Glu Met Val Leu
        195                 200                 205

Thr Asp Ser Asn Gly Glu Gln Pro Leu Ser Ala Met Val Ser Met Val
    210                 215                 220

Thr Lys Asp Asn Pro Gly Val Val Thr Cys Leu Asp Glu Ala Arg His
225                 230                 235                 240

Gly Phe Glu Thr Gly Asp Phe Val Ser Phe Ser Glu Val Gln Gly Met
                245                 250                 255

```
Val Gln Leu Asn Gly Cys Gln Pro Ile Glu Ile Lys Val Leu Gly Pro
            260                 265                 270

Tyr Thr Phe Ser Ile Cys Asp Thr Ser Asn Phe Ser Asp Tyr Ile Arg
        275                 280                 285

Gly Gly Ile Val Ser Gln Val Lys Val Pro Lys Lys Ile Ser Phe Lys
    290                 295                 300

Ser Leu Pro Ala Ser Leu Ala Glu Pro Asp Phe Val Met Thr Asp Phe
305                 310                 315                 320

Ala Lys Tyr Ser Arg Pro Ala Gln Leu His Ile Gly Phe Gln Ala Leu
                325                 330                 335

His Gln Phe Cys Ala Gln His Asn Arg Pro Pro Arg Pro Arg Asn Glu
            340                 345                 350

Glu Asp Ala Thr Glu Leu Val Thr Leu Ala Gln Ala Val Asn Ala Arg
        355                 360                 365

Ser Pro Pro Ala Val Gln Gln Asp Asn Val Asp Glu Asp Leu Ile Arg
    370                 375                 380

Lys Leu Ala Tyr Val Ala Ala Gly Asp Leu Ala Pro Ile Asn Ala Phe
385                 390                 395                 400

Ile Gly Gly Leu Ala Ala Gln Glu Val Met Lys Ala Cys Ser Gly Lys
                405                 410                 415

Phe Met Pro Ile Met Gln Trp Leu Tyr Phe Asp Ala Leu Glu Cys Leu
            420                 425                 430

Pro Glu Asp Lys Glu Ala Leu Thr Glu Asp Lys Cys Leu Pro Arg Gln
        435                 440                 445

Asn Arg Tyr Asp Gly Gln Val Ala Val Phe Gly Ser Asp Leu Gln Glu
    450                 455                 460

Lys Leu Gly Lys Gln Lys Tyr Phe Leu Val Gly Ala Gly Ala Ile Gly
465                 470                 475                 480

Cys Glu Leu Leu Lys Asn Phe Ala Met Ile Gly Leu Gly Cys Gly Glu
                485                 490                 495

Gly Gly Glu Val Val Val Thr Asp Met Asp Thr Ile Glu Lys Ser Asn
            500                 505                 510

Leu Asn Arg Gln Phe Leu Phe Arg Pro Trp Asp Val Thr Lys Leu Lys
        515                 520                 525

Ser Asp Thr Ala Ala Ala Ala Val Arg Gln Met Asn Pro Tyr Ile Gln
    530                 535                 540

Val Thr Ser His Gln Asn Arg Val Gly Pro Asp Thr Glu Arg Ile Tyr
545                 550                 555                 560

Asp Asp Asp Phe Phe Gln Asn Leu Asp Gly Val Ala Asn Ala Leu Asp
                565                 570                 575

Asn Val Asp Ala Arg Met Tyr Met Asp Arg Arg Cys Val Tyr Tyr Arg
            580                 585                 590

Lys Pro Leu Leu Glu Ser Gly Thr Leu Gly Thr Lys Gly Asn Val Gln
        595                 600                 605

Val Val Ile Pro Phe Leu Thr Glu Ser Tyr Ser Ser Ser Gln Asp Pro
    610                 615                 620

Pro Glu Lys Ser Ile Pro Ile Cys Thr Leu Lys Asn Phe Pro Asn Ala
625                 630                 635                 640

Ile Glu His Thr Leu Gln Trp Ala Arg Asp Glu Phe Glu Gly Leu Phe
                645                 650                 655

Lys Gln Pro Ala Glu Asn Val Asn Gln Tyr Leu Thr Asp Ser Lys Phe
            660                 665                 670
```

Val Glu Arg Thr Leu Arg Leu Ala Gly Thr Gln Pro Leu Glu Val Leu
            675                 680                 685

Glu Ala Val Gln Arg Ser Leu Val Leu Gln Arg Pro Gln Thr Trp Gly
690                 695                 700

Asp Cys Val Thr Trp Ala Cys His His Trp His Thr Gln Tyr Cys Asn
705                 710                 715                 720

Asn Ile Arg Gln Leu Leu His Asn Phe Pro Pro Asp Gln Leu Thr Ser
            725                 730                 735

Ser Gly Ala Pro Phe Trp Ser Gly Pro Lys Arg Cys Pro His Pro Leu
            740                 745                 750

Thr Phe Asp Val Asn Asn Thr Leu His Leu Asp Tyr Val Met Ala Ala
            755                 760                 765

Ala Asn Leu Phe Ala Gln Thr Tyr Gly Leu Thr Gly Ser Gln Asp Arg
770                 775                 780

Ala Ala Val Ala Ser Leu Leu Gln Ser Val Gln Val Pro Glu Phe Thr
785                 790                 795                 800

Pro Lys Ser Gly Val Lys Ile His Val Ser Asp Gln Glu Leu Gln Ser
            805                 810                 815

Ala Asn Ala Ser Val Asp Asp Ser Arg Leu Glu Glu Leu Lys Ala Thr
            820                 825                 830

Leu Pro Ser Pro Asp Lys Leu Pro Gly Phe Lys Met Tyr Pro Ile Asp
            835                 840                 845

Phe Glu Lys Asp Asp Asp Ser Asn Phe His Met Asp Phe Ile Val Ala
            850                 855                 860

Ala Ser Asn Leu Arg Ala Glu Asn Tyr Asp Ile Ser Pro Ala Asp Arg
865                 870                 875                 880

His Lys Ser Lys Leu Ile Ala Gly Lys Ile Ile Pro Ala Ile Ala Thr
            885                 890                 895

Thr Thr Ala Ala Val Val Gly Leu Val Cys Leu Glu Leu Tyr Lys Val
            900                 905                 910

Val Gln Gly His Gln Leu Asp Ser Tyr Lys Asn Gly Phe Leu Asn
            915                 920                 925

Leu Ala Leu Pro Phe Phe Gly Phe Ser Glu Pro Leu Ala Ala Pro Arg
930                 935                 940

His Gln Tyr Tyr Asn Gln Glu Trp Thr Leu Trp Asp Arg Phe Glu Val
945                 950                 955                 960

Gln Gly Leu Gln Pro Asn Gly Glu Glu Met Thr Leu Lys Gln Phe Leu
            965                 970                 975

Asp Tyr Phe Lys Thr Glu His Lys Leu Glu Ile Thr Met Leu Ser Gln
            980                 985                 990

Gly Val Ser Met Leu Tyr Ser Phe Phe Met Pro Ala Ala Lys Leu Lys
            995                 1000                1005

Glu Arg Leu Asp Gln Pro Met Thr Glu Ile Val Ser Arg Val Ser
   1010                1015                1020

Lys Arg Lys Leu Gly Arg His Val Arg Ala Leu Val Leu Glu Leu
   1025                1030                1035

Cys Cys Asn Asp Glu Ser Gly Glu Asp Val Glu Val Pro Tyr Val
   1040                1045                1050

Arg Tyr Thr Ile Arg
   1055

<210> SEQ ID NO 17
<211> LENGTH: 148
<212> TYPE: PRT

-continued

<213> ORGANISM: Saccharomyces cerevisiae

<400> SEQUENCE: 17

Met Ser Ser Ser Lys Arg Ile Ala Lys Glu Leu Ser Asp Leu Gly Arg
1               5                   10                  15

Asp Pro Pro Ala Ser Cys Ser Ala Gly Pro Val Gly Asp Asp Leu Tyr
            20                  25                  30

His Trp Gln Ala Ser Ile Met Gly Pro Ser Asp Ser Pro Tyr Ala Gly
        35                  40                  45

Gly Val Phe Phe Leu Ser Ile His Phe Pro Thr Asp Tyr Pro Phe Lys
    50                  55                  60

Pro Pro Lys Val Asn Phe Thr Thr Lys Ile Tyr His Pro Asn Ile Asn
65                  70                  75                  80

Ser Ser Gly Asn Ile Cys Leu Asp Ile Leu Lys Asp Gln Trp Ser Pro
                85                  90                  95

Ala Leu Thr Leu Ser Lys Val Leu Leu Ser Ile Cys Ser Leu Leu Thr
            100                 105                 110

Asp Ala Asn Pro Asp Asp Pro Leu Val Pro Glu Ile Ala Gln Ile Tyr
        115                 120                 125

Lys Thr Asp Lys Ala Lys Tyr Glu Ala Thr Ala Lys Glu Trp Thr Lys
130                 135                 140

Lys Tyr Ala Val
145

<210> SEQ ID NO 18
<211> LENGTH: 185
<212> TYPE: PRT
<213> ORGANISM: Arabidopsis lyrata

<400> SEQUENCE: 18

Met Ser Ser Pro Ser Lys Arg Arg Glu Met Asp Leu Met Lys Leu Met
1               5                   10                  15

Met Ser Asp Tyr Lys Val Glu Met Ile Asn Asp Gly Met Gln Glu Phe
            20                  25                  30

Tyr Val Glu Phe Asn Gly Pro Lys Asp Ser Ile Tyr Glu Gly Gly Val
        35                  40                  45

Trp Lys Ile Arg Val Glu Leu Pro Asp Ala Tyr Pro Tyr Lys Ser Pro
    50                  55                  60

Ser Val Gly Phe Ile Thr Lys Ile Tyr His Pro Asn Val Asp Glu Met
65                  70                  75                  80

Ser Gly Ser Val Cys Leu Asp Val Ile Asn Gln Thr Trp Ser Pro Met
                85                  90                  95

Phe Asp Leu Val Asn Val Phe Glu Thr Phe Leu Pro Gln Leu Leu Leu
            100                 105                 110

Tyr Pro Asn Pro Ser Asp Pro Leu Asn Gly Glu Ala Ala Ala Leu Met
        115                 120                 125

Met Arg Asp Arg Pro Thr Tyr Glu Gln Arg Val Lys Gly Tyr Cys Glu
130                 135                 140

Lys Tyr Ala Lys Pro Arg Ala Asp Thr Glu Glu Met Ser Ser Asp Asp
145                 150                 155                 160

Glu Met Ser Glu Asp Glu Tyr Ala Ser Asp Cys Asp Asp Glu Asp Asp
                165                 170                 175

Val Ala Ile Ala Gly Lys Leu Asp Pro
            180                 185

```
<210> SEQ ID NO 19
<211> LENGTH: 148
<212> TYPE: PRT
<213> ORGANISM: Saccharomyces cerevisiae

<400> SEQUENCE: 19

Met Ser Ser Ser Lys Arg Ile Ala Lys Glu Leu Ser Asp Leu Glu Arg
1               5                   10                  15

Asp Pro Pro Thr Ser Cys Ser Ala Gly Pro Val Gly Asp Asp Leu Tyr
                20                  25                  30

His Trp Gln Ala Ser Ile Met Gly Pro Ala Asp Ser Pro Tyr Ala Gly
            35                  40                  45

Gly Val Phe Phe Leu Ser Ile His Phe Pro Thr Asp Tyr Pro Phe Lys
    50                  55                  60

Pro Pro Lys Ile Ser Phe Thr Thr Lys Ile Tyr His Pro Asn Ile Asn
65                  70                  75                  80

Ala Asn Gly Asn Ile Cys Leu Asp Ile Leu Lys Asp Gln Trp Ser Pro
                85                  90                  95

Ala Leu Thr Leu Ser Lys Val Leu Leu Ser Ile Cys Ser Leu Leu Thr
                100                 105                 110

Asp Ala Asn Pro Asp Asp Pro Leu Val Pro Glu Ile Ala His Ile Tyr
            115                 120                 125

Lys Thr Asp Arg Pro Lys Tyr Glu Ala Thr Ala Arg Glu Trp Thr Lys
    130                 135                 140

Lys Tyr Ala Val
145

<210> SEQ ID NO 20
<211> LENGTH: 170
<212> TYPE: PRT
<213> ORGANISM: Arabidopsis thaliana

<400> SEQUENCE: 20

Met Met Ser Asp Tyr Lys Val Glu Met Ile Asn Asp Gly Met Gln Glu
1               5                   10                  15

Phe Phe Val Glu Phe Ser Gly Pro Lys Asp Ser Ile Tyr Glu Gly Gly
                20                  25                  30

Val Trp Lys Ile Arg Val Glu Leu Pro Asp Ala Tyr Pro Tyr Lys Ser
            35                  40                  45

Pro Ser Val Gly Phe Ile Thr Lys Ile Tyr His Pro Asn Val Asp Glu
    50                  55                  60

Met Ser Gly Ser Val Cys Leu Asp Val Ile Asn Gln Thr Trp Ser Pro
65                  70                  75                  80

Met Phe Asp Leu Val Asn Val Phe Glu Thr Phe Leu Pro Gln Leu Leu
                85                  90                  95

Leu Tyr Pro Asn Pro Ser Asp Pro Leu Asn Gly Glu Ala Ala Ala Leu
                100                 105                 110

Met Met Arg Asp Arg Pro Thr Tyr Glu Gln Arg Val Lys Glu Tyr Cys
            115                 120                 125

Glu Lys Tyr Ala Lys Pro Arg Ala Asp Thr Glu Glu Met Ser Ser Asp
    130                 135                 140

Asp Glu Met Ser Glu Asp Glu Tyr Ala Ser Asp Gly Asp Asp Glu Asp
145                 150                 155                 160

Asp Val Ala Ile Ala Gly Lys Leu Asp Pro
                165                 170
```

<210> SEQ ID NO 21
<211> LENGTH: 236
<212> TYPE: PRT
<213> ORGANISM: Homo sapiens

<400> SEQUENCE: 21

Met Ala Arg Pro Leu Val Pro Ser Ser Gln Lys Ala Leu Leu Leu Glu
1               5                   10                  15

Leu Lys Gly Leu Gln Glu Glu Pro Val Glu Gly Phe Arg Val Thr Leu
            20                  25                  30

Val Asp Glu Gly Asp Leu Tyr Asn Trp Glu Val Ala Ile Phe Gly Pro
        35                  40                  45

Pro Asn Thr Tyr Tyr Glu Gly Gly Tyr Phe Lys Ala Arg Leu Lys Phe
    50                  55                  60

Pro Ile Asp Tyr Pro Tyr Ser Pro Pro Ala Phe Arg Phe Leu Thr Lys
65                  70                  75                  80

Met Trp His Pro Asn Ile Tyr Glu Thr Gly Asp Val Cys Ile Ser Ile
                85                  90                  95

Leu His Pro Pro Val Asp Asp Pro Gln Ser Gly Glu Leu Pro Ser Glu
            100                 105                 110

Arg Trp Asn Pro Thr Gln Asn Val Arg Thr Ile Leu Leu Ser Val Ile
        115                 120                 125

Ser Leu Leu Asn Glu Pro Asn Thr Phe Ser Pro Ala Asn Val Asp Ala
    130                 135                 140

Ser Val Met Tyr Arg Lys Trp Lys Glu Ser Lys Gly Lys Asp Arg Glu
145                 150                 155                 160

Tyr Thr Asp Ile Ile Arg Lys Gln Val Leu Gly Thr Lys Val Asp Ala
                165                 170                 175

Glu Arg Asp Gly Val Lys Val Pro Thr Thr Leu Ala Glu Tyr Cys Val
            180                 185                 190

Lys Thr Lys Ala Pro Ala Pro Asp Glu Gly Ser Asp Leu Phe Tyr Asp
        195                 200                 205

Asp Tyr Tyr Glu Asp Gly Glu Val Glu Glu Glu Ala Asp Ser Cys Phe
    210                 215                 220

Gly Asp Asp Glu Asp Asp Ser Gly Thr Glu Glu Ser
225                 230                 235

<210> SEQ ID NO 22
<211> LENGTH: 147
<212> TYPE: PRT
<213> ORGANISM: Homo sapiens

<400> SEQUENCE: 22

Met Ala Leu Lys Arg Ile His Lys Glu Leu Asn Asp Leu Ala Arg Asp
1               5                   10                  15

Pro Pro Ala Gln Cys Ser Ala Gly Pro Val Gly Asp Asp Met Phe His
            20                  25                  30

Trp Gln Ala Thr Ile Met Gly Pro Asn Asp Ser Pro Tyr Gln Gly Gly
        35                  40                  45

Val Phe Phe Leu Thr Ile His Phe Pro Thr Asp Tyr Pro Phe Lys Pro
    50                  55                  60

Pro Lys Val Ala Phe Thr Thr Arg Ile Tyr His Pro Asn Ile Asn Ser
65                  70                  75                  80

Asn Gly Ser Ile Cys Leu Asp Ile Leu Arg Ser Gln Trp Ser Pro Ala
                85                  90                  95

Leu Thr Ile Ser Lys Val Leu Leu Ser Ile Cys Ser Leu Leu Cys Asp 100                 105                 110

Pro Asn Pro Asp Asp Pro Leu Val Pro Glu Ile Ala Arg Ile Tyr Lys
            115                 120                 125

Thr Asp Arg Glu Lys Tyr Asn Arg Ile Ala Arg Glu Trp Thr Gln Lys
130                 135                 140

Tyr Ala Met
145

<210> SEQ ID NO 23
<211> LENGTH: 147
<212> TYPE: PRT
<213> ORGANISM: Homo sapiens

<400> SEQUENCE: 23

Met Ala Leu Lys Arg Ile Asn Lys Glu Leu Ser Asp Leu Ala Arg Asp
1               5                   10                  15

Pro Pro Ala Gln Cys Ser Ala Gly Pro Val Gly Asp Asp Met Phe His
            20                  25                  30

Trp Gln Ala Thr Ile Met Gly Pro Asn Asp Ser Pro Tyr Gln Gly Gly
        35                  40                  45

Val Phe Phe Leu Thr Ile His Phe Pro Thr Asp Tyr Pro Phe Lys Pro
50                  55                  60

Pro Lys Val Ala Phe Thr Thr Arg Ile Tyr His Pro Asn Ile Asn Ser
65                  70                  75                  80

Asn Gly Ser Ile Cys Leu Asp Ile Leu Arg Ser Gln Trp Ser Pro Ala
                85                  90                  95

Leu Thr Ile Ser Lys Val Leu Leu Ser Ile Cys Ser Leu Leu Cys Asp
            100                 105                 110

Pro Asn Pro Asp Asp Pro Leu Val Pro Glu Ile Ala Arg Ile Tyr Lys
            115                 120                 125

Thr Asp Arg Asp Lys Tyr Asn Arg Ile Ser Arg Glu Trp Thr Gln Lys
130                 135                 140

Tyr Ala Met
145

<210> SEQ ID NO 24
<211> LENGTH: 200
<212> TYPE: PRT
<213> ORGANISM: Homo sapiens

<400> SEQUENCE: 24

Met Ala Asn Ile Ala Val Gln Arg Ile Lys Arg Glu Phe Lys Glu Val
1               5                   10                  15

Leu Lys Ser Glu Glu Thr Ser Lys Asn Gln Ile Lys Val Asp Leu Val
            20                  25                  30

Asp Glu Asn Phe Thr Glu Leu Arg Gly Glu Ile Ala Gly Pro Pro Asp
        35                  40                  45

Thr Pro Tyr Glu Gly Gly Arg Tyr Gln Leu Glu Ile Lys Ile Pro Glu
50                  55                  60

Thr Tyr Pro Phe Asn Pro Pro Lys Val Arg Phe Ile Thr Lys Ile Trp
65                  70                  75                  80

His Pro Asn Ile Ser Ser Val Thr Gly Ala Ile Cys Leu Asp Ile Leu
                85                  90                  95

Lys Asp Gln Trp Ala Ala Ala Met Thr Leu Arg Thr Val Leu Leu Ser
            100                 105                 110

Leu Gln Ala Leu Leu Ala Ala Ala Glu Pro Asp Asp Pro Gln Asp Ala

```
            115                 120                 125
Val Val Ala Asn Gln Tyr Lys Gln Asn Pro Glu Met Phe Lys Gln Thr
    130                 135                 140

Ala Arg Leu Trp Ala His Val Tyr Ala Gly Ala Pro Val Ser Ser Pro
145                 150                 155                 160

Glu Tyr Thr Lys Lys Ile Glu Asn Leu Cys Ala Met Gly Phe Asp Arg
                165                 170                 175

Asn Ala Val Ile Val Ala Leu Ser Ser Lys Ser Trp Asp Val Glu Thr
            180                 185                 190

Ala Thr Glu Leu Leu Leu Ser Asn
        195                 200

<210> SEQ ID NO 25
<211> LENGTH: 428
<212> TYPE: PRT
<213> ORGANISM: Arabidopsis thaliana

<400> SEQUENCE: 25

Met Ala Thr Ala Phe Ala Pro Thr Lys Leu Thr Ala Thr Val Pro Leu
1               5                   10                  15

His Gly Ser His Glu Asn Arg Leu Leu Leu Pro Ile Arg Leu Ala Pro
            20                  25                  30

Pro Ser Ser Phe Leu Gly Ser Thr Arg Ser Leu Ser Leu Arg Arg Leu
        35                  40                  45

Asn His Ser Asn Ala Thr Arg Arg Ser Pro Val Val Ser Val Gln Glu
    50                  55                  60

Val Val Lys Glu Lys Gln Ser Thr Asn Asn Thr Ser Leu Leu Ile Thr
65                  70                  75                  80

Lys Glu Glu Gly Leu Glu Leu Tyr Glu Asp Met Ile Leu Gly Arg Ser
                85                  90                  95

Phe Glu Asp Met Cys Ala Gln Met Tyr Tyr Arg Gly Lys Met Phe Gly
            100                 105                 110

Phe Val His Leu Tyr Asn Gly Gln Glu Ala Val Ser Thr Gly Phe Ile
        115                 120                 125

Lys Leu Leu Thr Lys Ser Asp Ser Val Val Ser Thr Tyr Arg Asp His
    130                 135                 140

Val His Ala Leu Ser Lys Gly Val Ser Ala Arg Ala Val Met Ser Glu
145                 150                 155                 160

Leu Phe Gly Lys Val Thr Gly Cys Cys Arg Gly Gln Gly Gly Ser Met
                165                 170                 175

His Met Phe Ser Lys Glu His Asn Met Leu Gly Gly Phe Ala Phe Ile
            180                 185                 190

Gly Glu Gly Ile Pro Val Ala Thr Gly Ala Ala Phe Ser Ser Lys Tyr
        195                 200                 205

Arg Arg Glu Val Leu Lys Gln Asp Cys Asp Asp Val Thr Val Ala Phe
    210                 215                 220

Phe Gly Asp Gly Thr Cys Asn Asn Gly Gln Phe Phe Glu Cys Leu Asn
225                 230                 235                 240

Met Ala Ala Leu Tyr Lys Leu Pro Ile Ile Phe Val Val Glu Asn Asn
                245                 250                 255

Leu Trp Ala Ile Gly Met Ser His Leu Arg Ala Thr Ser Asp Pro Glu
            260                 265                 270

Ile Trp Lys Lys Gly Pro Ala Phe Gly Met Pro Gly Val His Val Asp
        275                 280                 285
```

```
Gly Met Asp Val Leu Lys Val Arg Glu Val Ala Lys Glu Ala Val Thr
    290                 295                 300
Arg Ala Arg Arg Gly Glu Gly Pro Thr Leu Val Glu Cys Glu Thr Tyr
305                 310                 315                 320
Arg Phe Arg Gly His Ser Leu Ala Asp Pro Asp Glu Leu Arg Asp Ala
                325                 330                 335
Ala Glu Lys Ala Lys Tyr Ala Ala Arg Asp Pro Ile Ala Ala Leu Lys
            340                 345                 350
Lys Tyr Leu Ile Glu Asn Lys Leu Ala Lys Ala Glu Leu Lys Ser
        355                 360                 365
Ile Glu Lys Lys Ile Asp Glu Leu Val Glu Ala Val Glu Phe Ala
    370                 375                 380
Asp Ala Ser Pro Gln Pro Gly Arg Ser Gln Leu Leu Glu Asn Val Phe
385                 390                 395                 400
Ala Asp Pro Lys Gly Phe Gly Ile Gly Pro Asp Gly Arg Tyr Arg Cys
                405                 410                 415
Glu Asp Pro Lys Phe Thr Glu Gly Thr Ala Gln Val
                420                 425
```

<210> SEQ ID NO 26
<211> LENGTH: 235
<212> TYPE: PRT
<213> ORGANISM: Mus musculus

<400> SEQUENCE: 26

```
Met Ala Arg Pro Leu Val Pro Ser Ser Gln Lys Ala Leu Leu Leu Glu
1               5                   10                  15
Leu Lys Gly Leu Gln Glu Glu Pro Val Glu Gly Phe Arg Val Thr Leu
            20                  25                  30
Val Asp Glu Gly Asp Leu Tyr Asn Trp Glu Val Ala Ile Phe Gly Pro
        35                  40                  45
Pro Asn Thr Tyr Tyr Glu Gly Gly Tyr Phe Lys Ala Arg Leu Lys Phe
    50                  55                  60
Pro Ile Asp Tyr Pro Tyr Ser Pro Pro Ala Phe Arg Phe Leu Thr Lys
65                  70                  75                  80
Met Trp His Pro Asn Ile Tyr Glu Thr Gly Asp Val Cys Ile Ser Ile
                85                  90                  95
Leu His Pro Pro Val Asp Asp Pro Gln Ser Gly Glu Leu Pro Ser Glu
            100                 105                 110
Arg Trp Asn Pro Thr Gln Asn Val Arg Thr Ile Leu Leu Ser Val Ile
        115                 120                 125
Ser Leu Leu Asn Glu Pro Asn Thr Phe Ser Pro Ala Asn Val Asp Ala
    130                 135                 140
Ser Val Met Tyr Arg Lys Trp Lys Glu Ser Lys Gly Lys Asp Arg Glu
145                 150                 155                 160
Tyr Thr Asp Ile Ile Arg Lys Gln Val Leu Gly Thr Lys Val Asp Ala
                165                 170                 175
Glu Arg Asp Gly Val Lys Val Pro Thr Thr Leu Ala Glu Tyr Cys Val
            180                 185                 190
Lys Thr Lys Ala Pro Ala Pro Asp Glu Gly Ser Asp Leu Phe Tyr Asp
        195                 200                 205
Asp Tyr Tyr Glu Asp Gly Glu Val Glu Ala Asp Ser Cys Phe Gly
    210                 215                 220
Asp Glu Glu Asp Ser Gly Thr Glu Glu Ser
225                 230                 235
```

```
<210> SEQ ID NO 27
<211> LENGTH: 172
<212> TYPE: PRT
<213> ORGANISM: Saccharomyces cerevisiae

<400> SEQUENCE: 27

Met Ser Thr Pro Ala Arg Arg Leu Met Arg Asp Phe Lys Arg Met
1               5                   10                  15

Lys Glu Asp Ala Pro Pro Gly Val Ser Ala Ser Pro Leu Pro Asp Asn
                20                  25                  30

Val Met Val Trp Asn Ala Met Ile Ile Gly Pro Ala Asp Thr Pro Tyr
            35                  40                  45

Glu Asp Gly Thr Phe Arg Leu Leu Leu Glu Phe Asp Glu Glu Tyr Pro
        50                  55                  60

Asn Lys Pro Pro His Val Lys Phe Leu Ser Glu Met Phe His Pro Asn
65                  70                  75                  80

Val Tyr Ala Asn Gly Glu Ile Cys Leu Asp Ile Leu Gln Asn Arg Trp
                85                  90                  95

Thr Pro Thr Tyr Asp Val Ala Ser Ile Leu Thr Ser Ile Gln Ser Leu
            100                 105                 110

Phe Asn Asp Pro Asn Pro Ala Ser Pro Ala Asn Val Glu Ala Ala Thr
        115                 120                 125

Leu Phe Lys Asp His Lys Ser Gln Tyr Val Lys Arg Val Lys Glu Thr
    130                 135                 140

Val Glu Lys Ser Trp Glu Asp Met Asp Asp Met Asp Asp Asp Asp Asp
145                 150                 155                 160

Asp Asp Asp Asp Asp Asp Asp Asp Glu Ala Asp
                165                 170

<210> SEQ ID NO 28
<211> LENGTH: 200
<212> TYPE: PRT
<213> ORGANISM: Mus musculus

<400> SEQUENCE: 28

Met Ala Asn Ile Ala Val Gln Arg Ile Lys Arg Glu Phe Lys Glu Val
1               5                   10                  15

Leu Lys Ser Glu Glu Thr Ser Lys Asn Gln Ile Lys Val Asp Leu Val
                20                  25                  30

Asp Glu Asn Phe Thr Glu Leu Arg Gly Glu Ile Ala Gly Pro Pro Asp
            35                  40                  45

Thr Pro Tyr Glu Gly Gly Arg Tyr Gln Leu Glu Ile Lys Ile Pro Glu
        50                  55                  60

Thr Tyr Pro Phe Asn Pro Pro Lys Val Arg Phe Ile Thr Lys Ile Trp
65                  70                  75                  80

His Pro Asn Ile Ser Ser Val Thr Gly Ala Ile Cys Leu Asp Ile Leu
                85                  90                  95

Lys Asp Gln Trp Ala Ala Ala Met Thr Leu Arg Thr Val Leu Leu Ser
            100                 105                 110

Leu Gln Ala Leu Leu Ala Ala Ala Glu Pro Asp Asp Pro Gln Asp Ala
        115                 120                 125

Val Val Ala Asn Gln Tyr Lys Gln Asn Pro Glu Met Phe Lys Gln Thr
    130                 135                 140

Ala Arg Leu Trp Ala His Val Tyr Ala Gly Ala Pro Val Ser Ser Pro
145                 150                 155                 160
```

Glu Tyr Thr Lys Lys Ile Glu Asn Leu Cys Ala Met Gly Phe Asp Arg
                165                 170                 175

Asn Ala Val Ile Val Ala Leu Ser Ser Lys Ser Trp Asp Val Glu Thr
            180                 185                 190

Ala Thr Glu Leu Leu Leu Ser Asn
        195                 200

<210> SEQ ID NO 29
<211> LENGTH: 153
<212> TYPE: PRT
<213> ORGANISM: Arabidopsis thaliana

<400> SEQUENCE: 29

Met Ala Asn Ser Asn Leu Pro Arg Arg Ile Ile Lys Glu Thr Gln Arg
1               5                   10                  15

Leu Leu Ser Glu Pro Ala Pro Gly Ile Ser Ala Ser Pro Ser Glu Asp
            20                  25                  30

Asn Met Arg Tyr Phe Asn Val Met Ile Leu Gly Pro Thr Gln Ser Pro
        35                  40                  45

Tyr Glu Gly Gly Val Phe Lys Leu Glu Leu Phe Leu Pro Glu Glu Tyr
    50                  55                  60

Pro Met Ala Ala Pro Lys Val Arg Phe Leu Thr Lys Ile Tyr His Pro
65                  70                  75                  80

Asn Ile Asp Lys Leu Gly Arg Ile Cys Leu Asp Ile Leu Lys Asp Lys
                85                  90                  95

Trp Ser Pro Ala Leu Gln Ile Arg Thr Val Leu Leu Ser Ile Gln Ala
            100                 105                 110

Leu Leu Ser Ala Pro Asn Pro Asp Asp Pro Leu Ser Glu Asn Ile Ala
        115                 120                 125

Lys His Trp Lys Ser Asn Glu Ala Glu Ala Val Asp Thr Ala Lys Glu
    130                 135                 140

Trp Thr Arg Leu Tyr Ala Ser Gly Ala
145                 150

<210> SEQ ID NO 30
<211> LENGTH: 295
<212> TYPE: PRT
<213> ORGANISM: Saccharomyces cerevisiae

<400> SEQUENCE: 30

Met Ser Ser Arg Lys Ser Thr Ala Ser Ser Leu Leu Leu Arg Gln Tyr
1               5                   10                  15

Arg Glu Leu Thr Asp Pro Lys Lys Ala Ile Pro Ser Phe His Ile Glu
            20                  25                  30

Leu Glu Asp Asp Ser Asn Ile Phe Thr Trp Asn Ile Gly Val Met Val
        35                  40                  45

Leu Asn Glu Asp Ser Ile Tyr His Gly Gly Phe Phe Lys Ala Gln Met
    50                  55                  60

Arg Phe Pro Glu Asp Phe Pro Phe Ser Pro Pro Gln Phe Arg Phe Thr
65                  70                  75                  80

Pro Ala Ile Tyr His Pro Asn Val Tyr Arg Asp Gly Arg Leu Cys Ile
                85                  90                  95

Ser Ile Leu His Gln Ser Gly Asp Pro Met Thr Asp Glu Pro Asp Ala
            100                 105                 110

Glu Thr Trp Ser Pro Val Gln Thr Val Glu Ser Val Leu Ile Ser Ile
        115                 120                 125

```
Val Ser Leu Leu Glu Asp Pro Asn Ile Asn Ser Pro Ala Asn Val Asp
    130                 135                 140

Ala Ala Val Asp Tyr Arg Lys Asn Pro Glu Gln Tyr Lys Gln Arg Val
145                 150                 155                 160

Lys Met Glu Val Glu Arg Ser Lys Gln Asp Ile Pro Lys Gly Phe Ile
                165                 170                 175

Met Pro Thr Ser Glu Ser Ala Tyr Ile Ser Gln Ser Lys Leu Asp Glu
            180                 185                 190

Pro Glu Ser Asn Lys Asp Met Ala Asp Asn Phe Trp Tyr Asp Ser Asp
        195                 200                 205

Leu Asp Asp Asp Glu Asn Gly Ser Val Ile Leu Gln Asp Asp Asp Tyr
    210                 215                 220

Asp Asp Gly Asn Asn His Ile Pro Phe Glu Asp Asp Val Tyr Asn
225                 230                 235                 240

Tyr Asn Asp Asn Asp Asp Asp Glu Arg Ile Glu Phe Glu Asp Asp
                245                 250                 255

Asp Asp Asp Asp Asp Asp Ser Ile Asp Asn Asp Ser Val Met Asp Arg
                260                 265                 270

Lys Gln Pro His Lys Ala Glu Asp Glu Ser Glu Asp Val Glu Asp Val
            275                 280                 285

Glu Arg Val Ser Lys Lys Ile
    290                 295

<210> SEQ ID NO 31
<211> LENGTH: 145
<212> TYPE: PRT
<213> ORGANISM: Homo sapiens

<400> SEQUENCE: 31

Met Ala Val Ser Thr Gly Val Lys Val Pro Arg Asn Phe Arg Leu Leu
1               5                   10                  15

Glu Glu Leu Glu Glu Gly Gln Lys Gly Val Gly Asp Gly Thr Val Ser
                20                  25                  30

Trp Gly Leu Glu Asp Asp Glu Asp Met Thr Leu Thr Arg Trp Thr Gly
            35                  40                  45

Met Ile Ile Gly Pro Pro Arg Thr Asn Tyr Glu Asn Arg Ile Tyr Ser
        50                  55                  60

Leu Lys Val Glu Cys Gly Pro Lys Tyr Pro Glu Ala Pro Pro Ser Val
65                  70                  75                  80

Arg Phe Val Thr Lys Ile Asn Met Asn Gly Ile Asn Asn Ser Ser Gly
                85                  90                  95

Met Val Asp Ala Arg Ser Ile Pro Val Leu Ala Lys Trp Gln Asn Ser
            100                 105                 110

Tyr Ser Ile Lys Val Val Leu Gln Glu Leu Arg Arg Leu Met Met Ser
        115                 120                 125

Lys Glu Asn Met Lys Leu Pro Gln Pro Pro Glu Gly Gln Thr Tyr Asn
    130                 135                 140

Asn
145

<210> SEQ ID NO 32
<211> LENGTH: 215
<212> TYPE: PRT
<213> ORGANISM: Saccharomyces cerevisiae

<400> SEQUENCE: 32
```

```
Met Ser Arg Ala Lys Arg Ile Met Lys Glu Ile Gln Ala Val Lys Asp
1               5                   10                  15

Asp Pro Ala Ala His Ile Thr Leu Glu Phe Val Ser Glu Ser Asp Ile
            20                  25                  30

His His Leu Lys Gly Thr Phe Leu Gly Pro Pro Gly Thr Pro Tyr Glu
        35                  40                  45

Gly Gly Lys Phe Val Val Asp Ile Glu Val Pro Met Glu Tyr Pro Phe
    50                  55                  60

Lys Pro Pro Lys Met Gln Phe Asp Thr Lys Val Tyr His Pro Asn Ile
65                  70                  75                  80

Ser Ser Val Thr Gly Ala Ile Cys Leu Asp Ile Leu Lys Asn Ala Trp
                85                  90                  95

Ser Pro Val Ile Thr Leu Lys Ser Ala Leu Ile Ser Leu Gln Ala Leu
            100                 105                 110

Leu Gln Ser Pro Glu Pro Asn Asp Pro Gln Asp Ala Glu Val Ala Gln
        115                 120                 125

His Tyr Leu Arg Asp Arg Glu Ser Phe Asn Lys Thr Ala Ala Leu Trp
    130                 135                 140

Thr Arg Leu Tyr Ala Ser Glu Thr Ser Asn Gly Gln Lys Gly Asn Val
145                 150                 155                 160

Glu Glu Ser Asp Leu Tyr Gly Ile Asp His Asp Leu Ile Asp Glu Phe
                165                 170                 175

Glu Ser Gln Gly Phe Glu Lys Asp Lys Ile Val Glu Val Leu Arg Arg
            180                 185                 190

Leu Gly Val Lys Ser Leu Asp Pro Asn Asp Asn Asn Thr Ala Asn Arg
        195                 200                 205

Ile Ile Glu Glu Leu Leu Lys
    210                 215

<210> SEQ ID NO 33
<211> LENGTH: 250
<212> TYPE: PRT
<213> ORGANISM: Saccharomyces cerevisiae

<400> SEQUENCE: 33

Met Ala Thr Lys Gln Ala His Lys Arg Leu Thr Lys Glu Tyr Lys Leu
1               5                   10                  15

Met Val Glu Asn Pro Pro Tyr Ile Leu Ala Arg Pro Asn Glu Asp
            20                  25                  30

Asn Ile Leu Glu Trp His Tyr Ile Ile Thr Gly Pro Ala Asp Thr Pro
        35                  40                  45

Tyr Lys Gly Gly Gln Tyr His Gly Thr Leu Thr Phe Pro Ser Asp Tyr
    50                  55                  60

Pro Tyr Lys Pro Pro Ala Ile Arg Met Ile Thr Pro Asn Gly Arg Phe
65                  70                  75                  80

Lys Pro Asn Thr Arg Leu Cys Leu Ser Met Ser Asp Tyr His Pro Asp
                85                  90                  95

Thr Trp Asn Pro Gly Trp Ser Val Ser Thr Ile Leu Asn Gly Leu Leu
            100                 105                 110

Ser Phe Met Thr Ser Asp Glu Ala Thr Thr Gly Ser Ile Thr Thr Ser
        115                 120                 125

Asp His Gln Lys Lys Thr Leu Ala Arg Asn Ser Ile Ser Tyr Asn Thr
    130                 135                 140

Phe Gln Asn Val Arg Phe Lys Leu Ile Phe Pro Glu Val Val Gln Glu
```

```
                145                 150                 155                 160
Asn Val Glu Thr Leu Glu Lys Arg Lys Leu Asp Glu Gly Asp Ala Ala
                    165                 170                 175

Asn Thr Gly Asp Glu Thr Glu Asp Pro Phe Thr Lys Ala Ala Lys Glu
                    180                 185                 190

Lys Val Ile Ser Leu Glu Glu Ile Leu Asp Pro Glu Asp Arg Ile Arg
                    195                 200                 205

Ala Glu Gln Ala Leu Arg Gln Ser Glu Asn Asn Ser Lys Lys Asp Gly
                    210                 215                 220

Lys Glu Pro Asn Asp Ser Ser Ser Met Val Tyr Ile Gly Ile Ala Ile
225                 230                 235                 240

Phe Leu Phe Leu Val Gly Leu Phe Met Lys
                    245                 250

<210> SEQ ID NO 34
<211> LENGTH: 148
<212> TYPE: PRT
<213> ORGANISM: Arabidopsis thaliana

<400> SEQUENCE: 34

Met Ala Ser Lys Arg Ile Leu Lys Glu Leu Lys Asp Leu Gln Lys Asp
1               5                   10                  15

Pro Pro Thr Ser Cys Ser Ala Gly Pro Val Ala Glu Asp Met Phe His
                20                  25                  30

Trp Gln Ala Thr Ile Met Gly Pro Ser Glu Ser Pro Tyr Ala Gly Gly
                35                  40                  45

Val Phe Leu Val Thr Ile His Phe Pro Pro Asp Tyr Pro Phe Lys Pro
        50                  55                  60

Pro Lys Val Ala Phe Arg Thr Lys Val Phe His Pro Asn Ile Asn Ser
65                  70                  75                  80

Asn Gly Ser Ile Cys Leu Asp Ile Leu Lys Glu Gln Trp Ser Pro Ala
                85                  90                  95

Leu Thr Ile Ser Lys Val Leu Leu Ser Ile Cys Ser Leu Leu Thr Asp
                100                 105                 110

Pro Asn Pro Asp Asp Pro Leu Val Pro Glu Ile Ala His Met Tyr Lys
                115                 120                 125

Thr Asp Lys Asn Lys Tyr Glu Ser Thr Ala Arg Ser Trp Thr Gln Lys
                130                 135                 140

Tyr Ala Met Gly
145

<210> SEQ ID NO 35
<211> LENGTH: 318
<212> TYPE: PRT
<213> ORGANISM: Mus musculus

<400> SEQUENCE: 35

Met Glu Thr Arg Tyr Asn Leu Lys Ser Pro Ala Val Lys Arg Leu Met
1               5                   10                  15

Lys Glu Ala Ala Glu Leu Lys Asp Pro Thr Asp His Tyr His Ala Gln
                20                  25                  30

Pro Leu Glu Asp Asn Leu Phe Glu Trp His Phe Thr Val Arg Gly Pro
                35                  40                  45

Pro Asp Ser Asp Phe Asp Gly Gly Val Tyr His Gly Arg Ile Val Leu
        50                  55                  60

Pro Pro Glu Tyr Pro Met Lys Pro Pro Ser Ile Ile Leu Leu Thr Ala
```

```
                65                  70                  75                  80
Asn Gly Arg Phe Glu Val Gly Lys Lys Ile Cys Leu Ser Ile Ser Gly
                    85                  90                  95

His His Pro Glu Thr Trp Gln Pro Ser Trp Ser Ile Arg Thr Ala Leu
                100                 105                 110

Leu Ala Ile Ile Gly Phe Met Pro Thr Lys Gly Glu Gly Ala Ile Gly
                115                 120                 125

Ser Leu Asp Tyr Thr Pro Glu Glu Arg Arg Ala Leu Ala Lys Lys Ser
            130                 135                 140

Gln Asp Phe Cys Cys Glu Gly Cys Gly Ser Ala Met Lys Asp Val Leu
145                 150                 155                 160

Leu Pro Leu Lys Ser Gly Ser Gly Ser Ser Gln Ala Asp Gln Glu Ala
                165                 170                 175

Lys Glu Leu Ala Arg Gln Ile Ser Phe Lys Ala Glu Val Asn Ser Ser
                180                 185                 190

Gly Lys Thr Ile Ala Glu Ser Asp Leu Asn Gln Cys Phe Ser Leu Asn
            195                 200                 205

Asp Ser Gln Asp Leu Pro Thr Thr Phe Gln Gly Ala Thr Ala Ser
210                 215                 220

Thr Ser Tyr Gly Ala Gln Asn Pro Ser Gly Ala Pro Leu Pro Gln Pro
225                 230                 235                 240

Thr Gln Pro Ala Pro Lys Asn Thr Ser Met Ser Pro Arg Gln Arg Arg
                245                 250                 255

Ala Gln Gln Gln Ser Gln Arg Arg Pro Ser Thr Ser Pro Asp Val Leu
                260                 265                 270

Gln Gly Gln Pro Pro Arg Ala His His Thr Glu His Gly Gly Ser Ala
            275                 280                 285

Met Leu Ile Ile Ile Leu Thr Leu Ala Leu Ala Ala Leu Ile Phe Arg
290                 295                 300

Arg Ile Tyr Leu Ala Asn Glu Tyr Ile Phe Asp Phe Glu Leu
305                 310                 315

<210> SEQ ID NO 36
<211> LENGTH: 148
<212> TYPE: PRT
<213> ORGANISM: Arabidopsis thaliana

<400> SEQUENCE: 36

Met Ala Ser Lys Arg Ile Leu Lys Glu Leu Lys Asp Leu Gln Lys Asp
1               5                   10                  15

Pro Pro Ser Asn Cys Ser Ala Gly Pro Val Ala Glu Asp Met Phe His
                20                  25                  30

Trp Gln Ala Thr Ile Met Gly Pro Pro Glu Ser Pro Tyr Ala Gly Gly
            35                  40                  45

Val Phe Leu Val Ser Ile His Phe Pro Pro Asp Tyr Pro Phe Lys Pro
        50                  55                  60

Pro Lys Val Ser Phe Lys Thr Lys Val Tyr His Pro Asn Ile Asn Ser
65                  70                  75                  80

Asn Gly Ser Ile Cys Leu Asp Ile Leu Lys Glu Gln Trp Ser Pro Ala
                85                  90                  95

Leu Thr Ile Ser Lys Val Leu Leu Ser Ile Cys Ser Leu Leu Thr Asp
                100                 105                 110

Pro Asn Pro Asp Asp Pro Leu Val Pro Glu Ile Ala His Met Tyr Lys
            115                 120                 125
```

```
Thr Asp Arg Ser Lys Tyr Glu Ser Thr Ala Arg Ser Trp Thr Gln Lys
            130                 135                 140

Tyr Ala Met Gly
145

<210> SEQ ID NO 37
<211> LENGTH: 491
<212> TYPE: PRT
<213> ORGANISM: Homo sapiens

<400> SEQUENCE: 37

Met Cys Asn Thr Asn Met Ser Val Pro Thr Asp Gly Ala Val Thr Thr
  1               5                  10                  15

Ser Gln Ile Pro Ala Ser Glu Gln Glu Thr Leu Val Arg Pro Lys Pro
             20                  25                  30

Leu Leu Leu Lys Leu Leu Lys Ser Val Gly Ala Gln Lys Asp Thr Tyr
         35                  40                  45

Thr Met Lys Glu Val Leu Phe Tyr Leu Gly Gln Tyr Ile Met Thr Lys
     50                  55                  60

Arg Leu Tyr Asp Glu Lys Gln Gln His Ile Val Tyr Cys Ser Asn Asp
 65                  70                  75                  80

Leu Leu Gly Asp Leu Phe Gly Val Pro Ser Phe Ser Val Lys Glu His
                 85                  90                  95

Arg Lys Ile Tyr Thr Met Ile Tyr Arg Asn Leu Val Val Val Asn Gln
            100                 105                 110

Gln Glu Ser Ser Asp Ser Gly Thr Ser Val Ser Glu Asn Arg Cys His
        115                 120                 125

Leu Glu Gly Gly Ser Asp Gln Lys Asp Leu Val Gln Glu Leu Gln Glu
    130                 135                 140

Glu Lys Pro Ser Ser Ser His Leu Val Ser Arg Pro Ser Thr Ser Ser
145                 150                 155                 160

Arg Arg Arg Ala Ile Ser Glu Thr Glu Glu Asn Ser Asp Glu Leu Ser
                165                 170                 175

Gly Glu Arg Gln Arg Lys Arg His Lys Ser Asp Ser Ile Ser Leu Ser
            180                 185                 190

Phe Asp Glu Ser Leu Ala Leu Cys Val Ile Arg Glu Ile Cys Cys Glu
        195                 200                 205

Arg Ser Ser Ser Glu Ser Thr Gly Thr Pro Ser Asn Pro Asp Leu
    210                 215                 220

Asp Ala Gly Val Ser Glu His Ser Gly Asp Trp Leu Asp Gln Asp Ser
225                 230                 235                 240

Val Ser Asp Gln Phe Ser Val Glu Phe Glu Val Glu Ser Leu Asp Ser
                245                 250                 255

Glu Asp Tyr Ser Leu Ser Glu Glu Gly Gln Glu Leu Ser Asp Glu Asp
            260                 265                 270

Asp Glu Val Tyr Gln Val Thr Val Tyr Gln Ala Gly Glu Ser Asp Thr
        275                 280                 285

Asp Ser Phe Glu Glu Asp Pro Glu Ile Ser Leu Ala Asp Tyr Trp Lys
    290                 295                 300

Cys Thr Ser Cys Asn Glu Met Asn Pro Pro Leu Pro Ser His Cys Asn
305                 310                 315                 320

Arg Cys Trp Ala Leu Arg Glu Asn Trp Leu Pro Glu Asp Lys Gly Lys
                325                 330                 335

Asp Lys Gly Glu Ile Ser Glu Lys Ala Lys Leu Glu Asn Ser Thr Gln
            340                 345                 350
```

```
Ala Glu Glu Gly Phe Asp Val Pro Asp Cys Lys Lys Thr Ile Val Asn
            355                 360                 365

Asp Ser Arg Glu Ser Cys Val Glu Glu Asn Asp Asp Lys Ile Thr Gln
370                 375                 380

Ala Ser Gln Ser Gln Glu Ser Glu Asp Tyr Ser Gln Pro Ser Thr Ser
385                 390                 395                 400

Ser Ser Ile Ile Tyr Ser Ser Gln Glu Asp Val Lys Glu Phe Glu Arg
                405                 410                 415

Glu Glu Thr Gln Asp Lys Glu Glu Ser Val Glu Ser Ser Leu Pro Leu
            420                 425                 430

Asn Ala Ile Glu Pro Cys Val Ile Cys Gln Gly Arg Pro Lys Asn Gly
            435                 440                 445

Cys Ile Val His Gly Lys Thr Gly His Leu Met Ala Cys Phe Thr Cys
            450                 455                 460

Ala Lys Lys Leu Lys Lys Arg Asn Lys Pro Cys Pro Val Cys Arg Gln
465                 470                 475                 480

Pro Ile Gln Met Ile Val Leu Thr Tyr Phe Pro
            485                 490

<210> SEQ ID NO 38
<211> LENGTH: 465
<212> TYPE: PRT
<213> ORGANISM: Homo sapiens

<400> SEQUENCE: 38

Met Ile Val Phe Val Arg Phe Asn Ser Ser His Gly Phe Pro Val Glu
1               5                   10                  15

Val Asp Ser Asp Thr Ser Ile Phe Gln Leu Lys Glu Val Val Ala Lys
            20                  25                  30

Arg Gln Gly Val Pro Ala Asp Gln Leu Arg Val Ile Phe Ala Gly Lys
        35                  40                  45

Glu Leu Arg Asn Asp Trp Thr Val Gln Asn Cys Asp Leu Asp Gln Gln
50                  55                  60

Ser Ile Val His Ile Val Gln Arg Pro Trp Arg Lys Gly Gln Glu Met
65                  70                  75                  80

Asn Ala Thr Gly Gly Asp Asp Pro Arg Asn Ala Ala Gly Gly Cys Glu
                85                  90                  95

Arg Glu Pro Gln Ser Leu Thr Arg Val Asp Leu Ser Ser Ser Val Leu
            100                 105                 110

Pro Gly Asp Ser Val Gly Leu Ala Val Ile Leu His Thr Asp Ser Arg
        115                 120                 125

Lys Asp Ser Pro Pro Ala Gly Ser Pro Ala Gly Arg Ser Ile Tyr Asn
130                 135                 140

Ser Phe Tyr Val Tyr Cys Lys Gly Pro Cys Gln Arg Val Gln Pro Gly
145                 150                 155                 160

Lys Leu Arg Val Gln Cys Ser Thr Cys Arg Gln Ala Thr Leu Thr Leu
                165                 170                 175

Thr Gln Gly Pro Ser Cys Trp Asp Asp Val Leu Ile Pro Asn Arg Met
            180                 185                 190

Ser Gly Glu Cys Gln Ser Pro His Cys Pro Gly Thr Ser Ala Glu Phe
        195                 200                 205

Phe Phe Lys Cys Gly Ala His Pro Thr Ser Asp Lys Glu Thr Ser Val
210                 215                 220

Ala Leu His Leu Ile Ala Thr Asn Ser Arg Asn Ile Thr Cys Ile Thr
```

```
               225                 230                 235                 240
Cys Thr Asp Val Arg Ser Pro Val Leu Val Phe Gln Cys Asn Ser Arg
            245                 250                 255

His Val Ile Cys Leu Asp Cys Phe His Leu Tyr Cys Val Thr Arg Leu
            260                 265                 270

Asn Asp Arg Gln Phe Val His Asp Pro Gln Leu Gly Tyr Ser Leu Pro
            275                 280                 285

Cys Val Ala Gly Cys Pro Asn Ser Leu Ile Lys Glu Leu His His Phe
            290                 295                 300

Arg Ile Leu Gly Glu Glu Gln Tyr Asn Arg Tyr Gln Gln Tyr Gly Ala
305                 310                 315                 320

Glu Glu Cys Val Leu Gln Met Gly Gly Val Leu Cys Pro Arg Pro Gly
                325                 330                 335

Cys Gly Ala Gly Leu Leu Pro Glu Pro Asp Gln Arg Lys Val Thr Cys
            340                 345                 350

Glu Gly Gly Asn Gly Leu Gly Cys Gly Phe Ala Phe Cys Arg Glu Cys
            355                 360                 365

Lys Glu Ala Tyr His Glu Gly Glu Cys Ser Ala Val Phe Glu Ala Ser
            370                 375                 380

Gly Thr Thr Thr Gln Ala Tyr Arg Val Asp Glu Arg Ala Ala Glu Gln
385                 390                 395                 400

Ala Arg Trp Glu Ala Ala Ser Lys Glu Thr Ile Lys Lys Thr Thr Lys
                405                 410                 415

Pro Cys Pro Arg Cys His Val Pro Val Glu Lys Asn Gly Gly Cys Met
            420                 425                 430

His Met Lys Cys Pro Gln Pro Gln Cys Arg Leu Glu Trp Cys Trp Asn
            435                 440                 445

Cys Gly Cys Glu Trp Asn Arg Val Cys Met Gly Asp His Trp Phe Asp
            450                 455                 460

Val
465

<210> SEQ ID NO 39
<211> LENGTH: 1863
<212> TYPE: PRT
<213> ORGANISM: Homo sapiens

<400> SEQUENCE: 39

Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
                20                  25                  30

Glu Pro Val Ser Thr Lys Cys Asp His Ile Phe Cys Lys Phe Cys Met
            35                  40                  45

Leu Lys Leu Leu Asn Gln Lys Lys Gly Pro Ser Gln Cys Pro Leu Cys
        50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
            115                 120                 125
```

```
Gly Tyr Arg Asn Arg Ala Lys Arg Leu Leu Gln Ser Glu Pro Glu Asn
            130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
        195                 200                 205

Pro Gln Gly Thr Arg Asp Glu Ile Ser Leu Asp Ser Ala Lys Lys Ala
210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255

His Pro Glu Lys Tyr Gln Gly Ser Ser Val Ser Asn Leu His Val Glu
            260                 265                 270

Pro Cys Gly Thr Asn Thr His Ala Ser Ser Leu Gln His Glu Asn Ser
        275                 280                 285

Ser Leu Leu Leu Thr Lys Asp Arg Met Asn Val Glu Lys Ala Glu Phe
290                 295                 300

Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
                325                 330                 335

Glu Lys Lys Val Asp Leu Asn Ala Asp Pro Leu Cys Glu Arg Lys Glu
            340                 345                 350

Trp Asn Lys Gln Lys Leu Pro Cys Ser Glu Asn Pro Arg Asp Thr Glu
        355                 360                 365

Asp Val Pro Trp Ile Thr Leu Asn Ser Ser Ile Gln Lys Val Asn Glu
370                 375                 380

Trp Phe Ser Arg Ser Asp Glu Leu Leu Gly Ser Asp Asp Ser His Asp
385                 390                 395                 400

Gly Glu Ser Glu Ser Asn Ala Lys Val Ala Asp Val Leu Asp Val Leu
                405                 410                 415

Asn Glu Val Asp Glu Tyr Ser Gly Ser Ser Glu Lys Ile Asp Leu Leu
            420                 425                 430

Ala Ser Asp Pro His Glu Ala Leu Ile Cys Lys Ser Glu Arg Val His
        435                 440                 445

Ser Lys Ser Val Glu Ser Asn Ile Glu Asp Lys Ile Phe Gly Lys Thr
450                 455                 460

Tyr Arg Lys Lys Ala Ser Leu Pro Asn Leu Ser His Val Thr Glu Asn
465                 470                 475                 480

Leu Ile Ile Gly Ala Phe Val Thr Glu Pro Gln Ile Ile Gln Glu Arg
                485                 490                 495

Pro Leu Thr Asn Lys Leu Lys Arg Lys Arg Arg Pro Thr Ser Gly Leu
            500                 505                 510

His Pro Glu Asp Phe Ile Lys Lys Ala Asp Leu Ala Val Gln Lys Thr
        515                 520                 525

Pro Glu Met Ile Asn Gln Gly Thr Asn Gln Thr Glu Gln Asn Gly Gln
530                 535                 540

Val Met Asn Ile Thr Asn Ser Gly His Glu Asn Lys Thr Lys Gly Asp
```

-continued

```
545                 550                 555                 560
Ser Ile Gln Asn Glu Lys Asn Pro Asn Pro Ile Glu Ser Leu Glu Lys
                    565                 570                 575

Glu Ser Ala Phe Lys Thr Lys Ala Glu Pro Ile Ser Ser Ile Ser
            580                 585                 590

Asn Met Glu Leu Glu Leu Asn Ile His Asn Ser Lys Ala Pro Lys Lys
            595                 600                 605

Asn Arg Leu Arg Arg Lys Ser Ser Thr Arg His Ile His Ala Leu Glu
610                 615                 620

Leu Val Val Ser Arg Asn Leu Ser Pro Pro Asn Cys Thr Glu Leu Gln
625                 630                 635                 640

Ile Asp Ser Cys Ser Ser Ser Glu Glu Ile Lys Lys Lys Lys Tyr Asn
                    645                 650                 655

Gln Met Pro Val Arg His Ser Arg Asn Leu Gln Leu Met Glu Gly Lys
                660                 665                 670

Glu Pro Ala Thr Gly Ala Lys Lys Ser Asn Lys Pro Asn Glu Gln Thr
            675                 680                 685

Ser Lys Arg His Asp Ser Asp Thr Phe Pro Glu Leu Lys Leu Thr Asn
        690                 695                 700

Ala Pro Gly Ser Phe Thr Lys Cys Ser Asn Thr Ser Glu Leu Lys Glu
705                 710                 715                 720

Phe Val Asn Pro Ser Leu Pro Arg Glu Glu Lys Glu Glu Lys Leu Glu
                    725                 730                 735

Thr Val Lys Val Ser Asn Asn Ala Glu Asp Pro Lys Asp Leu Met Leu
                740                 745                 750

Ser Gly Glu Arg Val Leu Gln Thr Glu Arg Ser Val Glu Ser Ser Ser
            755                 760                 765

Ile Ser Leu Val Pro Gly Thr Asp Tyr Gly Thr Gln Glu Ser Ile Ser
        770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
                    805                 810                 815

Gly Cys Ser Lys Asp Asn Arg Asn Asp Thr Glu Gly Phe Lys Tyr Pro
                820                 825                 830

Leu Gly His Glu Val Asn His Ser Arg Glu Thr Ser Ile Glu Met Glu
            835                 840                 845

Glu Ser Glu Leu Asp Ala Gln Tyr Leu Gln Asn Thr Phe Lys Val Ser
850                 855                 860

Lys Arg Gln Ser Phe Ala Pro Phe Ser Asn Pro Gly Asn Ala Glu Glu
865                 870                 875                 880

Glu Cys Ala Thr Phe Ser Ala His Ser Gly Ser Leu Lys Lys Gln Ser
                    885                 890                 895

Pro Lys Val Thr Phe Glu Cys Glu Gln Lys Glu Glu Asn Gln Gly Lys
                900                 905                 910

Asn Glu Ser Asn Ile Lys Pro Val Gln Thr Val Asn Ile Thr Ala Gly
            915                 920                 925

Phe Pro Val Val Gly Gln Lys Asp Lys Pro Val Asp Asn Ala Lys Cys
        930                 935                 940

Ser Ile Lys Gly Gly Ser Arg Phe Cys Leu Ser Ser Gln Phe Arg Gly
945                 950                 955                 960

Asn Glu Thr Gly Leu Ile Thr Pro Asn Lys His Gly Leu Leu Gln Asn
                    965                 970                 975
```

```
Pro Tyr Arg Ile Pro Pro Leu Phe Pro Ile Lys Ser Phe Val Lys Thr
            980                 985                 990

Lys Cys Lys Lys Asn Leu Leu Glu Glu Asn Phe Glu Glu His Ser Met
        995                 1000                1005

Ser Pro Glu Arg Glu Met Gly Asn Glu Asn Ile Pro Ser Thr Val
    1010                1015                1020

Ser Thr Ile Ser Arg Asn Asn Ile Arg Glu Asn Val Phe Lys Glu
    1025                1030                1035

Ala Ser Ser Ser Asn Ile Asn Glu Val Gly Ser Ser Thr Asn Glu
    1040                1045                1050

Val Gly Ser Ser Ile Asn Glu Ile Gly Ser Ser Asp Glu Asn Ile
    1055                1060                1065

Gln Ala Glu Leu Gly Arg Asn Arg Gly Pro Lys Leu Asn Ala Met
    1070                1075                1080

Leu Arg Leu Gly Val Leu Gln Pro Glu Val Tyr Lys Gln Ser Leu
    1085                1090                1095

Pro Gly Ser Asn Cys Lys His Pro Glu Ile Lys Lys Gln Glu Tyr
    1100                1105                1110

Glu Glu Val Val Gln Thr Val Asn Thr Asp Phe Ser Pro Tyr Leu
    1115                1120                1125

Ile Ser Asp Asn Leu Glu Gln Pro Met Gly Ser Ser His Ala Ser
    1130                1135                1140

Gln Val Cys Ser Glu Thr Pro Asp Asp Leu Leu Asp Asp Gly Glu
    1145                1150                1155

Ile Lys Glu Asp Thr Ser Phe Ala Glu Asn Asp Ile Lys Glu Ser
    1160                1165                1170

Ser Ala Val Phe Ser Lys Ser Val Gln Lys Gly Glu Leu Ser Arg
    1175                1180                1185

Ser Pro Ser Pro Phe Thr His Thr His Leu Ala Gln Gly Tyr Arg
    1190                1195                1200

Arg Gly Ala Lys Lys Leu Glu Ser Ser Glu Glu Asn Leu Ser Ser
    1205                1210                1215

Glu Asp Glu Glu Leu Pro Cys Phe Gln His Leu Leu Phe Gly Lys
    1220                1225                1230

Val Asn Asn Ile Pro Ser Gln Ser Thr Arg His Ser Thr Val Ala
    1235                1240                1245

Thr Glu Cys Leu Ser Lys Asn Thr Glu Glu Asn Leu Leu Ser Leu
    1250                1255                1260

Lys Asn Ser Leu Asn Asp Cys Ser Asn Gln Val Ile Leu Ala Lys
    1265                1270                1275

Ala Ser Gln Glu His His Leu Ser Glu Glu Thr Lys Cys Ser Ala
    1280                1285                1290

Ser Leu Phe Ser Ser Gln Cys Ser Glu Leu Glu Asp Leu Thr Ala
    1295                1300                1305

Asn Thr Asn Thr Gln Asp Pro Phe Leu Ile Gly Ser Ser Lys Gln
    1310                1315                1320

Met Arg His Gln Ser Glu Ser Gln Gly Val Gly Leu Ser Asp Lys
    1325                1330                1335

Glu Leu Val Ser Asp Asp Glu Glu Arg Gly Thr Gly Leu Glu Glu
    1340                1345                1350

Asn Asn Gln Glu Glu Gln Ser Met Asp Ser Asn Leu Gly Glu Ala
    1355                1360                1365
```

```
Ala Ser Gly Cys Glu Ser Glu Thr Ser Val Ser Glu Asp Cys Ser
1370                1375                1380

Gly Leu Ser Ser Gln Ser Asp Ile Leu Thr Thr Gln Gln Arg Asp
1385                1390                1395

Thr Met Gln His Asn Leu Ile Lys Leu Gln Gln Glu Met Ala Glu
1400                1405                1410

Leu Glu Ala Val Leu Glu Gln His Gly Ser Gln Pro Ser Asn Ser
1415                1420                1425

Tyr Pro Ser Ile Ile Ser Asp Ser Ser Ala Leu Glu Asp Leu Arg
1430                1435                1440

Asn Pro Glu Gln Ser Thr Ser Glu Lys Ala Val Leu Thr Ser Gln
1445                1450                1455

Lys Ser Ser Glu Tyr Pro Ile Ser Gln Asn Pro Glu Gly Leu Ser
1460                1465                1470

Ala Asp Lys Phe Glu Val Ser Ala Asp Ser Ser Thr Ser Lys Asn
1475                1480                1485

Lys Glu Pro Gly Val Glu Arg Ser Ser Pro Ser Lys Cys Pro Ser
1490                1495                1500

Leu Asp Asp Arg Trp Tyr Met His Ser Cys Ser Gly Ser Leu Gln
1505                1510                1515

Asn Arg Asn Tyr Pro Ser Gln Glu Glu Leu Ile Lys Val Val Asp
1520                1525                1530

Val Glu Glu Gln Gln Leu Glu Glu Ser Gly Pro His Asp Leu Thr
1535                1540                1545

Glu Thr Ser Tyr Leu Pro Arg Gln Asp Leu Glu Gly Thr Pro Tyr
1550                1555                1560

Leu Glu Ser Gly Ile Ser Leu Phe Ser Asp Asp Pro Glu Ser Asp
1565                1570                1575

Pro Ser Glu Asp Arg Ala Pro Glu Ser Ala Arg Val Gly Asn Ile
1580                1585                1590

Pro Ser Ser Thr Ser Ala Leu Lys Val Pro Gln Leu Lys Val Ala
1595                1600                1605

Glu Ser Ala Gln Ser Pro Ala Ala Ala His Thr Thr Asp Thr Ala
1610                1615                1620

Gly Tyr Asn Ala Met Glu Glu Ser Val Ser Arg Glu Lys Pro Glu
1625                1630                1635

Leu Thr Ala Ser Thr Glu Arg Val Asn Lys Arg Met Ser Met Val
1640                1645                1650

Val Ser Gly Leu Thr Pro Glu Glu Phe Met Leu Val Tyr Lys Phe
1655                1660                1665

Ala Arg Lys His His Ile Thr Leu Thr Asn Leu Ile Thr Glu Glu
1670                1675                1680

Thr Thr His Val Val Met Lys Thr Asp Ala Glu Phe Val Cys Glu
1685                1690                1695

Arg Thr Leu Lys Tyr Phe Leu Gly Ile Ala Gly Gly Lys Trp Val
1700                1705                1710

Val Ser Tyr Phe Trp Val Thr Gln Ser Ile Lys Glu Arg Lys Met
1715                1720                1725

Leu Asn Glu His Asp Phe Glu Val Arg Gly Asp Val Val Asn Gly
1730                1735                1740

Arg Asn His Gln Gly Pro Lys Arg Ala Arg Glu Ser Gln Asp Arg
1745                1750                1755

Lys Ile Phe Arg Gly Leu Glu Ile Cys Cys Tyr Gly Pro Phe Thr
```

```
                1760                1765                1770
Asn Met Pro Thr Asp Gln Leu Glu Trp Met Val Gln Leu Cys Gly
    1775                1780                1785

Ala Ser Val Val Lys Glu Leu Ser Ser Phe Thr Leu Gly Thr Gly
    1790                1795                1800

Val His Pro Ile Val Val Val Gln Pro Asp Ala Trp Thr Glu Asp
    1805                1810                1815

Asn Gly Phe His Ala Ile Gly Gln Met Cys Glu Ala Pro Val Val
    1820                1825                1830

Thr Arg Glu Trp Val Leu Asp Ser Val Ala Leu Tyr Gln Cys Gln
    1835                1840                1845

Glu Leu Asp Thr Tyr Leu Ile Pro Gln Ile Pro His Ser His Tyr
    1850                1855                1860

<210> SEQ ID NO 40
<211> LENGTH: 809
<212> TYPE: PRT
<213> ORGANISM: Saccharomyces cerevisiae

<400> SEQUENCE: 40

Met Pro Ser Ser Ile Ser Val Lys Leu Val Ala Ala Glu Ser Leu Tyr
1               5                   10                  15

Lys Arg Asp Val Phe Arg Ser Pro Asp Pro Phe Ala Val Leu Thr Ile
                20                  25                  30

Asp Gly Tyr Gln Thr Lys Ser Thr Ser Ala Ala Lys Lys Thr Leu Asn
            35                  40                  45

Pro Tyr Trp Asn Glu Thr Phe Lys Phe Asp Asp Ile Asn Glu Asn Ser
    50                  55                  60

Ile Leu Thr Ile Gln Val Phe Asp Gln Lys Lys Phe Lys Lys Lys Asp
65                  70                  75                  80

Gln Gly Phe Leu Gly Val Val Asn Val Arg Val Gly Asp Val Leu Gly
                85                  90                  95

His Leu Asp Glu Asp Thr Ala Thr Ser Ser Gly Arg Pro Arg Glu Glu
                100                 105                 110

Thr Ile Thr Arg Asp Leu Lys Lys Ser Asn Asp Gly Met Ala Val Ser
            115                 120                 125

Gly Arg Leu Ile Val Val Leu Ser Lys Leu Pro Ser Ser Ser Pro His
        130                 135                 140

Ser Gln Ala Pro Ser Gly His Thr Ala Ser Ser Ser Thr Asn Thr Ser
145                 150                 155                 160

Ser Thr Thr Arg Thr Asn Gly His Ser Thr Ser Ser Thr Arg Asn His
                165                 170                 175

Ser Thr Ser His Pro Ser Arg Gly Thr Ala Gln Ala Val Glu Ser Thr
            180                 185                 190

Leu Gln Ser Gly Thr Thr Ala Ala Thr Asn Thr Ala Thr Thr Ser His
        195                 200                 205

Arg Ser Thr Asn Ser Thr Ser Ser Ala Thr Arg Gln Tyr Ser Ser Phe
    210                 215                 220

Glu Asp Gln Tyr Gly Arg Leu Pro Pro Gly Trp Glu Arg Arg Thr Asp
225                 230                 235                 240

Asn Phe Gly Arg Thr Tyr Tyr Val Asp His Asn Thr Arg Thr Thr Thr
                245                 250                 255

Trp Lys Arg Pro Thr Leu Asp Thr Glu Ala Glu Arg Gly Asn Gln
            260                 265                 270
```

```
Leu Asn Ala Asn Thr Glu Leu Glu Arg Arg Gln His Arg Gly Arg Thr
            275                 280                 285
Leu Pro Gly Gly Ser Ser Asp Asn Ser Ser Val Thr Val Gln Val Gly
        290                 295                 300
Gly Gly Ser Asn Ile Pro Pro Val Asn Gly Ala Ala Ala Ala Phe
305                 310                 315                 320
Ala Ala Thr Gly Gly Thr Thr Ser Gly Leu Gly Leu Pro Ser Gly
            325                 330                 335
Trp Glu Gln Arg Phe Thr Pro Glu Gly Arg Ala Tyr Phe Val Asp His
            340                 345                 350
Asn Thr Arg Thr Thr Thr Trp Val Asp Pro Arg Gln Gln Tyr Ile
        355                 360                 365
Arg Thr Tyr Gly Pro Thr Asn Thr Thr Ile Gln Gln Gln Pro Val Ser
    370                 375                 380
Gln Leu Gly Pro Leu Pro Ser Gly Trp Glu Met Arg Leu Thr Asn Thr
385                 390                 395                 400
Ala Arg Val Tyr Phe Val Asp His Asn Thr Lys Thr Thr Thr Trp Asp
            405                 410                 415
Asp Pro Arg Leu Pro Ser Ser Leu Asp Gln Asn Val Pro Gln Tyr Lys
        420                 425                 430
Arg Asp Phe Arg Arg Lys Val Ile Tyr Phe Arg Ser Gln Pro Ala Leu
    435                 440                 445
Arg Ile Leu Pro Gly Gln Cys His Ile Lys Val Arg Arg Lys Asn Ile
    450                 455                 460
Phe Glu Asp Ala Tyr Gln Glu Ile Met Arg Gln Thr Pro Glu Asp Leu
465                 470                 475                 480
Lys Lys Arg Leu Met Ile Lys Phe Asp Gly Glu Glu Gly Leu Asp Tyr
            485                 490                 495
Gly Gly Val Ser Arg Glu Phe Phe Leu Leu Ser His Glu Met Phe
        500                 505                 510
Asn Pro Phe Tyr Cys Leu Phe Glu Tyr Ser Ala Tyr Asp Asn Tyr Thr
        515                 520                 525
Ile Gln Ile Asn Pro Asn Ser Gly Ile Asn Pro Glu His Leu Asn Tyr
    530                 535                 540
Phe Lys Phe Ile Gly Arg Val Val Gly Leu Gly Val Phe His Arg Arg
545                 550                 555                 560
Phe Leu Asp Ala Phe Phe Val Gly Ala Leu Tyr Lys Met Met Leu Arg
            565                 570                 575
Lys Lys Val Val Leu Gln Asp Met Glu Gly Val Asp Ala Glu Val Tyr
        580                 585                 590
Asn Ser Leu Asn Trp Met Leu Glu Asn Ser Ile Asp Gly Val Leu Asp
    595                 600                 605
Leu Thr Phe Ser Ala Asp Asp Glu Arg Phe Gly Glu Val Val Thr Val
    610                 615                 620
Asp Leu Lys Pro Asp Gly Arg Asn Ile Glu Val Thr Asp Gly Asn Lys
625                 630                 635                 640
Lys Glu Tyr Val Glu Leu Tyr Thr Gln Trp Arg Ile Val Asp Arg Val
            645                 650                 655
Gln Glu Gln Phe Lys Ala Phe Met Asp Gly Phe Asn Glu Leu Ile Pro
        660                 665                 670
Glu Asp Leu Val Thr Val Phe Asp Glu Arg Glu Leu Glu Leu Leu Ile
    675                 680                 685
Gly Gly Ile Ala Glu Ile Asp Ile Glu Asp Trp Lys Lys His Thr Asp
```

```
                690                 695                 700
Tyr Arg Gly Tyr Gln Glu Ser Asp Glu Val Ile Gln Trp Phe Trp Lys
705                 710                 715                 720

Cys Val Ser Glu Trp Asp Asn Glu Gln Arg Ala Arg Leu Leu Gln Phe
                725                 730                 735

Thr Thr Gly Thr Ser Arg Ile Pro Val Asn Gly Phe Lys Asp Leu Gln
            740                 745                 750

Gly Ser Asp Gly Pro Arg Arg Phe Thr Ile Glu Lys Ala Gly Glu Val
        755                 760                 765

Gln Gln Leu Pro Lys Ser His Thr Cys Phe Asn Arg Val Asp Leu Pro
    770                 775                 780

Gln Tyr Val Asp Tyr Asp Ser Met Lys Gln Lys Leu Thr Leu Ala Val
785                 790                 795                 800

Glu Glu Thr Ile Gly Phe Gly Gln Glu
                805

<210> SEQ ID NO 41
<211> LENGTH: 501
<212> TYPE: PRT
<213> ORGANISM: Homo sapiens

<400> SEQUENCE: 41

Met Ala Ala Ala Ser Val Thr Pro Pro Gly Ser Leu Glu Leu Leu Gln
1               5                   10                  15

Pro Gly Phe Ser Lys Thr Leu Leu Gly Thr Lys Leu Glu Ala Lys Tyr
            20                  25                  30

Leu Cys Ser Ala Cys Arg Asn Val Leu Arg Arg Pro Phe Gln Ala Gln
        35                  40                  45

Cys Gly His Arg Tyr Cys Ser Phe Cys Leu Ala Ser Ile Leu Ser Ser
    50                  55                  60

Gly Pro Gln Asn Cys Ala Ala Cys Val His Glu Gly Ile Tyr Glu Glu
65                  70                  75                  80

Gly Ile Ser Ile Leu Glu Ser Ser Ala Phe Pro Asp Asn Ala Ala
            85                  90                  95

Arg Arg Glu Val Glu Ser Leu Pro Ala Val Cys Pro Ser Asp Gly Cys
            100                 105                 110

Thr Trp Lys Gly Thr Leu Lys Glu Tyr Glu Ser Cys His Glu Gly Arg
        115                 120                 125

Cys Pro Leu Met Leu Thr Glu Cys Pro Ala Cys Lys Gly Leu Val Arg
    130                 135                 140

Leu Gly Glu Lys Glu Arg His Leu Glu His Glu Cys Pro Glu Arg Ser
145                 150                 155                 160

Leu Ser Cys Arg His Cys Arg Ala Pro Cys Cys Gly Ala Asp Val Lys
                165                 170                 175

Ala His His Glu Val Cys Pro Lys Phe Pro Leu Thr Cys Asp Gly Cys
            180                 185                 190

Gly Lys Lys Lys Ile Pro Arg Glu Lys Phe Gln Asp His Val Lys Thr
        195                 200                 205

Cys Gly Lys Cys Arg Val Pro Cys Arg Phe His Ala Ile Gly Cys Leu
    210                 215                 220

Glu Thr Val Glu Gly Glu Lys Gln Gln Glu His Glu Val Gln Trp Leu
225                 230                 235                 240

Arg Glu His Leu Ala Met Leu Leu Ser Ser Val Leu Glu Ala Lys Pro
                245                 250                 255
```

```
Leu Leu Gly Asp Gln Ser His Ala Gly Ser Glu Leu Leu Gln Arg Cys
            260                 265                 270

Glu Ser Leu Glu Lys Lys Thr Ala Thr Phe Glu Asn Ile Val Cys Val
        275                 280                 285

Leu Asn Arg Glu Val Glu Arg Val Ala Met Thr Ala Glu Ala Cys Ser
    290                 295                 300

Arg Gln His Arg Leu Asp Gln Asp Lys Ile Glu Ala Leu Ser Ser Lys
305                 310                 315                 320

Val Gln Gln Leu Glu Arg Ser Ile Gly Leu Lys Asp Leu Ala Met Ala
                325                 330                 335

Asp Leu Glu Gln Lys Val Leu Glu Met Glu Ala Ser Thr Tyr Asp Gly
            340                 345                 350

Val Phe Ile Trp Lys Ile Ser Asp Phe Ala Arg Lys Arg Gln Glu Ala
        355                 360                 365

Val Ala Gly Arg Ile Pro Ala Ile Phe Ser Pro Ala Phe Tyr Thr Ser
    370                 375                 380

Arg Tyr Gly Tyr Lys Met Cys Leu Arg Ile Tyr Leu Asn Gly Asp Gly
385                 390                 395                 400

Thr Gly Arg Gly Thr His Leu Ser Leu Phe Phe Val Val Met Lys Gly
                405                 410                 415

Pro Asn Asp Ala Leu Leu Arg Trp Pro Phe Asn Gln Lys Val Thr Leu
            420                 425                 430

Met Leu Leu Asp Gln Asn Asn Arg Glu His Val Ile Asp Ala Phe Arg
        435                 440                 445

Pro Asp Val Thr Ser Ser Ser Phe Gln Arg Pro Val Asn Asp Met Asn
    450                 455                 460

Ile Ala Ser Gly Cys Pro Leu Phe Cys Pro Val Ser Lys Met Glu Ala
465                 470                 475                 480

Lys Asn Ser Tyr Val Arg Asp Asp Ala Ile Phe Ile Lys Ala Ile Val
                485                 490                 495

Asp Leu Thr Gly Leu
            500

<210> SEQ ID NO 42
<211> LENGTH: 282
<212> TYPE: PRT
<213> ORGANISM: Homo sapiens

<400> SEQUENCE: 42

Met Ser Arg Gln Thr Ala Thr Ala Leu Pro Thr Gly Thr Ser Lys Cys
1               5                   10                  15

Pro Pro Ser Gln Arg Val Pro Ala Leu Thr Gly Thr Thr Ala Ser Asn
                20                  25                  30

Asn Asp Leu Ala Ser Leu Phe Glu Cys Pro Val Cys Phe Asp Tyr Val
            35                  40                  45

Leu Pro Pro Ile Leu Gln Cys Gln Ser Gly His Leu Val Cys Ser Asn
        50                  55                  60

Cys Arg Pro Lys Leu Thr Cys Cys Pro Thr Cys Arg Gly Pro Leu Gly
65                  70                  75                  80

Ser Ile Arg Asn Leu Ala Met Glu Lys Val Ala Asn Ser Val Leu Phe
                85                  90                  95

Pro Cys Lys Tyr Ala Ser Ser Gly Cys Glu Ile Thr Leu Pro His Thr
            100                 105                 110

Glu Lys Ala Asp His Glu Glu Leu Cys Glu Phe Arg Pro Tyr Ser Cys
        115                 120                 125
```

```
Pro Cys Pro Gly Ala Ser Cys Lys Trp Gln Gly Ser Leu Asp Ala Val
    130                 135                 140

Met Pro His Leu Met His Gln His Lys Ser Ile Thr Thr Leu Gln Gly
145                 150                 155                 160

Glu Asp Ile Val Phe Leu Ala Thr Asp Ile Asn Leu Pro Gly Ala Val
                165                 170                 175

Asp Trp Val Met Met Gln Ser Cys Phe Gly Phe His Phe Met Leu Val
                180                 185                 190

Leu Glu Lys Gln Glu Lys Tyr Asp Gly His Gln Gln Phe Ala Ile
    195                 200                 205

Val Gln Leu Ile Gly Thr Arg Lys Gln Ala Glu Asn Phe Ala Tyr Arg
    210                 215                 220

Leu Glu Leu Asn Gly His Arg Arg Leu Thr Trp Glu Ala Thr Pro
225                 230                 235                 240

Arg Ser Ile His Glu Gly Ile Ala Thr Ala Ile Met Asn Ser Asp Cys
                245                 250                 255

Leu Val Phe Asp Thr Ser Ile Ala Gln Leu Phe Ala Glu Asn Gly Asn
                260                 265                 270

Leu Gly Ile Asn Val Thr Ile Ser Met Cys
                275                 280

<210> SEQ ID NO 43
<211> LENGTH: 464
<212> TYPE: PRT
<213> ORGANISM: Mus musculus

<400> SEQUENCE: 43

Met Ile Val Phe Val Arg Phe Asn Ser Ser Tyr Gly Phe Pro Val Glu
1               5                   10                  15

Val Asp Ser Asp Thr Ser Ile Leu Gln Leu Lys Glu Val Val Ala Lys
                20                  25                  30

Arg Gln Gly Val Pro Ala Asp Gln Leu Arg Val Ile Phe Ala Gly Lys
            35                  40                  45

Glu Leu Pro Asn His Leu Thr Val Gln Asn Cys Asp Leu Glu Gln Gln
50                  55                  60

Ser Ile Val His Ile Val Gln Arg Pro Arg Arg Arg Ser His Glu Thr
65                  70                  75                  80

Asn Ala Ser Gly Gly Asp Glu Pro Gln Ser Thr Ser Glu Gly Ser Ile
                85                  90                  95

Trp Glu Ser Arg Ser Leu Thr Arg Val Asp Leu Ser Ser His Thr Leu
            100                 105                 110

Pro Val Asp Ser Val Gly Leu Ala Val Ile Leu Asp Thr Asp Ser Lys
            115                 120                 125

Arg Asp Ser Glu Ala Ala Arg Gly Pro Val Lys Pro Thr Tyr Asn Ser
    130                 135                 140

Phe Phe Ile Tyr Cys Lys Gly Pro Cys His Lys Val Gln Pro Gly Lys
145                 150                 155                 160

Leu Arg Val Gln Cys Gly Thr Cys Lys Gln Ala Thr Leu Thr Leu Ala
                165                 170                 175

Gln Gly Pro Ser Cys Trp Asp Asp Val Leu Ile Pro Asn Arg Met Ser
                180                 185                 190

Gly Glu Cys Gln Ser Pro Asp Cys Pro Gly Thr Arg Ala Glu Phe Phe
            195                 200                 205

Phe Lys Cys Gly Ala His Pro Thr Ser Asp Lys Asp Thr Ser Val Ala
```

```
            210                 215                 220
Leu Asn Leu Ile Thr Ser Asn Arg Arg Ser Ile Pro Cys Ile Ala Cys
225                 230                 235                 240

Thr Asp Val Arg Ser Pro Val Leu Val Phe Gln Cys Asn His Arg His
                245                 250                 255

Val Ile Cys Leu Asp Cys Phe His Leu Tyr Cys Val Thr Arg Leu Asn
                260                 265                 270

Asp Arg Gln Phe Val His Asp Ala Gln Leu Gly Tyr Ser Leu Pro Cys
            275                 280                 285

Val Ala Gly Cys Pro Asn Ser Leu Ile Lys Glu Leu His His Phe Arg
290                 295                 300

Ile Leu Gly Glu Glu Gln Tyr Thr Arg Tyr Gln Gln Tyr Gly Ala Glu
305                 310                 315                 320

Glu Cys Val Leu Gln Met Gly Val Leu Cys Pro Arg Pro Gly Cys
                325                 330                 335

Gly Ala Gly Leu Leu Pro Glu Gln Gly Gln Arg Lys Val Thr Cys Glu
                340                 345                 350

Gly Gly Asn Gly Leu Gly Cys Gly Phe Val Phe Cys Arg Asp Cys Lys
                355                 360                 365

Glu Ala Tyr His Glu Gly Asp Cys Asp Ser Leu Leu Glu Pro Ser Gly
                370                 375                 380

Ala Thr Ser Gln Ala Tyr Arg Val Asp Lys Arg Ala Ala Glu Gln Ala
385                 390                 395                 400

Arg Trp Glu Glu Ala Ser Lys Glu Thr Ile Lys Lys Thr Thr Lys Pro
                405                 410                 415

Cys Pro Arg Cys Asn Val Pro Ile Glu Lys Asn Gly Gly Cys Met His
                420                 425                 430

Met Lys Cys Pro Gln Pro Gln Cys Lys Leu Glu Trp Cys Trp Asn Cys
                435                 440                 445

Gly Cys Glu Trp Asn Arg Ala Cys Met Gly Asp His Trp Phe Asp Val
                450                 455                 460

<210> SEQ ID NO 44
<211> LENGTH: 303
<212> TYPE: PRT
<213> ORGANISM: Homo sapiens

<400> SEQUENCE: 44

Met Lys Gly Lys Glu Glu Lys Glu Gly Gly Ala Arg Leu Gly Ala Gly
1               5                   10                  15

Gly Gly Ser Pro Glu Lys Ser Pro Ser Ala Gln Glu Leu Lys Glu Gln
                20                  25                  30

Gly Asn Arg Leu Phe Val Gly Arg Lys Tyr Pro Glu Ala Ala Ala Cys
                35                  40                  45

Tyr Gly Arg Ala Ile Thr Arg Asn Pro Leu Val Ala Val Tyr Tyr Thr
                50                  55                  60

Asn Arg Ala Leu Cys Tyr Leu Lys Met Gln Gln His Glu Gln Ala Leu
65                  70                  75                  80

Ala Asp Cys Arg Arg Ala Leu Glu Leu Asp Gly Gln Ser Val Lys Ala
                85                  90                  95

His Phe Phe Leu Gly Gln Cys Gln Leu Glu Met Glu Ser Tyr Asp Glu
                100                 105                 110

Ala Ile Ala Asn Leu Gln Arg Ala Tyr Ser Leu Ala Lys Glu Gln Arg
                115                 120                 125
```

```
Leu Asn Phe Gly Asp Asp Ile Pro Ser Ala Leu Arg Ile Ala Lys Lys
            130                 135                 140

Lys Arg Trp Asn Ser Ile Glu Glu Arg Ile His Gln Glu Ser Glu
145                 150                 155                 160

Leu His Ser Tyr Leu Ser Arg Leu Ile Ala Ala Glu Arg Glu Arg Glu
                165                 170                 175

Leu Glu Glu Cys Gln Arg Asn His Glu Gly Asp Glu Asp Ser His
            180                 185                 190

Val Arg Ala Gln Gln Ala Cys Ile Glu Ala Lys His Asp Lys Tyr Met
            195                 200                 205

Ala Asp Met Asp Glu Leu Phe Ser Gln Val Asp Glu Lys Arg Lys Lys
210                 215                 220

Arg Asp Ile Pro Asp Tyr Leu Cys Gly Lys Ile Ser Phe Glu Leu Met
225                 230                 235                 240

Arg Glu Pro Cys Ile Thr Pro Ser Gly Ile Thr Tyr Asp Arg Lys Asp
                245                 250                 255

Ile Glu Glu His Leu Gln Arg Val Gly His Phe Asp Pro Val Thr Arg
            260                 265                 270

Ser Pro Leu Thr Gln Glu Gln Leu Ile Pro Asn Leu Ala Met Lys Glu
            275                 280                 285

Val Ile Asp Ala Phe Ile Ser Glu Asn Gly Trp Val Glu Asp Tyr
            290                 295                 300

<210> SEQ ID NO 45
<211> LENGTH: 1030
<212> TYPE: PRT
<213> ORGANISM: Danio rerio

<400> SEQUENCE: 45

Met Thr Thr Gly Arg Asn Asn Arg Val Met Met Glu Gly Val Gly Ala
1               5                   10                  15

Arg Val Ile Arg Gly Pro Asp Trp Lys Trp Gly Lys Gln Asp Gly Gly
            20                  25                  30

Glu Gly His Val Gly Thr Val Arg Ser Phe Glu Ser Pro Glu Glu Val
        35                  40                  45

Val Val Val Trp Asp Asn Gly Thr Ala Ala Asn Tyr Arg Cys Ser Gly
    50                  55                  60

Ala Tyr Asp Val Arg Ile Leu Asp Ser Ala Pro Thr Gly Ile Lys His
65                  70                  75                  80

Asp Gly Thr Met Cys Asp Thr Cys Arg Gln Gln Pro Ile Ile Gly Ile
                85                  90                  95

Arg Trp Lys Cys Ala Glu Cys Thr Asn Tyr Asp Leu Cys Thr Thr Cys
            100                 105                 110

Tyr His Gly Asp Lys His His Leu Arg His Arg Phe Tyr Arg Ile Thr
        115                 120                 125

Thr Pro Gly Ser Glu Arg Val Leu Leu Glu Ser Arg Arg Lys Ser Lys
    130                 135                 140

Lys Ile Thr Ala Arg Gly Ile Phe Ala Gly Gly Arg Val Val Arg Gly
145                 150                 155                 160

Val Asp Trp Gln Trp Glu Asp Gln Asp Gly Gly Asn Gly Arg Arg Gly
                165                 170                 175

Lys Val Thr Glu Ile Gln Asp Trp Ser Ala Ala Ser Pro His Ser Ala
            180                 185                 190

Ala Tyr Val Leu Trp Asp Asn Gly Ala Lys Asn Leu Tyr Arg Val Gly
        195                 200                 205
```

```
Phe Glu Gly Met Ser Asp Leu Lys Cys Val Gln Asp Ala Lys Gly Gly
    210                 215                 220

Thr Phe Tyr Arg Asp His Cys Pro Val Leu Gly Glu Gln Asn Gly Asn
225                 230                 235                 240

Arg Asn Pro Gly Gly Leu Gln Ile Gly Asp Leu Val Asn Ile Asp Leu
                245                 250                 255

Asp Leu Glu Ile Val Gln Ser Leu Gln His Gly His Gly Gly Trp Thr
            260                 265                 270

Asp Gly Met Phe Glu Thr Leu Thr Thr Gly Thr Val Cys Gly Ile
        275                 280                 285

Asp Glu Asp His Asp Ile Val Val Gln Tyr Pro Ser Gly Asn Arg Trp
    290                 295                 300

Thr Phe Asn Pro Ala Val Leu Thr Lys Ala Asn Val Val Arg Ser Gly
305                 310                 315                 320

Glu Val Ala Ala Gly Ala Glu Gly Gly Ser Ser Gln Phe Met Val Gly
                325                 330                 335

Asp Leu Val Gln Ile Cys Tyr Asp Ile Asp Arg Ile Lys Leu Leu Gln
            340                 345                 350

Arg Gly His Gly Glu Trp Ala Glu Ala Met Leu Pro Thr Leu Gly Lys
        355                 360                 365

Val Gly Arg Val Gln Gln Ile Tyr Ser Asp Ser Asp Leu Lys Val Glu
    370                 375                 380

Val Cys Gly Thr Ser Trp Thr Tyr Asn Pro Ala Ala Val Thr Lys Val
385                 390                 395                 400

Ala Pro Ala Gly Ser Ala Val Thr Asn Ala Ser Gly Glu Arg Leu Ser
                405                 410                 415

Gln Leu Leu Lys Lys Leu Phe Glu Thr Gln Glu Ser Gly Asp Ile Asn
            420                 425                 430

Glu Glu Leu Val Lys Ala Ala Asn Gly Asp Leu Ala Lys Val Glu
        435                 440                 445

Asp Ile Leu Lys Arg Pro Asp Val Asp Val Asn Gly Gln Cys Ala Gly
    450                 455                 460

His Thr Ala Met Gln Ala Ala Ser Gln Asn Gly His Val Asp Val Leu
465                 470                 475                 480

Lys Leu Leu Leu Lys His Ser Val Asp Leu Glu Ala Glu Asp Lys Asp
                485                 490                 495

Gly Asp Arg Ala Val His His Ala Ser Phe Gly Asp Glu Gly Ser Val
            500                 505                 510

Ile Glu Val Leu His Arg Gly Gly Ala Asp Leu Asn Ala Arg Asn Lys
        515                 520                 525

Arg Arg Gln Thr Pro Leu His Ile Ala Val Asn Lys Gly His Leu Gln
    530                 535                 540

Val Val Lys Thr Leu Leu Asp Phe Gly Cys His Pro Ser Leu Gln Asp
545                 550                 555                 560

Ser Glu Gly Asp Thr Pro Leu His Asp Ala Ile Ser Lys Lys Arg Asp
                565                 570                 575

Asp Met Leu Ser Val Leu Leu Glu Ala Gly Ala Asp Val Thr Ile Thr
            580                 585                 590

Asn Asn Asn Gly Phe Asn Ala Leu His His Ala Ala Leu Arg Gly Asn
        595                 600                 605

Pro Ser Ala Met Arg Val Leu Leu Ser Lys Leu Pro Arg Pro Trp Ile
    610                 615                 620
```

```
Val Asp Glu Lys Lys Asp Asp Gly Tyr Thr Ala Leu His Leu Ala Ala
625                 630                 635                 640

Leu Asn Asn His Val Glu Val Ala Glu Leu Leu Val His Gln Gly Asn
            645                 650                 655

Ala Asn Leu Asp Val Gln Asn Val Asn Gln Gln Thr Ala Leu His Leu
                660                 665                 670

Ala Val Glu Arg Gln His Thr Gln Ile Val Arg Leu Leu Val Arg Ala
            675                 680                 685

Glu Ala Lys Leu Asp Val Gln Asp Lys Asp Gly Asp Thr Pro Leu His
            690                 695                 700

Glu Ala Leu Arg His His Thr Leu Ser Gln Leu Arg Gln Leu Gln Asp
705                 710                 715                 720

Met Gln Asp Val Ser Lys Val Glu Pro Trp Glu Pro Ser Lys Asn Thr
                725                 730                 735

Leu Ile Met Gly Leu Gly Thr Gln Gly Ala Glu Lys Lys Ser Ala Ala
                740                 745                 750

Ser Ile Ala Cys Phe Leu Ala Ala Asn Gly Ala Asp Leu Thr Ile Arg
            755                 760                 765

Asn Lys Lys Gly Gln Ser Pro Leu Asp Leu Cys Pro Asp Pro Ser Leu
770                 775                 780

Cys Lys Ala Leu Ala Lys Cys His Lys Glu Lys Thr Ser Gly Gln Val
785                 790                 795                 800

Gly Ser Arg Ser Pro Ser Leu Asn Ser Asn Asn Glu Thr Leu Glu Glu
            805                 810                 815

Cys Met Val Cys Ser Asp Met Lys Arg Asp Thr Leu Phe Gly Pro Cys
            820                 825                 830

Gly His Ile Ala Thr Cys Ser Leu Cys Ser Pro Arg Val Lys Lys Cys
            835                 840                 845

Leu Ile Cys Lys Glu Gln Val Gln Ser Arg Thr Lys Ile Glu Glu Cys
850                 855                 860

Val Val Cys Ser Asp Lys Lys Ala Ala Val Leu Phe Gln Pro Cys Gly
865                 870                 875                 880

His Met Cys Ala Cys Glu Asn Cys Ala Ser Leu Met Lys Lys Cys Val
            885                 890                 895

Gln Cys Arg Ala Val Val Glu Arg Arg Thr Pro Phe Val Leu Cys Cys
            900                 905                 910

Gly Lys Gly Met Glu Asp Ala Thr Asp Glu Asp Leu Thr Gly
    915                 920                 925

Gly Ser Asn Ser Met Ala Gly Gly Ser Gln Asp Leu Leu Gln Pro Asn
    930                 935                 940

Asn Leu Ala Leu Ser Trp Ser Ser Gly Asn Ile Pro Ala Leu Gln Arg
945                 950                 955                 960

Asp Lys Asp Asn Thr Asn Val Asn Ala Asp Val Gln Lys Leu Gln Gln
            965                 970                 975

Gln Leu Gln Asp Ile Lys Glu Gln Thr Met Cys Pro Val Cys Leu Asp
            980                 985                 990

Arg Leu Lys Asn Met Ile Phe Met Cys Gly His Gly Thr Cys Gln Leu
            995                 1000                1005

Cys Gly Asp Arg Met Ser Glu Cys Pro Ile Cys Arg Lys Ala Ile
        1010                1015                1020

Glu Arg Arg Ile Leu Leu Tyr
1025                1030
```

<210> SEQ ID NO 46
<211> LENGTH: 757
<212> TYPE: PRT
<213> ORGANISM: Homo sapiens

<400> SEQUENCE: 46

```
Met Ser Asn Pro Gly Thr Arg Arg Asn Gly Ser Ser Ile Lys Ile Arg
1               5                   10                  15

Leu Thr Val Leu Cys Ala Lys Asn Leu Ala Lys Lys Asp Phe Phe Arg
            20                  25                  30

Leu Pro Asp Pro Phe Ala Lys Ile Val Val Asp Gly Ser Gly Gln Cys
        35                  40                  45

His Ser Thr Asp Thr Val Lys Asn Thr Leu Asp Pro Lys Trp Asn Gln
    50                  55                  60

His Tyr Asp Leu Tyr Val Gly Lys Thr Asp Ser Ile Thr Ile Ser Val
65                  70                  75                  80

Trp Asn His Lys Lys Ile His Lys Lys Gln Gly Ala Gly Phe Leu Gly
                85                  90                  95

Cys Val Arg Leu Leu Ser Asn Ala Ile Ser Arg Leu Lys Asp Thr Gly
            100                 105                 110

Tyr Gln Arg Leu Asp Leu Cys Lys Leu Asn Pro Ser Asp Thr Asp Ala
        115                 120                 125

Val Arg Gly Gln Ile Val Val Ser Leu Gln Thr Arg Asp Arg Ile Gly
    130                 135                 140

Thr Gly Gly Ser Val Val Asp Cys Arg Gly Leu Leu Glu Asn Glu Gly
145                 150                 155                 160

Thr Val Tyr Glu Asp Ser Gly Pro Gly Arg Pro Leu Ser Cys Phe Met
                165                 170                 175

Glu Glu Pro Ala Pro Tyr Thr Asp Ser Thr Gly Ala Ala Ala Gly Gly
            180                 185                 190

Gly Asn Cys Arg Phe Val Glu Ser Pro Ser Gln Asp Gln Arg Leu Gln
        195                 200                 205

Ala Gln Arg Leu Arg Asn Pro Asp Val Arg Gly Ser Leu Gln Thr Pro
    210                 215                 220

Gln Asn Arg Pro His Gly His Gln Ser Pro Glu Leu Pro Glu Gly Tyr
225                 230                 235                 240

Glu Gln Arg Thr Thr Val Gln Gly Gln Val Tyr Phe Leu His Thr Gln
                245                 250                 255

Thr Gly Val Ser Thr Trp His Asp Pro Arg Ile Pro Ser Pro Ser Gly
            260                 265                 270

Thr Ile Pro Gly Gly Asp Ala Ala Phe Leu Tyr Glu Phe Leu Leu Gln
        275                 280                 285

Gly His Thr Ser Glu Pro Arg Asp Leu Asn Ser Val Asn Cys Asp Glu
    290                 295                 300

Leu Gly Pro Leu Pro Pro Gly Trp Glu Val Arg Ser Thr Val Ser Gly
305                 310                 315                 320

Arg Ile Tyr Phe Val Asp His Asn Asn Arg Thr Thr Gln Phe Thr Asp
                325                 330                 335

Pro Arg Leu His His Ile Met Asn His Gln Cys Gln Leu Lys Glu Pro
            340                 345                 350

Ser Gln Pro Leu Pro Leu Pro Ser Glu Gly Ser Leu Glu Asp Glu Glu
        355                 360                 365

Leu Pro Ala Gln Arg Tyr Glu Arg Asp Leu Val Gln Lys Leu Lys Val
    370                 375                 380
```

```
Leu Arg His Glu Leu Ser Leu Gln Gln Pro Gln Ala Gly His Cys Arg
385                 390                 395                 400

Ile Glu Val Ser Arg Glu Glu Ile Phe Glu Glu Ser Tyr Arg Gln Ile
            405                 410                 415

Met Lys Met Arg Pro Lys Asp Leu Lys Lys Arg Leu Met Val Lys Phe
        420                 425                 430

Arg Gly Glu Glu Gly Leu Asp Tyr Gly Gly Val Ala Arg Glu Trp Leu
    435                 440                 445

Tyr Leu Leu Cys His Glu Met Leu Asn Pro Tyr Tyr Gly Leu Phe Gln
450                 455                 460

Tyr Ser Thr Asp Asn Ile Tyr Met Leu Gln Ile Asn Pro Asp Ser Ser
465                 470                 475                 480

Ile Asn Pro Asp His Leu Ser Tyr Phe His Phe Val Gly Arg Ile Met
                485                 490                 495

Gly Leu Ala Val Phe His Gly His Tyr Ile Asn Gly Gly Phe Thr Val
            500                 505                 510

Pro Phe Tyr Lys Gln Leu Leu Gly Lys Pro Ile Gln Leu Ser Asp Leu
        515                 520                 525

Glu Ser Val Asp Pro Glu Leu His Lys Ser Leu Val Trp Ile Leu Glu
530                 535                 540

Asn Asp Ile Thr Pro Val Leu Asp His Thr Phe Cys Val Glu His Asn
545                 550                 555                 560

Ala Phe Gly Arg Ile Leu Gln His Glu Leu Lys Pro Asn Gly Arg Asn
                565                 570                 575

Val Pro Val Thr Glu Glu Asn Lys Lys Glu Tyr Val Arg Leu Tyr Val
            580                 585                 590

Asn Trp Arg Phe Met Arg Gly Ile Glu Ala Gln Phe Leu Ala Leu Gln
        595                 600                 605

Lys Gly Phe Asn Glu Leu Ile Pro Gln His Leu Leu Lys Pro Phe Asp
610                 615                 620

Gln Lys Glu Leu Glu Leu Ile Ile Gly Gly Leu Asp Lys Ile Asp Leu
625                 630                 635                 640

Asn Asp Trp Lys Ser Asn Thr Arg Leu Lys His Cys Val Ala Asp Ser
                645                 650                 655

Asn Ile Val Arg Trp Phe Trp Gln Ala Val Glu Thr Phe Asp Glu Glu
            660                 665                 670

Arg Arg Ala Arg Leu Leu Gln Phe Val Thr Gly Ser Thr Arg Val Pro
        675                 680                 685

Leu Gln Gly Phe Lys Ala Leu Gln Gly Ser Thr Gly Ala Ala Gly Pro
690                 695                 700

Arg Leu Phe Thr Ile His Leu Ile Asp Ala Asn Thr Asp Asn Leu Pro
705                 710                 715                 720

Lys Ala His Thr Cys Phe Asn Arg Ile Asp Ile Pro Pro Tyr Glu Ser
                725                 730                 735

Tyr Glu Lys Leu Tyr Glu Lys Leu Leu Thr Ala Val Glu Glu Thr Cys
            740                 745                 750

Gly Phe Ala Val Glu
        755

<210> SEQ ID NO 47
<211> LENGTH: 1319
<212> TYPE: PRT
<213> ORGANISM: Homo sapiens

<400> SEQUENCE: 47
```

-continued

```
Met Ala Gln Ser Leu Arg Leu His Phe Ala Arg Arg Ser Asn Thr
1               5                   10                  15

Tyr Pro Leu Ser Glu Thr Ser Gly Asp Leu Asp Ser His Val His
                20                  25                  30

Met Cys Phe Lys Arg Pro Thr Arg Ile Ser Thr Ser Asn Val Val Gln
        35                  40                  45

Met Lys Leu Thr Pro Arg Gln Thr Ala Leu Ala Pro Leu Ile Lys Glu
    50                  55                  60

Asn Val Gln Ser Gln Glu Arg Ser Ser Val Pro Ser Ser Glu Asn Val
65                  70                  75                  80

Asn Lys Lys Ser Ser Cys Leu Gln Ile Ser Leu Gln Pro Thr Arg Tyr
                85                  90                  95

Ser Gly Tyr Leu Gln Ser Ser Asn Val Leu Ala Asp Ser Asp Asp Ala
                100                 105                 110

Ser Phe Thr Cys Ile Leu Lys Asp Gly Ile Tyr Ser Ser Ala Val Val
            115                 120                 125

Asp Asn Glu Leu Asn Ala Val Asn Asp Gly His Leu Val Ser Ser Pro
130                 135                 140

Ala Ile Cys Ser Gly Ser Leu Ser Asn Phe Ser Thr Ser Asp Asn Gly
145                 150                 155                 160

Ser Tyr Ser Ser Asn Gly Ser Asp Phe Gly Ser Cys Ala Ser Ile Thr
                165                 170                 175

Ser Gly Gly Ser Tyr Thr Asn Ser Val Ile Ser Asp Ser Ser Ser Tyr
                180                 185                 190

Thr Phe Pro Pro Ser Asp Asp Thr Phe Leu Gly Gly Asn Leu Pro Ser
                195                 200                 205

Asp Ser Thr Ser Asn Arg Ser Val Pro Asn Arg Asn Thr Thr Pro Cys
210                 215                 220

Glu Ile Phe Ser Arg Ser Thr Ser Thr Asp Pro Phe Val Gln Asp Asp
225                 230                 235                 240

Leu Glu His Gly Leu Glu Ile Met Lys Leu Pro Val Ser Arg Asn Thr
                245                 250                 255

Lys Ile Pro Leu Lys Arg Tyr Ser Ser Leu Val Ile Phe Pro Arg Ser
                260                 265                 270

Pro Ser Thr Thr Arg Pro Thr Ser Pro Thr Ser Leu Cys Thr Leu Leu
                275                 280                 285

Ser Lys Gly Ser Tyr Gln Thr Ser His Gln Phe Ile Ile Ser Pro Ser
290                 295                 300

Glu Ile Ala His Asn Glu Asp Gly Thr Ser Ala Lys Gly Phe Leu Ser
305                 310                 315                 320

Thr Ala Val Asn Gly Leu Arg Leu Ser Lys Thr Ile Cys Thr Pro Gly
                325                 330                 335

Glu Val Arg Asp Ile Arg Pro Leu His Arg Lys Gly Ser Leu Gln Lys
                340                 345                 350

Lys Ile Val Leu Ser Asn Asn Thr Pro Arg Gln Thr Val Cys Glu Lys
                355                 360                 365

Ser Ser Glu Gly Tyr Ser Cys Val Ser Val His Phe Thr Gln Arg Lys
370                 375                 380

Ala Ala Thr Leu Asp Cys Glu Thr Thr Asn Gly Asp Cys Lys Pro Glu
385                 390                 395                 400

Met Ser Glu Ile Lys Leu Asn Ser Asp Ser Glu Tyr Ile Lys Leu Met
                405                 410                 415
```

His Arg Thr Ser Ala Cys Leu Pro Ser Ser Gln Asn Val Asp Cys Gln
                420                 425                 430

Ile Asn Ile Asn Gly Glu Leu Glu Arg Pro His Ser Gln Met Asn Lys
                435                 440                 445

Asn His Gly Ile Leu Arg Arg Ser Ile Ser Leu Gly Gly Ala Tyr Pro
450                 455                 460

Asn Ile Ser Cys Leu Ser Ser Leu Lys His Asn Cys Ser Lys Gly Gly
465                 470                 475                 480

Pro Ser Gln Leu Leu Ile Lys Phe Ala Ser Gly Asn Glu Gly Lys Val
                485                 490                 495

Asp Asn Leu Ser Arg Asp Ser Asn Arg Asp Cys Thr Asn Glu Leu Ser
                500                 505                 510

Asn Ser Cys Lys Thr Arg Asp Asp Phe Leu Gly Gln Val Asp Val Pro
515                 520                 525

Leu Tyr Pro Leu Pro Thr Glu Asn Pro Arg Leu Glu Arg Pro Tyr Thr
                530                 535                 540

Phe Lys Asp Phe Val Leu His Pro Arg Ser His Lys Ser Arg Val Lys
545                 550                 555                 560

Gly Tyr Leu Arg Leu Lys Met Thr Tyr Leu Pro Lys Thr Ser Gly Ser
                565                 570                 575

Glu Asp Asp Asn Ala Glu Gln Ala Glu Glu Leu Glu Pro Gly Trp Val
                580                 585                 590

Val Leu Asp Gln Pro Asp Ala Ala Cys His Leu Gln Gln Gln Gln Glu
                595                 600                 605

Pro Ser Pro Leu Pro Pro Gly Trp Glu Glu Arg Gln Asp Ile Leu Gly
610                 615                 620

Arg Thr Tyr Tyr Val Asn His Glu Ser Arg Arg Thr Gln Trp Lys Arg
625                 630                 635                 640

Pro Thr Pro Gln Asp Asn Leu Thr Asp Ala Glu Asn Gly Asn Ile Gln
                645                 650                 655

Leu Gln Ala Gln Arg Ala Phe Thr Thr Arg Arg Gln Ile Ser Glu Glu
                660                 665                 670

Thr Glu Ser Val Asp Asn Arg Glu Ser Ser Glu Asn Trp Glu Ile Ile
                675                 680                 685

Arg Glu Asp Glu Ala Thr Met Tyr Ser Asn Gln Ala Phe Pro Ser Pro
690                 695                 700

Pro Pro Ser Ser Asn Leu Asp Val Pro Thr His Leu Ala Glu Glu Leu
705                 710                 715                 720

Asn Ala Arg Leu Thr Ile Phe Gly Asn Ser Ala Val Ser Gln Pro Ala
                725                 730                 735

Ser Ser Ser Asn His Ser Ser Arg Arg Gly Ser Leu Gln Ala Tyr Thr
                740                 745                 750

Phe Glu Glu Gln Pro Thr Leu Pro Val Leu Leu Pro Thr Ser Ser Gly
                755                 760                 765

Leu Pro Pro Gly Trp Glu Glu Lys Gln Asp Glu Arg Gly Arg Ser Tyr
                770                 775                 780

Tyr Val Asp His Asn Ser Arg Thr Thr Thr Trp Thr Lys Pro Thr Val
785                 790                 795                 800

Gln Ala Thr Val Glu Thr Ser Gln Leu Thr Ser Ser Gln Ser Ser Ala
                805                 810                 815

Gly Pro Gln Ser Gln Ala Ser Thr Ser Asp Ser Gly Gln Gln Val Thr
                820                 825                 830

Gln Pro Ser Glu Ile Glu Gln Gly Phe Leu Pro Lys Gly Trp Glu Val

```
                835                 840                 845
Arg His Ala Asn Gly Arg Pro Phe Phe Ile Asp His Asn Thr Lys
    850                 855                 860
Thr Thr Thr Trp Glu Asp Pro Arg Leu Lys Ile Pro Ala His Leu Arg
865                 870                 875                 880
Gly Lys Thr Ser Leu Asp Thr Ser Asn Asp Leu Gly Pro Leu Pro Pro
                885                 890                 895
Gly Trp Glu Glu Arg Thr His Thr Asp Gly Arg Ile Phe Tyr Ile Asn
                900                 905                 910
His Asn Ile Lys Arg Thr Gln Trp Glu Asp Pro Arg Leu Glu Asn Val
            915                 920                 925
Ala Ile Thr Gly Pro Ala Val Pro Tyr Ser Arg Asp Tyr Lys Arg Lys
    930                 935                 940
Tyr Glu Phe Phe Arg Arg Lys Leu Lys Lys Gln Asn Asp Ile Pro Asn
945                 950                 955                 960
Lys Phe Glu Met Lys Leu Arg Arg Ala Thr Val Leu Glu Asp Ser Tyr
                965                 970                 975
Arg Arg Ile Met Gly Val Lys Arg Ala Asp Phe Leu Lys Ala Arg Leu
            980                 985                 990
Trp Ile Glu Phe Asp Gly Glu Lys Gly Leu Asp Tyr Gly Gly Val Ala
            995                 1000                1005
Arg Glu Trp Phe Phe Leu Ile Ser Lys Glu Met Phe Asn Pro Tyr
    1010                1015                1020
Tyr Gly Leu Phe Glu Tyr Ser Ala Thr Asp Asn Tyr Thr Leu Gln
    1025                1030                1035
Ile Asn Pro Asn Ser Gly Leu Cys Asn Glu Asp His Leu Ser Tyr
    1040                1045                1050
Phe Lys Phe Ile Gly Arg Val Ala Gly Met Ala Val Tyr His Gly
    1055                1060                1065
Lys Leu Leu Asp Gly Phe Phe Ile Arg Pro Phe Tyr Lys Met Met
    1070                1075                1080
Leu His Lys Pro Ile Thr Leu His Asp Met Glu Ser Val Asp Ser
    1085                1090                1095
Glu Tyr Tyr Asn Ser Leu Arg Trp Ile Leu Glu Asn Asp Pro Thr
    1100                1105                1110
Glu Leu Asp Leu Arg Phe Ile Ile Asp Glu Glu Leu Phe Gly Gln
    1115                1120                1125
Thr His Gln His Glu Leu Lys Asn Gly Gly Ser Glu Ile Val Val
    1130                1135                1140
Thr Asn Lys Asn Lys Lys Glu Tyr Ile Tyr Leu Val Ile Gln Trp
    1145                1150                1155
Arg Phe Val Asn Arg Ile Gln Lys Gln Met Ala Ala Phe Lys Glu
    1160                1165                1170
Gly Phe Phe Glu Leu Ile Pro Gln Asp Leu Ile Lys Ile Phe Asp
    1175                1180                1185
Glu Asn Glu Leu Glu Leu Leu Met Cys Gly Leu Gly Asp Val Asp
    1190                1195                1200
Val Asn Asp Trp Arg Glu His Thr Lys Tyr Lys Asn Gly Tyr Ser
    1205                1210                1215
Ala Asn His Gln Val Ile Gln Trp Phe Trp Lys Ala Val Leu Met
    1220                1225                1230
Met Asp Ser Glu Lys Arg Ile Arg Leu Leu Gln Phe Val Thr Gly
    1235                1240                1245
```

```
Thr Ser Arg Val Pro Met Asn Gly Phe Ala Glu Leu Tyr Gly Ser
    1250                1255                1260

Asn Gly Pro Gln Ser Phe Thr Val Glu Gln Trp Gly Thr Pro Glu
    1265                1270                1275

Lys Leu Pro Arg Ala His Thr Cys Phe Asn Arg Leu Asp Leu Pro
    1280                1285                1290

Pro Tyr Glu Ser Phe Glu Glu Leu Trp Asp Lys Leu Gln Met Ala
    1295                1300                1305

Ile Glu Asn Thr Gln Gly Phe Asp Gly Val Asp
    1310                1315

<210> SEQ ID NO 48
<211> LENGTH: 887
<212> TYPE: PRT
<213> ORGANISM: Mus musculus

<400> SEQUENCE: 48

Met Ser Ser Asp Met Ala Ala Asp Glu Ser Glu Ala Pro Val Leu Ser
1               5                   10                  15

Glu Asp Glu Val Trp Glu Phe Cys Leu Asp Lys Thr Glu Asp Gly Gly
                20                  25                  30

Gly Ser Pro Gly Ser Asp Val Thr Asp Thr Cys Glu Pro Pro Cys Gly
            35                  40                  45

Cys Trp Glu Leu Asn Pro Asn Ser Leu Glu Glu Glu His Val Leu Phe
        50                  55                  60

Thr Ala Asp Pro Tyr Leu Glu Leu His Asn Asp Asp Thr Arg Val Val
65                  70                  75                  80

Arg Val Lys Val Ile Ala Gly Ile Gly Leu Ala Lys Lys Asp Ile Leu
                85                  90                  95

Gly Ala Ser Asp Pro Tyr Val Arg Val Thr Leu Tyr Asp Pro Met Ser
            100                 105                 110

Gly Ile Leu Thr Ser Val Gln Thr Lys Thr Ile Lys Lys Ser Leu Asn
        115                 120                 125

Pro Lys Trp Asn Glu Glu Ile Leu Phe Arg Val Leu Pro Gln Arg His
    130                 135                 140

Arg Ile Leu Phe Glu Val Phe Asp Glu Asn Arg Leu Thr Arg Asp Asp
145                 150                 155                 160

Phe Leu Gly Gln Val Asp Val Pro Leu Tyr Pro Leu Pro Thr Glu Asn
                165                 170                 175

Pro Arg Met Glu Arg Pro Tyr Thr Phe Lys Asp Phe Val Leu His Pro
            180                 185                 190

Arg Ser His Lys Ser Arg Val Lys Gly Tyr Leu Arg Leu Lys Met Thr
        195                 200                 205

Tyr Leu Pro Lys Asn Gly Ser Glu Asp Glu Asn Ala Asp Gln Ala Glu
    210                 215                 220

Glu Leu Glu Pro Gly Trp Val Leu Asp Gln Pro Asp Ala Ala Thr
225                 230                 235                 240

His Leu Pro His Pro Pro Glu Pro Ser Pro Leu Pro Pro Gly Trp Glu
                245                 250                 255

Glu Arg Gln Asp Val Leu Gly Arg Thr Tyr Tyr Val Asn His Glu Ser
            260                 265                 270

Arg Arg Thr Gln Trp Lys Arg Pro Ser Pro Asp Asp Asp Leu Thr Asp
        275                 280                 285

Glu Asp Asn Asp Asp Met Gln Leu Gln Ala Gln Arg Ala Phe Thr Thr
```

```
              290                 295                 300
Arg Arg Gln Ile Ser Glu Asp Val Asp Gly Pro Asp Asn Arg Glu Ser
305                 310                 315                 320

Pro Glu Asn Trp Glu Ile Val Arg Glu Asp Glu Asn Thr Glu Tyr Ser
                325                 330                 335

Gly Gln Ala Val Gln Ser Pro Pro Ser Gly His Ile Asp Val Gln Thr
                340                 345                 350

His Leu Ala Glu Glu Phe Asn Thr Arg Leu Ala Val Cys Gly Asn Pro
                355                 360                 365

Ala Thr Ser Gln Pro Val Thr Ser Ser Asn His Ser Ser Arg Gly Gly
                370                 375                 380

Ser Leu Gln Thr Cys Ile Phe Glu Glu Gln Pro Thr Leu Pro Val Leu
385                 390                 395                 400

Leu Pro Thr Ser Ser Gly Leu Pro Pro Gly Trp Glu Glu Lys Gln Asp
                405                 410                 415

Asp Arg Gly Arg Ser Tyr Tyr Val Asp His Asn Ser Lys Thr Thr Thr
                420                 425                 430

Trp Ser Lys Pro Thr Met Gln Asp Asp Pro Arg Ser Lys Ile Pro Ala
                435                 440                 445

His Leu Arg Gly Lys Thr Asp Ser Asn Asp Leu Gly Pro Leu Pro Pro
                450                 455                 460

Gly Trp Glu Glu Arg Thr His Thr Asp Gly Arg Val Phe Phe Ile Asn
465                 470                 475                 480

His Asn Ile Lys Lys Thr Gln Trp Glu Asp Pro Arg Leu Gln Asn Val
                485                 490                 495

Ala Ile Thr Gly Pro Ala Val Pro Tyr Ser Arg Asp Tyr Lys Arg Lys
                500                 505                 510

Tyr Glu Phe Phe Arg Arg Lys Leu Lys Lys Gln Thr Asp Ile Pro Asn
                515                 520                 525

Lys Phe Glu Met Lys Leu Arg Arg Ala Asn Ile Leu Glu Asp Ser Tyr
                530                 535                 540

Arg Arg Ile Met Gly Val Lys Arg Ala Asp Leu Leu Lys Ala Arg Leu
545                 550                 555                 560

Trp Ile Glu Phe Asp Gly Glu Lys Gly Leu Asp Tyr Gly Gly Val Ala
                565                 570                 575

Arg Glu Trp Phe Phe Leu Ile Ser Lys Glu Met Phe Asn Pro Tyr Tyr
                580                 585                 590

Gly Leu Phe Glu Tyr Ser Ala Thr Asp Asn Tyr Thr Leu Gln Ile Asn
                595                 600                 605

Pro Asn Ser Gly Leu Cys Asn Glu Asp His Leu Ser Tyr Phe Lys Phe
                610                 615                 620

Ile Gly Arg Val Ala Gly Met Ala Val Tyr His Gly Lys Leu Leu Asp
625                 630                 635                 640

Gly Phe Phe Ile Arg Pro Phe Tyr Lys Met Met Leu Gln Lys Leu Ile
                645                 650                 655

Thr Leu His Asp Met Glu Ser Val Asp Ser Glu Tyr Tyr Ser Ser Leu
                660                 665                 670

Arg Trp Ile Leu Glu Asn Asp Pro Thr Glu Leu Asp Leu Arg Phe Ile
                675                 680                 685

Ile Asp Glu Glu Leu Phe Gly Gln Thr His Gln His Glu Leu Lys Thr
                690                 695                 700

Gly Gly Ser Glu Ile Val Val Thr Asn Lys Asn Lys Lys Glu Tyr Ile
705                 710                 715                 720
```

```
Tyr Leu Val Ile Gln Trp Arg Phe Val Asn Arg Ile Gln Lys Gln Met
                725                 730                 735

Ala Ala Phe Lys Glu Gly Phe Phe Glu Leu Ile Pro Gln Asp Leu Ile
            740                 745                 750

Lys Ile Phe Asp Glu Asn Glu Leu Glu Leu Leu Met Cys Gly Leu Gly
        755                 760                 765

Asp Val Asp Val Asn Asp Trp Arg Glu His Thr Lys Tyr Lys Asn Gly
    770                 775                 780

Tyr Ser Met Asn His Gln Val Ile His Trp Phe Trp Lys Ala Val Trp
785                 790                 795                 800

Met Met Asp Ser Glu Lys Arg Ile Arg Leu Leu Gln Phe Val Thr Gly
                805                 810                 815

Thr Ser Arg Val Pro Met Asn Gly Phe Ala Glu Leu Tyr Gly Ser Asn
            820                 825                 830

Gly Pro Gln Ser Phe Thr Val Glu Gln Trp Gly Thr Pro Asp Lys Leu
        835                 840                 845

Pro Arg Ala His Thr Cys Phe Asn Arg Leu Asp Leu Pro Pro Tyr Glu
    850                 855                 860

Ser Phe Asp Glu Leu Trp Asp Lys Leu Gln Met Ala Ile Glu Asn Thr
865                 870                 875                 880

Gln Gly Phe Asp Gly Val Asp
                885

<210> SEQ ID NO 49
<211> LENGTH: 324
<212> TYPE: PRT
<213> ORGANISM: Homo sapiens

<400> SEQUENCE: 49

Met Ser Arg Pro Ser Ser Thr Gly Pro Ser Ala Asn Lys Pro Cys Ser
1               5                   10                  15

Lys Gln Pro Pro Gln Pro Gln His Thr Pro Ser Pro Ala Ala Pro
            20                  25                  30

Pro Ala Ala Ala Thr Ile Ser Ala Ala Gly Pro Gly Ser Ser Ala Val
            35                  40                  45

Pro Ala Ala Ala Val Ile Ser Gly Pro Gly Gly Gly Gly Ala
        50                  55                  60

Gly Pro Val Ser Pro Gln His His Glu Leu Thr Ser Leu Phe Glu Cys
65                  70                  75                  80

Pro Val Cys Phe Asp Tyr Val Leu Pro Pro Ile Leu Gln Cys Gln Ala
                85                  90                  95

Gly His Leu Val Cys Asn Gln Cys Arg Gln Lys Leu Ser Cys Cys Pro
            100                 105                 110

Thr Cys Arg Gly Ala Leu Thr Pro Ser Ile Arg Asn Leu Ala Met Glu
        115                 120                 125

Lys Val Ala Ser Ala Val Leu Phe Pro Cys Lys Tyr Ala Thr Thr Gly
    130                 135                 140

Cys Ser Leu Thr Leu His His Thr Glu Lys Pro Glu His Glu Asp Ile
145                 150                 155                 160

Cys Glu Tyr Arg Pro Tyr Ser Cys Pro Cys Pro Gly Ala Ser Cys Lys
                165                 170                 175

Trp Gln Gly Ser Leu Glu Ala Val Met Ser His Leu Met His Ala His
            180                 185                 190

Lys Ser Ile Thr Thr Leu Gln Gly Glu Asp Ile Val Phe Leu Ala Thr
```

```
                195                 200                 205
Asp Ile Asn Leu Pro Gly Ala Val Asp Trp Val Met Met Gln Ser Cys
    210                 215                 220

Phe Gly His His Phe Met Leu Val Leu Glu Lys Gln Glu Lys Tyr Glu
225                 230                 235                 240

Gly His Gln Gln Phe Ala Ile Val Leu Ile Gly Thr Arg Lys
                245                 250                 255

Gln Ala Glu Asn Phe Ala Tyr Arg Leu Glu Leu Asn Gly Asn Arg Arg
                260                 265                 270

Arg Leu Thr Trp Glu Ala Thr Pro Arg Ser Ile His Asp Gly Val Ala
            275                 280                 285

Ala Ala Ile Met Asn Ser Asp Cys Leu Val Phe Asp Thr Ala Ile Ala
            290                 295                 300

His Leu Phe Ala Asp Asn Gly Asn Leu Gly Ile Asn Val Thr Ile Ser
305                 310                 315                 320

Thr Cys Cys Pro

<210> SEQ ID NO 50
<211> LENGTH: 301
<212> TYPE: PRT
<213> ORGANISM: Arabidopsis thaliana

<400> SEQUENCE: 50

Met Ala Phe Asn His Arg Lys Met Leu Leu Ser Cys Leu Gln Phe Lys
1               5                   10                  15

Asp Leu Arg Phe Cys Phe Arg Gln Tyr Pro Pro Pro Pro Pro Pro Pro
            20                  25                  30

Pro Pro Pro Arg Glu Leu Ser Leu Leu Leu Pro Thr Ser Ile Cys Val
        35                  40                  45

Val Gly Ser Ile Ile Leu Phe Leu Phe Leu Val Phe Phe Leu Tyr Leu
    50                  55                  60

His Ile Thr Gln Gln Arg Arg Ile Ser Ala Ala Ser Val Thr Pro Gly
65                  70                  75                  80

Asp Thr Asn Gln Gln Glu Asp Glu Asp Glu Thr Glu Glu Arg Asp Phe
                85                  90                  95

Ser Asp Phe His His Val Trp Gln Ile Pro Thr Val Gly Leu His Arg
            100                 105                 110

Ser Ala Ile Asn Ser Ile Thr Val Val Gly Phe Lys Lys Gly Glu Gly
        115                 120                 125

Ile Ile Asp Gly Thr Glu Cys Ser Val Cys Leu Asn Glu Phe Glu Glu
    130                 135                 140

Asp Glu Ser Leu Arg Leu Leu Pro Lys Cys Ser His Ala Phe His Leu
145                 150                 155                 160

Asn Cys Ile Asp Thr Trp Leu Leu Ser His Lys Asn Cys Pro Leu Cys
                165                 170                 175

Arg Ala Pro Val Leu Leu Ile Thr Glu Pro Pro His Gln Glu Thr Glu
            180                 185                 190

Thr Asn His Gln Pro Asp Ser Glu Ser Ser Asn Asp Leu Arg Gly Arg
        195                 200                 205

Gln Asp Ser Ser Arg Ser Arg Arg Asn His Asn Ile Phe Leu Pro Arg
    210                 215                 220

Ala Gln Ser Asp Leu Ala Asn Tyr Cys Gly Ser Gly Arg Val Glu Asn
225                 230                 235                 240

Val Arg Arg Ser Phe Ser Ile Gly Gly Ser Leu Ser Leu Cys Asp Gly
```

```
                    245                 250                 255
Ile Asn Asn Ala Thr Arg Ser Gly Arg Gln Phe Tyr Thr Ser Phe Ser
            260                 265                 270

Ala Asn Leu Phe Ser Ser Arg Arg Val Arg Asn Glu Gln Pro Ile
            275                 280                 285

Pro Gln Asn Gln Met Pro Ser Val Thr Gly Asn Thr Ser
            290                 295                 300

<210> SEQ ID NO 51
<211> LENGTH: 1030
<212> TYPE: PRT
<213> ORGANISM: Danio rerio

<400> SEQUENCE: 51

Met Thr Thr Gly Arg Asn Asn Arg Val Met Met Glu Gly Val Gly Ala
1               5                   10                  15

Arg Val Ile Arg Gly Pro Asp Trp Lys Trp Gly Lys Gln Asp Gly Gly
            20                  25                  30

Glu Gly His Val Gly Thr Val Arg Ser Phe Glu Ser Pro Glu Glu Val
        35                  40                  45

Val Val Val Trp Asp Asn Gly Thr Ala Ala Asn Tyr Arg Cys Ser Gly
50                  55                  60

Ala Tyr Asp Val Arg Ile Leu Asp Ser Ala Pro Thr Gly Ile Lys His
65                  70                  75                  80

Asp Gly Thr Met Cys Asp Thr Cys Arg Gln Gln Pro Ile Ile Gly Ile
                85                  90                  95

Arg Trp Lys Cys Ala Glu Cys Thr Asn Tyr Asp Leu Cys Thr Thr Cys
            100                 105                 110

Tyr His Gly Asp Lys His His Leu Arg His Arg Phe Tyr Arg Ile Thr
        115                 120                 125

Thr Pro Gly Ser Glu Arg Val Leu Leu Glu Ser Arg Arg Lys Ser Lys
    130                 135                 140

Lys Ile Thr Ala Arg Gly Ile Phe Ala Gly Gly Arg Val Val Arg Gly
145                 150                 155                 160

Val Asp Trp Gln Trp Glu Asp Gln Asp Gly Gly Asn Gly Arg Arg Gly
                165                 170                 175

Lys Val Thr Glu Ile Gln Asp Trp Ser Ala Ala Ser Pro His Ser Ala
            180                 185                 190

Ala Tyr Val Leu Trp Asp Asn Gly Ala Lys Asn Leu Tyr Arg Val Gly
        195                 200                 205

Phe Glu Gly Met Ser Asp Leu Lys Cys Val Gln Asp Ala Lys Gly Gly
    210                 215                 220

Thr Phe Tyr Arg Asp His Cys Pro Val Leu Gly Glu Gln Asn Gly Asn
225                 230                 235                 240

Arg Asn Pro Gly Gly Leu Gln Ile Gly Asp Leu Val Asn Ile Asp Leu
                245                 250                 255

Asp Leu Glu Ile Val Gln Ser Leu Gln His Gly His Gly Gly Trp Thr
            260                 265                 270

Asp Gly Met Phe Glu Thr Leu Thr Thr Thr Gly Thr Val Cys Gly Ile
        275                 280                 285

Asp Glu Asp His Asp Ile Val Val Gln Tyr Pro Ser Gly Asn Arg Trp
    290                 295                 300

Thr Phe Asn Pro Ala Val Leu Thr Lys Ala Asn Val Val Arg Ser Gly
305                 310                 315                 320
```

```
Glu Val Ala Ala Gly Ala Glu Gly Gly Ser Ser Gln Phe Met Val Gly
            325                 330                 335

Asp Leu Val Gln Ile Cys Tyr Asp Ile Asp Arg Ile Lys Leu Leu Gln
        340                 345                 350

Arg Gly His Gly Glu Trp Ala Glu Ala Met Leu Pro Thr Leu Gly Lys
            355                 360                 365

Val Gly Arg Val Gln Gln Ile Tyr Ser Asp Ser Asp Leu Lys Val Glu
    370                 375                 380

Val Cys Gly Thr Ser Trp Thr Tyr Asn Pro Ala Val Thr Lys Val
385                 390                 395                 400

Ala Pro Ala Gly Ser Ala Val Thr Asn Ala Ser Gly Glu Arg Leu Ser
                405                 410                 415

Gln Leu Leu Lys Lys Leu Phe Glu Thr Gln Glu Ser Gly Asp Ile Asn
            420                 425                 430

Glu Glu Leu Val Lys Ala Ala Asn Gly Asp Leu Ala Lys Val Glu
        435                 440                 445

Asp Ile Leu Lys Arg Pro Asp Val Asp Val Asn Gly Gln Cys Ala Gly
    450                 455                 460

His Thr Ala Met Gln Ala Ala Ser Gln Asn Gly His Val Asp Val Leu
465                 470                 475                 480

Lys Leu Leu Leu Lys His Ser Val Asp Leu Glu Ala Glu Asp Lys Asp
                485                 490                 495

Gly Asp Arg Ala Val His His Ala Ser Phe Gly Asp Glu Gly Ser Val
            500                 505                 510

Ile Glu Val Leu His Arg Gly Gly Ala Asp Leu Asn Ala Arg Asn Lys
        515                 520                 525

Arg Arg Gln Thr Pro Leu His Ile Ala Val Asn Lys Gly His Leu Gln
    530                 535                 540

Val Val Lys Thr Leu Leu Asp Phe Gly Cys His Pro Ser Leu Gln Asp
545                 550                 555                 560

Ser Glu Gly Asp Thr Pro Leu His Asp Ala Ile Ser Lys Lys Arg Asp
                565                 570                 575

Asp Met Leu Ser Val Leu Leu Glu Ala Gly Ala Asp Val Thr Ile Thr
            580                 585                 590

Asn Asn Asn Gly Phe Asn Ala Leu His His Ala Ala Leu Arg Gly Asn
        595                 600                 605

Pro Ser Ala Met Arg Val Leu Leu Ser Lys Leu Pro Arg Pro Trp Ile
    610                 615                 620

Val Asp Glu Lys Lys Asp Asp Gly Tyr Thr Ala Leu His Leu Ala Ala
625                 630                 635                 640

Leu Asn Asn His Val Glu Val Ala Glu Leu Leu Val His Gln Gly Asn
                645                 650                 655

Ala Asn Leu Asp Val Gln Asn Val Asn Gln Gln Thr Ala Leu His Leu
            660                 665                 670

Ala Val Glu Arg Gln His Thr Gln Ile Val Arg Leu Leu Val Arg Ala
        675                 680                 685

Glu Ala Lys Leu Asp Val Gln Asp Lys Asp Gly Asp Thr Pro Leu His
    690                 695                 700

Glu Ala Leu Arg His His Thr Leu Ser Gln Leu Arg Gln Leu Gln Asp
705                 710                 715                 720

Met Gln Asp Val Ser Lys Val Glu Pro Trp Glu Pro Ser Lys Asn Thr
                725                 730                 735

Leu Ile Met Gly Leu Gly Thr Gln Gly Ala Glu Lys Lys Ser Ala Ala
```

740                 745                 750

Ser Ile Ala Cys Phe Leu Ala Ala Asn Gly Ala Asp Leu Thr Ile Arg
            755                 760                 765

Asn Lys Lys Gly Gln Ser Pro Leu Asp Leu Cys Pro Asp Pro Ser Leu
        770                 775                 780

Cys Lys Ala Leu Ala Lys Cys His Lys Glu Lys Thr Ser Gly Gln Val
785                 790                 795                 800

Gly Ser Arg Ser Pro Ser Leu Asn Ser Asn Asn Glu Thr Leu Glu Glu
                805                 810                 815

Cys Met Val Cys Ser Asp Met Lys Arg Asp Thr Leu Phe Gly Pro Cys
            820                 825                 830

Gly His Ile Ala Thr Cys Ser Leu Cys Ser Pro Arg Val Lys Lys Cys
        835                 840                 845

Leu Ile Cys Lys Glu Gln Val Gln Ser Arg Thr Lys Ile Glu Glu Cys
        850                 855                 860

Val Val Cys Ser Asp Lys Lys Ala Ala Val Leu Phe Gln Pro Cys Gly
865                 870                 875                 880

His Met Cys Ala Cys Glu Asn Cys Ala Ser Leu Met Lys Lys Cys Val
                885                 890                 895

Gln Cys Arg Ala Val Val Glu Arg Arg Thr Pro Phe Val Leu Cys Cys
            900                 905                 910

Gly Gly Lys Gly Met Glu Asp Ala Thr Asp Asp Glu Asp Leu Thr Gly
        915                 920                 925

Gly Ser Asn Ser Met Ala Gly Gly Ser Gln Asp Leu Leu Gln Pro Asn
        930                 935                 940

Asn Leu Ala Leu Ser Trp Ser Ser Gly Asn Ile Pro Ala Leu Gln Arg
945                 950                 955                 960

Asp Lys Asp Asn Thr Asn Val Asn Ala Asp Val Gln Lys Leu Gln Gln
                965                 970                 975

Gln Leu Gln Asp Ile Lys Glu Gln Thr Met Cys Pro Val Cys Leu Asp
            980                 985                 990

Arg Leu Lys Asn Met Ile Phe Met Cys Gly His Gly Thr Cys Gln Leu
        995                 1000                1005

Cys Gly Asp Arg Met Ser Glu Cys Pro Ile Cys Arg Lys Ala Ile
        1010                1015                1020

Glu Arg Arg Ile Leu Leu Tyr
        1025                1030

<210> SEQ ID NO 52
<211> LENGTH: 522
<212> TYPE: PRT
<213> ORGANISM: Arabidopsis thaliana

<400> SEQUENCE: 52

Met Ser Val Lys Asn Asn Ser Phe Ser Ala Glu Ile Pro Asp Val
1               5                   10                  15

Ala Asp Gln Pro Arg Asp Arg Phe Asn Pro Glu Ala Thr Gln Asp Leu
            20                  25                  30

Gln Glu Lys Asp Glu Thr Lys Glu Lys Glu Gly Asp Glu Glu Val
        35                  40                  45

Lys His Asp Glu Ala Glu Glu Asp Gln Glu Val Val Lys Pro Asn Asp
    50                  55                  60

Ala Glu Glu Asp Asp Asp Gly Asp Asp Ala Glu Glu Asp Glu Glu Glu
65                  70                  75                  80

```
Glu Val Glu Ala Glu Glu Asp Glu Glu Ala Glu Glu Glu Glu Glu
                 85                  90                  95

Glu Glu Glu Glu Glu Glu Glu Glu Asp Ser Lys Glu Arg Ser Pro
            100                 105                 110

Ser Ser Ile Ser Gly Asp Gln Ser Glu Phe Met Glu Ile Asp Leu Gly
            115                 120                 125

Glu Ile Arg Lys Asp Val Gln Cys Pro Ile Cys Leu Gly Ile Ile Lys
            130                 135                 140

Lys Thr Arg Thr Val Met Glu Cys Leu His Arg Phe Cys Arg Glu Cys
145                 150                 155                 160

Ile Asp Lys Ser Met Arg Leu Gly Asn Asn Glu Cys Pro Ala Cys Arg
            165                 170                 175

Lys His Cys Ala Ser Arg Arg Ser Leu Arg Asp Asp Pro Lys Phe Asp
            180                 185                 190

Ala Leu Ile Ala Ala Leu Phe Thr Asn Ile Asp Ser Tyr Glu Glu Glu
            195                 200                 205

Glu Leu Ala Phe His Glu Asp Glu Met Ala Arg Asn Lys Gln Ile Gln
            210                 215                 220

Ala Ser Ile Ala Gln Ile Ser Gln Arg Gln Ser Glu Ala Leu Val Lys
225                 230                 235                 240

Arg Arg Ser Leu Gly Lys Glu Ala Ala Val Leu Met Arg Ser Pro Arg
            245                 250                 255

Ile Ala Ser Gly Ser Arg Arg Arg Asn Ser Arg Asn Met Glu Gln
            260                 265                 270

Gln Asn Ala Ser Glu Ala His Glu Asp Asp Asn Asp Asp Asn Asn
            275                 280                 285

Asn Arg Gly Arg Asp Lys Asp Ser Ser Asp Glu Arg Gly Thr Glu
            290                 295                 300

Val Arg Gln Lys Lys Arg Arg Lys Arg Ser Thr Ser Arg Ser Thr Gln
305                 310                 315                 320

His Pro Ser Ser Ser Gly Ala Asn Lys Asn Asn Gly Asn Cys Ala Asp
            325                 330                 335

Asn Asp Thr Glu Val Tyr Arg Asp Thr Lys Gly Ile Ser Pro Gly Leu
            340                 345                 350

Val Trp Asn Pro Glu Ile Leu Ala Trp Gly Arg Gly Thr Arg Ser
            355                 360                 365

Asn Thr Arg His Gly Asn Asn Thr Ser Gly Gly Ser Ser Lys Ser Val
            370                 375                 380

Arg Asn Ala Arg Val Asn Lys Leu Val Glu Tyr Leu Arg Ser Val
385                 390                 395                 400

Asp Gly Ser Ser Val Glu Leu Asp Ile His Val Lys Leu Val Ser Leu
            405                 410                 415

Asp Thr Lys Cys Ile Pro Asp Leu Pro Gln Pro Tyr Leu Cys Cys Arg
            420                 425                 430

Pro Thr Leu Leu Val Lys Gln Leu Arg Glu Phe Val Ala Leu Gln Ile
            435                 440                 445

His Leu Lys Thr Glu Glu Val Glu Leu Leu Val Thr Arg Arg Val
450                 455                 460

Gly Glu Asp Ala Ala Ile Glu Asn Leu Pro Val Thr Pro Ala Ser
465                 470                 475                 480

Ala Ala Ala Ser Lys Asp Glu Met Leu Ser Leu Glu Asp Asn Glu Thr
            485                 490                 495

Leu Ser Arg Leu Lys Ile Asp Phe Ile Ser Ser His Glu Gln His Leu
```

Ile Ile Ala Tyr Arg Lys Lys Gln Thr Glu
          515                 520

<210> SEQ ID NO 53
<211> LENGTH: 574
<212> TYPE: PRT
<213> ORGANISM: Homo sapiens

<400> SEQUENCE: 53

Met Ala Thr Leu Val Val Asn Lys Leu Gly Ala Gly Val Asp Ser Gly
1               5                   10                  15

Arg Gln Gly Ser Arg Gly Thr Ala Val Val Lys Val Leu Glu Cys Gly
            20                  25                  30

Val Cys Glu Asp Val Phe Ser Leu Gln Gly Asp Lys Val Pro Arg Leu
        35                  40                  45

Leu Leu Cys Gly His Thr Val Cys His Asp Cys Leu Thr Arg Leu Pro
    50                  55                  60

Leu His Gly Arg Ala Ile Arg Cys Pro Phe Asp Arg Gln Val Thr Asp
65                  70                  75                  80

Leu Gly Asp Ser Gly Val Trp Gly Leu Lys Lys Asn Phe Ala Leu Leu
                85                  90                  95

Glu Leu Leu Glu Arg Leu Gln Asn Gly Pro Ile Gly Gln Tyr Gly Ala
            100                 105                 110

Ala Glu Glu Ser Ile Gly Ile Ser Gly Glu Ser Ile Ile Arg Cys Asp
        115                 120                 125

Glu Asp Glu Ala His Leu Ala Ser Val Tyr Cys Thr Val Cys Ala Thr
    130                 135                 140

His Leu Cys Ser Glu Cys Ser Gln Val Thr His Ser Thr Lys Thr Leu
145                 150                 155                 160

Ala Lys His Arg Arg Val Pro Leu Ala Asp Lys Pro His Glu Lys Thr
                165                 170                 175

Met Cys Ser Gln His Gln Val His Ala Ile Glu Phe Val Cys Leu Glu
            180                 185                 190

Glu Gly Cys Gln Thr Ser Pro Leu Met Cys Val Cys Lys Glu Tyr
        195                 200                 205

Gly Lys His Gln Gly His Lys His Ser Val Leu Glu Pro Glu Ala Asn
    210                 215                 220

Gln Ile Arg Ala Ser Ile Leu Asp Met Ala His Cys Ile Arg Thr Phe
225                 230                 235                 240

Thr Glu Glu Ile Ser Asp Tyr Ser Arg Lys Leu Val Gly Ile Val Gln
                245                 250                 255

His Ile Glu Gly Gly Glu Gln Ile Val Glu Asp Gly Ile Gly Met Ala
            260                 265                 270

His Thr Glu His Val Pro Gly Thr Ala Glu Asn Ala Arg Ser Cys Ile
        275                 280                 285

Arg Ala Tyr Phe Tyr Asp Leu His Glu Thr Leu Cys Arg Gln Glu Glu
    290                 295                 300

Met Ala Leu Ser Val Val Asp Ala His Val Arg Glu Lys Leu Ile Trp
305                 310                 315                 320

Leu Arg Gln Gln Gln Glu Asp Met Thr Ile Leu Leu Ser Glu Val Ser
                325                 330                 335

Ala Ala Cys Leu His Cys Glu Lys Thr Leu Gln Gln Asp Asp Cys Arg
            340                 345                 350

```
Val Val Leu Ala Lys Gln Glu Ile Thr Arg Leu Leu Glu Thr Leu Gln
            355                 360                 365

Lys Gln Gln Gln Gln Phe Thr Glu Val Ala Asp His Ile Gln Leu Asp
370                 375                 380

Ala Ser Ile Pro Val Thr Phe Thr Lys Asp Asn Arg Val His Ile Gly
385                 390                 395                 400

Pro Lys Met Glu Ile Arg Val Val Thr Leu Gly Leu Asp Gly Ala Gly
                405                 410                 415

Lys Thr Thr Ile Leu Phe Lys Leu Lys Gln Asp Glu Phe Met Gln Pro
            420                 425                 430

Ile Pro Thr Ile Gly Phe Asn Val Glu Thr Val Glu Tyr Lys Asn Leu
        435                 440                 445

Lys Phe Thr Ile Trp Asp Val Gly Gly Lys His Lys Leu Arg Pro Leu
    450                 455                 460

Trp Lys His Tyr Tyr Leu Asn Thr Gln Ala Val Val Phe Val Val Asp
465                 470                 475                 480

Ser Ser His Arg Asp Arg Ile Ser Glu Ala His Ser Glu Leu Ala Lys
                485                 490                 495

Leu Leu Thr Glu Lys Glu Leu Arg Asp Ala Leu Leu Leu Ile Phe Ala
            500                 505                 510

Asn Lys Gln Asp Val Ala Gly Ala Leu Ser Val Glu Glu Ile Thr Glu
        515                 520                 525

Leu Leu Ser Leu His Lys Leu Cys Cys Gly Arg Ser Trp Tyr Ile Gln
    530                 535                 540

Gly Cys Asp Ala Arg Ser Gly Met Gly Leu Tyr Glu Gly Leu Asp Trp
545                 550                 555                 560

Leu Ser Arg Gln Leu Val Ala Ala Gly Val Leu Asp Val Ala
                565                 570

<210> SEQ ID NO 54
<211> LENGTH: 864
<212> TYPE: PRT
<213> ORGANISM: Mus musculus

<400> SEQUENCE: 54

Met Ser Asp Ser Gly Pro Gln Leu Asp Ser Met Gly Ser Leu Thr Met
1               5                   10                  15

Lys Ser Gln Leu Gln Ile Thr Val Ile Ser Ala Lys Leu Lys Glu Asn
            20                  25                  30

Lys Lys Asn Trp Phe Gly Pro Ser Pro Tyr Val Glu Val Thr Val Asp
        35                  40                  45

Gly Gln Ser Lys Lys Thr Glu Lys Cys Asn Asn Thr Asn Ser Pro Lys
    50                  55                  60

Trp Lys Gln Pro Leu Thr Val Ile Val Thr Pro Thr Ser Lys Leu Cys
65                  70                  75                  80

Phe Arg Val Trp Ser His Gln Thr Leu Lys Ser Asp Val Leu Leu Gly
                85                  90                  95

Thr Ala Gly Leu Asp Ile Tyr Glu Thr Leu Lys Ser Asn Asn Met Lys
            100                 105                 110

Leu Glu Glu Val Val Met Thr Leu Gln Leu Val Gly Asp Lys Glu Pro
        115                 120                 125

Thr Glu Thr Met Gly Asp Leu Ser Val Cys Leu Asp Gly Leu Gln Val
    130                 135                 140

Glu Ala Glu Val Val Thr Asn Gly Glu Thr Ser Cys Ser Glu Ser Thr
145                 150                 155                 160
```

```
Thr Gln Asn Asp Asp Gly Cys Arg Thr Arg Asp Asp Thr Arg Val Ser
                165                 170                 175

Thr Asn Gly Ser Glu Asp Pro Glu Val Ala Ala Ser Gly Glu Asn Lys
            180                 185                 190

Arg Ala Asn Gly Asn Asn Ser Pro Ser Leu Ser Asn Gly Gly Phe Lys
            195                 200                 205

Pro Ser Arg Pro Pro Arg Pro Ser Arg Pro Pro Pro Thr Pro Arg
210                 215                 220

Arg Pro Ala Ser Val Asn Gly Ser Pro Ser Thr Asn Ser Asp Ser Asp
225                 230                 235                 240

Gly Ser Ser Thr Gly Ser Leu Pro Pro Thr Asn Thr Asn Val Asn Thr
                245                 250                 255

Ser Thr Ser Glu Gly Ala Thr Ser Gly Leu Ile Ile Pro Leu Thr Ile
            260                 265                 270

Ser Gly Gly Ser Gly Pro Arg Pro Leu Asn Thr Val Ser Gln Ala Pro
            275                 280                 285

Leu Pro Pro Gly Trp Glu Gln Arg Val Asp Gln His Gly Arg Val Tyr
        290                 295                 300

Tyr Val Asp His Val Glu Lys Arg Thr Thr Trp Asp Arg Pro Glu Pro
305                 310                 315                 320

Leu Pro Pro Gly Trp Glu Arg Arg Val Asp Asn Met Gly Arg Ile Tyr
            325                 330                 335

Tyr Val Asp His Phe Thr Arg Thr Thr Thr Trp Gln Arg Pro Thr Leu
            340                 345                 350

Glu Ser Val Arg Asn Tyr Glu Gln Trp Gln Leu Gln Arg Ser Gln Leu
        355                 360                 365

Gln Gly Ala Met Gln Gln Phe Asn Gln Arg Phe Ile Tyr Gly Asn Gln
    370                 375                 380

Asp Leu Phe Ala Thr Ser Gln Asn Lys Glu Phe Asp Pro Leu Gly Pro
385                 390                 395                 400

Leu Pro Pro Gly Trp Glu Lys Arg Thr Asp Ser Asn Gly Arg Val Tyr
            405                 410                 415

Phe Val Asn His Asn Thr Arg Ile Thr Gln Trp Glu Asp Pro Arg Ser
            420                 425                 430

Gln Gly Gln Leu Asn Glu Lys Pro Leu Pro Glu Gly Trp Glu Met Arg
        435                 440                 445

Phe Thr Val Asp Gly Ile Pro Tyr Phe Val Asp His Asn Arg Arg Ala
    450                 455                 460

Thr Thr Tyr Ile Asp Pro Arg Thr Gly Lys Ser Ala Leu Asp Asn Gly
465                 470                 475                 480

Pro Gln Ile Ala Tyr Val Arg Asp Phe Lys Ala Lys Val Gln Tyr Phe
            485                 490                 495

Arg Phe Trp Cys Gln Gln Leu Ala Met Pro Gln His Ile Lys Ile Thr
            500                 505                 510

Val Thr Arg Lys Thr Leu Phe Glu Asp Ser Phe Gln Gln Ile Met Ser
        515                 520                 525

Phe Ser Pro Gln Asp Leu Arg Arg Arg Leu Trp Val Ile Phe Pro Gly
    530                 535                 540

Glu Glu Gly Leu Asp Tyr Gly Gly Val Ala Arg Glu Trp Phe Phe Leu
545                 550                 555                 560

Leu Ser His Glu Val Leu Asn Pro Met Tyr Cys Leu Phe Glu Tyr Ala
            565                 570                 575
```

```
Gly Lys Asp Asn Tyr Cys Leu Gln Ile Asn Pro Ala Ser Tyr Ile Asn
                580                 585                 590

Pro Asp His Leu Lys Tyr Phe Arg Phe Ile Gly Arg Phe Ile Ala Met
            595                 600                 605

Ala Leu Phe His Gly Lys Phe Ile Asp Thr Gly Phe Ser Leu Pro Phe
        610                 615                 620

Tyr Lys Arg Ile Leu Asn Lys Pro Val Gly Leu Lys Asp Leu Glu Ser
625                 630                 635                 640

Ile Asp Pro Glu Phe Tyr Asn Ser Leu Ile Trp Val Lys Glu Asn Asn
                645                 650                 655

Ile Glu Glu Cys Gly Leu Glu Met Tyr Phe Ser Val Asp Lys Glu Ile
            660                 665                 670

Leu Gly Glu Ile Lys Ser His Asp Leu Lys Pro Asn Gly Gly Asn Ile
        675                 680                 685

Leu Val Thr Glu Glu Asn Lys Glu Glu Tyr Ile Arg Met Val Ala Glu
690                 695                 700

Trp Arg Leu Ser Arg Gly Val Glu Glu Gln Thr Gln Ala Phe Phe Glu
705                 710                 715                 720

Gly Phe Asn Glu Ile Leu Pro Gln Gln Tyr Leu Gln Tyr Phe Asp Ala
                725                 730                 735

Lys Glu Leu Glu Val Leu Leu Cys Gly Met Gln Glu Ile Asp Leu Asn
            740                 745                 750

Asp Trp Gln Arg His Ala Ile Tyr Arg His Tyr Thr Arg Thr Ser Lys
        755                 760                 765

Gln Ile Met Trp Phe Trp Gln Phe Val Lys Glu Ile Asp Asn Glu Lys
770                 775                 780

Arg Met Arg Leu Leu Gln Phe Val Thr Gly Thr Cys Arg Leu Pro Val
785                 790                 795                 800

Gly Gly Phe Ala Asp Leu Met Gly Ser Asn Gly Pro Gln Lys Phe Cys
                805                 810                 815

Ile Glu Lys Val Gly Lys Glu Asn Trp Leu Pro Arg Ser His Thr Cys
            820                 825                 830

Phe Asn Arg Leu Asp Leu Pro Pro Tyr Lys Ser Tyr Glu Gln Leu Lys
        835                 840                 845

Glu Lys Leu Leu Phe Ala Ile Glu Glu Thr Glu Gly Phe Gly Gln Glu
850                 855                 860

<210> SEQ ID NO 55
<211> LENGTH: 353
<212> TYPE: PRT
<213> ORGANISM: Homo sapiens

<400> SEQUENCE: 55

Met Asp Tyr Lys Ser Ser Leu Ile Gln Asp Gly Asn Pro Met Glu Asn
1               5                   10                  15

Leu Glu Lys Gln Leu Ile Cys Pro Ile Cys Leu Glu Met Phe Thr Lys
                20                  25                  30

Pro Val Val Ile Leu Pro Cys Gln His Asn Leu Cys Arg Lys Cys Ala
            35                  40                  45

Asn Asp Ile Phe Gln Ala Ala Asn Pro Tyr Trp Thr Ser Arg Gly Ser
        50                  55                  60

Ser Val Ser Met Ser Gly Gly Arg Phe Arg Cys Pro Thr Cys Arg His
65                  70                  75                  80

Glu Val Ile Met Asp Arg His Gly Val Tyr Gly Leu Gln Arg Asn Leu
                85                  90                  95
```

```
Leu Val Glu Asn Ile Ile Asp Ile Tyr Lys Gln Cys Ser Ser Arg
                100                 105                 110

Pro Leu Gln Lys Gly Ser His Pro Met Cys Lys Glu His Glu Asp Glu
            115                 120                 125

Lys Ile Asn Ile Tyr Cys Leu Thr Cys Glu Val Pro Thr Cys Ser Met
    130                 135                 140

Cys Lys Val Phe Gly Ile His Lys Ala Cys Glu Val Ala Pro Leu Gln
145                 150                 155                 160

Ser Val Phe Gln Gly Gln Lys Thr Glu Leu Asn Asn Cys Ile Ser Met
                165                 170                 175

Leu Val Ala Gly Asn Asp Arg Val Gln Thr Ile Ile Thr Gln Leu Glu
            180                 185                 190

Asp Ser Arg Arg Val Thr Lys Glu Asn Ser His Gln Val Lys Glu Glu
                195                 200                 205

Leu Ser Gln Lys Phe Asp Thr Leu Tyr Ala Ile Leu Asp Glu Lys Lys
        210                 215                 220

Ser Glu Leu Leu Gln Arg Ile Thr Gln Glu Gln Lys Lys Leu Ser
225                 230                 235                 240

Phe Ile Glu Ala Leu Ile Gln Gln Tyr Gln Gln Leu Asp Lys Ser
                245                 250                 255

Thr Lys Leu Val Glu Thr Ala Ile Gln Ser Leu Asp Glu Pro Gly Gly
                260                 265                 270

Ala Thr Phe Leu Leu Thr Ala Lys Gln Leu Ile Lys Ser Ile Val Glu
            275                 280                 285

Ala Ser Lys Gly Cys Gln Leu Gly Lys Thr Glu Gln Gly Phe Glu Asn
            290                 295                 300

Met Asp Phe Phe Thr Leu Asp Leu Glu His Ile Ala Asp Ala Leu Arg
305                 310                 315                 320

Ala Ile Asp Phe Gly Thr Asp Glu Glu Glu Glu Phe Ile Glu Glu
                325                 330                 335

Glu Asp Gln Glu Glu Glu Glu Ser Thr Glu Gly Lys Glu Glu Gly His
                340                 345                 350

Gln

<210> SEQ ID NO 56
<211> LENGTH: 870
<212> TYPE: PRT
<213> ORGANISM: Homo sapiens

<400> SEQUENCE: 56

Met Ala Ser Ala Ser Ser Ser Arg Ala Gly Val Ala Leu Pro Phe Glu
1               5                   10                  15

Lys Ser Gln Leu Thr Leu Lys Val Val Ser Ala Lys Pro Lys Val His
                20                  25                  30

Asn Arg Gln Pro Arg Ile Asn Ser Tyr Val Glu Val Ala Val Asp Gly
            35                  40                  45

Leu Pro Ser Glu Thr Lys Lys Thr Gly Lys Arg Ile Gly Ser Ser Glu
        50                  55                  60

Leu Leu Trp Asn Glu Ile Ile Ile Leu Asn Val Thr Ala Gln Ser His
65                  70                  75                  80

Leu Asp Leu Lys Val Trp Ser Cys His Thr Leu Arg Asn Glu Leu Leu
                85                  90                  95

Gly Thr Ala Ser Val Asn Leu Ser Asn Val Leu Lys Asn Asn Gly Gly
            100                 105                 110
```

```
Lys Met Glu Asn Met Gln Leu Thr Leu Asn Leu Gln Thr Glu Asn Lys
            115                 120                 125
Gly Ser Val Val Ser Gly Gly Glu Leu Thr Ile Phe Leu Asp Gly Pro
        130                 135                 140
Thr Val Asp Leu Gly Asn Val Pro Asn Gly Ser Ala Leu Thr Asp Gly
145                 150                 155                 160
Ser Gln Leu Pro Ser Arg Asp Ser Ser Gly Thr Ala Val Ala Pro Glu
                165                 170                 175
Asn Arg His Gln Pro Pro Ser Thr Asn Cys Phe Gly Gly Arg Ser Arg
            180                 185                 190
Thr His Arg His Ser Gly Ala Ser Ala Arg Thr Thr Pro Ala Thr Gly
        195                 200                 205
Glu Gln Ser Pro Gly Ala Arg Ser Arg His Arg Gln Pro Val Lys Asn
    210                 215                 220
Ser Gly His Ser Gly Leu Ala Asn Gly Thr Val Asn Asp Glu Pro Thr
225                 230                 235                 240
Thr Ala Thr Asp Pro Glu Pro Ser Val Val Gly Val Thr Ser Pro
                245                 250                 255
Pro Ala Ala Pro Leu Ser Val Thr Pro Asn Pro Asn Thr Thr Ser Leu
            260                 265                 270
Pro Ala Pro Ala Thr Pro Ala Glu Gly Glu Glu Pro Ser Thr Ser Gly
        275                 280                 285
Thr Gln Gln Leu Pro Ala Ala Ala Gln Ala Pro Asp Ala Leu Pro Ala
    290                 295                 300
Gly Trp Glu Gln Arg Glu Leu Pro Asn Gly Arg Val Tyr Tyr Val Asp
305                 310                 315                 320
His Asn Thr Lys Thr Thr Thr Trp Glu Arg Pro Leu Pro Pro Gly Trp
                325                 330                 335
Glu Lys Arg Thr Asp Pro Arg Gly Arg Phe Tyr Tyr Val Asp His Asn
            340                 345                 350
Thr Arg Thr Thr Thr Trp Gln Arg Pro Thr Ala Glu Tyr Val Arg Asn
        355                 360                 365
Tyr Glu Gln Trp Gln Ser Gln Arg Asn Gln Leu Gln Gly Ala Met Gln
    370                 375                 380
His Phe Ser Gln Arg Phe Leu Tyr Gln Ser Ser Ser Ala Ser Thr Asp
385                 390                 395                 400
His Asp Pro Leu Gly Pro Leu Pro Pro Gly Trp Glu Lys Arg Gln Asp
                405                 410                 415
Asn Gly Arg Val Tyr Tyr Val Asn His Asn Thr Arg Thr Thr Gln Trp
            420                 425                 430
Glu Asp Pro Arg Thr Gln Gly Met Ile Gln Glu Pro Ala Leu Pro Pro
        435                 440                 445
Gly Trp Glu Met Lys Tyr Thr Ser Glu Gly Val Arg Tyr Phe Val Asp
    450                 455                 460
His Asn Thr Arg Thr Thr Thr Phe Lys Asp Pro Arg Pro Gly Phe Glu
465                 470                 475                 480
Ser Gly Thr Lys Gln Gly Ser Pro Gly Ala Tyr Asp Arg Ser Phe Arg
                485                 490                 495
Trp Lys Tyr His Gln Phe Arg Phe Leu Cys His Ser Asn Ala Leu Pro
            500                 505                 510
Ser His Val Lys Ile Ser Val Ser Arg Gln Thr Leu Phe Glu Asp Ser
        515                 520                 525
```

```
Phe Gln Gln Ile Met Asn Met Lys Pro Tyr Asp Leu Arg Arg Leu
        530                 535                 540

Tyr Ile Ile Met Arg Gly Glu Glu Gly Leu Asp Tyr Gly Gly Ile Ala
545                 550                 555                 560

Arg Glu Trp Phe Phe Leu Leu Ser His Glu Val Leu Asn Pro Met Tyr
                565                 570                 575

Cys Leu Phe Glu Tyr Ala Gly Lys Asn Asn Tyr Cys Leu Gln Ile Asn
                580                 585                 590

Pro Ala Ser Ser Ile Asn Pro Asp His Leu Thr Tyr Phe Arg Phe Ile
            595                 600                 605

Gly Arg Phe Ile Ala Met Ala Leu Tyr His Gly Lys Phe Ile Asp Thr
610                 615                 620

Gly Phe Thr Leu Pro Phe Tyr Lys Arg Met Leu Asn Lys Arg Pro Thr
625                 630                 635                 640

Leu Lys Asp Leu Glu Ser Ile Asp Pro Glu Phe Tyr Asn Ser Ile Val
                645                 650                 655

Trp Ile Lys Glu Asn Asn Leu Glu Glu Cys Gly Leu Glu Leu Tyr Phe
                660                 665                 670

Ile Gln Asp Met Glu Ile Leu Gly Lys Val Thr Thr His Glu Leu Lys
                675                 680                 685

Glu Gly Gly Glu Ser Ile Arg Val Thr Glu Glu Asn Lys Glu Glu Tyr
            690                 695                 700

Ile Met Leu Leu Thr Asp Trp Arg Phe Thr Arg Gly Val Glu Glu Gln
705                 710                 715                 720

Thr Lys Ala Phe Leu Asp Gly Phe Asn Glu Val Ala Pro Leu Glu Trp
                725                 730                 735

Leu Arg Tyr Phe Asp Glu Lys Glu Leu Glu Leu Met Leu Cys Gly Met
                740                 745                 750

Gln Glu Ile Asp Met Ser Asp Trp Gln Lys Ser Thr Ile Tyr Arg His
            755                 760                 765

Tyr Thr Lys Asn Ser Lys Gln Ile Gln Trp Phe Trp Gln Val Val Lys
770                 775                 780

Glu Met Asp Asn Glu Lys Arg Ile Arg Leu Leu Gln Phe Val Thr Gly
785                 790                 795                 800

Thr Cys Arg Leu Pro Val Gly Gly Phe Ala Glu Leu Ile Gly Ser Asn
                805                 810                 815

Gly Pro Gln Lys Phe Cys Ile Asp Lys Val Gly Lys Glu Thr Trp Leu
                820                 825                 830

Pro Arg Ser His Thr Cys Phe Asn Arg Leu Asp Leu Pro Pro Tyr Lys
                835                 840                 845

Ser Tyr Glu Gln Leu Arg Glu Lys Leu Leu Tyr Ala Ile Glu Glu Thr
850                 855                 860

Glu Gly Phe Gly Gln Glu
865                 870

<210> SEQ ID NO 57
<211> LENGTH: 180
<212> TYPE: PRT
<213> ORGANISM: Homo sapiens

<400> SEQUENCE: 57

Met Ala Ala Ala Glu Glu Asp Gly Gly Pro Glu Gly Pro Asn Arg
1               5                   10                  15

Glu Arg Gly Gly Ala Gly Ala Thr Phe Glu Cys Asn Ile Cys Leu Glu
                20                  25                  30
```

```
Thr Ala Arg Glu Ala Val Val Ser Val Cys Gly His Leu Tyr Cys Trp
        35                  40                  45

Pro Cys Leu His Gln Trp Leu Glu Thr Arg Pro Glu Arg Gln Glu Cys
    50                  55                  60

Pro Val Cys Lys Ala Gly Ile Ser Arg Glu Lys Val Val Pro Leu Tyr
65                  70                  75                  80

Gly Arg Gly Ser Gln Lys Pro Gln Asp Pro Arg Leu Lys Thr Pro Pro
                85                  90                  95

Arg Pro Gln Gly Gln Arg Pro Ala Pro Glu Ser Arg Gly Gly Phe Gln
            100                 105                 110

Pro Phe Gly Asp Thr Gly Gly Phe His Phe Ser Phe Gly Val Gly Ala
            115                 120                 125

Phe Pro Phe Gly Phe Phe Thr Thr Val Phe Asn Ala His Glu Pro Phe
        130                 135                 140

Arg Arg Gly Thr Gly Val Asp Leu Gly Gln Gly His Pro Ala Ser Ser
145                 150                 155                 160

Trp Gln Asp Ser Leu Phe Leu Phe Leu Ala Ile Phe Phe Phe Phe Trp
                165                 170                 175

Leu Leu Ser Ile
            180

<210> SEQ ID NO 58
<211> LENGTH: 875
<212> TYPE: PRT
<213> ORGANISM: Homo sapiens

<400> SEQUENCE: 58

Met Glu Lys Leu His Gln Cys Tyr Trp Lys Ser Gly Glu Pro Gln Ser
1               5                   10                  15

Asp Asp Ile Glu Ala Ser Arg Met Lys Arg Ala Ala Lys His Leu
            20                  25                  30

Ile Glu Arg Tyr Tyr His Gln Leu Thr Glu Gly Cys Gly Asn Glu Ala
        35                  40                  45

Cys Thr Asn Glu Phe Cys Ala Ser Cys Pro Thr Phe Leu Arg Met Asp
    50                  55                  60

Asn Asn Ala Ala Ala Ile Lys Ala Leu Glu Leu Tyr Lys Ile Asn Ala
65                  70                  75                  80

Lys Leu Cys Asp Pro His Pro Ser Lys Lys Gly Ala Ser Ser Ala Tyr
                85                  90                  95

Leu Glu Asn Ser Lys Gly Ala Pro Asn Asn Ser Cys Ser Glu Ile Lys
            100                 105                 110

Met Asn Lys Lys Gly Ala Arg Ile Asp Phe Lys Asp Val Thr Tyr Leu
            115                 120                 125

Thr Glu Glu Lys Val Tyr Glu Ile Leu Glu Leu Cys Arg Glu Arg Glu
        130                 135                 140

Asp Tyr Ser Pro Leu Ile Arg Val Ile Gly Arg Val Phe Ser Ser Ala
145                 150                 155                 160

Glu Ala Leu Val Gln Ser Phe Arg Lys Val Lys Gln His Thr Lys Glu
                165                 170                 175

Glu Leu Lys Ser Leu Gln Ala Lys Asp Glu Lys Asp Glu Asp
            180                 185                 190

Lys Glu Lys Ala Ala Cys Ser Ala Ala Ala Met Glu Glu Asp Ser Glu
            195                 200                 205

Ala Ser Ser Ser Arg Ile Gly Asp Ser Ser Gln Gly Asp Asn Asn Leu
```

```
            210                 215                 220
Gln Lys Leu Gly Pro Asp Asp Val Ser Val Asp Ile Asp Ala Ile Arg
225                 230                 235                 240

Arg Val Tyr Thr Arg Leu Leu Ser Asn Glu Lys Ile Glu Thr Ala Phe
                245                 250                 255

Leu Asn Ala Leu Val Tyr Leu Ser Pro Asn Val Glu Cys Asp Leu Thr
                260                 265                 270

Tyr His Asn Val Tyr Ser Arg Asp Pro Asn Tyr Leu Asn Leu Phe Ile
                275                 280                 285

Ile Val Met Glu Asn Arg Asn Leu His Ser Pro Glu Tyr Leu Glu Met
            290                 295                 300

Ala Leu Pro Leu Phe Cys Lys Ala Met Ser Lys Leu Pro Leu Ala Ala
305                 310                 315                 320

Gln Gly Lys Leu Ile Arg Leu Trp Ser Lys Tyr Asn Ala Asp Gln Ile
                325                 330                 335

Arg Arg Met Met Glu Thr Phe Gln Gln Leu Ile Thr Tyr Lys Val Ile
                340                 345                 350

Ser Asn Glu Phe Asn Ser Arg Asn Leu Val Asn Asp Asp Ala Ile
                355                 360                 365

Val Ala Ala Ser Lys Cys Leu Lys Met Val Tyr Tyr Ala Asn Val Val
            370                 375                 380

Gly Gly Glu Val Asp Thr Asn His Asn Glu Glu Asp Asp Glu Glu Pro
385                 390                 395                 400

Ile Pro Glu Ser Ser Glu Leu Thr Leu Gln Glu Leu Leu Gly Glu Glu
                405                 410                 415

Arg Arg Asn Lys Lys Gly Pro Arg Val Asp Pro Leu Glu Thr Glu Leu
                420                 425                 430

Gly Val Lys Thr Leu Asp Cys Arg Lys Pro Leu Ile Pro Phe Glu Glu
            435                 440                 445

Phe Ile Asn Glu Pro Leu Asn Glu Val Leu Glu Met Asp Lys Asp Tyr
                450                 455                 460

Thr Phe Phe Lys Val Glu Thr Glu Asn Lys Phe Ser Phe Met Thr Cys
465                 470                 475                 480

Pro Phe Ile Leu Asn Ala Val Thr Lys Asn Leu Gly Leu Tyr Tyr Asp
                485                 490                 495

Asn Arg Ile Arg Met Tyr Ser Glu Arg Arg Ile Thr Val Leu Tyr Ser
                500                 505                 510

Leu Val Gln Gly Gln Gln Leu Asn Pro Tyr Leu Arg Leu Lys Val Arg
                515                 520                 525

Arg Asp His Ile Ile Asp Asp Ala Leu Val Arg Leu Glu Met Ile Ala
                530                 535                 540

Met Glu Asn Pro Ala Asp Leu Lys Lys Gln Leu Tyr Val Glu Phe Glu
545                 550                 555                 560

Gly Glu Gln Gly Val Asp Glu Gly Val Ser Lys Glu Phe Phe Gln
                565                 570                 575

Leu Val Val Glu Glu Ile Phe Asn Pro Asp Ile Gly Met Phe Thr Tyr
                580                 585                 590

Asp Glu Ser Thr Lys Leu Phe Trp Phe Asn Pro Ser Ser Phe Glu Thr
                595                 600                 605

Glu Gly Gln Phe Thr Leu Ile Gly Ile Val Leu Gly Leu Ala Ile Tyr
            610                 615                 620

Asn Asn Cys Ile Leu Asp Val His Phe Pro Met Val Val Tyr Arg Lys
625                 630                 635                 640
```

```
Leu Met Gly Lys Lys Gly Thr Phe Arg Asp Leu Gly Asp Ser His Pro
                645                 650                 655

Val Leu Tyr Gln Ser Leu Lys Asp Leu Leu Glu Tyr Glu Gly Asn Val
            660                 665                 670

Glu Asp Asp Met Met Ile Thr Phe Gln Ile Ser Gln Thr Asp Leu Phe
            675                 680                 685

Gly Asn Pro Met Met Tyr Asp Leu Lys Glu Asn Gly Asp Lys Ile Pro
690                 695                 700

Ile Thr Asn Glu Asn Arg Lys Glu Phe Val Asn Leu Tyr Ser Asp Tyr
705                 710                 715                 720

Ile Leu Asn Lys Ser Val Glu Lys Gln Phe Lys Ala Phe Arg Arg Gly
                725                 730                 735

Phe His Met Val Thr Asn Glu Ser Pro Leu Lys Tyr Leu Phe Arg Pro
            740                 745                 750

Glu Glu Ile Glu Leu Leu Ile Cys Gly Ser Arg Asn Leu Asp Phe Gln
            755                 760                 765

Ala Leu Glu Glu Thr Thr Glu Tyr Asp Gly Gly Tyr Thr Arg Asp Ser
        770                 775                 780

Val Leu Ile Arg Glu Phe Trp Glu Ile Val His Ser Phe Thr Asp Glu
785                 790                 795                 800

Gln Lys Arg Leu Phe Leu Gln Phe Thr Thr Gly Thr Asp Arg Ala Pro
                805                 810                 815

Val Gly Gly Leu Gly Lys Leu Lys Met Ile Ile Ala Lys Asn Gly Pro
            820                 825                 830

Asp Thr Glu Arg Leu Pro Thr Ser His Thr Cys Phe Asn Val Leu Leu
        835                 840                 845

Leu Pro Glu Tyr Ser Ser Lys Glu Lys Leu Lys Glu Arg Leu Leu Lys
        850                 855                 860

Ala Ile Thr Tyr Ala Lys Gly Phe Gly Met Leu
865                 870                 875

<210> SEQ ID NO 59
<211> LENGTH: 1068
<212> TYPE: PRT
<213> ORGANISM: Homo sapiens

<400> SEQUENCE: 59

Met Phe Thr Leu Ser Gln Thr Ser Arg Ala Trp Phe Ile Asp Arg Ala
1               5                   10                  15

Arg Gln Ala Arg Glu Glu Arg Leu Val Gln Lys Glu Arg Glu Arg Ala
                20                  25                  30

Ala Val Val Ile Gln Ala His Val Arg Ser Phe Leu Cys Arg Ser Arg
            35                  40                  45

Leu Gln Arg Asp Ile Arg Arg Glu Ile Asp Asp Phe Phe Lys Ala Asp
        50                  55                  60

Asp Pro Glu Ser Thr Lys Arg Ser Ala Leu Cys Ile Phe Lys Ile Ala
65                  70                  75                  80

Arg Lys Leu Leu Phe Leu Phe Arg Ile Lys Glu Asp Asn Glu Arg Phe
                85                  90                  95

Glu Lys Leu Cys Arg Ser Ile Leu Ser Ser Met Asp Ala Glu Asn Glu
            100                 105                 110

Pro Lys Val Trp Tyr Val Ser Leu Ala Cys Ser Lys Asp Leu Thr Leu
        115                 120                 125

Leu Trp Ile Gln Gln Ile Lys Asn Ile Leu Trp Tyr Cys Cys Asp Phe
```

```
            130                 135                 140
Leu Lys Gln Leu Lys Pro Glu Ile Leu Gln Asp Ser Arg Leu Ile Thr
145                 150                 155                 160

Leu Tyr Leu Thr Met Leu Val Thr Phe Thr Asp Thr Ser Thr Trp Lys
                165                 170                 175

Ile Leu Arg Gly Lys Gly Glu Ser Leu Arg Pro Ala Met Asn His Ile
            180                 185                 190

Cys Ala Asn Ile Met Gly His Leu Asn Gln His Gly Phe Tyr Ser Val
            195                 200                 205

Leu Gln Ile Leu Leu Thr Arg Gly Leu Ala Arg Pro Arg Pro Cys Leu
            210                 215                 220

Ser Lys Gly Thr Leu Thr Ala Ala Phe Ser Leu Ala Leu Arg Pro Val
225                 230                 235                 240

Ile Ala Ala Gln Phe Ser Asp Asn Leu Ile Arg Pro Phe Leu Ile His
                245                 250                 255

Ile Met Ser Val Pro Ala Leu Val Thr His Leu Ser Thr Val Thr Pro
                260                 265                 270

Glu Arg Leu Thr Val Leu Glu Ser His Asp Met Leu Arg Lys Phe Ile
                275                 280                 285

Ile Phe Leu Arg Asp Gln Asp Arg Cys Arg Asp Val Cys Glu Ser Leu
            290                 295                 300

Glu Gly Cys His Thr Leu Cys Leu Met Gly Asn Leu Leu His Leu Gly
305                 310                 315                 320

Ser Leu Ser Pro Arg Val Leu Glu Glu Thr Asp Gly Phe Val Ser
                325                 330                 335

Leu Leu Thr Gln Thr Leu Cys Tyr Cys Arg Lys Tyr Val Ser Gln Lys
            340                 345                 350

Lys Ser Asn Leu Thr His Trp His Pro Val Leu Gly Trp Phe Ser Gln
            355                 360                 365

Ser Val Asp Tyr Gly Leu Asn Glu Ser Met His Leu Ile Thr Lys Gln
            370                 375                 380

Leu Gln Phe Leu Trp Gly Val Pro Leu Ile Arg Ile Phe Phe Cys Asp
385                 390                 395                 400

Ile Leu Ser Lys Lys Leu Leu Glu Ser Gln Glu Pro Ala His Ala Gln
                405                 410                 415

Pro Ala Ser Pro Gln Asn Val Leu Pro Val Lys Ser Leu Leu Lys Arg
                420                 425                 430

Ala Phe Gln Lys Ser Ala Ser Val Arg Asn Ile Leu Arg Pro Val Gly
            435                 440                 445

Gly Lys Arg Val Asp Ser Ala Glu Val Gln Lys Val Cys Asn Ile Cys
            450                 455                 460

Val Leu Tyr Gln Thr Ser Leu Thr Leu Thr Gln Ile Arg Leu Gln
465                 470                 475                 480

Ile Leu Thr Gly Leu Thr Tyr Leu Asp Asp Leu Leu Pro Lys Leu Trp
                485                 490                 495

Ala Phe Ile Cys Glu Leu Gly Pro His Gly Leu Lys Leu Phe Leu
                500                 505                 510

Glu Cys Leu Asn Asn Asp Thr Glu Glu Ser Lys Gln Leu Leu Ala Met
            515                 520                 525

Leu Met Leu Phe Cys Asp Cys Ser Arg His Leu Ile Thr Ile Leu Asp
            530                 535                 540

Asp Ile Glu Val Tyr Glu Glu Gln Ile Ser Phe Lys Leu Glu Glu Leu
545                 550                 555                 560
```

```
Val Thr Ile Ser Ser Phe Leu Asn Ser Phe Val Phe Lys Met Ile Trp
            565                 570                 575

Asp Gly Ile Val Glu Asn Ala Lys Gly Glu Thr Leu Glu Leu Phe Gln
            580                 585                 590

Ser Val His Gly Trp Leu Met Val Leu Tyr Glu Arg Asp Cys Arg Arg
        595                 600                 605

Arg Phe Thr Pro Glu Asp His Trp Leu Arg Lys Asp Leu Lys Pro Ser
        610                 615                 620

Val Leu Phe Gln Glu Leu Asp Arg Asp Arg Lys Arg Ala Gln Leu Ile
625                 630                 635                 640

Leu Gln Tyr Ile Pro His Val Ile Pro His Lys Asn Arg Val Leu Leu
                645                 650                 655

Phe Arg Thr Met Val Thr Lys Glu Lys Glu Lys Leu Gly Leu Val Glu
                660                 665                 670

Thr Ser Ser Ala Ser Pro His Val Thr His Ile Thr Ile Arg Arg Ser
            675                 680                 685

Arg Met Leu Glu Asp Gly Tyr Glu Gln Leu Arg Gln Leu Ser Gln His
        690                 695                 700

Ala Met Lys Gly Val Ile Arg Val Lys Phe Val Asn Asp Leu Gly Val
705                 710                 715                 720

Asp Glu Ala Gly Ile Asp Gln Asp Gly Val Phe Lys Glu Phe Leu Glu
                725                 730                 735

Glu Ile Ile Lys Arg Val Phe Asp Pro Ala Leu Asn Leu Phe Lys Thr
                740                 745                 750

Thr Ser Gly Asp Glu Arg Leu Tyr Pro Ser Pro Thr Ser Tyr Ile His
            755                 760                 765

Glu Asn Tyr Leu Gln Leu Phe Glu Phe Val Gly Lys Met Leu Gly Lys
        770                 775                 780

Ala Val Tyr Glu Gly Ile Val Val Asp Val Pro Phe Ala Ser Phe Phe
785                 790                 795                 800

Leu Ser Gln Leu Leu Gly His His His Ser Val Phe Tyr Ser Ser Val
                805                 810                 815

Asp Glu Leu Pro Ser Leu Asp Ser Glu Phe Tyr Lys Asn Leu Thr Ser
                820                 825                 830

Ile Lys Arg Tyr Asp Gly Asp Ile Thr Asp Leu Gly Leu Thr Leu Ser
            835                 840                 845

Tyr Asp Glu Asp Val Met Gly Gln Leu Val Cys His Glu Leu Ile Pro
        850                 855                 860

Gly Gly Lys Thr Ile Pro Val Thr Asn Glu Asn Lys Ile Ser Tyr Ile
865                 870                 875                 880

His Leu Met Ala His Phe Arg Met His Thr Gln Ile Lys Asn Gln Thr
                885                 890                 895

Ala Ala Leu Ile Ser Gly Phe Arg Ser Ile Ile Lys Pro Glu Trp Ile
                900                 905                 910

Arg Met Phe Ser Thr Pro Glu Leu Gln Arg Leu Ile Ser Gly Asp Asn
            915                 920                 925

Ala Glu Ile Asp Leu Glu Asp Leu Lys Lys His Thr Val Tyr Tyr Gly
        930                 935                 940

Gly Phe His Gly Ser His Arg Val Ile Ile Trp Leu Trp Asp Ile Leu
945                 950                 955                 960

Ala Ser Asp Phe Thr Pro Asp Glu Arg Ala Met Phe Leu Lys Phe Val
                965                 970                 975
```

-continued

```
Thr Ser Cys Ser Arg Pro Pro Leu Leu Gly Phe Ala Tyr Leu Lys Pro
            980                 985                 990

Pro Phe Ser Ile Arg Cys Val Glu Val Ser Asp Asp Gln Asp Thr Gly
        995                1000                1005

Asp Thr Leu Gly Ser Val Leu Arg Gly Phe Phe Thr Ile Arg Lys
    1010                1015                1020

Arg Glu Pro Gly Gly Arg Leu Pro Thr Ser Ser Thr Cys Phe Asn
    1025                1030                1035

Leu Leu Lys Leu Pro Asn Tyr Ser Lys Lys Ser Val Leu Arg Glu
    1040                1045                1050

Lys Leu Arg Tyr Ala Ile Ser Met Asn Thr Gly Phe Glu Leu Ser
    1055                1060                1065

<210> SEQ ID NO 60
<211> LENGTH: 216
<212> TYPE: PRT
<213> ORGANISM: Escherichia coli

<400> SEQUENCE: 60

Met Pro Phe Ser Phe Asn Leu Ser Ser Gly Asn Tyr Leu Ser Thr Gln
1               5                   10                  15

Asp Val Glu Val Leu Gln Arg Ala Thr Arg Asp His Gln Met Glu Arg
            20                  25                  30

Leu Thr Ile Gly Glu Arg Ser Phe Ser Val Arg Tyr Gln Ser Ala Met
        35                  40                  45

Asp Ala Phe Ile Val Asp Pro Val Gln Gly Glu Leu Tyr Ser Gly Leu
    50                  55                  60

Ser His Thr Glu Leu Ala Asp Ile Ile Arg Leu Ala Asp Ser Val Glu
65                  70                  75                  80

Asn Gln Leu Asn Gly Gly Asn Ser Phe Leu Asp Val Phe Ser Thr Tyr
                85                  90                  95

Met Gly Gln Val Ile Ser Glu Phe Met His Ser Asn Asp Asn Arg Ile
            100                 105                 110

Glu Leu Leu Gln Arg Arg Leu His Ser Cys Ser Phe Leu Val Asn Ile
        115                 120                 125

Glu Glu Met Ser Tyr Ile Asp Glu Ala Leu Gln Cys Pro Ile Thr Leu
    130                 135                 140

Ala Ile Pro Gln Arg Gly Val Phe Leu Arg Asn Ala Glu Gly Ser Arg
145                 150                 155                 160

Val Cys Ser Leu Tyr Asp Glu Met Ala Leu Ser Arg Ile Ile Asn Asp
                165                 170                 175

Gly Met His His Pro Leu Ser Arg Glu Pro Ile Thr Leu Ser Met Leu
            180                 185                 190

Val Ala Arg Glu Gln Cys Glu Phe Asp Cys Ser Ile Gly His Phe Thr
        195                 200                 205

Val Arg Ser Asp Cys Tyr Ser Val
    210                 215

<210> SEQ ID NO 61
<211> LENGTH: 140
<212> TYPE: PRT
<213> ORGANISM: Escherichia coli

<400> SEQUENCE: 61

Met Glu Arg Arg Ala Val Ala Leu Glu Arg Gln Leu Asn Gly Gly Val
1               5                   10                  15
```

Asp Phe Leu Arg Ser Val Asn Asn Tyr Phe Gln Ser Val Met Ala Glu
            20                  25                  30

His Arg Glu Asn Lys Thr Ser Asn Lys Ile Leu Met Glu Lys Ile Asn
        35                  40                  45

Ser Cys Val Phe Gly Thr Asp Ser Asn His Phe Ser Cys Pro Glu Ser
    50                  55                  60

Phe Leu Thr Cys Pro Ile Thr Leu Asp Thr Pro Ala Asn Gly Val Phe
65                  70                  75                  80

Met Arg Asn Ser Gln Gly Ala Glu Ile Cys Ser Leu Tyr Asp Lys Asp
                85                  90                  95

Thr Leu Val Gln Leu Val Glu Thr Gly Gly Ala His Pro Leu Ser Arg
            100                 105                 110

Glu Pro Ile Thr Glu Ser Met Ile Met Arg Lys Asp Glu Cys His Phe
        115                 120                 125

Asp Ser Lys Lys Glu Ser Phe Val Ala Ser Asp Ala
    130                 135                 140

<210> SEQ ID NO 62
<211> LENGTH: 123
<212> TYPE: PRT
<213> ORGANISM: Escherichia coli

<400> SEQUENCE: 62

Met Leu Gln Leu Ser Ser Asn Ile Gly Trp Lys Gly Ala Glu Asn
1               5                   10                  15

Ala Leu Lys Asn Lys Ile His Ser His Ser Phe Val Val Asn Pro Asp
            20                  25                  30

Glu Phe Ser Cys Asp Thr Gln Phe Leu Lys Cys Pro Ile Thr Leu Cys
        35                  40                  45

Val Pro Glu Lys Gly Val Phe Val Lys Asn Ala Leu Asn Ser Asn Ile
    50                  55                  60

Cys Thr Leu Tyr Asp Lys Ser Ala Phe Met Asn Leu Thr Arg Glu His
65                  70                  75                  80

Leu Pro His Pro Leu Ser Arg Glu Lys Ile Val Lys Glu Met Ile Ile
                85                  90                  95

Glu Arg Asn Met Cys Tyr Phe Asp Thr Ile Ser Gln His Phe Ile Ile
            100                 105                 110

Met Asp Ala Asp Gln Gln Lys Gln His Cys Lys
        115                 120

<210> SEQ ID NO 63
<211> LENGTH: 660
<212> TYPE: DNA
<213> ORGANISM: Artificial sequence
<220> FEATURE:
<223> OTHER INFORMATION: An exemplary DNA sequence that encodes full
      length CAT

<400> SEQUENCE: 63
atggagaaaa aaatcactgg atataccacc gttgatatat cccaatggca tcgtaaagaa      60
cattttgagg catttcagtc agttgctcaa tgtacctata accagaccgt tcagctggat     120
attacggcct ttttaaagac cgtaaagaaa aataagcaca gtttatcc ggcctttatt      180 cacattcttg cccgcctgat gaatgctcat ccggaattcc gtatggcaat gaaagacggt     240
gagctggtga tatgggatag tgttcaccct tgttacaccg ttttccatga gcaaactgaa     300
acgttttcat cgctctggag tgaataccac gacgatttcc ggcagtttct acacatatat     360

```
tcgcaagatg tggcgtgtta cggtgaaaac ctggcctatt tccctaaagg gtttattgag    420
aatatgtttt tcgtctcagc caatccctgg gtgagtttca ccagttttga tttaaacgtg    480
gccaatatgg acaacttctt cgcccccgtt ttcaccatgg gcaaatatta tacgcaaggc    540
gacaaggtgc tgatgccgct ggcgattcag gttcatcatg ccgtctgtga tggcttccat    600
gtcggcagaa tgcttaatga attacaacag tactgcgatg agtggcaggg cggggcgtaa    660
```

<210> SEQ ID NO 64
<211> LENGTH: 219
<212> TYPE: PRT
<213> ORGANISM: Artificial sequence
<220> FEATURE:
<223> OTHER INFORMATION: amino acid sequence of CAT

<400> SEQUENCE: 64

Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
            20                  25                  30

Tyr Asn Gln Thr Val Gln Leu Asp Ile Thr Ala Phe Leu Lys Thr Val
        35                  40                  45

Lys Lys Asn Lys His Lys Phe Tyr Pro Ala Phe Ile His Ile Leu Ala
    50                  55                  60

Arg Leu Met Asn Ala His Pro Glu Phe Arg Met Ala Met Lys Asp Gly
65                  70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190

His Ala Val Cys Asp Gly Phe His Val Gly Arg Met Leu Asn Glu Leu
        195                 200                 205

Gln Gln Tyr Cys Asp Glu Trp Gln Gly Gly Ala
    210                 215

<210> SEQ ID NO 65
<211> LENGTH: 93
<212> TYPE: DNA
<213> ORGANISM: Artificial sequence
<220> FEATURE:
<223> OTHER INFORMATION: CAT N-terminal fragment nucleic acid sequence

<400> SEQUENCE: 65

```
atggagaaaa aaatcactgg atataccacc gttgatatat cccaatggca tcgtaaagaa    60
cattttgagg catttcagtc agttgctcaa taa                                 93
```

<210> SEQ ID NO 66
<211> LENGTH: 573

<212> TYPE: DNA
<213> ORGANISM: Artificial sequence
<220> FEATURE:
<223> OTHER INFORMATION: CAT C-terminal fragment nucleic acid sequence

<400> SEQUENCE: 66

```
atgtgtacct ataaccagac cgttcagctg gatattacgg ccttttttaaa gaccgtaaag      60
aaaaataagc acaagtttta tccggccttt attcacattc ttgcccgcct gatgaatgct     120
catccggaat tccgtatggc aatgaaagac ggtgagctgg tgatatggga tagtgttcac     180
ccttgttaca ccgttttcca tgagcaaact gaaacgtttt catcgctctg gagtgaatac     240
cacgacgatt tccggcagtt tctacacata tattcgcaag atgtggcgtg ttacggtgaa     300
aacctggcct atttccctaa agggtttatt gagaatatgt ttttcgtctc agccaatccc     360
tgggtgagtt tcaccagttt tgatttaaac gtggccaata tggacaactt cttcgccccc     420
gttttcacca tgggcaaata ttatacgcaa ggcgacaagg tgctgatgcc gctggcgatt     480
caggttcatc atgccgtctg tgatggcttc catgtcggca gaatgcttaa tgaattacaa     540
cagtactgcg atgagtggca gggcggggcg taa                                  573
```

<210> SEQ ID NO 67
<211> LENGTH: 30
<212> TYPE: PRT
<213> ORGANISM: Artificial sequence
<220> FEATURE:
<223> OTHER INFORMATION: CAT N-terminal fragment amino acid sequence

<400> SEQUENCE: 67

```
Met Glu Lys Lys Ile Thr Gly Tyr Thr Thr Val Asp Ile Ser Gln Trp
1               5                   10                  15
His Arg Lys Glu His Phe Glu Ala Phe Gln Ser Val Ala Gln
            20                  25                  30
```

<210> SEQ ID NO 68
<211> LENGTH: 190
<212> TYPE: PRT
<213> ORGANISM: Artificial sequence
<220> FEATURE:
<223> OTHER INFORMATION: CAT C-terminal fragment amino acid sequence

<400> SEQUENCE: 68

```
Met Cys Thr Tyr Asn Gln Thr Val Gln Leu Asp Ile Thr Ala Phe Leu
1               5                   10                  15
Lys Thr Val Lys Lys Asn Lys His Lys Phe Tyr Pro Ala Phe Ile His
            20                  25                  30
Ile Leu Ala Arg Leu Met Asn Ala His Pro Glu Phe Arg Met Ala Met
        35                  40                  45
Lys Asp Gly Glu Leu Val Ile Trp Asp Ser Val His Pro Cys Tyr Thr
    50                  55                  60
Val Phe His Glu Gln Thr Glu Thr Phe Ser Ser Leu Trp Ser Glu Tyr
65                  70                  75                  80
His Asp Asp Phe Arg Gln Phe Leu His Ile Tyr Ser Gln Asp Val Ala
                85                  90                  95
Cys Tyr Gly Glu Asn Leu Ala Tyr Phe Pro Lys Gly Phe Ile Glu Asn
            100                 105                 110
Met Phe Phe Val Ser Ala Asn Pro Trp Val Ser Phe Thr Ser Phe Asp
        115                 120                 125
Leu Asn Val Ala Asn Met Asp Asn Phe Phe Ala Pro Val Phe Thr Met
    130                 135                 140
```

```
Gly Lys Tyr Tyr Thr Gln Gly Asp Lys Val Leu Met Pro Leu Ala Ile
145                 150                 155                 160

Gln Val His His Ala Val Cys Asp Gly Phe His Val Gly Arg Met Leu
                165                 170                 175

Asn Glu Leu Gln Gln Tyr Cys Asp Glu Trp Gln Gly Gly Ala
            180                 185                 190
```